US011684643B2

(12) United States Patent
Gibson et al.

(10) Patent No.: US 11,684,643 B2
(45) Date of Patent: Jun. 27, 2023

(54) PROBIOTIC COMPOSITIONS AND USES THEREOF

(71) Applicant: The University of British Columbia, Vancouver (CA)

(72) Inventors: Deanna Gibson, Kelowna (CA); Artem Godovannyi, Moscow (RU); Sandeep Gill, Kelowna (CA)

( * ) Notice: Subject to any disclaimer, the term of this patent is extended or adjusted under 35 U.S.C. 154(b) by 26 days.

(21) Appl. No.: 16/486,803

(22) PCT Filed: Feb. 19, 2018

(86) PCT No.: PCT/CA2018/050188
§ 371 (c)(1),
(2) Date: Aug. 16, 2019

(87) PCT Pub. No.: WO2018/148847
PCT Pub. Date: Aug. 23, 2018

(65) Prior Publication Data
US 2020/0069747 A1 Mar. 5, 2020

Related U.S. Application Data

(60) Provisional application No. 62/460,185, filed on Feb. 17, 2017.

(51) Int. Cl.

| | |
|---|---|
| ***A61K 35/747*** | (2015.01) |
| ***A61K 35/741*** | (2015.01) |
| ***C07K 14/255*** | (2006.01) |
| ***C07K 14/24*** | (2006.01) |
| ***C07K 14/28*** | (2006.01) |
| ***A61K 35/00*** | (2006.01) |
| ***A61P 1/00*** | (2006.01) |
| ***C07K 14/195*** | (2006.01) |
| ***C07K 14/335*** | (2006.01) |

(52) U.S. Cl.
CPC .......... *A61K 35/747* (2013.01); *A61K 35/741* (2013.01); *A61P 1/00* (2018.01); *C07K 14/195* (2013.01); *C07K 14/24* (2013.01); *C07K 14/255* (2013.01); *C07K 14/28* (2013.01); *C07K 14/335* (2013.01); *A61K 2035/115* (2013.01)

(58) Field of Classification Search
None
See application file for complete search history.

(56) References Cited

FOREIGN PATENT DOCUMENTS

WO WO 2012/138570 A2 10/2012

OTHER PUBLICATIONS

Nishiyama et al. Biosci. Biotechnol. Biochem. 79: 271-279, 2014.*
Hansen-Wester et al. Infect. Immun. 72: 2879-2888, 2004.*
Hensel M et al. Mol. Microbiol. 31: 489-498, 1999) (Hensel M et al., 1999.*
GenEmbl accession No. AJ224978.*
Hinsley et al. FEBS Letters 497: 45-49, 2001.*
Hinsley et al. Microbiology 148: 3631-3638, 2002.*
Rao et al. PNAS 102: 11993-11998, 2005.*
Skolnick et al. Trends in Biotechnology 18: 34-39, 2000.*
Rudinger J. In: Peptide Hormones. (Ed) JA Parsons, University Park Press, pp. 1-7, 1976.*
Lazar et al. Mol. Cellular Biol. 8: 1247-1252, 1988.*
Seffernick et al. J. Bacteriol. 183: 2405-2410, 2001.*
Sriramulu et al. J. Bacteriol. 190: 4559-4567, 2008.*
Partial Supplemental Search Report for Corresponding European Patent Application No. EP 18 755 048.8, dated Dec. 11, 2020, 11 pages.
Gill, S K et al, "Novel strategies that enhance the bioavailability of probiotics for therapeutic use during inflammatory bowel disease", Journal of Clinical Gastroenterology United States, Lippincott Williams & Wilkins, US, vol. 52, Jan. 1, 2018, 1 page.
Alander, M. et al., "Persistence of Colonization of Human Colonic Mucosa by a Probiotic Strain, Lactobacillus thamnosus GG, after Oral Consumption", (1999) Appl & Environ Microbiol. 65(1):351-354.
Almagro-Moren, S. et al., "Intestinal Colonization Dynamics of Vibrio cholerae", PLOS Pathog, May 21, 2015, vol. 11, No. 5, e1004787, pp. 1-11.
Baker, J. et al., Medicinal lavender modulates the enteric microbiota to protect against Citrobacter rodentium-induced colitis, 2012, Am J Physiol Gastrintest Liver Physiol, 303(7):G825-G836.
Beltran, S. et al., "The expression of heterologous MAM-7 in Lactobacillus rhamnosus reduces its intrinsic capacity to inhibit colonization of pathogen Vibrio parahaemolyticus in vitro", Biol Res., Jan. 7, 2016, vol. 49, nNo. 2, pp. 1-10.
Bergstrom, KS et al., Muc2 Protects Against Lethal Infectious Colitis by Disassociating Pathogenic and Commensal Bacteria from the Colonic Mucosa, PLOS Pathogens, 2010;13(6), e1000902, pp. 1-25.
Culligan, E.P. et al., "Probiotics and gastrointestinal disease: successes, problems and future prospects", Gut Pathogens, Nov. 23, 2009, vol. 1, No. 19, pp. 1-12.
Datsenko, K.A. et al., "One-step inactivation of chromosomal genes in *Escherichia coli* K-12 using PCR Products", 2000, Proc Nat Acad Sci, 97(12):6640-6645.
Quigley, Eamonn W.W., "Do patients with functional gastrointestinal disorders have an altered gut flora?", Therapeutic Advances in Gastroenterology, 2009, Suppl. 1, S23-S30.
Haldimann, A. et al. "Conditional-Republication, Integration, Excision, and Retrieval Plasmid-Host Systems for Gene Structure-Function Studies of Bacteria", 2001, Journal of Bacteriology, vol. 183, No. 21, pp. 6384-6393.
Hensel, M. et al., "The genetic basis of tetrathionate respiration in *Salmonella typhimurium*", Mol. Microbiol., Apr. 1999, vol. 32, No. 2, pp. 275-287 (Same as Hensel et al. 1999 Mol Microbiol 32:275-287).

(Continued)

*Primary Examiner* — S. Devi

(57) ABSTRACT

The present invention relates to probiotic compositions. More specifically, the present invention relates to probiotic compositions that are useful in reducing inflammation and/or that exhibit increased colonization or persistence in the gastrointestinal tract of a mammal.

19 Claims, 59 Drawing Sheets

Specification includes a Sequence Listing.

(56) References Cited

OTHER PUBLICATIONS

Vankov, D.N. et al., "How many signal peptides are there in bacteria?", Environmental Microbiology, 2013, 15 (4):983-990.
Lock, H.E. et al., "Combining the Polymerase incomplete primer extension method for cloning and mutagenesis with microscreening to accelerate structural genomics efforts", 2008, Proteins, 71:982-994.
Li, Jingru et al., "Lactobacillus reuteri-produced cyclic dipeptides quench agr-mediated expression of toxic shock syndrome toxin-1 in staphylococci", PNAS, Feb. 22, 2011, vol. 8, No. 8, pp. 3360-3365.
Morampudi, V. et al., "The goblet cell-derived mediator RELM-B drives spontaneous colitis in Muc2-deficient mice by promoting commensal microbial dysbiosis", Mucosal. Immunolgy, 2016, vol. 9, No. 5, pp. 1-16.
Morrison, D.J. et al., "Formation of short chain fatty acids by the gut microbiota and their impact on human metabolism", Gut Microbes, 2016, vol. 7, No. 3, pp. 189-200.
Neurath, M F, "Cytokines in inflammatory bowel disease", Nature Reviews, Immunology, 2014, vol. 14, pp. 329-342.
Payne, S. H. et al. "Unexpected Diversity of Signal Peptides in Prokaryotes", M Bio. 2012, vol. 3, Issue 6, e00339, pp. 1-12.
Ratsimandresy, R. A. et al., "The AIM2 inflammasome is a central regulator of intestinal homeostasis through the IL-18/IL-22/STAT3 pathway", Cellular & Molecular Immunology (2017) 14, 127-142.
Winter, Sebastian et al., "Gut inflammation provides a respiratory electron acceptor for *Salmonella*", Nature (2010) vol. 467, pp. 426-429.
Wong, E. et al., "The Vibrio cholera Colonization Factor GbpA Possesses a Modular Structure that Governs Binding to Different Host Surfaces", PLOS Pathog., 2012, vol. 8, No. 1, e1002373, pp. 1-12.
Zhao, G. et al., "Rapid determination of short-chain fatty acids in colonic contents and faeces of humans and rats by acidified water-extraction and direct-injection gas chromatography", Biomedical Chromatography, 2006, vol. 20, No. 8, pp. 674-682.
International Search Report and Written Opinion issued in corresponding International Application No. PCT/CA2018/050188 dated May 14, 2018, 14 pages.

* cited by examiner

MKKQPKMTAIALILSGISGLAYGHGYVSAVENGVAEGRVTLCKFAANGTGEKNTHCGAIQY
EPQSVEGPDGFPVTGPRDGKIASAESALAAALDEQTADRWVKRPIQAGPQTFEWTFTANH
VTKDWKYYITKPNWNPNQPLSRDAFDLNPFCVVEGNMVQPPKRVSHECIVPEREGYQVILA
VWDVGDTAASFYNVIDVKFDGNGPVLPDWNPAGQIIPSMDLSIGDTVYTRVFDNDGENPAY
RTELKIDSETLTKANQWSYALATKINQTQKQQRAGQLNGDQFVPVYGTNPIYLKEGSGLKS
VEIGYQIEAPQPEYSLTVSGLAKEYEIGEQPIQLDLTLEAQGEMSAELTVYNHHQKPLASWS
QAMTDGELKSITLELSEAKAGHHMLVSRIKDRDGNLQDQQTLDFMLVEPQTPPTPGDYDFV
FPNGLKEYVAGTKVLASDGAIYQCKPWPYSGYCQQWTSNATQYQPGTGSHWEMAWDKR
(SEQ ID NO: 19)

FIGURE 30A atgaaaaaacaacctaaaatgaccgctattgccctgatcctctctggtatcagtggattagcgtatgg
acacggctacgtttccgcagtggaaaacggtgtcgccgaaggacgtgtcaccttgtgtaaatttgccg
ctaacggcactggagagaaaaacactcactgtggcgcgattcaatacgaaccacaaagtgtcgaaggc
ccagatggcttcccggtcactggccctcgtgatggcaaaattgccagtgcggaatcggcactggcggc
agcgctggatgagcaaaccgccgaccgttgggtaaagcgcccaattcaagctggcccacaaaccttcg
agtggacgttcaccgccaaccacgtcacaaaggattggaaatactacattaccaaaccaaactggaac
ccaaaccagccattgtcgcgtgatgcatttgacctcaatccgttctgtgtcgttgaaggaaatatggt
gcagccaccaaaacgtgtcagccacgaatgtatcgtgcctgagcgcgaagggtatcaggtcatcctcg
ccgtatgggatgttggcgataccgcagcttccttctacaacgtgatcgacgtgaaatttgacggtaac
ggcccagtgttacccgattggaacccagcaggtcaaatcattccaagtatggatctcagcattggcga
taccgtgtacactcgcgtgtttgataacgatggggaaaaccctgcttatcgcactgagctaaaaattg
actctgagacgctaaccaaagccaatcaatggtcttacgctctggcgactaaaattaaccaaacgcaa
aaacagcaacgtgctggtcagcttaatggcgatcaatttgttcccgtttacggcaccaacccgattta
tctgaaagaaggcagtggcttgaagagtgttgaaattggctaccaaattgaagcgccacagcctgagt
attcactgacggtttctggtctagcgaaagagtatgagattggcgaacaaccgattcagcttgacctg
actttagaagcgcaaggtgaaatgagcgcagagctgaccgtgtataaccaccaccaaaaaccgctggc
aagttggtcacaagcgatgacggatggcgagctgaaatccatcacgctagagctgagcgaagctaaag
cgggacatcatatgttggtttctcgcatcaaagatcgcgatggcaatctgcaagatcaacaaactctc
gatttcatgctggttgaaccgcaaacaccaccaacaccgggtgactacgactttgtgttcccgaatgg
cctgaaagagtacgtggctggcaccaaagtgctcgctagtgatggcgcaatctaccaatgtaagccat
ggccatactctggctactgccagcaatggacaagtaacgctactcaataccaaccgggtactggcagt
cattgggaaatggcgtgggataaacgttaa (SEQ ID NO: 26)

FIGURE 30B

HGYVSAVENGVAEGRVTLCKFAANGTGEKNTHCGAIQYEPQSVEGPDGFPVTGPRDGKIA
SAESALAAALDEQTADRWVKRPIQAGPQTFEWTFTANHVTKDWKYYITKPNWNPNQPLSR
DAFDLNPFCVVEGNMVQPPKRVSHECIVPEREGYQVILAVWDVGDTAASFYNVIDVKFDG
(SEQ ID NO: 20)

FIGURE 31A atgaaaaaacaacctaaaatgaccgctattgccctgatcctctctggtatcagtggattagcgtatggacacggctacgtttccgcagtggaaaa
cggtgtcgccgaaggacgtgtcaccttgtgtaaatttgccgctaacggcactggagagaaaaacactcactgtggcgcgattcaatacgaacca
caaagtgtcgaaggcccagatggcttcccggtcactggccctcgtgatggcaaaattgccagtgcggaatcggcactggcggcagcgctggatg
agcaaaccgccgaccgttgggtaaagcgcccaattcaagctggcccacaaaccttcgagtggacgttcaccgccaaccacgtcacaaaggatt
ggaaatactacattaccaaaccaaactggaacccaaaccagccattgtcgcgtgatgcatttgacctcaatccgttctgtgtcgttgaaggaaat
atggtgcagccaccaaaacgtgtcagccacgaatgtatcgtgcctgagcgcgaagggtatcaggtcatc (SEQ ID NO: 27)

FIGURE 31B

CACGGTTACGTATCGGCAGTTGAAAACGGTGTAGCCGAAGGGCGTGTAACTCTTTGTA
AATTTGCAGCCAACGGTACAGGGGAGAAAAACACACACTGTGGTGCAATTCAATATGAA
CCTCAATCTGTAGAAGGTCCTGATGGTTTCCCTGTAACAGGTCCTCGTGATGGTAAAAT
TGCCTCTGCAGAATCTGCCCTTGCAGCCGCACTTGATGAACAAACTGCAGACCGTTGG
GTCAAGCGTCCTATTCAAGCAGGTCCTCAAACTTTCGAGTGGACCTTCACTGCAAACCA
CGTAACGAAGGATTGGAAGTACTACATTACTAAGCCAAACTGGAACCCAAACCAGCCTC
TTAGCCGTGATGCATTTGACTTGAACCCTTTCTGTGTCGTAGAAGGGAACATGGTTCAG
CCTCCTAAGCGTGTATCTCACGAATGTATTGTTCCTGAACGTGAAGGGTACCAGGTAAT
CCTAGCAGTCTGGGATGTAGGTGATACTGCAGCCTCGTTCTACAACGTTATTGACGTTA
AGTTTGACGGT (SEQ ID NO: 22)

FIGURE 31C

MYLGGLIMLSRKNYKETIRKQTPTKQYYTIKKLTVGVTSVLIGLSFMGELEGDSVHADTMTA
SSESTSVTSTTAQDGLKKSPQLYLQVTDTNNPSTPLSASSTGTSKNVTSSAAVQVKSASDE
EDSDSTLAKGENKFARSAVKDSVTDGKTSTAEINPAKLSSPALITQLNQSLAKSSTSDAAKA
NDELEIKATDPTNYPNCGDVYGPLFELDASGQLVNKDEVISLKDMYIFQILKLVNTKDSDFQY
VILTMNRKDTADRSVYLFVTGSNYSNAVVVKVKPNDTYELSKTGYSVTYTEPTTINGHYVDG
TFYVTGSTYDDGFIMPDWQLQHLQIIYSLGNYDPSNTDATSVCEIMPSYEKVPVIKYSGVPS
NISQPKVYITGFTGQEFNVTDIINNYKKVFKGYYLQNPNVASMGTLSQFENGGYYLKTYYDN
DGNVDFKGLYHQIDDQGTMSVSVLNADNKTIVGPENILAGKSHNFNFNGHNWIARNPYVTS
SAHEVILKYAKLGSVIPVDENGNKINDGWQYVNDPDDASKATSPYEKAPVIDGYVAVNPDET
IVLPHNLSSDTKIYYRKRIKVTYSGSDSKTYDGNPANFEPTTVQWSGLKGLNTSTLTSADFT
WNTADKKAPTDAGKYTLSLNTTGEAALRKANPNYDLKTISGSYTYTINPLGIDKVTYSGSDS
KTYDGNPANFEPTTVQWSGLKGLNTSTLTSADFTWNTADKKAPTDAGKYTLSLNTTGEAAL
RKANPNYDLKTISGSYTYTINPLGIDKVTYSGSDSKTYDGNPANFEPTTVQWSGLKGLNTST
LTSADFTWNTADKKAPTDAGKYTLSLNTTGEAALRKANPNYDLKTISGSYTYTINPLGIDKVT
YSGSDSKTYDGNPANFEPTTVQWSGLKGLNTSTLTSADFTWNTADKKAPTDAGKYTLSLN
TTGEAALRKANPNYDLKTISGSYTYTINPLGIDKVTYSGSDSKTYDGNPANFEPTTVQWSGL
KGLNTSTLTSADFTWNTADKKAPTDAGKYTLSLNTTGEAALRKANPNYDLKTISGSYTYTIN
PLGIVTVNYKGYDKKVYDGQPGTINPGKLTWSKLPDGTSLKMPTWSIDDFAWETADGLAPT
AVGTYRIILTDAGKAALKKINPNYDLSSITGVFTYEIKPAQTPEILGQTPEQQPGQNTNQSGA
ENGFGSSTRPNASTNSNLNQLPQTGNEHSNTALAGLALAFLTAMLGLGKKRKHD (SEQ ID NO: 21)

FIGURE 32A

```
   1 mlsrknyket irkqtptkqy ytikkltvgv tsvliglsfm gelegdsvha dtmtassest
  61 svtsttaqdg lkkspqlylq vtdtnnpstp lsasstgtsk nvtssaavqv ksasdeedsd
 121 stlakgenkf arsavkdsvt dgktstaein paklsspali tqlnqslaks stsdaakand
 181 eleikatdpt nypncgdvyg plfeldasgq lvnkdevisl kdmyifqilk lvntkdsdfq
 241 yviltmnrkd tadrsvylfv tgsnysnavv vkvkpndtye lsktgysvty tepttinghy
 301 vdgtfyvtgs tyddgfimpd wqlqhlqiiy slgnydpsnt datsvceimp syekvpviky
 361 sgvpsnisqp kvyitgftgq efnvtdiinn ykkvfkgyyl qnpnvasmgt lsqfenggyy
 421 lktyydndgn vdfkglyhqi ddqgtmsvsv lnadnktivg penilagksh nfnfnghnwi
 481 arnpyvtssa hevilkyakl gsvipvdeng nkindgwqyv ndpddaskat spyekapvid
 541 gyvavnpdet ivlphnlssd tkiyyrkrik vtysgsdskt ydgnpanfep ttvqwsglkg
 601 lntstltsad ftwntadkka ptdagkytls lnttgeaalr kanpnydlkt isgsytytin
 661 plgidkvtys gsdsktydgn panfepttvq wsglkglnts tltsadftwn tadkkaptda
 721 gkytlslntt geaalrkanp nydlktisgs ytytinplgi dkvtysgsds ktydgnpanf
 781 epttvqwsgl kglntstlts adftwntadk kaptdagkyt lslnttgeaa lrkanpnydl
 841 ktisgsytyt inplgidkvt ysgsdsktyd gnpanfeptt vqwsglkgln tstltsadft
 901 wntadkkapt dagkytlsln ttgeaalrka npnydlktis gsytytinpl gidkvtysgs
 961 dsktydgnpa nfepttvqws glkglntstl tsadftwnta dkkaptdagk ytlslnttge
1021 aalrkanpny dlktisgsyt ytinplgivt vnykgydkkv ydgqpgtinp gkltwsklpd
1081 gtslkmptws iddfawetad glaptavgty riiltdagka alkkinpnyd lssitgvfty
1141 eikpaqtpei lgqtpeqqpg qntnqsgaen gfgsstrpna stnsnlnqlp qtgnehsnta
1201 laglalaflt amlglgkkrk hd (SEQ ID NO: 28)
```

FIGURE 32B atgCTATCAA GAAAAAATTA TAAGGAAACT ATACGAAAAC AGACACCTAC AAAACAGTAC
TATACTATTA AGAAATTAAC TGTTGGGGTT ACTTCGGTAT TAATTGGTCT ATCCTTTATG
GGAGAACTAG AAGGGGATAG CGTTCATGCG GACACGATGA CAGCAAGCAG TGAGTCAACA
AGTGTTACGT CGACGACTGC TCAGGATGGT TTAAAAAAAT CTCCACAACT CTATTTGCAA
GTTACTGATA CAAATAACCC AAGTACACCA TTAAGTGCTT CATCCACAGG GACTAGTAAG
AATGTTACCT CATCAGCTGC GGTACAAGTG AAGTCCGCTA GTGATGAAGA AGATAGTGAT
TCTACACTAG CTAAGGGAGA AAATAAATTT GCTCGGTCAG CAGTAAAAGA TTCAGTCACT
GATGGGAAAA CAAGTACAGC AGAAATTAAT CCGGCAAAAT TAAGCAGTCC TGCTTTAATA
ACGCAACTCA ACCAATCCTT AGCTAAGAGC AGTACGAGTG ATGCAGCAAA AGCTAATGAT
GAGTTAGAAA TTAAAGCAAC AGATCCGACT AATTATCCAA ACTGTGGCGA TGTGTATGGG
CCATTATTTG AATTGGATGC TAGCGGACAG CTTGTTAATA AAGATGAAGT TATATCTCTT
AAAGATATGT ATATTTTCCA AATATTGAAA TTAGTAAATA CAAAAGATAG TGACTTTCAA
TATGTAATAT TAACAATGAA TCGTAAAGAT ACTGCAGATA GGTCTGTATA TCTTTTTGTA
ACTGGAAGCA ATTATAGTAA TGCTGTTGTT GTTAAAGTAA AGCCAAATGA TACTTATGAA
TTAAGTAAAA CTGGATATAG TGTTACTTAT ACAGAACCAA CAACTATAAA TGGACATTAT
GTTGATGGAA CTTTTTATGT TACAGGAAGT ACTTACGATG ATGGTTTTAT AATGCCAGAT
TGGCAACTGC AGCACCTTCA GATTATATAT AGTTTAGGAA ATTATGATCC AAGCAATACT
GACGCAACAT CAGTTTGTGA AATAATGCCA AGTTATGAAA AGGTACCGGT AATTAAATAT
AGTGGAGTAC CTTCAAATAT TAGCCAACCT AAGGTTTACA TTACCGGGTT TACGGGTCAA
GAGTTTAACG TTACAGATAT TATTAACAAT TATAAGAAAG TTTTTAAGGG CTACTATCTT
CAAAATCCTA ATGTGGCGTC CATGGGAACT CTTTCCCAAT TTGAGAATGG TGGTTATTAC
TTAAAGACAT ATTATGATAA TGATGGTAAT GTTGACTTTA AGGGCTTGTA TCATCAAATT
GATGATCAGG GAACAATGAG TGTGAGTGTT CTTAATGCAG ATAATAAAAC AATTGTTGGA
CCTGAAAATA TTCTTGCTGG TAAATCGCAT AACTTTAACT TTAATGGTCA TAACTGGATT
GCGCGGAATC CTTATGTCAC TAGTTCAGCT CACGAAGTCA TATTAAAGTA TGCTAAGTTA
GGTTCAGTTA TTCCTGTTGA TGAAAACGGA AATAAAATAA ACGATGGATG GCAATATGTT
AATGATCCAG ATGATGCTTC CAAAGCCACT AGCCCATATG AAAAAGCGCC AGTTATCGAT
GGTTATGTAG CTGTAAATCC AGATGAAACG ATCGTTCTTC CTCATAACTT AAGTAGTGAC
ACAAAGATTT ATTACCGAAA GAGGATTAAA GTTACCTATA GTGGTAGTGA CAGCAAGACC
TACGATGGTA ACCCAGCTAA CTTCGAGCCA ACGACAGTTC AGTGGAGTGG CTTGAAAGGA
CTGAACACTT CAACCTTAAC GTCCGCTGAC TTCACGTGGA ATACTGCGGA TAAGAAGGCA
CCAACGGATG CCGGTAAGTA CACACTTAGT TTGAATACGA CCGGAGAAGC AGCCTTACGT
AAGGCTAACC CGAACTATGA TCTCAAGACA ATTAGCGGTA GTTACACCTA CACGATTAAT
CCACTAGGGA TTGATAAAGT TACCTATAGT GGTAGTGACA GCAAGACCTA CGATGGTAAC
CCAGCTAACT TCGAGCCAAC GACAGTTCAG TGGAGTGGCT TGAAAGGACT GAACACTTCA
ACCTTAACGT CCGCTGACTT CACGTGGAAT ACTGCGGATA AGAAGGCACC AACGGATGCC
GGTAAGTACA CACTTAGTTT GAATACGACC GGAGAAGCAG CCTTACGTAA GGCTAACCCG
AACTATGATC TCAAGACAAT TAGCGGTAGT TACACCTACA CGATTAATCC ACTAGGGATT
GATAAAGTTA CCTATAGTGG TAGTGACAGC AAGACCTACG ATGGTAACCC AGCTAACTTC
GAGCCAACGA CAGTTCAGTG GAGTGGCTTG AAAGGACTGA ACACTTCAAC CTTAACGTCC
GCTGACTTCA CGTGGAATAC TGCGGATAAG AAGGCACCAA CGGATGCCGG TAAGTACACA
CTTAGTTTGA ATACGACCGG AGAAGCAGCC TTACGTAAGG CTAACCCGAA CTATGATCTC
AAGACAATTA GCGGTAGTTA CACCTACACG ATTAATCCAC TAGGGATTGA TAAAGTTACC
TATAGTGGTA GTGACAGCAA GACCTACGAT GGTAACCCAG CTAACTTCGA GCCAACGACA
GTTCAGTGGA GTGGCTTGAA AGGACTGAAC ACTTCAACCT TAACGTCCGC TGACTTCACG
TGGAATACTG CGGATAAGAA GGCACCAACG GATGCCGGTA AGTACACACT TAGTTTGAAT
ACGACCGGAG AAGCAGCCTT ACGTAAGGCT AACCCGAACT ATGATCTCAA GACAATTAGC
GGTAGTTACA CCTACACGAT TAATCCACTA GGGATTGATA AAGTTACCTA TAGTGGTAGT
GACAGCAAGA CCTACGATGG TAACCCAGCT AACTTCGAGC CAACGACAGT TCAGTGGAGT
GGCTTGAAAG GACTGAACAC TTCAACCTTA ACGTCCGCTG ACTTCACGTG GAATACTGCG
GATAAGAAGG CACCAACGGA TGCCGGTAAG TACACACTTA GTTTGAATAC GACCGGAGAA
GCAGCCTTAC GTAAGGCTAA CCCGAACTAT GATCTCAAGA CAATTAGCGG TAGTTACACC

FIGURE 32C-1

TACACGATTA ATCCACTAGG GATTGTGACT GTAAATTACA AGGGCTATGA TAAGAAAGTC
TATGATGGTC AACCTGGAAC GATTAATCCG GGTAAATTAA CGTGGAGTAA GTTGCCAGAT
GGTACTTCAT TGAAGATGCC AACATGGAGT ATAGATGATT TCGCTTGGGA AACAGCTGAT
GGCTTAGCAC CAACGGCAGT AGGAACTTAT CGGATTATCT TGACGGATGC TGGTAAGGCT
GCACTAAAGA AGATTAATCC AAATTATGAC TTAAGCAGTA TTACTGGTGT CTTTACTTAT
GAAATTAAGC CAGCACAGAC ACCAGAAATC TTAGGCCAAA CACCTGAGCA ACAACCAGGC
CAAAATACTA ATCAATCAGG AGCTGAAAAC GGCTTTGGTT CTTCTACAAG GCCTAATGCA
TCAACTAACT CCAATCTTAA TCAACTTCCA CAGACTGGTA ATGAGCATTC TAATACTGCA
CTTGCTGGTC TAGCATTGGC TTTCTTGACT GCTATGCTTG GTTTGGGCAA GAAGCGTAAA
CATGATtag (SEQ ID NO: 53).

FIGURE 32C-2 (contd.)

TTGTATTTAGGAGGGTTAATAATGCTATCAAGAAAAAATTATAAGGAAACTATACGAAAACAGACACCTA
CAAAACAGTACTATACTATTAAGAAATTAACTGTTGGGGTTACTTCGGTATTAATTGGTCTATCCTTTAT
GGGAGAACTAGAAGGGGATAGCGTTCATGCGGACACGATGACAGCAAGCAGTGAGTCAACAAGTGTTACG
TCGACGACTGCTCAGGATGGTTTAAAAAAATCTCCACAACTCTATTTGCAAGTTACTGATACAAATAACC
CAAGTACACCATTAAGTGCTTCATCCACAGGGACTAGTAAGAATGTTACCTCATCAGCTGCGGTACAAGT
GAAGTCCGCTAGTGATGAAGAAGATAGTGATTCTACACTAGCTAAGGGAGAAAATAAATTTGCTCGGTCA
GCAGTAAAAGATTCAGTCACTGATGGGAAAACAAGTACAGCAGAAATTAATCCGGCAAAATTAAGCAGTC
CTGCTTTAATAACGCAACTCAACCAATCCTTAGCTAAGAGCAGTACGAGTGATGCAGCAAAAGCTAATGA
TGAGTTAGAAATTAAAGCAACAGATCCGACTAATTATCCAAACTGTGGCGATGTGTATGGGCCATTATTT
GAATTGGATGCTAGCGGACAGCTTGTTAATAAAGATGAAGTTATATCTCTTAAAGATATGTATATTTTCC
AAATATTGAAATTAGTAAATACAAAAGATAGTGACTTTCAATATGTAATATTAACAATGAATCGTAAAGA
TACTGCAGATAGGTCTGTATATCTTTTTGTAACTGGAAGCAATTATAGTAATGCTGTTGTTGTTAAAGTA
AAGCCAAATGATACTTATGAATTAAGTAAAACTGGATATAGTGTTACTTATACAGAACCAACAACTATAA
ATGGACATTATGTTGATGGAACTTTTTATGTTACAGGAAGTACTTACGATGATGGTTTTATAATGCCAGA
TTGGCAACTGCAGCACCTTCAGATTATATATAGTTTAGGAAATTATGATCCAAGCAATACTGACGCAACA
TCAGTTTGTGAAATAATGCCAAGTTATGAAAAGGTACCGGTAATTAAATATAGTGGAGTACCTTCAAATA
TTAGCCAACCTAAGGTTTACATTACCGGGTTTACGGGTCAAGAGTTTAACGTTACAGATATTATTAACAA
TTATAAGAAAGTTTTTAAGGGCTACTATCTTCAAAATCCTAATGTGGCGTCCATGGGAACTCTTTCCCAA
TTTGAGAATGGTGGTTATTACTTAAAGACATATTATGATAATGATGGTAATGTTGACTTTAAGGGCTTGT
ATCATCAAATTGATGATCAGGGAACAATGAGTGTGAGTGTTCTTAATGCAGATAATAAAACAATTGTTGG
ACCTGAAAATATTCTTGCTGGTAAATCGCATAACTTTAACTTTAATGGTCATAACTGGATTGCGCGGAAT
CCTTATGTCACTAGTTCAGCTCACGAAGTCATATTAAAGTATGCTAAGTTAGGTTCAGTTATTCCTGTTG
ATGAAAACGGAAATAAAATAAACGATGGATGGCAATATGTTAATGATCCAGATGATGCTTCCAAAGCCAC
TAGCCCATATGAAAAAGCGCCAGTTATCGATGGTTATGTAGCTGTAAATCCAGATGAAACGATCGTTCTT
CCTCATAACTTAAGTAGTGACACAAAGATTTATTACCGAAAGAGGATTAAAGTTACCTATAGTGGTAGTG
ACAGCAAGACCTACGATGGTAACCCAGCTAACTTCGAGCCAACGACAGTTCAGTGGAGTGGCTTGAAAGG
ACTGAACACTTCAACCTTAACGTCCGCTGACTTCACGTGGAATACTGCGGATAAGAAGGCACCAACGGAT
GCCGGTAAGTACACACTTAGTTTGAATACGACCGGAGAAGCAGCCTTACGTAAGGCTAACCCGAACTATG
ATCTCAAGACAATTAGCGGTAGTTACACCTACACGATTAATCCACTAGGGATTGATAAAGTTACCTATAG
TGGTAGTGACAGCAAGACCTACGATGGTAACCCAGCTAACTTCGAGCCAACGACAGTTCAGTGGAGTGGC
TTGAAAGGACTGAACACTTCAACCTTAACGTCCGCTGACTTCACGTGGAATACTGCGGATAAGAAGGCAC
CAACGGATGCCGGTAAGTACACACTTAGTTTGAATACGACCGGAGAAGCAGCCTTACGTAAGGCTAACCC
GAACTATGATCTCAAGACAATTAGCGGTAGTTACACCTACACGATTAATCCACTAGGGATTGATAAAGTT
ACCTATAGTGGTAGTGACAGCAAGACCTACGATGGTAACCCAGCTAACTTCGAGCCAACGACAGTTCAGT
GGAGTGGCTTGAAAGGACTGAACACTTCAACCTTAACGTCCGCTGACTTCACGTGGAATACTGCGGATAA
GAAGGCACCAACGGATGCCGGTAAGTACACACTTAGTTTGAATACGACCGGAGAAGCAGCCTTACGTAAG
GCTAACCCGAACTATGATCTCAAGACAATTAGCGGTAGTTACACCTACACGATTAATCCACTAGGGATTG
ATAAAGTTACCTATAGTGGTAGTGACAGCAAGACCTACGATGGTAACCCAGCTAACTTCGAGCCAACGAC
AGTTCAGTGGAGTGGCTTGAAAGGACTGAACACTTCAACCTTAACGTCCGCTGACTTCACGTGGAATACT
GCGGATAAGAAGGCACCAACGGATGCCGGTAAGTACACACTTAGTTTGAATACGACCGGAGAAGCAGCCT
TACGTAAGGCTAACCCGAACTATGATCTCAAGACAATTAGCGGTAGTTACACCTACACGATTAATCCACT
AGGGATTGATAAAGTTACCTATAGTGGTAGTGACAGCAAGACCTACGATGGTAACCCAGCTAACTTCGAG
CCAACGACAGTTCAGTGGAGTGGCTTGAAAGGACTGAACACTTCAACCTTAACGTCCGCTGACTTCACGT
GGAATACTGCGGATAAGAAGGCACCAACGGATGCCGGTAAGTACACACTTAGTTTGAATACGACCGGAGA
AGCAGCCTTACGTAAGGCTAACCCGAACTATGATCTCAAGACAATTAGCGGTAGTTACACCTACACGATT
AATCCACTAGGGATTGTGACTGTAAATTACAAGGGCTATGATAAGAAAGTCTATGATGGTCAACCTGGAA
CGATTAATCCGGGTAAATTAACGTGGAGTAAGTTGCCAGATGGTACTTCATTGAAGATGCCAACATGGAG
TATAGATGATTTCGCTTGGGAAACAGCTGATGGCTTAGCACCAACGGCAGTAGGAACTTATCGGATTATC
TTGACGGATGCTGGTAAGGCTGCACTAAAGAAGATTAATCCAAATTATGACTTAAGCAGTATTACTGGTG
TCTTTACTTATGAAATTAAGCCAGCACAGACACCAGAAATCTTAGGCCAAACACCTGAGCAACAACCAGG
CCAAAATACTAATCAATCAGGAGCTGAAAACGGCTTTGGTTCTTCTACAAGGCCTAATGCATCAACTAAC
TCCAATCTTAATCAACTTCCACAGACTGGTAATGAGCATTCTAATACTGCACTTGCTGGTCTAGCATTGG
CTTTCTTGACTGCTATGCTTGGTTTGGGCAAGAAGCGTAAACATGATTAG (SEQ ID NO: 23).

FIGURE 32D

TTGTATTTAGGAGGGTTAATAatgCTATCAA GAAAAAATTA TAAGGAAACT ATACGAAAAC
AGACACCTAC AAAACAGTACTATACTATTA AGAAATTAAC TGTTGGGGTT ACTTCGGTAT
TAATTggtctatcctttatgggagaactagaaggggatagcgttcatgcggacacgatgacagcaagc
agtgagtcaacaagtgttacgtcgacgactgctcaggatggtttaaaaaaatctccacaactctattt
gcaagttactgatacaaataacccaagtacaccattaagtgcttcatccacagggactagtaagaatg
ttacctcatcagctgcggtacaagtgaagtccgctagtgatgaagaagatagtgattctacactagct
aagggagaaaataaatttgctcggtcagcagtaaaagattcagtcactgatgggaaaacaagtacagc
agaaattaatccggcaaaattaagcagtcctgctttaataacgcaactcaaccaatccttagctaaga
gcagtacgagtgatgcagcaaaagctaatgatgagttagaaattaaagcaacagatccgactaattat
ccaaactgtggcgatgtgtatgggccattatttgaattggatgctagcggacagcttgttaataaaga
tgaagttatatctcttaaagatatgtatattttccaaatattgaaattagtaaatacaaaagatagtg
actttcaatatgtaatattaacaatgaatcgtaaagatactgcagataggtctgtatatctttttgta
actggaagcaattatagtaatgctgttgttgttaaagtaaagccaaatgatacttatgaattaagtaa
aactggatatagtgttacttatacagaaccaacaactataaatggacattatgttgatggaacttttt
atgttacaggaagtacttacgatgatggttttataatgccagattggcaactgcagcaccttcagatt
atatatagtttaggaaattatgatccaagcaatactgacgcaacatcagtttgtgaaataatgccaag
ttatgaaaaggtaccggtaattaaatatagtggagtaccttcaaatattagccaacctaaggtttaca
ttaccgggtttacgggtcaagagtttaacgttacagatattattaacaattataagaaagtttttaag
ggctactatcttcaaaatcctaatgtggcgtccatgggaactctttcccaatttgagaatggtggtta
ttacttaaagacatattatgataatgatggtaatgttgactttaagggcttgtatcatcaaattgatg
atcagggaacaatgagtgtgagtgttcttaatgcagataataaaacaattgttggacctgaaaatatt
cttgctggtaaatcgcataactttaactttaatggtcataactggattgcgcggaatccttatgtcac
tagttcagctcacgaagtcatattaaagtatgctaagttaggttcagttattcctgttgatgaaaacg
gaaataaaataaacgatggatggcaatatgttaatgatccagatgatgcttccaaagccactagccca
tatgaaaaagcgccagttatcgatggttatgtagctgtaaatccagatgaaacgatcgttcttcctca
taacttaagtagtgacacaaagatttattaccgaaagaggattggtagtgctggtagtgctgaagctg
gtagtaattggagtcatccacaatttgaaaaaggtagtgctggtagtgctgctggtagtcacggttac
gtatcggcagttgaaaacggtgtagccgaagggcgtgtaactctttgtaaatttgcagccaacggtac
aggggagaaaaacacacactgtggtgcaattcaatatgaacctcaatctgtagaaggtcctgatggtt
tccctgtaacaggtcctcgtgatggtaaaattgcctctgcagaatctgcccttgcagccgcacttgat
gaacaaactgcagaccgttgggtcaagcgtcctattcaagcaggtcctcaaactttcgagtggacctt
cactgcaaaccacgtaacgaaggattggaagtactacattactaagccaaactggaacccaaaccagc
ctcttagccgtgatgcatttgacttgaaccctttctgtgtcgtagaagggaacatggttcagcctcct
aagcgtgtatctcacgaatgtattgttcctgaacgtgaagggtaccaggtaatcctagcagtctggga
tgtaggtgatactgcagcctcgttctacaacgttattgacgttaagtttgacggtggtagtgctggta
gtgctgctggtagtggtgaatttAAAGTTACCTATAGTGGTAGTGACAGCAAGACCTACGATGGTA
ACCCAGCTAA CTTCGAGCCA ACGACAGTTC AGTGGAGTGGCTTGAAAGGACTGAACACTT
CAACCTTAAC GTCCGCTGAC TTCACGTGGA ATACTGCGGA TAAGAAGGCA CCAACGGATG
CCGGTAAGTA CACACTTAGT TTGAATACGA CCGGAGAAGC AGCCTTACGT AAGGCTAACC
CGAACTATGA TCTCAAGACA ATTAGCGGTA GTTACACCTA CACGATTAAT CCACTAGGGA
TTGATAAAGT TACCTATAGT GGTAGTGACA GCAAGACCTA CGATGGTAAC CCAGCTAACT
TCGAGCCAAC GACAGTTCAG TGGAGTGGCT TGAAAGGACT GAACACTTCA ACCTTAACGT
CCGCTGACTT CACGTGGAAT ACTGCGGATA AGAAGGCACC AACGGATGCC GGTAAGTACA
CACTTAGTTT GAATACGACC GGAGAAGCAG CCTTACGTAA GGCTAACCCG AACTATGATC
TCAAGACAAT TAGCGGTAGT TACACCTACA CGATTAATCC ACTAGGGATT GATAAAGTTA
CCTATAGTGG TAGTGACAGC AAGACCTACG ATGGTAACCC AGCTAACTTC GAGCCAACGA
CAGTTCAGTG GAGTGGCTTG AAAGGACTGA ACACTTCAAC CTTAACGTCC GCTGACTTCA
CGTGGAATAC TGCGGATAAG AAGGCACCAA CGGATGCCGG TAAGTACACA CTTAGTTTGA
ATACGACCGG AGAAGCAGCC TTACGTAAGG CTAACCCGAA CTATGATCTC AAGACAATTA
GCGGTAGTTA CACCTACACG ATTAATCCAC TAGGGATTGA TAAAGTTACC TATAGTGGTA
GTGACAGCAA GACCTACGAT GGTAACCCAG CTAACTTCGA GCCAACGACA GTTCAGTGGA
GTGGCTTGAA AGGACTGAAC ACTTCAACCT TAACGTCCGC TGACTTCACG TGGAATACTG

FIGURE 33A-1

CGGATAAGAA GGCACCAACG GATGCCGGTA AGTACACACT TAGTTTGAAT ACGACCGGAG
AAGCAGCCTT ACGTAAGGCT AACCCGAACT ATGATCTCAA GACAATTAGC GGTAGTTACA
CCTACACGAT TAATCCACTA GGGATTGATA AAGTTACCTA TAGTGGTAGT GACAGCAAGA
CCTACGATGG TAACCCAGCT AACTTCGAGC CAACGACAGT TCAGTGGAGT GGCTTGAAAG
GACTGAACAC TTCAACCTTA ACGTCCGCTG ACTTCACGTG GAATACTGCG GATAAGAAGG
CACCAACGGA TGCCGGTAAG TACACACTTA GTTTGAATAC GACCGGAGAA GCAGCCTTAC
GTAAGGCTAA CCCGAACTAT GATCTCAAGA CAATTAGCGG TAGTTACACC TACACGATTA
ATCCACTAGG GATTGTGACT GTAAATTACA AGGGCTATGA TAAGAAAGTC TATGATGGTC
AACCTGGAAC GATTAATCCG GGTAAATTAA CGTGGAGTAA GTTGCCAGAT GGTACTTCAT
TGAAGATGCC AACATGGAGT ATAGATGATT TCGCTTGGGA AACAGCTGAT GGCTTAGCAC
CAACGGCAGT AGGAACTTAT CGGATTATCT TGACGGATGC TGGTAAGGCT GCACTAAAGA
AGATTAATCC AAATTATGAC TTAAGCAGTA TTACTGGTGT CTTTACTTAT GAAATTAAGC
CAGCACAGAC ACCAGAAATC TTAGGCCAAA CACCTGAGCA ACAACCAGGC CAAAATACTA
ATCAATCAGG AGCTGAAAAC GGCTTTGGTT CTTCTACAAG GCCTAATGCA TCAACTAACT
CCAATCTTAA TCAACTTCCA CAGACTGGTA ATGAGCATTC TAATACTGCA CTTGCTGGTC
TAGCATTGGC TTTCTTGACT GCTATGCTTG GTTTGGGCAA GAAGCGTAAA CATGATtag
(SEQ ID NO: 24)

FIGURE 33A-2 (contd.)

MLSRKNYKETIRKQTPTKQYYTIKKLTVGVTSVLIGLSFMGELEGDSVHADTMTASSESTSV
TSTTAQDGLKKSPQLYLQVTDTNNPSTPLSASSTGTSKNVTSSAAVQVKSASDEEDSDSTL
AKGENKFARSAVKDSVTDGKTSTAEINPAKLSSPALITQLNQSLAKSSTSDAAKANDELEIKA
TDPTNYPNCGDVYGPLFELDASGQLVNKDEVISLKDMYIFQILKLVNTKDSDFQYVILTMNR
KDTADRSVYLFVTGSNYSNAVVVKVKPNDTYELSKTGYSVTYTEPTTINGHYVDGTFYVTG
STYDDGFIMPDWQLQHLQIIYSLGNYDPSNTDATSVCEIMPSYEKVPVIKYSGVPSNISQPK
VYITGFTGQEFNVTDIINNYKKVFKGYYLQNPNVASMGTLSQFENGGYYLKTYYDNDGNVD
FKGLYHQIDDQGTMSVSVLNADNKTIVGPENILAGKSHNFNFNGHNWIARNPYVTSSAHEVI
LKYAKLGSVIPVDENGNKINDGWQYVNDPDDASKATSPYEKAPVIDGYVAVNPDETIVLPHN
LSSDTKIYYRKRIGSAGSAEAGSNWSHPQFEKGSAGSAAGSHGYVSAVENGVAEGRVTL
CKFAANGTGEKNTHCGAIQYEPQSVEGPDGFPVTGPRDGKIASAESALAAALDEQTADRW
VKRPIQAGPQTFEWTFTANHVTKDWKYYITKPNWNPNQPLSRDAFDLNPFCVVEGNMVQP
PKRVSHECIVPEREGYQVILAVWDVGDTAASFYNVIDVKFDGGSAGSAAGSGEFKVTYSG
SDSKTYDGNPANFEPTTVQWSGLKGLNTSTLTSADFTWNTADKKAPTDAGKYTLSLNTTG
EAALRKANPNYDLKTISGSYTYTINPLGIDKVTYSGSDSKTYDGNPANFEPTTVQWSGLKGL
NTSTLTSADFTWNTADKKAPTDAGKYTLSLNTTGEAALRKANPNYDLKTISGSYTYTINPLGI
DKVTYSGSDSKTYDGNPANFEPTTVQWSGLKGLNTSTLTSADFTWNTADKKAPTDAGKYT
LSLNTTGEAALRKANPNYDLKTISGSYTYTINPLGIDKVTYSGSDSKTYDGNPANFEPTTVQ
WSGLKGLNTSTLTSADFTWNTADKKAPTDAGKYTLSLNTTGEAALRKANPNYDLKTISGSY
TYTINPLGIDKVTYSGSDSKTYDGNPANFEPTTVQWSGLKGLNTSTLTSADFTWNTADKKA
PTDAGKYTLSLNTTGEAALRKANPNYDLKTISGSYTYTINPLGIVTVNYKGYDKKVYDGQPG
TINPGKLTWSKLPDGTSLKMPTWSIDDFAWETADGLAPTAVGTYRIILTDAGKAALKKINPNY
DLSSITGVFTYEIKPAQTPEILGQTPEQQPGQNTNQSGAENGFGSSTRPNASTNSNLNQLP
QTGNEHSNTALAGLALAFLTAMLGLGKKRKHD (SEQ ID NO: 29)

FIGURE 33B atgCTATCAA GAAAAAATTA TAAGGAAACT ATACGAAAAC AGACACCTAC
AAAACAGTACTATACTATTA AGAAATTAAC TGTTGGGGTT ACTTCGGTAT
TAATTggtctatcctttatgggagaactagaaggggatagcgttcatgcggacacgatgacagcaagc
agtgagtcaacaagtgttacgtcgacgactgctcaggatggtttaaaaaaatctccacaactctattt
gcaagttactgatacaaataacccaagtacaccattaagtgcttcatccacagggactagtaagaatg
ttacctcatcagctgcggtacaagtgaagtccgctagtgatgaagaagatagtgattctacactagct
aagggagaaaataaatttgctcggtcagcagtaaaagattcagtcactgatgggaaaacaagtacagc
agaaattaatccggcaaaattaagcagtcctgctttaataacgcaactcaaccaatccttagctaaga
gcagtacgagtgatgcagcaaaagctaatgatgagttagaaattaaagcaacagatccgactaattat
ccaaactgtggcgatgtgtatgggccattatttgaattggatgctagcggacagcttgttaataaaga
tgaagttatatctcttaaagatatgtatattttccaaatattgaaattagtaaatacaaaagatagtg
actttcaatatgtaatattaacaatgaatcgtaaagatactgcagataggtctgtatatctttttgta
actggaagcaattatagtaatgctgttgttgttaaagtaaagccaaatgatacttatgaattaagtaa
aactggatatagtgttacttatacagaaccaacaactataaatggacattatgttgatggaactttt
atgttacaggaagtacttacgatgatggttttataatgccagattggcaactgcagcaccttcagatt
atatatagtttaggaaattatgatccaagcaatactgacgcaacatcagtttgtgaaataatgccaag
ttatgaaaaggtaccggtaattaaatatagtggagtaccttcaaatattagccaacctaaggtttaca
ttaccgggtttacgggtcaagagtttaacgttacagatattattaacaattataagaaagtttttaag
ggctactatcttcaaaatcctaatgtggcgtccatgggaactctttcccaatttgagaatggtggtta
ttacttaaagacatattatgataatgatggtaatgttgactttaagggcttgtatcatcaaattgatg
atcagggaacaatgagtgtgagtgttcttaatgcagataataaaacaattgttggacctgaaaatatt
cttgctggtaaatcgcataactttaactttaatggtcataactggattgcgcggaatccttatgtcac
tagttcagctcacgaagtcatattaaagtatgctaagttaggttcagttattcctgttgatgaaaacg
gaaataaaataaacgatggatggcaatatgttaatgatccagatgatgcttccaaagccactagccca
tatgaaaaagcgccagttatcgatggttatgtagctgtaaatccagatgaaacgatcgttcttcctca
taacttaagtagtgacacaaagatttattaccgaaagaggattggtagtgctggtagtgctgaagctg
gtagtaattggagtcatccacaatttgaaaaaggtagtgctggtagtgctgctggtagtcacggttac
gtatcggcagttgaaaacggtgtagccgaagggcgtgtaactctttgtaaatttgcagccaacggtac
aggggagaaaaacacacactgtggtgcaattcaatatgaacctcaatctgtagaaggtcctgatggtt
tccctgtaacaggtcctcgtgatggtaaaattgcctctgcagaatctgcccttgcagccgcacttgat
gaacaaactgcagaccgttgggtcaagcgtcctattcaagcaggtcctcaaactttcgagtggacctt
cactgcaaaccacgtaacgaaggattggaagtactacattactaagccaaactggaacccaaaccagc
ctcttagccgtgatgcatttgacttgaaccctttctgtgtcgtagaagggaacatggttcagcctcct
aagcgtgtatctcacgaatgtattgttcctgaacgtgaagggtaccaggtaatcctagcagtctggga
tgtaggtgatactgcagcctcgttctacaacgttattgacgttaagtttgacggtggtagtgctggta
gtgctgctggtagtggtgaatttAAAGTTACCTATAGTGGTAGTGACAGCAAGACCTACGATGGTA
ACCCAGCTAA CTTCGAGCCA ACGACAGTTC AGTGGAGTGGCTTGAAAGGACTGAACACTT
CAACCTTAAC GTCCGCTGAC TTCACGTGGA ATACTGCGGA TAAGAAGGCA
CCAACGGATG CCGGTAAGTA CACACTTAGT TTGAATACGA CCGGAGAAGC AGCCTTACGT
AAGGCTAACC CGAACTATGA TCTCAAGACA ATTAGCGGTA GTTACACCTA CACGATTAAT
CCACTAGGGA TTGATAAAGT TACCTATAGT GGTAGTGACA GCAAGACCTA CGATGGTAAC
CCAGCTAACT TCGAGCCAAC GACAGTTCAG TGGAGTGGCT TGAAAGGACT GAACACTTCA
ACCTTAACGT CCGCTGACTT CACGTGGAAT ACTGCGGATA AGAAGGCACC AACGGATGCC
GGTAAGTACA CACTTAGTTT GAATACGACC GGAGAAGCAG CCTTACGTAA GGCTAACCCG
AACTATGATC TCAAGACAAT TAGCGGTAGT TACACCTACA CGATTAATCC ACTAGGGATT
GATAAAGTTA CCTATAGTGG TAGTGACAGC AAGACCTACG ATGGTAACCC AGCTAACTTC
GAGCCAACGA CAGTTCAGTG GAGTGGCTTG AAAGGACTGA ACACTTCAAC CTTAACGTCC
GCTGACTTCA CGTGGAATAC TGCGGATAAG AAGGCACCAA CGGATGCCGG TAAGTACACA
CTTAGTTTGA ATACGACCGG AGAAGCAGCC TTACGTAAGG CTAACCCGAA CTATGATCTC
AAGACAATTA GCGGTAGTTA CACCTACACG ATTAATCCAC TAGGGATTGA TAAAGTTACC
TATAGTGGTA GTGACAGCAA GACCTACGAT GGTAACCCAG CTAACTTCGA GCCAACGACA

FIGURE 33C-1

GTTCAGTGGA GTGGCTTGAA AGGACTGAAC ACTTCAACCT TAACGTCCGC TGACTTCACG
TGGAATACTG CGGATAAGAA GGCACCAACG GATGCCGGTA AGTACACACT TAGTTTGAAT
ACGACCGGAG AAGCAGCCTT ACGTAAGGCT AACCCGAACT ATGATCTCAA GACAATTAGC
GGTAGTTACA CCTACACGAT TAATCCACTA GGGATTGATA AAGTTACCTA TAGTGGTAGT
GACAGCAAGA CCTACGATGG TAACCCAGCT AACTTCGAGC CAACGACAGT TCAGTGGAGT
GGCTTGAAAG GACTGAACAC TTCAACCTTA ACGTCCGCTG ACTTCACGTG GAATACTGCG
GATAAGAAGG CACCAACGGA TGCCGGTAAG TACACACTTA GTTTGAATAC GACCGGAGAA
GCAGCCTTAC GTAAGGCTAA CCCGAACTAT GATCTCAAGA CAATTAGCGG TAGTTACACC
TACACGATTA ATCCACTAGG GATTGTGACT GTAAATTACA AGGGCTATGA TAAGAAAGTC
TATGATGGTC AACCTGGAAC GATTAATCCG GGTAAATTAA CGTGGAGTAA GTTGCCAGAT
GGTACTTCAT TGAAGATGCC AACATGGAGT ATAGATGATT TCGCTTGGGA AACAGCTGAT
GGCTTAGCAC CAACGGCAGT AGGAACTTAT CGGATTATCT TGACGGATGC TGGTAAGGCT
GCACTAAAGA AGATTAATCC AAATTATGAC TTAAGCAGTA TTACTGGTGT CTTTACTTAT
GAAATTAAGC CAGCACAGAC ACCAGAAATC TTAGGCCAAA CACCTGAGCA ACAACCAGGC
CAAAATACTA ATCAATCAGG AGCTGAAAAC GGCTTTGGTT CTTCTACAAG GCCTAATGCA
TCAACTAACT CCAATCTTAA TCAACTTCCA CAGACTGGTA ATGAGCATTC TAATACTGCA
CTTGCTGGTC TAGCATTGGC TTTCTTGACT GCTATGCTTG GTTTGGGCAA GAAGCGTAAA
CATGATtag (SEQ ID NO: 30)

FIGURE 33C-2 (contd.)

TTATTCATGGCTCATACGTTGTTCGTATTCTGGTCTCTGGCGAGGCCATTTTTTCGAAAC
GCCTAATCAGTTCCGCCAGGCTACCGGCCTGCATTTTTTCCATGACTCTGGCGCGGTG
CACCTCTACGGTACGCACCGCGATATTCATCGCTTCCGCAATTTCACGGTTCATAAATC
CTTTTGCCACCAGGCTGGCCAGCTCACGCTCTTTCGGCGTCAACTGCTGGTAACACAG
TATAATCTCACGACGCGCCACCGCTGCCGATGAAACCGTCAGCGCACGCTCCAGCGCC
GCCTGTAGCGGTTTTACCGATACCGGTTTTTGCAGAAAATCGACGGCGCCGCGTTTCAT
CTGCTCCACGGCCATCGGTACATCGCCATGCCCGGTAAGAAAAACAACCGCCAGGGTA
CTTCCGCACTGGCGCAACGCATCATGAACGCCCTGCCCATCCAGTACCGGCATTCGCA
TATCCAGTAATACGACCCCGGCCTGATACAGACTGGCCTGCGCCAAAAAATCCGCCCC
CTGCGTCCAGCATTTTACGTCATATCCCAGACTTTCCAGTAAAAACGCGCACGCGTTAG
TGACCGCCGTATCATCATCCAGTAGATGAATTGTCGCCATCCCTGCCCCCATTTTCATG
TAAGAAATGTATCGTAACCACCGTTCCCGACAGACCGTCCGGCGCGGTCTGGTTCCTG
ATGCTGATATCGCCCCGCCCATACCGCACCAGCCGCTGGCAAATCGCCAGCCCTAAGC
CCATCCCCTCTTTACGGGTGGTCATAAACGGCTGAAACGCCTGACGTAATAGCGCCTC
ATCGATTCCCCCGGCGTTATCCTGTAAAACAATACTGATGCCGTTTTCAGTGCGTTCAG
CAACGATCCATAAATGGGTGGCGCCCGCCTGAGCCGCATTAAGAATGATATTCGCCAG
CACCTGTTCCAGCAGCACTGACGGCAGCGTTACGCGCAGCGCAGCGCTAACCTCGGT
ATGCAGAGTCACTGTCGGAAACTGTTGCGCCATACGCAACAATTGCCAGACATGATCAA
TCGCCTCGCGAATGGCTATGGCCTTCCACGCTTCGGTTAGCACCGGGTTGCCCTGCGC
CTGGCTGACCCAGTGACGCAGGTTACGCAGAGTATCCGCACCGCGTTGCGCCTGCTG
GTCAATCTGCTCCAGCGCCGGCAGCAAGGGATGCTGTTCATCTGCAGCGCGCAGTCG
AATCAGGCACCCCTGGGCATAATGTCGAATCGCGGAAAGCGGCTGATTAAGCTCATGG
GCAAACCCGGAGGTCATTTCACCCAACACGCTCATTTGCCGGGCGGTTTCCAGCGCCC
GCTCATGCTGATGAAGAACTACGCTATTACGTTCCAGTTGCTTTCCACGTCGACGCACC
AGCAGCATGACCCAAATATAATTGAGCGTGAGCAACAAGAACGCCAGAATCACGCCGC
CGACCATTAGCTGGTGCTGGATTAACCAACTTTTGACATCCAGCCACAGTCGACGCTGC
TGAGGGTGCTGACGAACATCACGCAGCAAGGCTTCCACCTGACTGGTGGACGCAGGC
GCGCCCCAGTGAAATGACGCGGCGGCGGGCGCGTTGAATAGCGCTCGCGTTACGCGA
TCCGCCAGCGCATCGCTTACCGCAGGTAGCGCCGCGAACGACCAGTCAGGATATAAC
GGCGTACTGGTTAAGCAAGGCAGGGGCGTCGGTCGGGAAAGCAGCGCGATAAAGTCC
TTTTTATTAATCAATCCTTCCTGATCCATATTTTCTAACAGGCACACTGGCACAATTGCC
GCCTGCACCGCTTTTTCGCGCAGCATATAGACTAAGGCATCGCCAGGAAATCCGGTAA
AACGGAGATGAAAATCGCGCTCCGGGCGTAAGCCCGCGTCGCTGAGCGCTTTATAGC
CTAATAAATAGCCGCCAAACGCCTGAGCATCAATCGCGCCGACGGTCTTACCGATGAG
ATCATGCGCCGTGGTGATGCCGCTATCGCGCCGGGTCAAAATCACGCTGCCAATAACA
TTACTCACCGCTTTCCCATCGCGCGTGGAGCGCAGGGAAGCTAACCAGCGCAGCGGC
GCATGGCTGTTCAGTTGGACAAATTGCGCCGGGTTGGTTATCACAAACTGCACGGTTC
CCTGGTTAACGGCCTCCTGCATTTGATGCAGATCCAGCGGCTGGATGTGAAAGGTTTC
GCCTGGAAGCTGTTGGCTTAATGTCTTTGCCAACGGTTGCCAGTGGCTACGCGTAGAC
GCCTCGCCGCGCATGGCCAAAATACCGATATTCCACGTCCCTGCCCACGCGCCATGAC
AAAGTAGCCCTACTGCCGCCAACACCGCCAGGCGCCTTACGGTTTTACCTCTCACCCC
AATATCCCTGTCAATTATGTTGTTTTAGATCAACAACAAGCCGGGTATGTGGTTAACCAC
AATAGAGCGCACCCCGCCTCGATTTTTACACTGTAAATCATCGACATTTTTTATTCATTA
CACATGAACCAACATCGTGACAAATGTTTCATTGTTGGCAATGTGGACGGGAGTCAATA
TGGACAGCAGTAAACGGCAATTTCTCCAGCAGCTTGGCGTCCTGACCGCTGGCGCCTC
GCTGGTTCCGCTGGCTGAAGCGAAATTTCCTTTTTCGCCGGAGCGGCATGAAGGCTCT
CCCCGACACCGTTACGCCATGCTTATCGATCTGCGGCGTTGTATCGGCTGTCAGTCCT
GTACCGTAAGTTGCACTATTGAAAACCAAACGCCGCAAGGCGCGTTTCGTACGACGGT
GAACCAATACCAGGTCCAGCGTGAAGGTAGTCAGGAAGTCACGAATGTGCTGTTGCCG

FIGURE 34A-1

CGTCTGTGCAACCATTGCGATAACCCCCCCTGTGTGCCGGTCTGCCCGGTACAAGCCA
CCTTTCAGCGGGAAGATGGCATTGTGGTGGTGGATAACAAACGCTGCGTCGGCTGCGC
CTATTGTGTCCAGGCGTGTCCTTACGACGCCCGATTTATCAATCATGAAACGCAAACTG
CCGATAAATGCACGTTTTGCGTCCATCGTCTGGAAGCCGGACTGTTACCCGCTTGCGT
AGAGTCCTGCGTCGGCGGCGCGCGTATTATTGGCGATATCAAAGATCCCCATAGCCGC
ATCGCCACCATGCTTCATCAGCATCGCGACGCTATCAAGGTATTAAAGCCGGAAAACG
GCACGTCGCCCCATGTTTTCTACCTGGGTCTGGACGACGCCTTTGTCACCCCATTAATG
GGCCGTGCGCAGCCCGCGCTTTGGCAGGAGGTCTGAATGACGCATTCACTCATCATTG
AAGAAGTGCTGGCTCACCCGCAGGACATTAGCTGGCTGCCGTGGGCGGTACAATATTT
CTTTTTTATTGGCATTGCCGCCTGCGCCGCACTGTTTGCCTGTTATCTTCACTGGCGGA
AAAAAGACGCCGCAACAGAAGAAAATCGGGCATTACTGATTGCCATTACCTGTGCGATT
ACCGCACCGCTGGCGCTGACGGCGGATCTGCACCAGACCGCCCGCGTCTGGCATTTC
TATGCCTGGCCGACGCCCTGGTCGTGGATGCCCTGGGGAGCGTTATTCCTGCCGCTG
TTTACCGGATTTCTCGCTCTGTGGTTCCTGGCGCAGCAGATTAAACGATTATTCAATAAA
AGTTACAACGTCACTAAATGGTTGGCGTTAGCCAGCGCGCTTTGCGCGGTGGCCTGT
TGATTTATACCGGCCGCGAAGTCTCCGTTGTGCTGGCGCGCCCAATCTGGTTTAGCTA
CGCCTTCCCCGTGGCGATGTTTCTTAGCGCCTTACAGGCGTTCTTCGCGCTGATGATT
GTCGCCGCCCGACGCGACTCGGTAAGGCTGCCAAAAATATTGTGGGGACAAATCTGGA
CGCTGGCGGCGCTGGGGCTGGTTGTGGCCATGTGGGTTAGCGGCGATACGCTTTCCG
GCACGGCAATCCGTCAGTGGATTACCGTCGCCCTGTCAGCCAAATATTACGCTGTCGG
CTGGGTAGCGCTGTGGGTATGCACACTGCTGTTCTGTAGCCTGGCGCTACGCCATCCG
TTATCACAGCTAAGACGCGTCCTGCTGGTTCTCAGCGCGCTGGCGCTATGTTGGCTGA
TGCGCTGGACATTGTTGATTCAGGTACAAACCGTCCCCAAGTTCAACGCGCAATTTAAC
CCTTACTCGTTACCAGGCGGAACGGATGGCTGGCTGGCTATTCTCGGCACCTTCGGCC
TGTGGATAGCGCTACTGATTATTATTCGTGAAACGCTGAACGGACTCACCAGGAGATTA
CAACATGGCTAATTTAACCCGTCGTCAGTGGCTAAAAGTCGGTCTCGCCGTCGGTGGG
ATGGTCACTTTTGGTCTGAGCTACCGTGATGTGGCGAAACGCGCAATTGATGGCCTGTT
AAACGGGACGTCCGGCAAGGTAACGCGCGACCGCATCTTTGGCAATGCGTTAATTCCG
GAGGCGCAGGCGCAAACACACTGGCAGCAAAATCCACAACAAACCATCGCCATGACGC
AATGCTTCGGCTGTTGGACACAGTGCGGTATCCGCGCCCGGGTTAATGCCGATGGCAA
AGTGATACGCATCGCCGGCAATCCCTATCACCCCTTGTCGCAGGAACACCCGATTGAC
TCGTCCGTCCCTTTTAGCGAAGCCATGGAGCAACTGGCGGGAGAAAGCGGTCTTGACG
CCCGCTCAACCGCCTGCGCGCGCGGCGCCACGCTGCTGGAAAGCCTGTACAGTCCGC
TACGACTGCTTGAACCGATGAAACGCGTGGGTAAACGCGGCGAAGGGAAATGGCAGC
GCATCAGCTTTGAGCAACTTATTGAAGAAGTCGTGGAAGGCGGCGATCTGTTTGGCGA
AGGTCATGTGGACGGACTGCGCGCTATTCATGCGCCGGATACGCCAATTGACGCAAAG
CACCCCAGTTTCGGGCCCAAAACCAATCAGTTACTGGTCACGAATACCAGCGACGAAG
GCCGCGATGCGTTTCTGCGTCGTTTTGCGCTAAATAGCTTCGGCAGCAAGAATTTCGG
CGCGCATGGCGCCTACTGTGGACTGGCTTACCGGGCCGGCTCCGGGGCATTGATGGG
CGATCTGGATAAAAACCCGCATGTCAAACCCGACTGGGAAAACGTGGAGTTTGCGCTC
TTTATGGGCACCTCCCCGGCACAGTCCGGCAATCCGTTTAAACGCCAGGCACGTCAGT
TGGCGAGCGCCCGACTGCGTGAGAATTTTCAATACGTCGTGGTCGCCCCCGCCCTCCC
CTTATCAACGGTGCTCGCCGATCCTCGCGGTCGCTGGCAACCGGTCATGCCCGGCAG
TGATTCGGCGCTGGCAATGGGGATGATCCGCTGGATCATGGATAATCAACGTTATAATG
CTGATTATCTGGCGATTCCCGGCGTACAGGCGATGCAGCAGGCCGGCGAGCAAAGTT
GGACCAACGCCACGCACCTGGTCATTGCGGATGAGCTGCCGACGCTTGCCGGACAAC
ACCTGACGCTGCGCCATCTTACGCCCGATGGCGAAGAGACCCCTGTCGTACTGAATAC
CGACGGCGAGTTGGTCGATGCGTCCACTTGCCGACAGGCACGGCTTTTCGTGACGCA
GTACGTTACGCTCGCCGACGGCCAACGGGTCACGGTGAAGAGCGGGTTGCAACGCCT
GAAAGAGGCGGCAGAAAAGCTCTCGTTGGCGCAATACAGCGAACAGTGCGGCGTGCC
GGAAGCGCAAATTATCGCGCTGGCGGAAACCTTTACCAGTCACGGACGTAAAGCTGCG

FIGURE 34A-2 (contd.)

GTCATCAGTCACGGCGGCATGATGGCCGGCAATGGGTTTTATAACGCCTGGTCGGTCA
TGATGCTTAACGCGCTGATCGGCAACCTCAGCTTGTCCGGCGGCGTCTTTGTCGGCGG
CGGCAAATTCAACGGCGTTAGCGACGGCCCCCGCTACAACATGAACAGTTTTGCCGGA
AAAGTGAAACCGTCCGGGTTAAGTATTGCCCGTAGCAAAACCGCTTATGAAGCATCGG
AAGAATACCGCGACAAAATTGCCGGTGGGCAATCCCCTTATCCAGCCAAAGCGCCGTG
GTATCCCTTTGTGGCAGGCCAGCTTACCGAACTGTTGACCTCCGCGCTCGAAGGCTAT
CCTTATCCGCTTAAAGCCTGGATTTCCAATATGAGCAACCCGTTTTACGGTGTTCCCGG
TCTACGCGCCGTGGCGGAAGAAAAACTAAAAGACCCTCGCCGACTGCCGCTCTTTATC
GCGATTGACGCCTTTATGAATGAAACGACGGCGCTGGCGGATTACATTGTGCCGGATA
CGCACAATTTTGAGAGCTGGGGCTTTACGGCGCCCTGGGGCGGCGTAGCCAGTAAAG
CCACTACCGCCCGCTGGCCGGTTGTCGCCCCCGCCACTCACCGCACGGCGGACGGG
CAACCTGTCTCAATGGAAGCATTTTGTATTGCGGTAGCAAAACGGCTCCATCTGCCCGG
CTTCGGCGACCGGGCGATAACCGATCCGCAGGGCAATACTTTTCCACTGAACCGGGC
GGAAGACTTCTATCTGCGCGTAGCCGCTAATATCGCCTTTATGGGCAAGACGCCGGTC
GCGCTGGCAAATCAGGAAGATATTTCGCTTACCGGCGTCAGCCGCATTCTGCCAGCAA
TTCAGCACACGCTTAAAGCTGATGAGGTCGGTCGCGTGGCGTTTATCTACTCGCGTGG
CGGCCGGTTTGCGCCCGAGGATAGCGGCTATACGGAGCAACGGTTAGGTAACGCGTG
GAAAAAACCCTTACAGATCTGGAATGCAGATGTCGCCGCCCACCGTCACGCCATCACC
GGGGAGCGCTTCAGCGGTTGCCCGGTCTGGTATCCGGCGCGTTTGTCAGATGGTCGT
GCGATTGACGACCAGTTTCCCATTGGGCAATGGCCGCTGAAACTGATTTCATTTAAATC
AAATACCATGTCCAGCTCAACAGCCGTCATCCCGCGCTTACACCATGTGAAGCCAGCA
AACCTGGTGGCGCTGAATCCGCAAGACGGCGAGCGTTATGGACTGCAACATGGCGAT
CGGGTACGGATCATTACGCCGGGCGGTCAGGTCGTGGCGCAAATCAGTTTGTTAAATG
GCGTGATGCCAGGCGTCATCGCCATCGAACACGGATATGGCCACCGCGAGATGGGCG
CAACGCAGCACTCTCTGGATGGCGTGCCTATGCCGTATGATCCACAAATCAGGGCAGG
CATAAATCTTAACGATCTGGGCTTTGCCGATCCGACAAGAACCATTACCAACACCTGGC
TCGACTGGGTTTCTGGCGCGGCAGTACGTCAGGGGCTGCCGGCAAAAATCGAGCGTA
TATAAC (SEQ ID NO: 25)

FIGURE 34A-3 (contd.)

cccaatatccctgtcaattatgttgttttagatcaacaacaagccgggtatgtggttaaccacaatagagcgcaccccgcctcgattt
ttacactgtaaatcatcgacatttttattcattacacatgaaccaacatcgtgacaaatgtttcattgttggcaatgtggacgggagtc
aatatggacagcagtaaacggcaatttctccagcagcttggcgtcctgaccgctggcgcctcgctggttccgctggctgaagcga
aatttcctttttcgccggagcggcatgaaggctctccccgacaccgttacgccatgcttatcgatctgcggcgttgtatcggctgtcag
tcctgtaccgtaagttgcactattgaaaaccaaacgccgcaaggcgcgtttcgtacgacggtgaaccaataccaggtccagcgt
gaaggtagtcaggaagtcacgaatgtgctgttgccgcgtctgtgcaaccattgcgataaccccccctgtgtgccggtctgcccggt
acaagccacctttcagcgggaagatggcattgtggtggtggataacaaacgctgcgtcggctgcgcctattgtgtccaggcgtgt
ccttacgacgcccgatttatcaatcatgaaacgcaaactgccgataaatgcacgttttgcgtccatcgtctggaagccggactgtta
cccgcttgcgtagagtcctgcgtcggcggcgcgcgtattattggcgatatcaaagatccccatagccgcatcgccaccatgcttca
tcagcatcgcgacgctatcaaggtattaaagccggaaaacggcacgtcgccccatgttttctacctgggtctggacgacgcctttg
tcaccccattaatgggccgtgcgcagcccgcgctttggcaggaggtctgaatgacgcattcactcatcattgaagaagtgctggct
cacccgcaggacattagctggctgccgtgggcggtacaatatttctttttattggcattgccgcctgcgccgcactgtttgcctgttat
cttcactggcggaaaaaagacgccgcaacagaagaaaatcgggcattactgattgccattacctgtgcgattaccgcaccgctg
gcgctgacggcggatctgcaccagaccgcccgcgtctggcatttctatgcctggccgacgccctggtcgtggatgccctgggga
gcgttattcctgccgctgtttaccggatttctcgctctgtggttcctggcgcagcagattaaacgattattcaataaaagttacaacgtc
actaaatggttggcgttagccagcgcgctttgcgcggtgggcctgttgatttataccggccgcgaagtctccgttgtgctggcgcgc
ccaatctggtttagctacgccttccccgtggcgatgtttcttagcgccttacaggcgttcttcgcgctgatgattgtcgccgcccgacg
cgactcggtaaggctgccaaaaatattgtggggacaaatctggacgctggcggcgctggggctggttgtggccatgtgggttagc
ggcgatacgctttccggcacggcaatccgtcagtggattaccgtcgccctgtcagccaaatattacgctgtcggctgggtagcgct
gtgggtatgcacactgctgttctgtagcctggcgctacgccatccgttatcacagctaagacgcgtcctgctggttctcagcgcgctg
gcgctatgttggctgatgcgctggacattgttgattcaggtacaaaccgtccccaagttcaacgcgcaatttaacccttactcgttac
caggcggaacggatggctggctggctattctcggcaccttcggcctgtggatagcgctactgattattattcgtgaaacgctgaac
ggactcaccaggagattacaacatggctaatttaacccgtcgtcagtggctaaaagtcggtctcgccgtcggtgggatggtcactt
ttggtctgagctaccgtgatgtggcgaaacgcgcaattgatggcctgttaaacgggacgtccggcaaggtaacgcgcgaccgc
atctttggcaatgcgttaattccggaggcgcaggcgcaaacacactggcagcaaaatccacaacaaaccatcgccatgacgc
aatgcttcggctgttggacacagtgcggtatccgcgcccgggttaatgccgatggcaaagtgatacgcatcgccggcaatccta
tcaccccttgtcgcaggaacacccgattgactcgtccgtcccttttagcgaagccatggagcaactggcgggagaaagcggtctt
gacgcccgctcaaccgcctgcgcgcgcggcgccacgctgctggaaagcctgtacagtccgctacgactgcttgaaccgatga
aacgcgtgggtaaacgcggcgaagggaaatggcagcgcatcagctttgagcaacttattgaagaagtcgtggaaggcggcg
atctgtttggcgaaggtcatgtggacggactgcgcgctattcatgcgccggatacgccaattgacgcaaagcaccccagtttcgg
gcccaaaaccaatcagttactggtcacgaataccagcgacgaaggccgcgatgcgtttctgcgtcgttttgcgctaaatagcttcg
gcagcaagaatttcggcgcgcatggcgcctactgtggactggcttaccgggccggctccggggcattgatgggcgatctggata
aaaacccgcatgtcaaacccgactgggaaaacgtggagtttgcgctctttatgggcacctccccggcacagtccggcaatccgtt
taaacgccaggcacgtcagttggcgagcgcccgactgcgtgagaattttcaatacgtcgtggtcgcccccgccctccccttatca
acggtgctcgccgatcctcgcggtcgctggcaaccggtcatgcccggcagtgattcggcgctggcaatggggatgatccgctgg
atcatggataatcaacgttataatgctgattatctggcgattcccggcgtacaggcgatgcagcaggccggcgagcaaagttgga
ccaacgccacgcacctggtcattgcggatgagctgccgacgcttgccggacaacacctgacgctgcgccatcttacgcccgatg
gcgaagagacccctgtcgtactgaataccgacggcgagttggtcgatgcgtccacttgccgacaggcacggcttttcgtgacgc
agtacgttacgctcgccgacggccaacgggtcacggtgaagagcgggttgcaacgcctgaaagaggcggcagaaaagctct
cgttggcgcaatacagcgaacagtgcggcgtgccggaagcgcaaattatcgcgctggcggaaacctttaccagtcacggacgt
aaagctgcggtcatcagtcacggcggcatgatggccggcaatgggttttataacgcctggtcggtcatgatgcttaacgcgctgat
cggcaacctcagcttgtccggcggcgtctttgtcggcggcggcaaattcaacggcgttagcgacggcccccgctacaacatgaa
cagttttgccggaaaagtgaaaccgtccgggttaagtattgcccgtagcaaaaccgcttatgaagcatcggaagaataccgcga
caaaattgccggtgggcaatccccttatccagccaaagcgccgtggtatccctttgtggcaggccagcttaccgaactgttgacct
ccgcgctcgaaggctatccttatccgcttaaagcctggatttccaatatgagcaacccgttttacggtgttcccggtctacgcgccgt
ggcggaagaaaaactaaaagaccctcgccgactgccgctctttatcgcgattgacgcctttatgaatgaaacgacggcgctggc

FIGURE 34B-1 ggattacattgtgccggatacgcacaattttgagagctggggctttacggcgccctggggcggcgtagccagtaaagccactacc
gcccgctggccggttgtcgcccccgccactcaccgcacggcggacgggcaacctgtctcaatggaagcattttgtattgcggtag
caaaacggctccatctgcccggcttcggcgaccgggcgataaccgatccgcagggcaatacttttccactgaaccgggcggaa
gacttctatctgcgcgtagccgctaatatcgcctttatgggcaagacgccggtcgcgctggcaaatcaggaagatatttcgcttacc
ggcgtcagccgcattctgccagcaattcagcacacgcttaaagctgatgaggtcggtcgcgtggcgtttatctactcgcgtggcgg
ccggtttgcgcccgaggatagcggctatacggagcaacggttaggtaacgcgtggaaaaaacccttacagatctggaatgcag
atgtcgccgcccaccgtcacgccatcaccggggagcgcttcagcggttgcccggtctggtatccggcgcgtttgtcagatggtcgt
gcgattgacgaccagtttcccattgggcaatggccgctgaaactgatttcatttaaatcaaataccatgtccagctcaacagccgtc
atcccgcgcttacaccatgtgaagccagcaaacctggtggcgctgaatccgcaagacggcgagcgttatggactgcaacatgg
cgatcgggtacggatcattacgccgggcggtcaggtcgtggcgcaaatcagtttgttaaatggcgtgatgccaggcgtcatcgcc
atcgaacacggatatggccaccgcgagatgggcgcaacgcagcactctctggatggcgtgcctatgccgtatgatccacaaat
cagggcaggcataaatcttaacgatctgggctttgccgatccgacaagaaccattaccaacacctggctcgactgggtttctggc
gcggcagtacgtcaggggctgccggcaaaaatcgagcgtata (SEQ ID NO: 31)

FIGURE 34B-2 (contd.)

tcatggctcatacgttgttcgtattctggtctctggcgaggccatttttcgaaacgcctaatcagttccgccaggctaccggcctgcat
tttttccatgactctggcgcggtgcacctctacggtacgcaccgcgatattcatcgcttccgcaatttcacggttcataaatccttttgcc
accaggctggccagctcacgctctttcggcgtcaactgctggtaacacagtataatctcacgacgcgccaccgctgccgatgaa
accgtcagcgcacgctccagcgccgcctgtagcggttttaccgataccggtttttgcagaaaatcgacggcgccgcgtttcatctg
ctccacggccatcggtacatcgccatgcccggtaagaaaaacaaccgccagggtacttccgcactggcgcaacgcatcatga
acgccctgcccatccagtaccggcattcgcatatccagtaatacgaccccggcctgatacagactggcctgcgccaaaaaatcc
gccccctgcgtccagcattttacgtcatatcccagactttccagtaaaaacgcgcacgcgttagtgaccgccgtatcatcatccagt
agatgaattgtcgccatccctgcccccattttcatgtaagaaatgtatcgtaaccaccgttcccgacagaccgtccggcgcggtctg
gttcctgatgctgatatcgccccgcccataccgcaccagccgctggcaaatcgccagccctaagcccatcccctctttacgggtg
gtcataaacggctgaaacgcctgacgtaatagcgcctcatcgattcccccggcgttatcctgtaaaacaatactgatgccgttttca
gtgcgttcagcaacgatccataaatgggtggcgcccgcctgagccgcattaagaatgatattcgccagcacctgttccagcagc
actgacggcagcgttacgcgcagcgcagcgctaacctcggtatgcagagtcactgtcggaaactgttgcgccatacgcaacaa
ttgccagacatgatcaatcgcctcgcgaatggctatggccttccacgcttcggttagcaccgggttgccctgcgcctggctgaccc
agtgacgcaggttacgcagagtatccgcaccgcgttgcgcctgctggtcaatctgctccagcgccggcagcaagggatgctgtt
catctgcagcgcgcagtcgaatcaggcacccctgggcataatgtcgaatcgcggaaagcggctgattaagctcatgggcaaac
ccggaggtcatttcacccaacacgctcatttgccgggcggtttccagcgcccgctcatgctgatgaagaactacgctattacgttcc
agttgctttccacgtcgacgcaccagcagcatgacccaaatataattgagcgtgagcaacaagaacgccagaatcacgccgc
cgaccattagctggtgctggattaaccaacttttgacatccagccacagtcgacgctgctgagggtgctgacgaacatcacgcag
caaggcttccacctgactggtggacgcaggcgcgccccagtgaaatgacgcggcggcgggcgcgttgaatagcgctcgcgtt
acgcgatccgccagcgcatcgcttaccgcaggtagcgccgcgaacgaccagtcaggatataacggcgtactggttaagcaag
gcaggggcgtcggtcgggaaagcagcgcgataaagtccttttattaatcaatccttcctgatccatattttctaacaggcacactg
gcacaattgccgcctgcaccgctttttcgcgcagcatatagactaaggcatcgccaggaaatccggtaaaacggagatgaaaat
cgcgctccgggcgtaagcccgcgtcgctgagcgctttatagcctaataaatagccgccaaacgcctgagcatcaatcgcgccg
acggtcttaccgatgagatcatgcgccgtggtgatgccgctatcgcgccgggtcaaaatcacgctgccaataacattactcaccg
ctttcccatcgcgcgtggagcgcagggaagctaaccagcgcagcggcgcatggctgttcagttggacaaattgcgccgggttgg
ttatcacaaactgcacggttccctggttaacggcctcctgcatttgatgcagatccagcggctggatgtgaaaggtttcgcctggaa
gctgttggcttaatgtctttgccaacggttgccagtggctacgcgtagacgcctcgccgcgcatggccaaaataccgatattccac
gtccctgcccacgcgccatgacaaagtagccctactgccgccaacaccgccaggcgccttacggttttacctctcac (SEQ
ID NO: 32)

FIGURE 34C atggctaatttaacccgtcgtcagtggctaaaagtcggtctcgccgtcggtgggatggtcacttttgg
tctgagctaccgtgatgtggcgaaacgcgcaattgatggcctgttaaacgggacgtccggcaaggtaa
cgcgcgaccgcatctttggcaatgcgttaattccggaggcgcaggcgcaaacacactggcagcaaaat
ccacaacaaaccatcgccatgacgcaatgcttcggctgttggacacagtgcggtatccgcgcccgggt
taatgccgatggcaaagtgatacgcatcgccggcaatccctatcaccccttgtcgcaggaacacccga
ttgactcgtccgtcccttttagcgaagccatggagcaactggcgggagaaagcggtcttgacgcccgc
tcaaccgcctgcgcgcgcggcgccacgctgctggaaagcctgtacagtccgctacgactgcttgaacc
gatgaaacgcgtgggtaaacgcggcgaagggaaatggcagcgcatcagctttgagcaacttattgaag
aagtcgtggaaggcggcgatctgtttggcgaaggtcatgtggacggactgcgcgctattcatgcgccg
gatacgccaattgacgcaaagcaccccagtttcgggcccaaaaccaatcagttactggtcacgaatac
cagcgacgaaggccgcgatgcgtttctgcgtcgttttgcgctaaatagcttcggcagcaagaatttcg
gcgcgcatggcgcctactgtggactggcttaccgggccggctccggggcattgatgggcgatctggat
aaaaacccgcatgtcaaacccgactgggaaaacgtggagtttgcgctctttatgggcacctccccggc
acagtccggcaatccgtttaaacgccaggcacgtcagttggcgagcgcccgactgcgtgagaatttc
aatacgtcgtggtcgcccccgccctccccttatcaacggtgctcgccgatcctcgcggtcgctggcaa
ccggtcatgcccggcagtgattcggcgctggcaatggggatgatccgctggatcatggataatcaacg
ttataatgctgattatctggcgattcccggcgtacaggcgatgcagcaggccggcgagcaaagttgga
ccaacgccacgcacctggtcattgcggatgagctgccgacgcttgccggacaacacctgacgctgcgc
catcttacgcccgatggcgaagagacccctgtcgtactgaataccgacggcgagttggtcgatgcgtc
cacttgccgacaggcacggcttttcgtgacgcagtacgttacgctcgccgacggccaacgggtcacgg
tgaagagcgggttgcaacgcctgaaagaggcggcagaaaagctctcgttggcgcaatacagcgaacag
tgcggcgtgccggaagcgcaaattatcgcgctggcggaaacctttaccagtcacggacgtaaagctgc
ggtcatcagtcacggcggcatgatggccggcaatgggttttataacgcctggtcggtcatgatgctta
acgcgctgatcggcaacctcagcttgtccggcggcgtctttgtcggcggcggcaaattcaacggcgtt
agcgacggcccccgctacaacatgaacagttttgccggaaaagtgaaaccgtccgggttaagtattgc
ccgtagcaaaaccgcttatgaagcatcggaagaataccgcgacaaaattgccggtgggcaatcccctt
atccagccaaagcgccgtggtatccctttgtggcaggccagcttaccgaactgttgacctccgcgctc
gaaggctatccttatccgcttaaagcctggatttccaatatgagcaacccgttttacggtgttcccgg
tctacgcgccgtggcggaagaaaaactaaaagaccctcgccgactgccgctctttatcgcgattgacg
cctttatgaatgaaacgacggcgctggcggattacattgtgccggatacgcacaattttgagagctgg
ggctttacggcgccctggggcggcgtagccagtaaagccactaccgcccgctggccggttgtcgcccc
cgccactcaccgcacggcggacgggcaacctgtctcaatggaagcattttgtattgcggtagcaaaac
ggctccatctgcccggcttcggcgaccgggcgataaccgatccgcagggcaatacttttccactgaac
cgggcggaagacttctatctgcgcgtagccgctaatatcgcctttatgggcaagacgccggtcgcgct
ggcaaatcaggaagatatttcgcttaccggcgtcagccgcattctgccagcaattcagcacacgctta
aagctgatgaggtcggtcgcgtggcgtttatctactcgcgtggcggccggtttgcgcccgaggatagc
ggctatacggagcaacggttaggtaacgcgtggaaaaaacccttacagatctggaatgcagatgtcgc
cgcccaccgtcacgccatcaccggggagcgcttcagcggttgcccggtctggtatccggcgcgtttgt
cagatggtcgtgcgattgacgaccagtttcccattgggcaatggccgctgaaactgatttcatttaaa
tcaaataccatgtccagctcaacagccgtcatcccgcgcttacaccatgtgaagccagcaaacctggt
ggcgctgaatccgcaagacggcgagcgttatggactgcaacatggcgatcgggtacggatcattacgc
cgggcggtcaggtcgtggcgcaaatcagtttgttaaatggcgtgatgccaggcgtcatcgccatcgaa
cacggatatggccaccgcgagatgggcgcaacgcagcactctctggatggcgtgcctatgccgtatga
tccacaaatcagggcaggcataaatcttaacgatctgggctttgccgatccgacaagaaccattacca
acacctggctcgactgggtttctggcgcggcagtacgtcaggggctgccggcaaaaatcgagcgtata
(SEQ ID NO: 33)

FIGURE 34D

MANLTRRQWL KVGLAVGGMV TFGLSYRDVA KRAIDGLLNG TSGKVTRDRI FGNALIPEAQ
AQTHWQQNPQ QTIAMTQCFG CWTQCGIRAR VNADGKVIRI AGNPYHPLSQ EHPIDSSVPF
SEAMEQLAGE SGLDARSTAC ARGATLLESL YSPLRLLEPM KRVGKRGEGK WQRISFEQLI
EEVVEGGDLF GEGHVDGLRA IHAPDTPIDA KHPSFGPKTN QLLVTNTSDE GRDAFLRRFA
LNSFGSKNFG AHGAYCGLAY RAGSGALMGD LDKNPHVKPD WENVEFALFM GTSPAQSGNP
FKRQARQLAS ARLRENFQYV VVAPALPLST VLADPRGRWQ PVMPGSDSAL AMGMIRWIMD
NQRYNADYLA IPGVQAMQQA GEQSWTNATH LVIADELPTL AGQHLTLRHL TPDGEETPVV
LNTDGELVDA STCRQARLFV TQYVTLADGQ RVTVKSGLQR LKEAAEKLSL AQYSEQCGVP
EAQIIALAET FTSHGRKAAV ISHGGMMAGN GFYNAWSVMM LNALIGNLSL SGGVFVGGGK
FNGVSDGPRY NMNSFAGKVK PSGLSIARSK TAYEASEEYR DKIAGGQSPY PAKAPWYPFV
AGQLTELLTS ALEGYPYPLK AWISNMSNPF YGVPGLRAVA EEKLKDPRRL PLFIAIDAFM
NETTALADYI VPDTHNFESW GFTAPWGGVA SKATTARWPV VAPATHRTAD GQPVSMEAFC
IAVAKRLHLP GFGDRAITDP QGNTFPLNRA EDFYLRVAAN IAFMGKTPVA LANQEDISLT
GVSRILPAIQ HTLKADEVGR VAFIYSRGGR FAPEDSGYTE QRLGNAWKKP LQIWNADVAA
HRHAITGERF SGCPVWYPAR LSDGRAIDDQ FPIGQWPLKL ISFKSNTMSS STAVIPRLHH
VKPANLVALN PQDGERYGLQ HGDRVRIITP GGQVVAQISL LNGVMPGVIA IEHGYGHREM
GATQHSLDGV PMPYDPQIRA GINLNDLGFA DPTRTITNTW LDWVSGAAVR QGLPAKIERI
(SEQ ID NO: 34)

FIGURE 34E

Atgtggacgggagtcaatatggacagcagtaaacggcaatttctccagcagcttggcgtcctgaccgc
tggcgcctcgctggttccgctggctgaagcgaaatttcctttttcgccggagcggcatgaaggctctc
cccgacaccgttacgccatgcttatcgatctgcggcgttgtatcggctgtcagtcctgtaccgtaagt
tgcactattgaaaaccaaacgccgcaaggcgcgtttcgtacgacggtgaaccaataccaggtccagcg
tgaaggtagtcaggaagtcacgaatgtgctgttgccgcgtctgtgcaaccattgcgataacccccccct
gtgtgccggtctgcccggtacaagccacctttcagcgggaagatggcattgtggtggtggataacaaa
cgctgcgtcggctgcgcctattgtgtccaggcgtgtccttacgacgcccgatttatcaatcatgaaac
gcaaactgccgataaatgcacgttttgcgtccatcgtctggaagccggactgttacccgcttgcgtag
agtcctgcgtcggcggcgcgcgtattattggcgatatcaaagatccccatagccgcatcgccaccatg
cttcatcagcatcgcgacgctatcaaggtattaaagccggaaaacggcacgtcgccccatgttttcta
cctgggtctggacgacgcctttgtcaccccattaatgggccgtgcgcagcccgcgctttggcaggagg
tctg (SEQ ID NO: 35)

FIGURE 34F

MWTGVNMDSS KRQFLQQLGV LTAGASLVPL AEAKFPFSPE RHEGSPRHRY AMLIDLRRCI
GCQSCTVSCT IENQTPQGAF RTTVNQYQVQ REGSQEVTNV LLPRLCNHCD NPPCVPVCPV
QATFQREDGI VVVDNKRCVG CAYCVQACPY DARFINHETQ TADKCTFCVH RLEAGLLPAC
VESCVGGARI IGDIKDPHSR IATMLHQHRD AIKVLKPENG TSPHVFYLGL DDAFVTPLMG
RAQPALWQEV (SEQ ID NO: 36)

FIGURE 34G

Atgacgcattcactcatcattgaagaagtgctggctcacccgcaggacattagctggctgccgtgggcggtacaatatttctttttattggcattg
ccgcctgcgccgcactgtttgcctgttatcttcactggcggaaaaaagacgccgcaacagaagaaaatcgggcattactgattgccattacctgt
gcgattaccgcaccgctggcgctgacggcggatctgcaccagaccgcccgcgtctggcatttctatgcctggccgacgccctggtcgtggatgcc
ctggggagcgttattcctgccgctgtttaccggatttctcgctctgtggttcctggcgcagcagattaaacgattattcaataaaagttacaacgtc
actaaatggttggcgttagccagcgcgctttgcgcggtgggcctgttgatttataccggccgcgaagtctccgttgtgctggcgcgcccaatctggt
ttagctacgccttccccgtggcgatgtttcttagcgccttacaggcgttcttcgcgctgatgattgtcgccgcccgacgcgactcggtaaggctgcc
aaaaatattgtggggacaaatctggacgctggcggcgctggggctggttgtggccatgtgggttagcggcgatacgctttccggcacggcaatcc
gtcagtggattaccgtcgccctgtcagccaaatattacgctgtcggctgggtagcgctgtgggtatgcacactgctgttctgtagcctggcgctacg
ccatccgttatcacagctaagacgcgtcctgctggttctcagcgcgctggcgctatgttggctgatgcgctggacattgttgattcaggtacaaacc
gtccccaagttcaacgcgcaatttaacccttactcgttaccaggcggaacggatggctggctggctattctcggcaccttcggcctgtggatagcg
ctactgattattattcgtgaaacgctgaacggactcaccaggagattacaacatgg (SEQ ID NO: 37)

FIGURE 34H

MTHSLIIEEV LAHPQDISWL PWAVQYFFFI GIAACAALFA CYLHWRKKDA ATEENRALLI
AITCAITAPL ALTADLHQTA RVWHFYAWPT PWSWMPWGAL FLPLFTGFLA LWFLAQQIKR
LFNKSYNVTK WLALASALCA VGLLIYTGRE VSVVLARPIW FSYAFPVAMF LSALQAFFAL
MIVAARHDSV RLPKILWGQI WTLAALGLVV AMWVSGDTLS GTAIRQWITV ALSAKYYAVG
WVALWVCTLL FCSLALRHPL SQLRRVLLVL SALALCWLMR WTLLIQVQTV PKFNAQFNPY
SLPGGTDGWL AILGTFGLWI ALLIIIRETL NGLTRRLQHG (SEQ ID NO: 38)

FIGURE 34I atgAAAATGG GGGCAGGGAT GGCGACAATT CATCTACTGG ATGATGATAC GGCGGTCACT
AACGCGTGCG CGTTTTTACT GGAAAGTCTG GGATATGACG TAAAATGCTG GACGCAGGGG
GCGGATTTTT TGGCGCAGGC CAGTCTGTAT CAGGCCGGGG TCGTATTACT GGATATGCGA
ATGCCGGTAC TGGATGGGCA GGGCGTTCAT GATGCGTTGC GCCAGTGCGG AAGTACCCTG
GCGGTTGTTT TTCTTACCGG GCATGGCGAT GTACCGATGG CCGTGGAGCA GATGAAACGC
GGCGCCGTCG ATTTTCTGCA AAAACCGGTA TCGGTAAAAC CGCTACAGGC GGCGCTGGAG
CGTGCGCTGA CGGTTTCATC GGCAGCGGTG GCGCGTCGTG AGATTATACT GTGTTACCAG
CAGTTGACGC CGAAAGAGCG TGAGCTGGCC AGCCTGGTGG CAAAAGGATT TATGAACCGT
GAAATTGCGG AAGCGATGAA TATCGCGGTG CGTACCGTAG AGGTGCACCG CGCCAGAGTC
ATGGAAAAAA TGCAGGCCGG TAGCCTGGCG GAACTGATTA GGCGTTTCGA AAAAATGGCC
TCGCCAGAGA CCAGAATACG AACAACGTAT GAGCCAtga (SEQ ID NO: 39)

FIGURE 34J

MKMGAGMATI HLLDDDTAVT NACAFLLESL GYDVKCWTQG ADFLAQASLY QAGVVLLDMR
MPVLDGQGVH DALRQCGSTL AVVFLTGHGD VPMAVEQMKR GAVDFLQKPV SVKPLQAALE
RALTVSSAAV ARREIILCYQ QLTPKERELA SLVAKGFMNR EIAEAMNIAV RTVEVHRARV
MEKMQAGSLA ELIRRFEKMA SPETRIRTTY EP (SEQ ID NO: 40)

FIGURE 34K gtgAGAGGTA AAACCGTAAG GCGCCTGGCG GTGTTGGCGG CAGTAGGGCT ACTTTGTCAT
GGCGCGTGGG CAGGGACGTG GAATATCGGT ATTTTGGCCA TGCGCGGCGA GGCGTCTACG
CGTAGCCACT GGCAACCGTT GGCAAAGACA TTAAGCCAAC AGCTTCCAGG CGAAACCTTT
CACATCCAGC CGCTGGATCT GCATCAAATG CAGGAGGCCG TTAACCAGGG AACCGTGCAG
TTTGTGATAA CCAACCCGGC GCAATTTGTC CAACTGAACA GCCATGCGCC GCTGCGCTGG
TTAGCTTCCC TGCGCTCCAC GCGCGATGGG AAAGCGGTGA GTAATGTTAT TGGCAGCGTG
ATTTTGACCC GGCGCGATAG CGGCATCACC ACGGCGCATG ATCTCATCGG TAAGACCGTC
GGCGCGATTG ATGCTCAGGC GTTTGGCGGC TATTTATTAG GCTATAAAGC GCTCAGCGAC
GCGGGCTTAC GCCCGGAGCG CGATTTTCAT CTCCGTTTTA CCGGATTTCC TGGCGATGCC
TTAGTCTATA TGCTGCGCGA AAAAGCGGTG CAGGCGGCAA TTGTGCCAGT GTGCCTGTTA
GAAAATATGG ATCAGGAAGG ATTGATTAAT AAAAAGGACT TTATCGCGCT GCTTTCCCGA
CCGACGCCCC TGCCTTGCTT AACCAGTACG CCGTTATATC CTGACTGGTC GTTCGCGGCG
CTACCTGCGG TAAGCGATGC GCTGGCGGAT CGCGTAACGC GAGCGCTATT CAACGCGCCC
GCCGCCGCGT CATTTCACTG GGGCGCGCCT GCGTCCACCA GTCAGGTGGA AGCCTTGCTG
CGTGATGTTC GTCAGCACCC TCAGCAGCGT CGACTGTGGC TGGATGTCAA AAGTTGGTTA
ATCCAGCACC AGCTAATGGT CGGCGGCGTG ATTCTGGCGT TCTTGTTGCT CACGCTCAAT
TATATTTGGG TCATGCTGCT GGTGCGTCGA CGTGGAAAGC AACTGGAACG TAATAGCGTA
GTTCTTCATC AGCATGAGCG GGCGCTGGAA ACCGCCCGGC AAATGAGCGT GTTGGGTGAA
ATGACCTCCG GGTTTGCCCA TGAGCTTAAT CAGCCGCTTT CCGCGATTCG ACATTATGCC
CAGGGGTGCC TGATTCGACT GCGCGCTGCA GATGAACAGC ATCCCTTGCT GCCGGCGCTG
GAGCAGATTG ACCAGCAGGC GCAACGCGGT GCGGATACTC TGCGTAACCT GCGTCACTGG
GTCAGCCAGG CGCAGGGCAA CCCGGTGCTA ACCGAAGCGT GGAAGGCCAT AGCCATTCGC
GAGGCGATTG ATCATGTCTG GCAATTGTTG CGTATGGCGC AACAGTTTCC GACAGTGACT
CTGCATACCG AGGTTAGCGC TGCGCTGCGC GTAACGCTGC CGTCAGTGCT GCTGGAACAG
GTGCTGGCGA ATATCATTCT TAATGCGGCT CAGGCGGGCG CCACCCATTT ATGGATCGTT
GCTGAACGCA CTGAAAACGG CATCAGTATT GTTTTACAGG ATAACGCCGG GGGAATCGAT
GAGGCGCTAT TACGTCAGGC GTTTCAGCCG TTTATGACCA CCCGTAAAGA GGGGATGGGC
TTAGGGCTGG CGATTTGCCA GCGGCTGGTG CGGTATGGGC GGGGCGATAT CAGCATCAGG
AACCAGACCG CGCCGGACGG TCTGTCGGGA ACGGTGGTTA CGATACATTT CTTACATGAA
AATGGGGGCA GGGATGGCGA CAATTCATCT ACTGGAtga (SEQ ID NO: 41)

FIGURE 34L

MRGKTVRRLA VLAAVGLLCH GAWAGTWNIG ILAMRGEAST RSHWQPLAKT LSQQLPGETF
HIQPLDLHQM QEAVNQGTVQ FVITNPAQFV QLNSHAPLRW LASLRSTRDG KAVSNVIGSV
ILTRRDSGIT TAHDLIGKTV GAIDAQAFGG YLLGYKALSD AGLRPERDFH LRFTGFPGDA
LVYMLREKAV QAAIVPVCLL ENMDQEGLIN KKDFIALLSR PTPLPCLTST PLYPDWSFAA
LPAVSDALAD RVTRALFNAP AAASFHWGAP ASTSQVEALL RDVRQHPQQR RLWLDVKSWL
IQHQLMVGGV ILAFLLLTLN YIWVMLLVRR RGKQLERNSV VLHQHERALE TARQMSVLGE
MTSGFAHELN QPLSAIRHYA QGCLIRLRAA DEQHPLLPAL EQIDQQAQRG ADTLRNLRHW
VSQAQGNPVL TEAWKAIAIR EAIDHVWQLL RMAQQFPTVT LHTEVSAALR VTLPSVLLEQ
VLANIILNAA QAGATHLWIV AERTENGISI VLQDNAGGID EALLRQAFQP FMTTRKEGMG
LGLAICQRLV RYGRGDISIR NQTAPDGLSG TVVTIHFLHE NGGRDGDNSS TG (SEQ ID NO: 42)

FIGURE 34M aggcacacgaaaaacaagttaagggatgcagtttatcgggcagcgttgggtcctggccacgggtgcgcatgatcgtgctcctgtcgttgaggac
ccggctaggctggcggggttgccttactggttagcagaatgaatcaccgatacgcgagcgaacgtgaagcgactgctgctgcaaaacgtctgcg
acctgagcaacaacatgaatggtcttcggtttccgtgtttcgtaaagtctggaaacgcggaagtcagcgccctgcaccattatgttccggatctgc
atcgcaggatgctgctggctaccctgtggaacacctacatctgtattaacgaagcgctggcattgaccctgagtgatttttctctggtcccgccgca
tccataccgccagttgtttaccctcacaacgttccagtaaccgggcatgttcatcatcagtaacccgtatcgtgagcatcctctctcgtttcatcggt
atcattacccccatgaacagaaatcccccttacacggaggcatcagtgaccaaacaggaaaaaaccgcccttaacatggcccgctttatcagaa
gccagacattaacgcttctggagaaactcaacgagctggacgcggatgaacaggcagacatctgtgaatcgcttcacgaccacgctgatgagct
ttaccgcagctgcctcgcgcgtttcggtgatgacggtgaaaacctctgacacatgcagctcccggagacggtcacagcttgtctgtaagcggatg
ccgggagcagacaagcccgtcagggcgcgtcagcgggtgttggcgggtgtcggggcgcagccatgacccagtcacgtagcgatagcggagtgt
atactggcttaactatgcggcatcagagcagattgtactgagagtgcaccatatgcggtgtgaaataccgcacagatgcgtaaggagaaaatac
cgcatcaggcgctcttccgcttcctcgctcactgactcgctgcgctcggtcgttcggctgcggcgagcggtatcagctcactcaaaggcggtaata
cggttatccacagaatcaggggataacgcaggaaagaacatgtgagcaaaaggccagcaaaaggccaggaaccgtaaaaaggccgcgttgc
tggcgtttttccataggctccgcccccctgacgagcatcacaaaaatcgacgctcaagtcagaggtggcgaaacccgacaggactataaagata
ccaggcgtttccccctggaagctccctcgtgcgctctcctgttccgaccctgccgcttaccggatacctgtccgcctttctcccttcgggaagcgtgg
cgctttctcatagctcacgctgtaggtatctcagttcggtgtaggtcgttcgctccaagctgggctgtgtgcacgaaccccccgttcagcccgaccg
ctgcgccttatccggtaactatcgtcttgagtccaacccggtaagacacgacttatcgccactggcagcagtcccttaacttacttattaaataatt
tatagctattgaaaagagataagaattgttcaaagctaatattgtttaaatcgtcaattcctgcatgttttaaggaattgttaaattgattttttgta
aatattttcttgtattctttgttaacccatttcataacgaaataattatacttttgtttatctttgtgtgatattcttgatttttttctacttaatctgataa
gtgagctattcactttaggtttaggatgaaaatattctcttggaaccatacttaatatagaaatatcaacttctgccattaaaagtaatgccaatga
gcgttttgtatttaataatcttttagcaaacccgtattccacgattaaataaatctcattagctatactatcaaaaacaattttgcgtattatatccgt
acttatgttataaggtatattaccatatattttataggattggtttttaggaaatttaaactgcaatatatccttgtttaaaacttggaaattatcgtg
atcaacaagtttattttctgtagttttgcataatttatggtctatttcaatggcagttacgaaattacacctctttactaattcaagggtaaaatggcc
ttttcctgagccgatttcaaagatattatcatgttcatttaatcttatatttgtcattattttatctatattatgttttgaagtaataaagttttgactgtg
ttttatatttttctcgttcattataaccctctttaatttggttatatgaattttgcttattaacgattcattataaccacttatttttttgtttggttgataat
gaactgtgctgattacaaaaatactaaaaatgcccatatttttttcctccttataaaattagtataattatagcacgagctctgataaatatgaacat
gatgagtgatcgttaaatttatactgcaatcggatgcgattattgaataaaagatatgagagatttatctaatttctttttttcttgtaaaaaaagaa
agttcttaaaggttttatagttttggtcgtagagcacacggtttaacgacttaattacgaagtaaataagtctagtgtgttagactttatgaaatcta
tatacgtttatatatatttattatccgatttttttattaaaacgtctcaaaatcgtttctgagacgttttagcgtttatttcgtttagttatcggcataatc
gttaaaacaggcgttatcgtagcgtaaaagcccttgagcgtagcgtggctttgcagcgaagatgttgtctgttagattatgaaagccgatgactg
aatgaaataataagcgcagcgcccttctatttcggttggaggaggctcaagggagtatgagggaatgaaattccctcatgggtttgattttaaaa
attgcttgcaattttgccgagcggtagcgctggaaaatttttgaaaaaaatttggaatttggaaaaaaatgggggggaaaggaagcgaattttgct
tccgtactacgacccccccattaagtgccgagtgccaatttttgtgccaaaaacgctctatcccaactggctcaagggtttaaggggtttttcaatcg
ccaacgaatcgccaacgttttcgccaacgtttttttataaatctatatttaagtagctttattgttgtttttatgattacaaagtgatacactaacttat
aaaattatttgattggagtttttttaaatggtgatttcagaatcgaaaaaaaagagttatgatttctctgacaaaagagcaagataaaaaaattaaca
gatatggcgaaacaaaaaggtttttcaaaatctgcggttgcggcgttagctatagaagaatatgcaagaaaggaatcagaacaaaaaaaaataa
gcgaaagctcgcgtttttagaaggatacgagttttcgctacttgtttttgataaggtaattatatcatggctattaaaaatactaaagctagaaatt
ttggatttttattatatcctgactcaattcctaatgattggaaagaaaaattagagagtttgggcgtatctatggctgtcagtcctttacacgatatg
gacgaaaaaaaaagataaagatacatggaataatagtaatattatacaaaatggaaagcactataaaaaaccacactatcacgttatatatatt
gcacgaaatcctgtaacaatagaaagcgttaggaacaagattaagcgaaaattggggaatagttcagttgctcatgttgagatacttgattatat
caaaggttcatatgaatatttgactcatgaatcaaaggacgctattgctaagaataaacatatatacgacaaaaaagatattttgaacattaatg
attttgatattgaccgctatataacacttgatgaaagccaaaaaagagaattgaagaatttacttttagatatagtggatgactataatttggtaa
atacaaaagatttaatggcttttattcgccttaggggagcggagtttggaattttaaatacaaagatattgtttcaacaaagaatgatgtactcta
gcgcctttagattatggtttgagggcaattatcagtgtggatatagagcaagttatgcaaaggttcttgatgctgaaacgggggaaataaaatga

FIGURE 35A-1 caaacaaagaaaaagagttatttgctgaaaatgaggaattaaaaaaagaaattaaggacttaaaagagcgtattgaaagatacagagaaatg
gaagttgaattaagtacaacaatagatttattgagaggagggattattgaataaataaaagccccctgacgaaagtcgaagggggtttttatttt
ggtttgatgttgcgattaatagcaatacaattgcaataaacaaaatgatcttccttcaggttatgaccatctgtgccagttcgtaatgtctggtcaa
ctttccgactctgagaaacttctggaatcgctagagaatttctggaatgggattcaggagtggacagaacgacacggatatatagtggatgtgtc
aaaacgcataccattttgaacgatgacctctaataattgttaatcatgttggttacgtatttattaacttctcctagtattagtaattatcatggctgt
catggcgcattaacggaataaagggtgtgcttaaatcgggccattttgcgtaataagaaaaaggattaattatgagcgaattgaattaataataa
ggtaatagatttacattagaaaatgaaaggggattttatgcgtgagaatgttacagtctatccctggcgaaagggggatgtgctgcaaggcgatt
aagttgggtaacgccagggttttcccagtcacgacgttgtaaaacgacggccagtgagcgcgcgtaatacgactcactatagggcgaattgggt
accgggccccccctcgaggtcgacggtatcgataagcttgatatcgaattcctgcagcccgggggatccactagttctagagcggccgccaccgc
ggtggagctccagcttttgttccctttagtgagggttaattgcgcgcttggcgtaatcatggtcatagctgtttcctgtgtgaaattgttatccgctca
caattccacacaacatacgagccggaagcataaagtgtaaagcctggggtgcctaatgagtgagctaactcacattaattgcgttgcgctcactg
cccgctttccagtcgggaaacctgtcgtgccag (SEQ ID NO: 43)

FIGURE 35A-2 (contd.)

aggcacacgaaaaacaagttaagggatgcagtttatcgggcagcgttgggtcctggccacgggtgcgcatgatcgtgctcctgtcgttgaggac
ccggctaggctggcggggttgccttactggttagcagaatgaatcaccgatacgcgagcgaacgtgaagcgactgctgctgcaaaacgtctgcg
acctgagcaacaacatgaatggtcttcggtttccgtgtttcgtaaagtctggaaacgcggaagtcagcgccctgcaccattatgttccggatctgc
atcgcaggatgctgctggctaccctgtggaacacctacatctgtattaacgaagcgctggcattgaccctgagtgatttttctctggtcccgccgca
tccataccgccagttgtttaccctcacaacgttccagtaaccgggcatgttcatcatcagtaacccgtatcgtgagcatcctctctcgtttcatcggt
atcattacccccatgaacagaaatcccccttacacggaggcatcagtgaccaaacaggaaaaaaccgcccttaacatggcccgctttatcagaa
gccagacattaacgcttctggagaaactcaacgagctggacgcggatgaacaggcagacatctgtgaatcgcttcacgaccacgctgatgagct
ttaccgcagctgcctcgcgcgtttcggtgatgacggtgaaaacctctgacacatgcagctcccggagacggtcacagcttgtctgtaagcggatg
ccgggagcagacaagcccgtcagggcgcgtcagcgggtgttggcgggtgtcggggcgcagccatgacccagtcacgtagcgatagcggagtgt
atactggcttaactatgcggcatcagagcagattgtactgagagtgcaccatatgcggtgtgaaataccgcacagatgcgtaaggagaaaatac
cgcatcaggcgctcttccgcttcctcgctcactgactcgctgcgctcggtcgttcggctgcggcgagcggtatcagctcactcaaaggcggtaata
cggttatccacagaatcaggggataacgcaggaaagaacatgtgagcaaaaggccagcaaaaggccaggaaccgtaaaaaggccgcgttgc
tggcgtttttccataggctccgcccccctgacgagcatcacaaaaatcgacgctcaagtcagaggtggcgaaacccgacaggactataaagata
ccaggcgtttccccctggaagctccctcgtgcgctctcctgttccgaccctgccgcttaccggatacctgtccgcctttctcccttcgggaagcgtgg
cgctttctcatagctcacgctgtaggtatctcagttcggtgtaggtcgttcgctccaagctgggctgtgtgcacgaaccccccgttcagcccgaccg
ctgcgccttatccggtaactatcgtcttgagtccaacccggtaagacacgacttatcgccactggcagcagtcccttaacttacttattaaataatt
tatagctattgaaaagagataagaattgttcaaagctaatattgtttaaatcgtcaattcctgcatgttttaaggaattgttaaattgatttttgta
aatattttcttgtattctttgttaacccatttcataacgaaataattatacttttgtttatctttgtgtgatattcttgatttttttctacttaatctgataa
gtgagctattcactttaggtttaggatgaaaatattctcttggaaccatacttaatatagaaatatcaacttctgccattaaaagtaatgccaatga
gcgttttgtatttaataatcttttagcaaacccgtattccacgattaaataaatctcattagctatactatcaaaaacaattttgcgtattatatccgt
acttatgttataaggtatattaccatatattttataggattggtttttaggaaatttaaactgcaatatatccttgtttaaaacttggaaattatcgtg
atcaacaagtttattttctgtagttttgcataatttatggtctatttcaatggcagttacgaaattacacctctttactaattcaagggtaaaatggcc
ttttcctgagccgatttcaaagatattatcatgttcatttaatcttatatttgtcattattttatctatattatgttttgaagtaataaagttttgactgtg
ttttatatttttctcgttcattataaccctctttaatttggttatatgaattttgcttattaacgattcattataaccacttatttttttgtttggttgataat
gaactgtgctgattacaaaaatactaaaaatgcccatattttttcctccttataaaattagtataattatagcacgagctctgataaatatgaacat
gatgagtgatcgttaaatttatactgcaatcggatgcgattattgaataaaagatatgagagatttatctaatttctttttcttgtaaaaaaagaa
agttcttaaaggttttatagttttggtcgtagagcacacggtttaacgacttaattacgaagtaaataagtctagtgtgttagactttatgaaatcta
tatacgtttatatatatttattatccgatttttattaaaacgtctcaaaatcgtttctgagacgttttagcgtttatttcgtttagttatcggcataatc
gttaaaacaggcgttatcgtagcgtaaaagcccttgagcgtagcgtggctttgcagcgaagatgttgtctgttagattatgaaagccgatgactg

FIGURE 35B-1 aatgaaataataagcgcagcgcccttctatttcggttggaggaggctcaagggagtatgagggaatgaaattccctcatgggtttgattttaaaa
attgcttgcaattttgccgagcggtagcgctggaaaatttttgaaaaaaatttggaatttggaaaaaaatgggggggaaaggaagcgaattttgct
tccgtactacgaccccccattaagtgccgagtgccaatttttgtgccaaaaacgctctatcccaactggctcaagggtttaaggggtttttcaatcg
ccaacgaatcgccaacgttttcgccaacgttttttataaatctatatttaagtagctttattgttgtttttatgattacaaagtgatacactaactttat
aaaattatttgattggagtttttaaatggtgatttcagaatcgaaaaaaagagttatgatttctctgacaaaagagcaagataaaaaattaaca
gatatggcgaaacaaaaaggtttttcaaaatctgcggttgcggcgttagctatagaagaatatgcaagaaaggaatcagaacaaaaaaaataa
gcgaaagctcgcgtttttagaaggatacgagttttcgctacttgtttttgataaggtaattatatcatggctattaaaaatactaaagctagaaatt
ttggatttttattatatcctgactcaattcctaatgattggaaagaaaaattagagagtttgggcgtatctatggctgtcagtcctttacacgatatg
gacgaaaaaaaagataaagatacatggaataatagtaatattatacaaaatggaaagcactataaaaaaccacactatcacgttatatatatt
gcacgaaatcctgtaacaatagaaagcgttaggaacaagattaagcgaaaattggggaatagttcagttgctcatgttgagatacttgattatat
caaaggttcatatgaatatttgactcatgaatcaaaggacgctattgctaagaataaacatatatacgacaaaaaagatattttgaacattaatg
attttgatattgaccgctatataacacttgatgaaagccaaaaaagagaattgaagaatttacttttagatatagtggatgactataatttggtaa
atacaaaagatttaatggcttttattcgccttaggggagcggagtttggaattttaaatacaaagatattgtttcaacaaagaatgatgtactcta
gcgcctttagattatggtttgagggcaattatcagtgtggatatagagcaagttatgcaaaggttcttgatgctgaaacggggaaataaaatga
caaacaaagaaaaagagttatttgctgaaaatgaggaattaaaaaaagaaattaaggacttaaaagagcgtattgaaagatacagagaaatg
gaagttgaattaagtacaacaatagatttattgagaggagggattattgaataaataaaagccccctgacgaaagtcgaagggggtttttatttt
ggtttgatgttgcgattaatagcaatacaattgcaataaacaaaatgatcttccttcaggttatgaccatctgtgccagttcgtaatgtctggtcaa
ctttccgactctgagaaacttctggaatcgctagagaatttctggaatgggattcaggagtggacagaacgacacggatatatagtggatgtgtc
aaaacgcataccattttgaacgatgacctctaataattgttaatcatgttggttacgtatttattaacttctcctagtattagtaattatcatggctgt
catggcgcattaacggaataaagggtgtgcttaaatcgggccattttgcgtaataagaaaaaggattaattatgagcgaattgaattaataataa
ggtaatagatttacattagaaaatgaaaggggattttatgcgtgagaatgttacagtctatccctggcgaaagggggatgtgctgcaaggcgatt
aagttgggtaacgccagggttttcccagtcacgacgttgtaaaacgacggccagtgagcgcgcgtaatacgactcactatagggcgaattgggt
accgggccccccctcgaggtcgacggtatcgataagcttgatatcgaattcctgcagcccgggggatccactagttctagagcggccgccaccgc
ggtggagctccagcttttgttccctttagtgagggttaattgcgcgcttggcgtaatcatggtcatagctgtttcctgtgtgaaattgttatccgctca
caattccacacaacatacgagccggaagcataaagtgtaaagcctggggtgcctaatgagtgagctaactcacattaattgcgttgcgctcactg
cccgctttccagtcgggaaacctgtcgtgccag (SEQ ID NO: 44)

FIGURE 35B-2 (contd.)

ttccccttctctgaaaatcaacgggcaggtcactgacttgcccgtttttttatcccttctccacaccgttgagctcgaattctcatgtttgacagc
ttatcactgatcagtgaattaatggcgatgacgcatcctcacgataatatccgggtaggcgcaatcactttcgtctctactccgttacaaag
cgaggctgggtatttcccggcctttctgttatccgaaatccactgaaagcacagcggctggctgaggagataaataataaacgagggg
ctgtatgcacaaagcatcttctgttgagttaagaacgagtatcgagatggcacatagccttgctcaaattggaatcaggtttgtgccaatac
cagtagaaacagacgaagaagctagaggtgaatcacgacaaagcgtatcaaaaacgtatggagtagggctctaaactctgtataaa
aagtttccagctagctgataacgggaaagaaacagagaagggcacaaatattgtgtactttaatgtgccctttaatttattgattggtggttg
aattgtccgtaactttttgatttaagtgcaaatttctaataaattagaacactttcttaaattgtcatttggcatattacgaacaattccgcgtaaa
aacgttctgttacgctaaacccttatccagcaggctttcaaggatgtaaaccataacactctgcgaactagtgttacattgcgtgtagctttg
agtgggcaactttgtgtacacttttgtgtacccaaaaacaaaaatgtgtacccattcaatgatcaccgacacaaagctcaggaaggcgc
tcggcaagaaaagagatgatatcgagattatttctgattcgcacgagctttctagacgctcaagttagtataaaaaagctgaacgagaa
acgtaaaatgatataaatatcaatatattaaattagattttgcataaaaaacagactacataatactgtaaaacacaacatatgcagtcac
tatgaatcaactacttagatggtattagtgacctgtaacagactgcgggcccaggttatgctgcttttaagacccactttcacatttaagttgtt
tttctaatccgcatatgatcaattcaaggccgaataagaaggctggctctgcaccttggtgatcaaataattcgatagcttgtcgtaataatg
gcggcatactatcagtagtaggtgtttccctttcttctttagcgacttgatgctcttgatcttccaatacgcaacctaaagtaaaatgccccac
agcgctgagtgcatataatgcattctctagtgaaaaaccttgttggcataaaaaggctaattgattttcgagagtttcatactgtttttctgtag
gccgtgtacctaaatgtacttttgctccatcgcgatgacttagtaaagcacatctaaaacttttagcgttattacgtaaaaaatcttgccagct
ttccccttctaaagggcaaaagtgagtatggtgcctatctaacatctcaatggctaaggcgtcgagcaaagcccgcttatttttacatgcc
aatacaatgtaggctgctctacacctagcttctgggcgagtttacgggttgttaaaccttcgattccgacctcattaagcagctctaatgcgc
tgttaatcactttacttttatctaatctagacatcattaattcctaatttttgttgacactctatcattgatagagttattttaccactccctatcagtga
tagagaaaagtgaaatgaatagttcgacaaagatcgcattggtaattacgttactcgatgccatggggattggccttatcatgccagtctt
gccaacgttattacgtgaatttattgcttcggaagatatcgctaaccactttggcgtattgcttgcactttatgcgttaatgcaggttatctttgct
ccttggcttggaaaaatgtctgaccgatttggtcggcgcccagtgctgttgttgtcattaataggcgcatcgctggattacttattgctggctttt
tcaagtgcgctttggatgctgtatttaggccgtttgctttcagggatcacaggagctactggggctgtcgcggcatcggtcattgccgatacc
acctcagcttctcaacgcgtgaagtggttcggttggttaggggcaagttttgggcttggtttaatagcggggcctattattggtggttttgcag
gagagatttcaccgcatagtcccttttttatcgctgcgttgctaaatattgtcactttccttgtggttatgttttggttccgtgaaaccaaaaatac
acgtgataatacagataccgaagtaggggttgagacgcaatcgaattcggtatacatcactttatttaaaacgatgcccattttgttgattat
ttatttttcagcgcaattgataggccaaattcccgcaacggtgtgggtgctatttaccgaaaatcgttttggatggaatagcatgatggttgg
cttttcattagcgggtcttggtcttttacactcagtattccaagcctttgtggcaggaagaatagccactaaatggggcgaaaaaacggca
gtactgctcgaatttattgcagatagtagtgcatttgcctttttagcgtttatatctgaaggttggttagatttccctgttttaattttattggctggtgg
tgggatcgctttacctgcattacagggagtgatgtctatccaaacaaagagtcatgagcaaggtgctttacagggattattggtgagcctt
accaatgcaaccggtgttattggcccattactgtttactgttatttataatcattcactaccaatttgggatggctggatttggattattggtttagc
gttttactgtattattatcctgctatcgatgaccttcatgttaacccctcaagctcaggggagtaaacaggagacaagtgcttagttatttcgtc
accaaatgatgttattccgcgaaatataatgaccctcttgataacccaagagggcatttttttacgagacgtcctaattcccatgtcagccgtt
aagtgttcctgtgtcactgaaaattgctttgagaggctctaagggcttctcagtgcgttacatccctggcttgttgtccacaaccgttaaacctt
aaaagctttaaaagccttatatattcttttttttcttataaaacttaaaaccttagaggctatttaagttgctgatttatattaattttattgttcaaaca
tgagagcttagtacgtgaaacatgagagcttagtacgttagccatgagagcttagtacgttagccatgagggtttagttcgttaaacatga
gagcttagtacgttaaacatgagagcttagtacgtgaaacatgagagcttagtacgtactatcaacaggttgaactgctgatcttcagatc
ctctacgccggacgcatcgtggccggatcttgcggccgcaaaaattaaaaatgaagttttggaggcctcatttggtgacgaaataacta
agcacttgtctcctgtttactcccctgagcttgaggggtcaacatgaaggtcattgatagcaggataataatacagtaaaacgctaaacc
aataatccaaatccagccatcccaaattggtagtgaatgattataaataacagtaaacagtaatgggccaataacaccggttgcattggt
aaggctcaccaataatccctgtaaagcaccttgctcatgactctttgtttggatagacatcactccctgtaatgcaggtaaagcgatccca
ccaccagccaataaaattaaaacagggaaatctaaccaaccttcagatataaacgctaaaaaggcaaatgcactactatctgcaata
aattcgagcagtactgccgtttttttcgccccatttagtggctattcttcctgccacaaaggcttggaatactgagtgtaaaagaccaagacc
cgctaatgaaaagccaaccatcatgctattccatccaaaacgattttcggtaaatagcacccacaccgttgcgggaatttggcctatcaa
ttcgaaatcaaataatgattttattttgactgatagtgacctgttcgttgcaacaaattgataagcaatgctttttttataatgccaacttagtataa
aaaagcaggcttcagagcgatggcccccgatggtagtgtggggtctccccatgcgagagtagggaactgccaggcatcaaataaaa
cgaaaggctcagtcgaaagactgggcctttcgttttatctgttgtttgtcggtgaacgctctcctgagtaggacaaatccgccgggagcgg
atttgaacgttgcgaagcaacggcccggagggtggcgggcaggacgcccgccataaactgccaggcatcaaattaagcagaaggc
catcctgacggatggcctttttgcgtggccagtgccaagcttgcatgc (SEQ ID NO: 45)

FIGURE 36A ctgcaggtcgactctagaggatccgttatatacgctcgatttttgccggcagcccctgacgtactgccgcgccagaaacccagtcgagccaggtg
ttggtaatggttcttgtcggatcggcaaagcccagatcgttaagatttatgcctgccctgatttgtggatcatacggcataggcacgccatccaga
gagtgctgcgttgcgcccatctcgcggtggccatatccgtgttcgatggcgatgacgcctggcatcacgccatttaacaaactgatttgcgccacg
acctgaccgcccggcgtaatgatccgtacccgatcgccatgttgcagtccataacgctcgccgtcttgcggattcagcgccaccaggtttgctggc
ttcacatggtgtaagcgcgggatgacggctgttgagctggacatggtatttgatttaaatgaaatcagtttcagcggccattgcccaatgggaaa
ctggtcgtcaatcgcacgaccatctgacaaacgcgccggataccagaccgggcaaccgctgaagcgctccccggtgatggcgtgacggtgggc
ggcgacatctgcattccagatctgtaagggtttttttccacgcgttacctaaccgttgctccgtatagccgctatcctcgggcgcaaaccggccgcca
cgcgagtagataaacgccacgcgaccgacctcatcagctttaagcgtgtgctgaattgctggcagaatgcggctgacgccggtaagcgaaatat
cttcctgatttgccagcgcgaccggcgtcttgcccataaaggcgatattagcggctacgcgcagatagaagtcttccgcccggttcagtggaaaa
gtattgccctgcggatcggttatcgcccggtcgccgaagccgggcagatggagccgttttgctaccgcaatacaaaatgcttccattgagacagg
ttgcccgtccgccgtgcggtgagtggcgggggcgacaaccggccagcgggcggtagtggctttactggctacgccgccccagggcgccgtaaag
ccccagctctcaaaattgtgcgtatccggcacaatgtaatccgccagcgccgtcgtttcattcataaaggcgtcaatcgcgataaagagcggcag
tcggcgagggtcttttagtttttcttccgccacggcgcgtagaccgggaacaccgtaaaacgggttgctcatattggaaatccaggctttaagcgg
ataaggatagccttcgagcgcggaggtcaacagttcggtaagctggcctgccacaaagggataccacggcgctttggctggataaggggattgc
ccaccggcaattttgtcgcggtattcttccgatgcttcataagcggttttgctacgggcaatacttaacccggacggtttcacttttccggcaaaact
gttcatgttgtagcgggggccgtcgctaacgccgttgaatttgccgccgccgacaaagacgccgccggacaagctgaggttgccgatcagcgcg
ttaagcatcatgaccgaccaggcgttataaaacccattgccggccatcatgccgccgtgactgatgaccgcagctttacgtccgtgactggtaaa
ggtttccgccagcgcgataatttgcgcttccggcacgccgcactgttcgctgtattgcgccaacgagagcttttctgccgcctctttcaggcgttgc
aacccgctcttcaccgtgacccgttggccgtcggcgagcgtaacgtactgcgtcacgaaaagccgtgcctgtcggcaagtggacgcatcgacca
actcgccgtcggtattcagtacgacaggggtctcttcgccatcgggcgtaagatggcgcagcgtcaggtgttgtccggcaagcgtcggcagctca
tccgcaatgaccaggtgcgtggcgttggtccaactttgctcgccggcctgctgcatcgcctgtacgccgggaatcgccagataatcagcattataa
cgttgattatccatgatccagcggatcatccccattgccagcgccgaatcactgccgggcatgaccggttgccagcgaccgcgaggatcggcga
gcaccgttgataaggggagggcgggggcgaccacgacgtattgaaaattctcacgcagtcgggcgctcgccaactgacgtgcctggcgtttaaa
cggattgccggactgtgccggggaggtgcccataaagagcgcaaactccacgttttcccagtcgggtttgacatgcgggtttttatccagatcgcc
catcaatgccccggagccggcccggtaagccagtccacagtaggcgccatgcgcgccgaaattcttgctgccgaagctatttagcgcaaaacga
cgcagaaacgcatcgcggccttcgtcgctggtattcgtgaccagtaactgattggttttgggcccgaaactggggtgctttgcgtcaattggcgta
tccggcgcatgaatagcgcgcagtccgtccacatgaccttcgccaaacagatcgccgccttccacgacttcttcaataagttgctcaaagctgatg
cgctgccatttcccttcgccgcgtttacccacgcgtttcatcggttcaagcagtcgtagcggactgtacaggctttccagcagcgtggcgccgcgcg
cgcaggcggttgagcgggcgtcaagaccgctttctcccgccagttgctccatggcttcgctaaaagggacggacgagtcaatcgggtgttcctgc
gacaaggggtgatagggattgccggcgatgcgtatcactttgccatcggcattaacccgggcgcggataccgcactgtgtccaacagccgaagc
attgcgtcatggcgatggtttgttgtggattttgctgccagtgtgtttgcgcctgcgcctccggaattaacgcattgccaaagatgcggtcgcgcgtt
accttgccggacgtcccgtttaacaggccatcaattgcgcgtttcgccacatcacggtagctcagaccaaaagtgaccatcccaccgacggcgag
accgacttttagccactgacgacgggttaaattagccatgttgtaatctcctggtgagtccgttcagcgtttcacgaataataatcagtagcgctat
ccacaggccgaaggtgccgagaatagccagccagccatccgttccgcctggtaacgagtaagggttaaattgcgcgttgaacttggggacggtt
tgtacctgaatcaacaatgtccagcgcatcagccaacatagcgccagcgcgctgagaaccagcaggacgcgtcttagctgtgataacggatggc
gtagcgccaggctacagaacagcagtgtgcatacccacagcgctacccagccgacagcgtaatatttggctgacagggcgacggtaatccact
gacggattgccgtgccggaaagcgtatcgccgctaacccacatggccacaaccagccccagcgccgccagcgtccagatttgtccccacaatat
ttttggcagccttaccgagtcgcgtcgggcggcgacaatcatcagcgcgaagaacgcctgtaaggcgctaagaaacatcgccacggggaaggc
gtagctaaaccagattgggcgcgccagcacaacggagacttcgcggccggtataaatcaacaggcccaccgcgcaaagcgcgctggctaacg
ccaaccatttagtgacgttgtaacttttattgaataatcgtttaatctgctgcgccaggaaccacagagcgagaaatccggtaaacagcggcagg
aataacgctccccagggcatccacgaccagggcgtcggccaggcatagaaatgccagacgcgggcggtctggtgcagatccgccgtcagcgcc
agcggtgcggtaatcgcacaggtaatggcaatcagtaatgcccgattttcttctgttgcggcgtctttttccgccagtgaagataacaggcaaac
agtgcggcgcaggcggcaatgccaataaaaaagaaatattgtaccgcccacggcagccagctaatgtcctgcgggtgagccagcacttcttca
atgatgagtgaatgcgtcattcagacctcctgccaaagcgcgggctgcgcacggcccattaatggggtgacaaaggcgtcgtccagacccaggt

FIGURE 36B-1 agaaaacatggggcgacgtgccgttttccggctttaataccttgatagcgtcgcgatgctgatgaagcatggtggcgatgcggctatggggatct
ttgatatcgccaataatacgcgcgccgccgacgcaggactctacgcaagcgggtaacagtccggcttccagacgatggacgcaaaacgtgcatt
tatcggcagtttgcgtttcatgattgataaatcgggcgtcgtaaggacacgcctggacacaataggcgcagccgacgcagcgtttgttatccacc
accacaatgccatcttcccgctgaaaggtggcttgtaccgggcagaccggcacacagggggggttatcgcaatggttgcacagacgcggcaac
agcacattcgtgacttcctgactaccttcacgctggacctggtattggttcaccgtcgtacgaaacgcgccttgcggcgtttggttttcaatagtgc
aacttacggtacaggactgacagccgatacaacgccgcagatcgataagcatggcgtaacggtgtcggggagagccttcatgccgctccggcg
aaaaaggaaatttcgcttcagccagcggaaccagcgaggcgccagcggtcaggacgccaagctgctggagaaattgccgtttactgctgtccat
attgactcccgtccacattgccaacaatgaaacatttgtcacgatgttggttcatgtgtaatgaataaaaaatgtcgatgatttacagtgtaaaaa
tcgaggcggggtgcgctctattgtggttaaccacatacccggcttgttgttgatctaaaacaacataattgacagggatattggggtgagaggta
aaaccgtaaggcgcctggcggtgttggcggcagtagggctactttgtcatggcgcgtgggcagggacgtggaatatcggtattttggccatgcgc
ggcgaggcgtctacgcgtagccactggcaaccgttggcaaagacattaagccaacagcttccaggcgaaacctttcacatccagccgctggatc
tgcatcaaatgcaggaggccgttaaccagggaaccgtgcagtttgtgataaccaacccggcgcaatttgtccaactgaacagccatgcgccgct
gcgctggttagcttccctgcgctccacgcgcgatgggaaagcggtgagtaatgttattggcagcgtgattttgacccggcgcgatagcggcatca
ccacggcgcatgatctcatcggtaagaccgtcggcgcgattgatgctcaggcgtttggcggctatttattaggctataaagcgctcagcgacgcg
ggcttacgcccggagcgcgattttcatctccgttttaccggatttcctggcgatgccttagtctatatgctgcgcgaaaaagcggtgcaggcggca
attgtgccagtgtgcctgttagaaaatatggatcaggaaggattgattaataaaaaggactttatcgcgctgctttcccgaccgacgcccctgcct
tgcttaaccagtacgccgttatatcctgactggtcgttcgcggcgctacctgcggtaagcgatgcgctggcggatcgcgtaacgcgagcgctattc
aacgcgcccgccgccgcgtcatttcactggggcgcgcctgcgtccaccagtcaggtggaagccttgctgcgtgatgttcgtcagcaccctcagca
gcgtcgactgtggctggatgtcaaaagttggttaatccagcaccagctaatggtcggcggcgtgattctggcgttcttgttgctcacgctcaattat
atttgggtcatgctgctggtgcgtcgacgtggaaagcaactggaacgtaatagcgtagttcttcatcagcatgagcgggcgctggaaaccgcccg
gcaaatgagcgtgttgggtgaaatgacctccgggtttgcccatgagcttaatcagccgctttccgcgattcgacattatgcccaggggtgcctgat
tcgactgcgcgctgcagatgaacagcatcccttgctgccggcgctggagcagattgaccagcaggcgcaacgcggtgcggatactctgcgtaac
ctgcgtcactgggtcagccaggcgcagggcaacccggtgctaaccgaagcgtggaaggccatagccattcgcgaggcgattgatcatgtctggc
aattgttgcgtatggcgcaacagtttccgacagtgactctgcataccgaggttagcgctgcgctgcgcgtaacgctgccgtcagtgctgctggaac
aggtgctggcgaatatcattcttaatgcggctcaggcgggcgccacccatttatggatcgttgctgaacgcactgaaaacggcatcagtattgttt
tacaggataacgccgggggaatcgatgaggcgctattacgtcaggcgtttcagccgtttatgaccacccgtaaagaggggatgggcttagggct
ggcgatttgccagcggctggtgcggtatgggcggggcgatatcagcatcaggaaccagaccgcgccggacggtctgtcgggaacggtggttac
gatacatttcttacatgaaaatgggggcagggatggcgacaattcatctactggatgatgatacggcggtcactaacgcgtgcgcgtttttactgg
aaagtctgggatatgacgtaaaatgctggacgcagggggcggatttttggcgcaggccagtctgtatcaggccggggtcgtattactggatatg
cgaatgccggtactggatgggcagggcgttcatgatgcgttgcgccagtgcggaagtaccctggcggttgtttttcttaccggcatggcgatgta
ccgatggccgtggagcagatgaaacgcggcgccgtcgattttctgcaaaaaccggtatcggtaaaaccgctacaggcggcgctggagcgtgcg
ctgacggtttcatcggcagcggtggcgcgtcgtgagattatactgtgttaccagcagttgacgccgaaagagcgtgagctggccagcctggtggc
aaaaggatttatgaaccgtgaaattgcggaagcgatgaatatcgcggtgcgtaccgtagaggtgcaccgcgccagagtcatggaaaaaatgca
ggccggtagcctggcggaactgattaggcgtttcgaaaaaatggcctcgccagagaccagaatacgaacaacgtatgagccatgaataagagc
tcgaattctcatgtttgacagcttatcactgatcagtgaattaatggcgatgacgcatcctcacgataatatccgggtaggcgcaatcactttcgtc
tctactccgttacaaagcgaggctgggtatttcccggcctttctgttatccgaaatccactgaaagcacagcggctggctgaggagataaataat
aaacgaggggctgtatgcacaaagcatcttctgttgagttaagaacgagtatcgagatggcacatagccttgctcaaattggaatcaggtttgtg
ccaataccagtagaaacagacgaagaagctagaggtgaatcacgacaaagcgtatcaaaaacgtatggagtagggctctaaactctgtataa
aaagtttccagctagctgataacgggaaagaaacagagaagggcacaaatattgtgtactttaatgtgccctttaatttattgattggtggttgaa
ttgtccgtaactttttgatttaagtgcaaatttctaataaattagaacactttcttaaattgtcatttggcatattacgaacaattccgcgtaaaaac
gttctgttacgctaaacccttatccagcaggctttcaaggatgtaaaccataacactctgcgaactagtgttacattgcgtgtagctttgagtgggc
aactttgtgtacacttttgtgtacccaaaaacaaaaatgtgtacccattcaatgatcaccgacacaaagctcaggaaggcgctcggcaagaaaa
gagatgatatcgagattatttctgattcgcacgggcccatggctaattcccatgtcagccgttaagtgttcctgtgtcactgaaaattgctttgaga
ggctctaagggcttctcagtgcgttacatccctggcttgttgtccacaaccgttaaaccttaaaagctttaaaagccttatatattcttttttttcttat FIGURE 36B-2 (contd.)

aaaacttaaaaccttagaggctatttaagttgctgatttatattaattttattgttcaaacatgagagcttagtacgtgaaacatgagagcttagta
cgttagccatgagagcttagtacgttagccatgagggtttagttcgttaaacatgagagcttagtacgttaaacatgagagcttagtacgtgaaa
catgagagcttagtacgtactatcaacaggttgaactgctgatcttcagatcctctacgccggacgcatcgtggccggatcttgcggccgcaaaa
attaaaaatgaagttttggaggcctcatttggtgacgaaataactaagcacttgtctcctgtttactcccctgagcttgaggggtcaacatgaagg
tcattgatagcaggataataatacagtaaaacgctaaaccaataatccaaatccagccatcccaaattggtagtgaatgattataaataacagt
aaacagtaatgggccaataacaccggttgcattggtaaggctcaccaataatccctgtaaagcaccttgctcatgactctttgtttggatagacat
cactccctgtaatgcaggtaaagcgatcccaccaccagccaataaaattaaaacagggaaatctaaccaaccttcagatataaacgctaaaaa
ggcaaatgcactactatctgcaataaattcgagcagtactgccgtttttcgccccatttagtggctattcttcctgccacaaaggcttggaatact
gagtgtaaaagaccaagacccgctaatgaaaagccaaccatcatgctattccatccaaaacgattttcggtaaatagcacccacaccgttgcgg
gaatttggcctatcaattgcgctgaaaaataaataatcaacaaaatgggcatcgttttaaataaagtgatgtacaccgaatttgattgcgtctcaa
cccctacttcggtatctgtattatcacgtgtatttttggtttcacggaaccaaaacataaccacaaggaaagtgacaatatttagcaacgcagcga
taaaaaagggactatgcggtgaaatctctcctgcaaaaccaccaataataggccccgctattaaaccaagcccaaaacttgcccctaaccaacc
gaaccacttcacgcgttgagaagctgaggtggtatcggcaatgaccgatgccgcgacagccccagtagctcctgtgatccctgaaagcaaacgg
cctaaatacagcatccaaagcgcacttgaaaaagccagcaataagtaatccagcgatgcgcctattaatgacaacaacagcactgggcgccga
ccaaatcggtcagacatttttccaagccaaggagcaaagataacctgcattaacgcataaagtgcaagcaatacgccaaagtggttagcgatat
cttccgaagcaataaattcacgtaataacgttggcaagactggcatgataaggccaatccccatggcatcgagtaacgtaattaccaatgcgatc
tttgtcgaactattcatttcacttttctctatcactgatagggagtgggaaaataactctatcaatgatagggtgtcaaatcgatggcccccgatgg
tagtgtggggtctccccatgcgagagtagggaactgccaggcatcaaataaaacgaaaggctcagtcgaaagactgggcctttcgttttatctgt
tgtttgtcggtgaacgctctcctgagtaggacaaatccgccgggagcggatttgaacgttgcgaagcaacggcccggagggtggcgggcagga
cgcccgccataaactgccaggcatcaaattaagcagaaggccatcctgacggatggcctttttgcgtggccagtgccaagcttgcatgc (SEQ ID NO: 46)

FIGURE 36B-3 (contd.)

GACCTATAAGGAAAGGCCAAACAAGAACACGGTTGCAAAAACCGTGCCCTTAAATATTGAATTTCTATTC

AGAACACTTTCTTAAATtgtcatttggcatattacgaacaattccgcgtaaaaacgttctgttacgctaaacccttatccagcaggctttca
aggatgtaaaccataacactctgcgaactagtgttacattgcgtgtagctttgagtgggcaactttgtgtacacttttgtgtacccaaaaacaaaa
atgtgtacccattcaatgatcaccgacacaaagctcaggaaggcgctcggcaagaaaagagatgatatcgagattatttctgattcgcacgggc
ccatggctaattcccatgtcagccgttaagtgttcctgtgtcactgaaaattgctttgagaggctctaagggcttctcagtgcgttacatccctggct
tgttgtccacaaccgttaaaccttaaaagctttaaaagccttatatattcttttttttcttataaaacttaaaaccttagaggctatttaagttgctga
tttatattaattttattgttcaaacatgagagcttagtacgtgaaacatgagagcttagtacgttagccatgagagcttagtacgttagccatgagg
gtttagttcgttaaacatgagagcttagtacgttaaacatgagagcttagtacgtgaaacatgagagcttagtacgtactatcaacaggttgaact
gctgatcttcagatcctctacgccggacgcatcgtggccggatcttgcggccgcaaaaattaaaaatgaagttttggaggcctcatttggtgacga
aataactaagcacttgtctcctgtttactcccctgagcttgaggggtcaacatgaaggtcattgatagcaggataataatacagtaaaacgctaa
accaataatccaaatccagccatcccaaattggtagtgaatgattataaataacagtaaacagtaatgggccaataacaccggttgcattggta
aggctcaccaataatccctgtaaagcaccttgctcatgactctttgtttggatagacatcactccctgtaatgcaggtaaagcgatcccaccacca
gccaataaaattaaaacagggaaatctaaccaaccttcagatataaacgctaaaaaggcaaatgcactactatctgcaataaattcgagcagt
actgccgtttttttcgccccatttagtggctattcttcctgccacaaaggcttggaatactgagtgtaaaagaccaagacccgctaatgaaaagcca
accatcatgctattccatccaaaacgattttcggtaaatagcacccacaccgttgcgggaatttggcctatcaattgcgctgaaaaataaataatc
aacaaaatgggcatcgttttaaataaagtgatgtacaccgaatttgattgcgtctcaacccctacttcggtatctgtattatcacgtgtatttttggt
ttcacggaaccaaaacataaccacaaggaaagtgacaatatttagcaacgcagcgataaaaaagggactatgcggtgaaatctctcctgcaaa
accaccaataataggccccgctattaaaccaagcccaaaacttgcccctaaccaaccgaaccacttcacgcgttgagaagctgaggtggtatcg
gcaatgaccgatgccgcgacagccccagtagctcctgtgatccctgaaagcaaacggcctaaatacagcatccaaagcgcacttgaaaaagcc
agcaataagtaatccagcgatgcgcctattaatgacaacaacagcactgggcgccgaccaaatcggtcagacatttttccaagccaaggagca
aagataacctgcattaacgcataaagtgcaagcaatacgccaaagtggttagcgatatcttccgaagcaataaattcacgtaataacgttggca
agactggcatgataaggccaatccccatggcatcgagtaacgtaattaccaatgcgatctttgtcgaactattcatttcacttttctctatcactgat
agggagtgggaaaataactctatcaatgatagggtgtcaaatcgatggcccccgatggtagtgtggggtctccccatgcgagagtagggaactg
ccaggcatcaaataaaacgaaaggctcagtcgaaagactgggcctttcgttttatctgttgtttgtcggtgaacgctctcctgagtaggacaaatc
cgccgggagcggatttgaacgttgcgaagcaacggcccggagggtggcgggcaggacgcccgccataaactgccaggcatcaaattaagcag
aaggccatcctgacggatggcctttttgcgtggccagtgccaagcttgcatgcctgcaggtcgactctagaggatccgttatatacgctcgatttt
gccggcagcccctgacgtactgccgcgccagaaacccagtcgagccaggtgttggtaatggttcttgtcggatcggcaaagcccagatcgttaa
gatttatgcctgccctgatttgtggatcatacggcataggcacgccatccagagagtgctgcgttgcgcccatctcgcggtggccatatccgtgttc
gatggcgatgacgcctggcatcacgccatttaacaaactgatttgcgccacgacctgaccgcccggcgtaatgatccgtacccgatcgccatgtt
gcagtccataacgctcgccgtcttgcggattcagcgccaccaggtttgctggcttcacatggtgtaagcgcgggatgacggctgttgagctggac
atggtatttgatttaaatgaaatcagtttcagcggccattgcccaatgggaaactggtcgtcaatcgcacgaccatctgacaaacgcgccggata
ccagaccgggcaaccgctgaagcgctccccggtgatggcgtgacggtgggcggcgacatctgcattccagatctgtaagggtttttccacgcgt
tacctaaccgttgctccgtatagccgctatcctcgggcgcaaaccggccgccacgcgagtagataaacgccacgcgaccgacctcatcagcttta
agcgtgtgctgaattgctggcagaatgcggctgacgccggtaagcgaaatatcttcctgatttgccagcgcgaccggcgtcttgcccataaaggc
gatattagcggctacgcgcagatagaagtcttccgcccggttcagtggaaaagtattgccctgcggatcggttatcgcccggtcgccgaagccgg
gcagatggagccgttttgctaccgcaatacaaaatgcttccattgagacaggttgcccgtccgccgtgcggtgagtggcgggggcgacaaccgg
ccagcgggcggtagtggctttactggctacgccgccccagggcgccgtaaagccccagctctcaaaattgtgcgtatccggcacaatgtaatccg
ccagcgccgtcgtttcattcataaaggcgtcaatcgcgataaagagcggcagtcggcgagggtcttttagtttttcttccgccacggcgcgtagac
cgggaacaccgtaaaacgggttgctcatattggaaatccaggctttaagcggataaggatagccttcgagcgcggaggtcaacagttcggtaag
ctggcctgccacaaagggataccacggcgctttggctggataaggggattgcccaccggcaattttgtcgcggtattcttccgatgcttcataagc
ggttttgctacgggcaatacttaacccggacggtttcacttttccggcaaaactgttcatgttgtagcgggggccgtcgctaacgccgttgaatttg
ccgccgccgacaaagacgccgccggacaagctgaggttgccgatcagcgcgttaagcatcatgaccgaccaggcgttataaaacccattgccg
gccatcatgccgccgtgactgatgaccgcagctttacgtccgtgactggtaaaggtttccgccagcgcgataatttgcgcttccggcacgccgcac
tgttcgctgtattgcgccaacgagagcttttctgccgcctctttcaggcgttgcaacccgctcttcaccgtgacccgttggccgtcggcgagcgtaa
cgtactgcgtcacgaaaagccgtgcctgtcggcaagtggacgcatcgaccaactcgccgtcggtattcagtacgacaggggtctcttcgccatcg
ggcgtaagatggcgcagcgtcaggtgttgtccggcaagcgtcggcagctcatccgcaatgaccaggtgcgtggcgttggtccaactttgctcgcc
ggcctgctgcatcgcctgtacgccgggaatcgccagataatcagcattataacgttgattatccatgatccagcggatcatccccattgccagcgc
cgaatcactgccgggcatgaccggttgccagcgaccgcgaggatcggcgagcaccgttgataaggggagggcgggggcgaccacgacgtatt

FIGURE 37A-1 gaaaattctcacgcagtcgggcgctcgccaactgacgtgcctggcgtttaaacggattgccggactgtgccggggaggtgcccataaagagcgc
aaactccacgttttcccagtcgggtttgacatgcgggtttttatccagatcgcccatcaatgccccggagccggcccggtaagccagtccacagta
ggcgccatgcgcgccgaaattcttgctgccgaagctatttagcgcaaaacgacgcagaaacgcatcgcggccttcgtcgctggtattcgtgacca
gtaactgattggttttgggcccgaaactggggtgctttgcgtcaattggcgtatccggcgcatgaatagcgcgcagtccgtccacatgaccttcgc
caaacagatcgccgccttccacgacttcttcaataagttgctcaaagctgatgcgctgccatttcccttcgccgcgtttacccacgcgtttcatcggt
tcaagcagtcgtagcggactgtacaggctttccagcagcgtggcgccgcgcgcgcaggcggttgagcgggcgtcaagaccgctttctcccgcca
gttgctccatggcttcgctaaaagggacggacgagtcaatcgggtgttcctgcgacaaggggtgatagggattgccggcgatgcgtatcactttg
ccatcggcattaacccgggcgcggataccgcactgtgtccaacagccgaagcattgcgtcatggcgatggtttgttgtggattttgctgccagtgt
gtttgcgcctgcgcctccggaattaacgcattgccaaagatgcggtcgcgcgttaccttgccggacgtcccgtttaacaggccatcaattgcgcgt
ttcgccacatcacggtagctcagaccaaaagtgaccatcccaccgacggcgagaccgacttttagccactgacgacgggttaaattagccatgtt
gtaatctcctggtgagtccgttcagcgtttcacgaataataatcagtagcgctatccacaggccgaaggtgccgagaatagccagccagccatcc
gttccgcctggtaacgagtaagggttaaattgcgcgttgaacttggggacggtttgtacctgaatcaacaatgtccagcgcatcagccaacatag
cgccagcgcgctgagaaccagcaggacgcgtcttagctgtgataacggatggcgtagcgccaggctacagaacagcagtgtgcatacccacag
cgctacccagccgacagcgtaatatttggctgacagggcgacggtaatccactgacggattgccgtgccggaaagcgtatcgccgctaacccac
atggccacaaccagccccagcgccgccagcgtccagatttgtccccacaatatttttggcagccttaccgagtcgcgtcgggcggcgacaatcat
cagcgcgaagaacgcctgtaaggcgctaagaaacatcgccacggggaaggcgtagctaaaccagattgggcgcgccagcacaacggagactt
cgcggccggtataaatcaacaggcccaccgcgcaaagcgcgctggctaacgccaaccatttagtgacgttgtaacttttattgaataatcgttta
atctgctgcgccaggaaccacagagcgagaaatccggtaaacagcggcaggaataacgctccccagggcatccacgaccagggcgtcggcca
ggcatagaaatgccagacgcgggcggtctggtgcagatccgccgtcagcgccagcggtgcggtaatcgcacaggtaatggcaatcagtaatgc
ccgattttcttctgttgcggcgtctttttccgccagtgaagataacaggcaaacagtgcggcgcaggcggcaatgccaataaaaaagaaatatt
gtaccgcccacggcagccagctaatgtcctgcgggtgagccagcacttcttcaatgatgagtgaatgcgtcattcagacctcctgccaaagcgcg
ggctgcgcacggcccattaatggggtgacaaaggcgtcgtccagacccaggtagaaaacatggggcgacgtgccgttttccggctttaatacctt
gatagcgtcgcgatgctgatgaagcatggtggcgatgcggctatggggatctttgatatcgccaataatacgcgcgccgccgacgcaggactct
acgcaagcgggtaacagtccggcttccagacgatggacgcaaaacgtgcatttatcggcagtttgcgtttcatgattgataaatcgggcgtcgta
aggacacgcctggacacaataggcgcagccgacgcagcgtttgttatccaccaccacaatgccatcttcccgctgaaaggtggcttgtaccggg
cagaccggcacacaggggggttatcgcaatggttgcacagacgcggcaacagcacattcgtgacttcctgactaccttcacgctggacctggt
attggttcaccgtcgtacgaaacgcgccttgcggcgtttggttttcaatagtgcaacttacggtacaggactgacagccgatacaacgccgcaga
tcgataagcatggcgtaacggtgtcggggagagccttcatgccgctccggcgaaaaaggaaatttcgcttcagccagcggaaccagcgaggcg
ccagcggtcaggacgccaagctgctggagaaattgccgtttactgctgtccatattgactcccgtccacattgccaacaatgaaacatttgtcacg
atgttggttcatgtgtaatgaataaaaaatgtcgatgatttacagtgtaaaaatcgaggcggggtgcgctctattgtggttaaccacatacccggc
ttgttgttgatctaaaacaacataattgacagggatattggggtgagaggtaaaaccgtaaggcgcctggcggtgttggcggcagtagggctact
ttgtcatggcgcgtgggcagggacgtggaatatcggtattttggccatgcgcggcgaggcgtctacgcgtagccactggcaaccgttggcaaag
acattaagccaacagcttccaggcgaaacctttcacatccagccgctggatctgcatcaaatgcaggaggccgttaaccagggaaccgtgcagt
ttgtgataaccaacccggcgcaatttgtccaactgaacagccatgcgccgctgcgctggttagcttccctgcgctccacgcgcgatgggaaagcg
gtgagtaatgttattggcagcgtgattttgacccggcgcgatagcggcatcaccacggcgcatgatctcatcggtaagaccgtcggcgcgattga
tgctcaggcgtttggcggctatttattaggctataaagcgctcagcgacgcgggcttacgcccggagcgcgattttcatctccgttttaccggattt
cctggcgatgccttagtctatatgctgcgcgaaaaagcggtgcaggcggcaattgtgccagtgtgcctgttagaaaatatggatcaggaaggatt
gattaataaaaaggactttatcgcgctgctttcccgaccgacgcccctgccttgcttaaccagtacgccgttatatcctgactggtcgttcgcggcg
ctacctgcggtaagcgatgcgctggcggatcgcgtaacgcgagcgctattcaacgcgcccgccgccgcgtcatttcactggggcgcgcctgcgtc
caccagtcaggtggaagccttgctgcgtgatgttcgtcagcaccctcagcagcgtcgactgtggctggatgtcaaaagttggttaatccagcacc
agctaatggtcggcggcgtgattctggcgttcttgttgctcacgctcaattatatttgggtcatgctgctggtgcgtcgacgtggaaagcaactgga
acgtaatagcgtagttcttcatcagcatgagcgggcgctggaaaccgcccggcaaatgagcgtgttgggtgaaatgacctccgggtttgcccatg
agcttaatcagccgctttccgcgattcgacattatgcccaggggtgcctgattcgactgcgcgctgcagatgaacagcatcccttgctgccggcgc
tggagcagattgaccagcaggcgcaacgcggtgcggatactctgcgtaacctgcgtcactgggtcagccaggcgcagggcaacccggtgctaa
ccgaagcgtggaaggccatagccattcgcgaggcgattgatcatgtctggcaattgttgcgtatggcgcaacagtttccgacagtgactctgcat
accgaggttagcgctgcgctgcgcgtaacgctgccgtcagtgctgctggaacaggtgctggcgaatatcattcttaatgcggctcaggcgggcgc
cacccatttatggatcgttgctgaacgcactgaaaacggcatcagtattgttttacaggataacgccgggggaatcgatgaggcgctattacgtc
aggcgtttcagccgtttatgaccacccgtaaagaggggatgggcttagggctggcgatttgccagcggctggtgcggtatgggcggggcgatat FIGURE 37A-2 (contd.)

cagcatcaggaaccagaccgcgccggacggtctgtcgggaacggtggttacgatacatttcttacatgaaaatgggggcagggatggcgacaa
ttcatctactggatgatgatacggcggtcactaacgcgtgcgcgtttttactggaaagtctgggatatgacgtaaaatgctggacgcagggggcg
gatttttggcgcaggccagtctgtatcaggccggggtcgtattactggatatgcgaatgccggtactggatgggcagggcgttcatgatgcgttg
cgccagtgcggaagtaccctggcggttgtttttcttaccgggcatggcgatgtaccgatggccgtggagcagatgaaacgcggcgccgtcgattt
tctgcaaaaaccggtatcggtaaaaccgctacaggcggcgctggagcgtgcgctgacggtttcatcggcagcggtggcgcgtcgtgagattata
ctgtgttaccagcagttgacgccgaaagagcgtgagctggccagcctggtggcaaaaggatttatgaaccgtgaaattgcggaagcgatgaata
tcgcggtgcgtaccgtagaggtgcaccgcgccagagtcatggaaaaaatgcaggccggtagcctggcggaactgattaggcgtttcgaaaaaa
tggcctcgccagagaccagaatacgaacaacgtatgagccatgaataagagctcgaattctcatgtttgacagcttatcactgatcagtgaatta
atggcgatgacgcatcctcacgataatatccgggtaggcgcaatcactttcgtctctactccgttacaaagcgaggctgggtatttcccggcctttc
tgttatccgaaatccactgaaagcacagcggctggctgaggagataaataataaacgaggggctgtatgcacaaagcatcttctgttgagttaa
gaacgagtatcgagatggcacatagccttgctcaaattggaatcaggtttgtgccaataccagtagaaacagacgaagaagctagaggtgaat
cacgacaaagcgtatcaaaaacgtatggagtagggctctaaactctgtataaaaagtttccagctagctgataacgggaaagaaacagagaag
ggcacaaatattgtgtactttaatgtgccctttaatttattgattggtggttgaattgtccgtaactttttgatttaagtgcaaatttctaataaattag
aacactttcttaaatGGTTTCACTGAAACGTGTTCATAGACTCCTGCCGCTACGTACGGGTCAGCATCGGCCCAAGC
CTGAGCTGCTTCCAGCGACTCAAATTCAGCAATAACGGTTGAGCCAGTAAATCCCGCAGCC (SEQ ID NO: 47)

FIGURE 37A-3 (contd.)

GACCTATAAGGAAAGGCCAAACAAGAACACGGTTGCAAAAACCGTGCCCTTAAATATTGAATTTCTATTC
AGAACACTTTCTTAAATtgtcatttggcatattacgaacaattccgcgtaaaaacgttctgttacgctaaacccttatccagcaggctttca
aggatgtaaaccataacactctgcgaactagtgttacattgcgtgtagctttgagtgggcaactttgtgtacacttttgtgtacccaaaaacaaaa
atgtgtacccattcaatgatcaccgacacaaagctcaggaaggcgctcggcaagaaaagagatgatatcgagattatttctgattcgcacgggc
ccatggctaattcccatgtcagccgttaagtgttcctgtgtcactgaaaattgctttgagaggctctaagggcttctcagtgcgttacatccctggct
tgttgtccacaaccgttaaaccttaaaagctttaaaagccttatatattcttttttttcttataaaacttaaaaccttagaggctatttaagttgctga
tttatattaattttattgttcaaacatgagagcttagtacgtgaaacatgagagcttagtacgttagccatgagagcttagtacgttagccatgagg
gtttagttcgttaaacatgagagcttagtacgttaaacatgagagcttagtacgtgaaacatgagagcttagtacgtactatcaacaggttgaact
gctgatcttcagatcctctacgccggacgcatcgtggccggatcttgcggccgcaaaaattaaaaatgaagttttggaggcctcatttggtgacga
aataactaagcacttgtctcctgtttactcccctgagcttgaggggtcaacatgaaggtcattgatagcaggataataatacagtaaaacgctaa
accaataatccaaatccagccatcccaaattggtagtgaatgattataaataacagtaaacagtaatgggccaataacaccggttgcattggta
aggctcaccaataatccctgtaaagcaccttgctcatgactctttgtttggatagacatcactccctgtaatgcaggtaaagcgatcccaccacca
gccaataaaattaaaacagggaaatctaaccaaccttcagatataaacgctaaaaaggcaaatgcactactatctgcaataaattcgagcagt
actgccgtttttttcgccccatttagtggctattcttcctgccacaaaggcttggaatactgagtgtaaaagaccaagacccgctaatgaaaagcca
accatcatgctattccatccaaaacgattttcggtaaatagcacccacaccgttgcgggaatttggcctatcaattgcgctgaaaaataaataatc
aacaaaatgggcatcgttttaaataaagtgatgtacaccgaatttgattgcgtctcaacccctacttcggtatctgtattatcacgtgtatttttggt
ttcacggaaccaaaacataaccacaaggaaagtgacaatatttagcaacgcagcgataaaaaagggactatgcggtgaaatctctcctgcaaa
accaccaataataggccccgctattaaaccaagcccaaaacttgcccctaaccaaccgaaccacttcacgcgttgagaagctgaggtggtatcg
gcaatgaccgatgccgcgacagccccagtagctcctgtgatccctgaaagcaaacggcctaaatacagcatccaaagcgcacttgaaaaagcc
agcaataagtaatccagcgatgcgcctattaatgacaacaacagcactgggcgccgaccaaatcggtcagacatttttccaagccaaggagca
aagataacctgcattaacgcataaagtgcaagcaatacgccaaagtggttagcgatatcttccgaagcaataaattcacgtaataacgttggca
agactggcatgataaggccaatccccatggcatcgagtaacgtaattaccaatgcgatctttgtcgaactattcatttcacttttctctatcactgat
agggagtgggaaaataactctatcaatgatagggtgtcaaatcgatggcccccgatggtagtgtggggtctccccatgcgagagtagggaactg
ccaggcatcaaataaaacgaaaggctcagtcgaaagactgggcctttcgttttatctgttgtttgtcggtgaacgctctcctgagtaggacaaatc
cgccgggagcggatttgaacgttgcgaagcaacggcccggagggtggcgggcaggacgcccgccataaactgccaggcatcaaattaagcag
aaggccatcctgacggatggcctttttgcgtggccagtgccaagcttgcatgcctgcaggtcgactctagaggatcc
attccggggatccgtcgacctgcagttcgaagttcctattctctagaaagtataggaacttcagagcgcttttgaagctcacgctgccgcaagcac
tcagggcgcaagggctgctaaaggaagcggaacacgtagaaagccagtccgcagaaacggtgctgaccccggatgaatgtcagctactgggc
tatctggacaagggaaaacgcaagcgcaaagagaaagcaggtagcttgcagtgggcttacatggcgatagctagactgggcggttttatggac
agcaagcgaaccggaattgccagctggggcgccctctggtaaggttgggaagccctgcaaagtaaactggatggctttcttgccgccaaggatc
tgatggcgcaggggatcaagatctgatcaagagacaggatgaggatcgtttcgcatgattgaacaagatggattgcacgcaggttctccggccg
cttgggtggagaggctattcggctatgactgggcacaacagacaatcggctgctctgatgccgccgtgttccggctgtcagcgcaggggcgcccg
gttctttttgtcaagaccgacctgtccggtgccctgaatgaactgcaggacgaggcagcgcggctatcgtggctggccacgacgggcgttccttgc
gcagctgtgctcgacgttgtcactgaagcgggaagggactggctgctattgggcgaagtgccggggcaggatctcctgtcatctcaccttgctcct
gccgagaaagtatccatcatggctgatgcaatgcggcggctgcatacgcttgatccggctacctgcccattcgaccaccaagcgaaacatcgca
tcgagcgagcacgtactcggatggaagccggtcttgtcgatcaggatgatctggacgaagagcatcaggggctcgcgccagccgaactgttcgc
caggctcaaggcgcgcatgcccgacggcgaggatctcgtcgtgacccatggcgatgcctgcttgccgaatatcatggtggaaaatggccgctttt
ctggattcatcgactgtggccggctgggtgtggcggaccgctatcaggacatagcgttggctacccgtgatattgctgaagagcttggcggcgaa
tgggctgaccgcttcctcgtgctttacggtatcgccgctcccgattcgcagcgcatcgccttctatcgccttcttgacgagttcttctaataaggga
tcttgaagttcctattccgaagttcctattctctagaaagtataggaacttcgaagcagctccagcctacagagctcgaattctcatgtttgacagc
ttatcactgatcagtgaattaatggcgatgacgcatcctcacgataatatccgggtaggcgcaatcactttcgtctctactccgttacaaagcgag
gctgggtatttcccggcctttctgttatccgaaatccactgaaagcacagcggctggctgaggagataaataataaacgaggggctgtatgcaca
aagcatcttctgttgagttaagaacgagtatcgagatggcacatagccttgctcaaattggaatcaggtttgtgccaataccagtagaaacagac
gaagaagctagaggtgaatcacgacaaagcgtatcaaaaacgtatggagtagggctctaaactctgtataaaaagtttccagctagctgataa
cgggaaagaaacagagaagggcacaaatattgtgtactttaatgtgccctttaatttattgattggtggttgaattgtccgtaactttttgatttaa
gtgcaaatttctaataaattagaacactttcttaaatGGTTTCACTGAAACGTGTTCATAGACTCCTGCCGCTACGTACGGGT
CAGCATCGGCCCAAGCCTGAGCTGCTTCCAGCGACTCAAATTCAGCAATAACGGTTGAGCCAGTAAATCCCGC
AGCC (SEQ ID NO: 48)

FIGURE 37B

SEQUENCE LISTING

<160> NUMBER OF SEQ ID NOS: 73

<210> SEQ ID NO 1
<211> LENGTH: 21
<212> TYPE: DNA
<213> ORGANISM: Artificial Sequence
<220> FEATURE:
<223> OTHER INFORMATION: Primer

<400> SEQUENCE: 1
gagctcgaat tctcatgttt g 21

<210> SEQ ID NO 2
<211> LENGTH: 21
<212> TYPE: DNA
<213> ORGANISM: Artificial Sequence
<220> FEATURE:
<223> OTHER INFORMATION: Primer

<400> SEQUENCE: 2
ggatcctcta gagtcgacct g 21

<210> SEQ ID NO 3
<211> LENGTH: 52
<212> TYPE: DNA
<213> ORGANISM: Artificial Sequence
<220> FEATURE:
<223> OTHER INFORMATION: Primer

<400> SEQUENCE: 3
gcatgcctgc aggtcgactc tagaggatcc gttatatacg ctcgattttt gc 52

<210> SEQ ID NO 4
<211> LENGTH: 51
<212> TYPE: DNA
<213> ORGANISM: Artificial Sequence
<220> FEATURE:
<223> OTHER INFORMATION: Primer

<400> SEQUENCE: 4
ataagctgtc aaacatgaga attcgagctc ttattcatgg ctcatacgtt g 51

<210> SEQ ID NO 5
<211> LENGTH: 20
<212> TYPE: DNA
<213> ORGANISM: Artificial Sequence
<220> FEATURE:
<223> OTHER INFORMATION: Primer

<400> SEQUENCE: 5
cgttatggac tgcaacatgg 20

<210> SEQ ID NO 6
<211> LENGTH: 20
<212> TYPE: DNA
<213> ORGANISM: Artificial Sequence
<220> FEATURE:
<223> OTHER INFORMATION: Primer

<400> SEQUENCE: 6
gcaaacggcc taaatacagc 20

<210> SEQ ID NO 7
<211> LENGTH: 60
<212> TYPE: DNA
<213> ORGANISM: Artificial Sequence
<220> FEATURE:
<223> OTHER INFORMATION: Primer

<400> SEQUENCE: 7
tgccaagctt gcatgcctgc aggtcgactc tagaggatcc attccgggga tccgtcgacc 60

<210> SEQ ID NO 8
<211> LENGTH: 60
<212> TYPE: DNA
<213> ORGANISM: Artificial Sequence
<220> FEATURE:
<223> OTHER INFORMATION: Primer

<400> SEQUENCE: 8
ctgatcagtg ataagctgtc aaacatgaga attcgagctc tgtaggctgg agctgcttcg 60

<210> SEQ ID NO 9
<211> LENGTH: 60
<212> TYPE: DNA
<213> ORGANISM: Artificial Sequence
<220> FEATURE:
<223> OTHER INFORMATION: Primer

<400> SEQUENCE: 9
ccaattacta ccagcttcag cactaccagc actaccaatc ctctttcggt aataaatctt 60

<210> SEQ ID NO 10
<211> LENGTH: 60
<212> TYPE: DNA
<213> ORGANISM: Artificial Sequence
<220> FEATURE:
<223> OTHER INFORMATION: Primer

<400> SEQUENCE: 10
gtgagcgcgc gtaatacgac tcactatagg gcggatccgg tctatccttt atgggagaac 60

<210> SEQ ID NO 11
<211> LENGTH: 90
<212> TYPE: DNA
<213> ORGANISM: Artificial Sequence
<220> FEATURE:
<223> OTHER INFORMATION: Primer

<400> SEQUENCE: 11
gtgctgaagc tggtagtaat tggagtcatc cacaatttga aaaaggtagt gctggtagtg 60
ctgctggtag tcacggttac gtatcggcag 90

<210> SEQ ID NO 12
<211> LENGTH: 60
<212> TYPE: DNA
<213> ORGANISM: Artificial Sequence
<220> FEATURE:
<223> OTHER INFORMATION: Primer

<400> SEQUENCE: 12
aattcaccac taccagcagc actaccagca ctaccaccgt caaacttaac gtcaataacg 60

<210> SEQ ID NO 13
<211> LENGTH: 60
<212> TYPE: DNA
<213> ORGANISM: Artificial Sequence
<220> FEATURE:
<223> OTHER INFORMATION: Primer

<400> SEQUENCE: 13

-continued

```
agtgctggta gtgctgctgg tagtggtgaa tttaaagtta cctatagtgg tagtgacagc      60


<210> SEQ ID NO 14
<211> LENGTH: 60
<212> TYPE: DNA
<213> ORGANISM: Artificial Sequence
<220> FEATURE:
<223> OTHER INFORMATION: Primer

<400> SEQUENCE: 14

cgatatcaag cttatcgata ccgtcgacct cgagaattcc cgtcaagata atccgataag      60


<210> SEQ ID NO 15
<211> LENGTH: 28
<212> TYPE: DNA
<213> ORGANISM: Artificial Sequence
<220> FEATURE:
<223> OTHER INFORMATION: Primer

<400> SEQUENCE: 15

gaattgggta ccgggccccc cctcgagg                                        28


<210> SEQ ID NO 16
<211> LENGTH: 28
<212> TYPE: DNA
<213> ORGANISM: Artificial Sequence
<220> FEATURE:
<223> OTHER INFORMATION: Primer

<400> SEQUENCE: 16

gccctatagt gagtcgtatt acgcgcgc                                        28


<210> SEQ ID NO 17
<211> LENGTH: 22
<212> TYPE: DNA
<213> ORGANISM: Artificial Sequence
<220> FEATURE:
<223> OTHER INFORMATION: Primer

<400> SEQUENCE: 17

aactgttggg gttacttcgg ta                                              22


<210> SEQ ID NO 18
<211> LENGTH: 21
<212> TYPE: DNA
<213> ORGANISM: Artificial Sequence
<220> FEATURE:
<223> OTHER INFORMATION: Primer

<400> SEQUENCE: 18

ctggttgttg ctcaggtgtt t                                               21


<210> SEQ ID NO 19
<211> LENGTH: 485
<212> TYPE: PRT
<213> ORGANISM: Vibrio cholerae

<400> SEQUENCE: 19

Met Lys Lys Gln Pro Lys Met Thr Ala Ile Ala Leu Ile Leu Ser Gly
1               5                   10                  15

Ile Ser Gly Leu Ala Tyr Gly His Gly Tyr Val Ser Ala Val Glu Asn
            20                  25                  30

Gly Val Ala Glu Gly Arg Val Thr Leu Cys Lys Phe Ala Ala Asn Gly
        35                  40                  45
```

-continued

```
Thr Gly Glu Lys Asn Thr His Cys Gly Ala Ile Gln Tyr Glu Pro Gln
    50                  55                  60

Ser Val Glu Gly Pro Asp Gly Phe Pro Val Thr Gly Pro Arg Asp Gly
65                  70                  75                  80

Lys Ile Ala Ser Ala Glu Ser Ala Leu Ala Ala Ala Leu Asp Glu Gln
                85                  90                  95

Thr Ala Asp Arg Trp Val Lys Arg Pro Ile Gln Ala Gly Pro Gln Thr
            100                 105                 110

Phe Glu Trp Thr Phe Thr Ala Asn His Val Thr Lys Asp Trp Lys Tyr
        115                 120                 125

Tyr Ile Thr Lys Pro Asn Trp Asn Pro Asn Gln Pro Leu Ser Arg Asp
    130                 135                 140

Ala Phe Asp Leu Asn Pro Phe Cys Val Val Glu Gly Asn Met Val Gln
145                 150                 155                 160

Pro Pro Lys Arg Val Ser His Glu Cys Ile Val Pro Glu Arg Glu Gly
                165                 170                 175

Tyr Gln Val Ile Leu Ala Val Trp Asp Val Gly Asp Thr Ala Ala Ser
            180                 185                 190

Phe Tyr Asn Val Ile Asp Val Lys Phe Asp Gly Asn Gly Pro Val Leu
        195                 200                 205

Pro Asp Trp Asn Pro Ala Gly Gln Ile Ile Pro Ser Met Asp Leu Ser
    210                 215                 220

Ile Gly Asp Thr Val Tyr Thr Arg Val Phe Asp Asn Asp Gly Glu Asn
225                 230                 235                 240

Pro Ala Tyr Arg Thr Glu Leu Lys Ile Asp Ser Glu Thr Leu Thr Lys
                245                 250                 255

Ala Asn Gln Trp Ser Tyr Ala Leu Ala Thr Lys Ile Asn Gln Thr Gln
            260                 265                 270

Lys Gln Gln Arg Ala Gly Gln Leu Asn Gly Asp Gln Phe Val Pro Val
        275                 280                 285

Tyr Gly Thr Asn Pro Ile Tyr Leu Lys Glu Gly Ser Gly Leu Lys Ser
    290                 295                 300

Val Glu Ile Gly Tyr Gln Ile Glu Ala Pro Gln Pro Glu Tyr Ser Leu
305                 310                 315                 320

Thr Val Ser Gly Leu Ala Lys Glu Tyr Glu Ile Gly Glu Gln Pro Ile
                325                 330                 335

Gln Leu Asp Leu Thr Leu Glu Ala Gln Gly Glu Met Ser Ala Glu Leu
            340                 345                 350

Thr Val Tyr Asn His His Gln Lys Pro Leu Ala Ser Trp Ser Gln Ala
        355                 360                 365

Met Thr Asp Gly Glu Leu Lys Ser Ile Thr Leu Glu Leu Ser Glu Ala
    370                 375                 380

Lys Ala Gly His His Met Leu Val Ser Arg Ile Lys Asp Arg Asp Gly
385                 390                 395                 400

Asn Leu Gln Asp Gln Gln Thr Leu Asp Phe Met Leu Val Glu Pro Gln
                405                 410                 415

Thr Pro Pro Thr Pro Gly Asp Tyr Asp Phe Val Phe Pro Asn Gly Leu
            420                 425                 430

Lys Glu Tyr Val Ala Gly Thr Lys Val Leu Ala Ser Asp Gly Ala Ile
        435                 440                 445

Tyr Gln Cys Lys Pro Trp Pro Tyr Ser Gly Tyr Cys Gln Gln Trp Thr
    450                 455                 460

Ser Asn Ala Thr Gln Tyr Gln Pro Gly Thr Gly Ser His Trp Glu Met
```

```
465                 470                 475                 480

Ala Trp Asp Lys Arg
                485


<210> SEQ ID NO 20
<211> LENGTH: 180
<212> TYPE: PRT
<213> ORGANISM: Vibrio cholerae

<400> SEQUENCE: 20

His Gly Tyr Val Ser Ala Val Glu Asn Gly Val Ala Glu Gly Arg Val
1               5                   10                  15

Thr Leu Cys Lys Phe Ala Ala Asn Gly Thr Gly Glu Lys Asn Thr His
            20                  25                  30

Cys Gly Ala Ile Gln Tyr Glu Pro Gln Ser Val Glu Gly Pro Asp Gly
        35                  40                  45

Phe Pro Val Thr Gly Pro Arg Asp Gly Lys Ile Ala Ser Ala Glu Ser
    50                  55                  60

Ala Leu Ala Ala Ala Leu Asp Glu Gln Thr Ala Asp Arg Trp Val Lys
65                  70                  75                  80

Arg Pro Ile Gln Ala Gly Pro Gln Thr Phe Glu Trp Thr Phe Thr Ala
                85                  90                  95

Asn His Val Thr Lys Asp Trp Lys Tyr Tyr Ile Thr Lys Pro Asn Trp
            100                 105                 110

Asn Pro Asn Gln Pro Leu Ser Arg Asp Ala Phe Asp Leu Asn Pro Phe
        115                 120                 125

Cys Val Val Glu Gly Asn Met Val Gln Pro Pro Lys Arg Val Ser His
    130                 135                 140

Glu Cys Ile Val Pro Glu Arg Glu Gly Tyr Gln Val Ile Leu Ala Val
145                 150                 155                 160

Trp Asp Val Gly Asp Thr Ala Ala Ser Phe Tyr Asn Val Ile Asp Val
                165                 170                 175

Lys Phe Asp Gly
            180


<210> SEQ ID NO 21
<211> LENGTH: 1229
<212> TYPE: PRT
<213> ORGANISM: Lactobacillus reuteri JCM 1112

<400> SEQUENCE: 21

Met Tyr Leu Gly Gly Leu Ile Met Leu Ser Arg Lys Asn Tyr Lys Glu
1               5                   10                  15

Thr Ile Arg Lys Gln Thr Pro Thr Lys Gln Tyr Tyr Thr Ile Lys Lys
            20                  25                  30

Leu Thr Val Gly Val Thr Ser Val Leu Ile Gly Leu Ser Phe Met Gly
        35                  40                  45

Glu Leu Glu Gly Asp Ser Val His Ala Asp Thr Met Thr Ala Ser Ser
    50                  55                  60

Glu Ser Thr Ser Val Thr Ser Thr Thr Ala Gln Asp Gly Leu Lys Lys
65                  70                  75                  80

Ser Pro Gln Leu Tyr Leu Gln Val Thr Asp Thr Asn Asn Pro Ser Thr
                85                  90                  95

Pro Leu Ser Ala Ser Ser Thr Gly Thr Ser Lys Asn Val Thr Ser Ser
            100                 105                 110

Ala Ala Val Gln Val Lys Ser Ala Ser Asp Glu Glu Asp Ser Asp Ser
```

```
        115                 120                 125

Thr Leu Ala Lys Gly Glu Asn Lys Phe Ala Arg Ser Ala Val Lys Asp
    130                 135                 140

Ser Val Thr Asp Gly Lys Thr Ser Thr Ala Glu Ile Asn Pro Ala Lys
145                 150                 155                 160

Leu Ser Ser Pro Ala Leu Ile Thr Gln Leu Asn Gln Ser Leu Ala Lys
                165                 170                 175

Ser Ser Thr Ser Asp Ala Ala Lys Ala Asn Asp Glu Leu Glu Ile Lys
            180                 185                 190

Ala Thr Asp Pro Thr Asn Tyr Pro Asn Cys Gly Asp Val Tyr Gly Pro
        195                 200                 205

Leu Phe Glu Leu Asp Ala Ser Gly Gln Leu Val Asn Lys Asp Glu Val
    210                 215                 220

Ile Ser Leu Lys Asp Met Tyr Ile Phe Gln Ile Leu Lys Leu Val Asn
225                 230                 235                 240

Thr Lys Asp Ser Asp Phe Gln Tyr Val Ile Leu Thr Met Asn Arg Lys
                245                 250                 255

Asp Thr Ala Asp Arg Ser Val Tyr Leu Phe Val Thr Gly Ser Asn Tyr
            260                 265                 270

Ser Asn Ala Val Val Val Lys Val Lys Pro Asn Asp Thr Tyr Glu Leu
        275                 280                 285

Ser Lys Thr Gly Tyr Ser Val Thr Tyr Thr Glu Pro Thr Thr Ile Asn
    290                 295                 300

Gly His Tyr Val Asp Gly Thr Phe Tyr Val Thr Gly Ser Thr Tyr Asp
305                 310                 315                 320

Asp Gly Phe Ile Met Pro Asp Trp Gln Leu Gln His Leu Gln Ile Ile
                325                 330                 335

Tyr Ser Leu Gly Asn Tyr Asp Pro Ser Asn Thr Asp Ala Thr Ser Val
            340                 345                 350

Cys Glu Ile Met Pro Ser Tyr Glu Lys Val Pro Val Ile Lys Tyr Ser
        355                 360                 365

Gly Val Pro Ser Asn Ile Ser Gln Pro Lys Val Tyr Ile Thr Gly Phe
    370                 375                 380

Thr Gly Gln Glu Phe Asn Val Thr Asp Ile Ile Asn Asn Tyr Lys Lys
385                 390                 395                 400

Val Phe Lys Gly Tyr Tyr Leu Gln Asn Pro Asn Val Ala Ser Met Gly
                405                 410                 415

Thr Leu Ser Gln Phe Glu Asn Gly Gly Tyr Tyr Leu Lys Thr Tyr Tyr
            420                 425                 430

Asp Asn Asp Gly Asn Val Asp Phe Lys Gly Leu Tyr His Gln Ile Asp
        435                 440                 445

Asp Gln Gly Thr Met Ser Val Ser Val Leu Asn Ala Asp Asn Lys Thr
    450                 455                 460

Ile Val Gly Pro Glu Asn Ile Leu Ala Gly Lys Ser His Asn Phe Asn
465                 470                 475                 480

Phe Asn Gly His Asn Trp Ile Ala Arg Asn Pro Tyr Val Thr Ser Ser
                485                 490                 495

Ala His Glu Val Ile Leu Lys Tyr Ala Lys Leu Gly Ser Val Ile Pro
            500                 505                 510

Val Asp Glu Asn Gly Asn Lys Ile Asn Asp Gly Trp Gln Tyr Val Asn
        515                 520                 525

Asp Pro Asp Asp Ala Ser Lys Ala Thr Ser Pro Tyr Glu Lys Ala Pro
    530                 535                 540
```

```
Val Ile Asp Gly Tyr Val Ala Val Asn Pro Asp Glu Thr Ile Val Leu
545                 550                 555                 560

Pro His Asn Leu Ser Ser Asp Thr Lys Ile Tyr Tyr Arg Lys Arg Ile
                565                 570                 575

Lys Val Thr Tyr Ser Gly Ser Asp Ser Lys Thr Tyr Asp Gly Asn Pro
            580                 585                 590

Ala Asn Phe Glu Pro Thr Thr Val Gln Trp Ser Gly Leu Lys Gly Leu
        595                 600                 605

Asn Thr Ser Thr Leu Thr Ser Ala Asp Phe Thr Trp Asn Thr Ala Asp
    610                 615                 620

Lys Lys Ala Pro Thr Asp Ala Gly Lys Tyr Thr Leu Ser Leu Asn Thr
625                 630                 635                 640

Thr Gly Glu Ala Ala Leu Arg Lys Ala Asn Pro Asn Tyr Asp Leu Lys
                645                 650                 655

Thr Ile Ser Gly Ser Tyr Thr Tyr Thr Ile Asn Pro Leu Gly Ile Asp
            660                 665                 670

Lys Val Thr Tyr Ser Gly Ser Asp Ser Lys Thr Tyr Asp Gly Asn Pro
        675                 680                 685

Ala Asn Phe Glu Pro Thr Thr Val Gln Trp Ser Gly Leu Lys Gly Leu
    690                 695                 700

Asn Thr Ser Thr Leu Thr Ser Ala Asp Phe Thr Trp Asn Thr Ala Asp
705                 710                 715                 720

Lys Lys Ala Pro Thr Asp Ala Gly Lys Tyr Thr Leu Ser Leu Asn Thr
                725                 730                 735

Thr Gly Glu Ala Ala Leu Arg Lys Ala Asn Pro Asn Tyr Asp Leu Lys
            740                 745                 750

Thr Ile Ser Gly Ser Tyr Thr Tyr Thr Ile Asn Pro Leu Gly Ile Asp
        755                 760                 765

Lys Val Thr Tyr Ser Gly Ser Asp Ser Lys Thr Tyr Asp Gly Asn Pro
    770                 775                 780

Ala Asn Phe Glu Pro Thr Thr Val Gln Trp Ser Gly Leu Lys Gly Leu
785                 790                 795                 800

Asn Thr Ser Thr Leu Thr Ser Ala Asp Phe Thr Trp Asn Thr Ala Asp
                805                 810                 815

Lys Lys Ala Pro Thr Asp Ala Gly Lys Tyr Thr Leu Ser Leu Asn Thr
            820                 825                 830

Thr Gly Glu Ala Ala Leu Arg Lys Ala Asn Pro Asn Tyr Asp Leu Lys
        835                 840                 845

Thr Ile Ser Gly Ser Tyr Thr Tyr Thr Ile Asn Pro Leu Gly Ile Asp
    850                 855                 860

Lys Val Thr Tyr Ser Gly Ser Asp Ser Lys Thr Tyr Asp Gly Asn Pro
865                 870                 875                 880

Ala Asn Phe Glu Pro Thr Thr Val Gln Trp Ser Gly Leu Lys Gly Leu
                885                 890                 895

Asn Thr Ser Thr Leu Thr Ser Ala Asp Phe Thr Trp Asn Thr Ala Asp
            900                 905                 910

Lys Lys Ala Pro Thr Asp Ala Gly Lys Tyr Thr Leu Ser Leu Asn Thr
        915                 920                 925

Thr Gly Glu Ala Ala Leu Arg Lys Ala Asn Pro Asn Tyr Asp Leu Lys
    930                 935                 940

Thr Ile Ser Gly Ser Tyr Thr Tyr Thr Ile Asn Pro Leu Gly Ile Asp
945                 950                 955                 960
```

```
Lys Val Thr Tyr Ser Gly Ser Asp Ser Lys Thr Tyr Asp Gly Asn Pro
                965                 970                 975

Ala Asn Phe Glu Pro Thr Thr Val Gln Trp Ser Gly Leu Lys Gly Leu
            980                 985                 990

Asn Thr Ser Thr Leu Thr Ser Ala  Asp Phe Thr Trp Asn  Thr Ala Asp
        995                 1000                 1005

Lys Lys  Ala Pro Thr Asp Ala  Gly Lys Tyr Thr Leu  Ser Leu Asn
    1010                 1015                 1020

Thr Thr  Gly Glu Ala Ala Leu  Arg Lys Ala Asn Pro  Asn Tyr Asp
    1025                 1030                 1035

Leu Lys  Thr Ile Ser Gly Ser  Tyr Thr Tyr Thr Ile  Asn Pro Leu
    1040                 1045                 1050

Gly Ile  Val Thr Val Asn Tyr  Lys Gly Tyr Asp Lys  Lys Val Tyr
    1055                 1060                 1065

Asp Gly  Gln Pro Gly Thr Ile  Asn Pro Gly Lys Leu  Thr Trp Ser
    1070                 1075                 1080

Lys Leu  Pro Asp Gly Thr Ser  Leu Lys Met Pro Thr  Trp Ser Ile
    1085                 1090                 1095

Asp Asp  Phe Ala Trp Glu Thr  Ala Asp Gly Leu Ala  Pro Thr Ala
    1100                 1105                 1110

Val Gly  Thr Tyr Arg Ile Ile  Leu Thr Asp Ala Gly  Lys Ala Ala
    1115                 1120                 1125

Leu Lys  Lys Ile Asn Pro Asn  Tyr Asp Leu Ser Ser  Ile Thr Gly
    1130                 1135                 1140

Val Phe  Thr Tyr Glu Ile Lys  Pro Ala Gln Thr Pro  Glu Ile Leu
    1145                 1150                 1155

Gly Gln  Thr Pro Glu Gln Gln  Pro Gly Gln Asn Thr  Asn Gln Ser
    1160                 1165                 1170

Gly Ala  Glu Asn Gly Phe Gly  Ser Ser Thr Arg Pro  Asn Ala Ser
    1175                 1180                 1185

Thr Asn  Ser Asn Leu Asn Gln  Leu Pro Gln Thr Gly  Asn Glu His
    1190                 1195                 1200

Ser Asn  Thr Ala Leu Ala Gly  Leu Ala Leu Ala Phe  Leu Thr Ala
    1205                 1210                 1215

Met Leu  Gly Leu Gly Lys Lys  Arg Lys His Asp
    1220                 1225
```

<210> SEQ ID NO 22
<211> LENGTH: 540
<212> TYPE: DNA
<213> ORGANISM: Artificial Sequence
<220> FEATURE:
<223> OTHER INFORMATION: Harmonized Sequence

<400> SEQUENCE: 22

```
cacggttacg tatcggcagt tgaaaacggt gtagccgaag ggcgtgtaac tctttgtaaa      60

tttgcagcca acggtacagg ggagaaaaac acacactgtg gtgcaattca atatgaacct     120

caatctgtag aaggtcctga tggtttccct gtaacaggtc ctcgtgatgg taaaattgcc     180

tctgcagaat ctgcccttgc agccgcactt gatgaacaaa ctgcagaccg ttgggtcaag     240

cgtcctattc aagcaggtcc tcaaactttc gagtggacct tcactgcaaa ccacgtaacg     300

aaggattgga agtactacat tactaagcca aactggaacc caaaccagcc tcttagccgt     360

gatgcatttg acttgaaccc tttctgtgtc gtagaaggga acatggttca gcctcctaag     420

cgtgtatctc acgaatgtat tgttcctgaa cgtgaagggt accaggtaat cctagcagtc     480
```

tgggatgtag gtgatactgc agcctcgttc tacaacgtta ttgacgttaa gtttgacggt 540

<210> SEQ ID NO 23
<211> LENGTH: 3690
<212> TYPE: DNA
<213> ORGANISM: Lactobacillus reuteri JCM 1112

<400> SEQUENCE: 23
ttgtatttag gagggttaat aatgctatca agaaaaaatt ataaggaaac tatacgaaaa 60
cagacaccta caaaacagta ctatactatt aagaaattaa ctgttggggt tacttcggta 120
ttaattggtc tatcctttat gggagaacta gaaggggata gcgttcatgc ggacacgatg 180
acagcaagca gtgagtcaac aagtgttacg tcgacgactg ctcaggatgg tttaaaaaaa 240
tctccacaac tctatttgca agttactgat acaaataacc caagtacacc attaagtgct 300
tcatccacag ggactagtaa gaatgttacc tcatcagctg cggtacaagt gaagtccgct 360
agtgatgaag aagatagtga ttctacacta gctaagggag aaaataaatt tgctcggtca 420
gcagtaaaag attcagtcac tgatgggaaa acaagtacag cagaaattaa tccggcaaaa 480
ttaagcagtc ctgctttaat aacgcaactc aaccaatcct tagctaagag cagtacgagt 540
gatgcagcaa aagctaatga tgagttagaa attaaagcaa cagatccgac taattatcca 600
aactgtggcg atgtgtatgg gccattattt gaattggatg ctagcggaca gcttgttaat 660
aaagatgaag ttatatctct taaagatatg tatattttcc aaatattgaa attagtaaat 720
acaaaagata gtgactttca atatgtaata ttaacaatga atcgtaaaga tactgcagat 780
aggtctgtat atctttttgt aactggaagc aattatagta atgctgttgt tgttaaagta 840
aagccaaatg atacttatga attaagtaaa actggatata gtgttactta tacagaacca 900
acaactataa atggacatta tgttgatgga actttttatg ttacaggaag tacttacgat 960
gatggtttta taatgccaga ttggcaactg cagcaccttc agattatata tagtttagga 1020
aattatgatc caagcaatac tgacgcaaca tcagtttgtg aaataatgcc aagttatgaa 1080
aaggtaccgg taattaaata tagtggagta ccttcaaata ttagccaacc taaggtttac 1140
attaccgggt ttacgggtca agagtttaac gttacagata ttattaacaa ttataagaaa 1200
gtttttaagg gctactatct tcaaaatcct aatgtggcgt ccatgggaac tctttcccaa 1260
tttgagaatg gtggttatta cttaaagaca tattatgata atgatggtaa tgttgacttt 1320
aagggcttgt atcatcaaat tgatgatcag ggaacaatga gtgtgagtgt tcttaatgca 1380
gataataaaa caattgttgg acctgaaaat attcttgctg gtaaatcgca taactttaac 1440
tttaatggtc ataactggat tgcgcggaat ccttatgtca ctagttcagc tcacgaagtc 1500
atattaaagt atgctaagtt aggttcagtt attcctgttg atgaaaacgg aaataaaata 1560
aacgatggat ggcaatatgt taatgatcca gatgatgctt ccaaagccac tagcccatat 1620
gaaaaagcgc cagttatcga tggttatgta gctgtaaatc cagatgaaac gatcgttctt 1680
cctcataact taagtagtga cacaaagatt tattaccgaa agaggattaa agttacctat 1740
agtggtagtg acagcaagac ctacgatggt aacccagcta acttcgagcc aacgacagtt 1800
cagtggagtg gcttgaaagg actgaacact tcaaccttaa cgtccgctga cttcacgtgg 1860
aatactgcgg ataagaaggc accaacggat gccggtaagt acacacttag tttgaatacg 1920
accggagaag cagccttacg taaggctaac ccgaactatg atctcaagac aattagcggt 1980
agttacacct acacgattaa tccactaggg attgataaag ttacctatag tggtagtgac 2040

```
agcaagacct acgatggtaa cccagctaac ttcgagccaa cgacagttca gtggagtggc   2100
ttgaaaggac tgaacacttc aaccttaacg tccgctgact tcacgtggaa tactgcggat   2160
aagaaggcac caacggatgc cggtaagtac acacttagtt tgaatacgac cggagaagca   2220
gccttacgta aggctaaccc gaactatgat ctcaagacaa ttagcggtag ttacacctac   2280
acgattaatc cactagggat tgataaagtt acctatagtg gtagtgacag caagacctac   2340
gatggtaacc cagctaactt cgagccaacg acagttcagt ggagtggctt gaaaggactg   2400
aacacttcaa ccttaacgtc cgctgacttc acgtggaata ctgcggataa gaaggcacca   2460
acggatgccg gtaagtacac acttagtttg aatacgaccg gagaagcagc cttacgtaag   2520
gctaacccga actatgatct caagacaatt agcggtagtt acacctacac gattaatcca   2580
ctagggattg ataaagttac ctatagtggt agtgacagca agacctacga tggtaaccca   2640
gctaacttcg agccaacgac agttcagtgg agtggcttga aaggactgaa cacttcaacc   2700
ttaacgtccg ctgacttcac gtggaatact gcggataaga aggcaccaac ggatgccggt   2760
aagtacacac ttagtttgaa tacgaccgga gaagcagcct tacgtaaggc taacccgaac   2820
tatgatctca agacaattag cggtagttac acctacacga ttaatccact agggattgat   2880
aaagttacct atagtggtag tgacagcaag acctacgatg gtaacccagc taacttcgag   2940
ccaacgacag ttcagtggag tggcttgaaa ggactgaaca cttcaacctt aacgtccgct   3000
gacttcacgt ggaatactgc ggataagaag gcaccaacgg atgccggtaa gtacacactt   3060
agtttgaata cgaccggaga agcagcctta cgtaaggcta acccgaacta tgatctcaag   3120
acaattagcg gtagttacac ctacacgatt aatccactag ggattgtgac tgtaaattac   3180
aagggctatg ataagaaagt ctatgatggt caacctggaa cgattaatcc gggtaaatta   3240
acgtggagta agttgccaga tggtacttca ttgaagatgc caacatggag tatagatgat   3300
ttcgcttggg aaacagctga tggcttagca ccaacggcag taggaactta tcggattatc   3360
ttgacggatg ctggtaaggc tgcactaaag aagattaatc caaattatga cttaagcagt   3420
attactggtg tctttactta tgaaattaag ccagcacaga caccagaaat cttaggccaa   3480
acacctgagc aacaaccagg ccaaaatact aatcaatcag gagctgaaaa cggctttggt   3540
tcttctacaa ggcctaatgc atcaactaac tccaatctta atcaacttcc acagactggt   3600
aatgagcatt ctaatactgc acttgctggt ctagcattgg ctttcttgac tgctatgctt   3660
ggtttgggca agaagcgtaa acatgattag                                  3690
```

<210> SEQ ID NO 24
<211> LENGTH: 4350
<212> TYPE: DNA
<213> ORGANISM: Artificial Sequence
<220> FEATURE:
<223> OTHER INFORMATION: GbpA-MBP Chimeric Sequence

<400> SEQUENCE: 24

```
ttgtatttag gagggttaat aatgctatca agaaaaaatt ataaggaaac tatacgaaaa     60
cagacaccta caaaacagta ctatactatt aagaaattaa ctgttggggt tacttcggta    120
ttaattggtc tatcctttat gggagaacta gaaggggata gcgttcatgc ggacacgatg    180
acagcaagca gtgagtcaac aagtgttacg tcgacgactg ctcaggatgg tttaaaaaaa    240
tctccacaac tctatttgca agttactgat acaaataacc caagtacacc attaagtgct    300
tcatccacag ggactagtaa gaatgttacc tcatcagctg cggtacaagt gaagtccgct    360
agtgatgaag aagatagtga ttctacacta gctaagggag aaaataaatt tgctcggtca    420
```

```
gcagtaaaag attcagtcac tgatgggaaa acaagtacag cagaaattaa tccggcaaaa    480
ttaagcagtc ctgctttaat aacgcaactc aaccaatcct tagctaagag cagtacgagt    540
gatgcagcaa aagctaatga tgagttagaa attaaagcaa cagatccgac taattatcca    600
aactgtggcg atgtgtatgg gccattattt gaattggatg ctagcggaca gcttgttaat    660
aaagatgaag ttatatctct taaagatatg tatattttcc aaatattgaa attagtaaat    720
acaaaagata gtgactttca atatgtaata ttaacaatga atcgtaaaga tactgcagat    780
aggtctgtat atctttttgt aactggaagc aattatagta atgctgttgt tgttaaagta    840
aagccaaatg atacttatga attaagtaaa actggatata gtgttactta tacagaacca    900
acaactataa atggacatta tgttgatgga actttttatg ttacaggaag tacttacgat    960
gatggtttta taatgccaga ttggcaactg cagcaccttc agattatata tagtttagga   1020
aattatgatc caagcaatac tgacgcaaca tcagtttgtg aaataatgcc aagttatgaa   1080
aaggtaccgg taattaaata tagtggagta ccttcaaata ttagccaacc taaggtttac   1140
attaccgggt ttacgggtca agagtttaac gttacagata ttattaacaa ttataagaaa   1200
gtttttaagg gctactatct tcaaaatcct aatgtggcgt ccatgggaac tctttcccaa   1260
tttgagaatg gtggttatta cttaaagaca tattatgata atgatggtaa tgttgacttt   1320
aagggcttgt atcatcaaat tgatgatcag ggaacaatga gtgtgagtgt tcttaatgca   1380
gataataaaa caattgttgg acctgaaaat attcttgctg gtaaatcgca taactttaac   1440
tttaatggtc ataactggat tgcgcggaat ccttatgtca ctagttcagc tcacgaagtc   1500
atattaaagt atgctaagtt aggttcagtt attcctgttg atgaaaacgg aaataaaata   1560
aacgatggat ggcaatatgt taatgatcca gatgatgctt ccaaagccac tagcccatat   1620
gaaaaagcgc cagttatcga tggttatgta gctgtaaatc cagatgaaac gatcgttctt   1680
cctcataact taagtagtga cacaaagatt tattaccgaa agaggattgg tagtgctggt   1740
agtgctgaag ctggtagtaa ttggagtcat ccacaatttg aaaaaggtag tgctggtagt   1800
gctgctggta gtcacggtta cgtatcggca gttgaaaacg gtgtagccga agggcgtgta   1860
actctttgta aatttgcagc caacggtaca ggggagaaaa acacacactg tggtgcaatt   1920
caatatgaac ctcaatctgt agaaggtcct gatggtttcc ctgtaacagg tcctcgtgat   1980
ggtaaaattg cctctgcaga atctgccctt gcagccgcac ttgatgaaca aactgcagac   2040
cgttgggtca agcgtcctat tcaagcaggt cctcaaactt tcgagtggac cttcactgca   2100
aaccacgtaa cgaaggattg gaagtactac attactaagc caaactggaa cccaaaccag   2160
cctcttagcc gtgatgcatt tgacttgaac cctttctgtg tcgtagaagg gaacatggtt   2220
cagcctccta agcgtgtatc tcacgaatgt attgttcctg aacgtgaagg gtaccaggta   2280
atcctagcag tctgggatgt aggtgatact gcagcctcgt tctacaacgt tattgacgtt   2340
aagtttgacg gtggtagtgc tggtagtgct gctggtagtg gtgaatttaa agttacctat   2400
agtggtagtg acagcaagac ctacgatggt aacccagcta acttcgagcc aacgacagtt   2460
cagtggagtg gcttgaaagg actgaacact tcaaccttaa cgtccgctga cttcacgtgg   2520
aatactgcgg ataagaaggc accaacggat gccggtaagt acacacttag tttgaatacg   2580
accggagaag cagccttacg taaggctaac ccgaactatg atctcaagac aattagcggt   2640
agttacacct acacgattaa tccactaggg attgataaag ttacctatag tggtagtgac   2700
agcaagacct acgatggtaa cccagctaac ttcgagccaa cgacagttca gtggagtggc   2760
```

ttgaaaggac tgaacacttc aaccttaacg tccgctgact tcacgtggaa tactgcggat 2820
aagaaggcac caacggatgc cggtaagtac acacttagtt tgaatacgac cggagaagca 2880
gccttacgta aggctaaccc gaactatgat ctcaagacaa ttagcggtag ttacacctac 2940
acgattaatc cactagggat tgataaagtt acctatagtg gtagtgacag caagacctac 3000
gatggtaacc cagctaactt cgagccaacg acagttcagt ggagtggctt gaaaggactg 3060
aacacttcaa ccttaacgtc cgctgacttc acgtggaata ctgcggataa gaaggcacca 3120
acggatgccg gtaagtacac acttagtttg aatacgaccg gagaagcagc cttacgtaag 3180
gctaacccga actatgatct caagacaatt agcggtagtt acacctacac gattaatcca 3240
ctagggattg ataaagttac ctatagtggt agtgacagca agacctacga tggtaaccca 3300
gctaacttcg agccaacgac agttcagtgg agtggcttga aaggactgaa cacttcaacc 3360
ttaacgtccg ctgacttcac gtggaatact gcggataaga aggcaccaac ggatgccggt 3420
aagtacacac ttagtttgaa tacgaccgga gaagcagcct tacgtaaggc taacccgaac 3480
tatgatctca agacaattag cggtagttac acctacacga ttaatccact agggattgat 3540
aaagttacct atagtggtag tgacagcaag acctacgatg gtaacccagc taacttcgag 3600
ccaacgacag ttcagtggag tggcttgaaa ggactgaaca cttcaacctt aacgtccgct 3660
gacttcacgt ggaatactgc ggataagaag gcaccaacgg atgccggtaa gtacacactt 3720
agtttgaata cgaccggaga agcagcctta cgtaaggcta acccgaacta tgatctcaag 3780
acaattagcg gtagttacac ctacacgatt aatccactag ggattgtgac tgtaaattac 3840
aagggctatg ataagaaagt ctatgatggt caacctggaa cgattaatcc gggtaaatta 3900
acgtggagta agttgccaga tggtacttca ttgaagatgc caacatggag tatagatgat 3960
ttcgcttggg aaacagctga tggcttagca ccaacggcag taggaactta tcggattatc 4020
ttgacggatg ctggtaaggc tgcactaaag aagattaatc caaattatga cttaagcagt 4080
attactggtg tctttactta tgaaattaag ccagcacaga caccagaaat cttaggccaa 4140
acacctgagc aacaaccagg ccaaaatact aatcaatcag gagctgaaaa cggctttggt 4200
tcttctacaa ggcctaatgc atcaactaac tccaatctta atcaacttcc acagactggt 4260
aatgagcatt ctaatactgc acttgctggt ctagcattgg ctttcttgac tgctatgctt 4320
ggtttgggca agaagcgtaa acatgattag 4350

<210> SEQ ID NO 25
<211> LENGTH: 7373
<212> TYPE: DNA
<213> ORGANISM: Salmonella enterica

<400> SEQUENCE: 25
ttattcatgg ctcatacgtt gttcgtattc tggtctctgg cgaggccatt ttttcgaaac 60
gcctaatcag ttccgccagg ctaccggcct gcattttttc catgactctg gcgcggtgca 120
cctctacggt acgcaccgcg atattcatcg cttccgcaat ttcacggttc ataaatcctt 180
ttgccaccag gctggccagc tcacgctctt tcggcgtcaa ctgctggtaa cacagtataa 240
tctcacgacg cgccaccgct gccgatgaaa ccgtcagcgc acgctccagc gccgcctgta 300
gcggttttac cgataccggt ttttgcagaa aatcgacggc gccgcgtttc atctgctcca 360
cggccatcgg tacatcgcca tgcccggtaa gaaaaacaac cgccagggta cttccgcact 420
ggcgcaacgc atcatgaacg ccctgcccat ccagtaccgg cattcgcata tccagtaata 480
cgaccccggc ctgatacaga ctggcctgcg ccaaaaaatc cgccccctgc gtccagcatt 540

-continued

```
ttacgtcata tcccagactt tccagtaaaa acgcgcacgc gttagtgacc gccgtatcat    600
catccagtag atgaattgtc gccatccctg cccccatttt catgtaagaa atgtatcgta    660
accaccgttc ccgacagacc gtccggcgcg gtctggttcc tgatgctgat atcgccccgc    720
ccataccgca ccagccgctg gcaaatcgcc agccctaagc ccatcccctc tttacgggtg    780
gtcataaacg gctgaaacgc ctgacgtaat agcgcctcat cgattccccc ggcgttatcc    840
tgtaaaacaa tactgatgcc gttttcagtg cgttcagcaa cgatccataa atgggtggcg    900
cccgcctgag ccgcattaag aatgatattc gccagcacct gttccagcag cactgacggc    960
agcgttacgc gcagcgcagc gctaacctcg gtatgcagag tcactgtcgg aaactgttgc   1020
gccatacgca acaattgcca gacatgatca atcgcctcgc gaatggctat ggccttccac   1080
gcttcggtta gcaccgggtt gccctgcgcc tggctgaccc agtgacgcag gttacgcaga   1140
gtatccgcac cgcgttgcgc ctgctggtca atctgctcca gcgccggcag caagggatgc   1200
tgttcatctg cagcgcgcag tcgaatcagg cacccctggg cataatgtcg aatcgcggaa   1260
agcggctgat taagctcatg ggcaaacccg gaggtcattt cacccaacac gctcatttgc   1320
cgggcggttt ccagcgcccg ctcatgctga tgaagaacta cgctattacg ttccagttgc   1380
tttccacgtc gacgcaccag cagcatgacc caaatataat tgagcgtgag caacaagaac   1440
gccagaatca cgccgccgac cattagctgg tgctggatta accaactttt gacatccagc   1500
cacagtcgac gctgctgagg gtgctgacga acatcacgca gcaaggcttc cacctgactg   1560
gtggacgcag gcgcgcccca gtgaaatgac gcggcggcgg gcgcgttgaa tagcgctcgc   1620
gttacgcgat ccgccagcgc atcgcttacc gcaggtagcg ccgcgaacga ccagtcagga   1680
tataacggcg tactggttaa gcaaggcagg ggcgtcggtc gggaaagcag cgcgataaag   1740
tcctttttat taatcaatcc ttcctgatcc atattttcta acaggcacac tggcacaatt   1800
gccgcctgca ccgctttttc gcgcagcata tagactaagg catcgccagg aaatccggta   1860
aaacggagat gaaaatcgcg ctccgggcgt aagcccgcgt cgctgagcgc tttatagcct   1920
aataaatagc cgccaaacgc ctgagcatca atcgcgccga cggtcttacc gatgagatca   1980
tgcgccgtgg tgatgccgct atcgcgccgg gtcaaaatca cgctgccaat aacattactc   2040
accgctttcc catcgcgcgt ggagcgcagg gaagctaacc agcgcagcgg cgcatggctg   2100
ttcagttgga caaattgcgc cgggttggtt atcacaaact gcacggttcc ctggttaacg   2160
gcctcctgca tttgatgcag atccagcggc tggatgtgaa aggtttcgcc tggaagctgt   2220
tggcttaatg tctttgccaa cggttgccag tggctacgcg tagacgcctc gccgcgcatg   2280
gccaaaatac cgatattcca cgtccctgcc cacgcgccat gacaaagtag ccctactgcc   2340
gccaacaccg ccaggcgcct tacggtttta cctctcaccc caatatccct gtcaattatg   2400
ttgttttaga tcaacaacaa gccgggtatg tggttaacca caatagagcg caccccgcct   2460
cgatttttac actgtaaatc atcgacattt tttattcatt acacatgaac caacatcgtg   2520
acaaatgttt cattgttggc aatgtggacg ggagtcaata tggacagcag taaacggcaa   2580
tttctccagc agcttggcgt cctgaccgct ggcgcctcgc tggttccgct ggctgaagcg   2640
aaatttcctt tttcgccgga gcggcatgaa ggctctcccc gacaccgtta cgccatgctt   2700
atcgatctgc ggcgttgtat cggctgtcag tcctgtaccg taagttgcac tattgaaaac   2760
caaacgccgc aaggcgcgtt tcgtacgacg gtgaaccaat accaggtcca gcgtgaaggt   2820
agtcaggaag tcacgaatgt gctgttgccg cgtctgtgca accattgcga taacccccc    2880
```

-continued tgtgtgccgg tctgcccggt acaagccacc tttcagcggg aagatggcat tgtggtggtg 2940
gataacaaac gctgcgtcgg ctgcgcctat tgtgtccagg cgtgtcctta cgacgcccga 3000
tttatcaatc atgaaacgca aactgccgat aaatgcacgt tttgcgtcca tcgtctggaa 3060
gccggactgt tacccgcttg cgtagagtcc tgcgtcggcg gcgcgcgtat tattggcgat 3120
atcaaagatc cccatagccg catcgccacc atgcttcatc agcatcgcga cgctatcaag 3180
gtattaaagc cggaaaacgg cacgtcgccc catgttttct acctgggtct ggacgacgcc 3240
tttgtcaccc cattaatggg ccgtgcgcag cccgcgcttt ggcaggaggt ctgaatgacg 3300
cattcactca tcattgaaga agtgctggct cacccgcagg acattagctg gctgccgtgg 3360
gcggtacaat atttcttttt tattggcatt gccgcctgcg ccgcactgtt tgcctgttat 3420
cttcactggc ggaaaaaaga cgccgcaaca gaagaaaatc gggcattact gattgccatt 3480
acctgtgcga ttaccgcacc gctggcgctg acggcggatc tgcaccagac cgcccgcgtc 3540
tggcatttct atgcctggcc gacgccctgg tcgtggatgc cctggggagc gttattcctg 3600
ccgctgttta ccggatttct cgctctgtgg ttcctggcgc agcagattaa acgattattc 3660
aataaaagtt acaacgtcac taaatggttg gcgttagcca gcgcgctttg cgcggtgggc 3720
ctgttgattt ataccggccg cgaagtctcc gttgtgctgg cgcgcccaat ctggtttagc 3780
tacgccttcc ccgtggcgat gtttcttagc gccttacagg cgttcttcgc gctgatgatt 3840
gtcgccgccc gacgcgactc ggtaaggctg ccaaaaatat tgtggggaca aatctggacg 3900
ctggcggcgc tggggctggt tgtggccatg tgggttagcg gcgatacgct ttccggcacg 3960
gcaatccgtc agtggattac cgtcgccctg tcagccaaat attacgctgt cggctgggta 4020
gcgctgtggg tatgcacact gctgttctgt agcctggcgc tacgccatcc gttatcacag 4080
ctaagacgcg tcctgctggt tctcagcgcg ctggcgctat gttggctgat gcgctggaca 4140
ttgttgattc aggtacaaac cgtccccaag ttcaacgcgc aatttaaccc ttactcgtta 4200
ccaggcggaa cggatggctg gctggctatt ctcggcacct tcggcctgtg gatagcgcta 4260
ctgattatta ttcgtgaaac gctgaacgga ctcaccagga gattacaaca tggctaattt 4320
aacccgtcgt cagtggctaa aagtcggtct cgccgtcggt gggatggtca cttttggtct 4380
gagctaccgt gatgtggcga aacgcgcaat tgatggcctg ttaaacggga cgtccggcaa 4440
ggtaacgcgc gaccgcatct ttggcaatgc gttaattccg gaggcgcagg cgcaaacaca 4500
ctggcagcaa aatccacaac aaaccatcgc catgacgcaa tgcttcggct gttggacaca 4560
gtgcggtatc cgcgcccggg ttaatgccga tggcaaagtg atacgcatcg ccggcaatcc 4620
ctatcacccc ttgtcgcagg aacacccgat tgactcgtcc gtccctttta gcgaagccat 4680
ggagcaactg gcgggagaaa gcggtcttga cgcccgctca accgcctgcg cgcgcggcgc 4740
cacgctgctg gaaagcctgt acagtccgct acgactgctt gaaccgatga aacgcgtggg 4800
taaacgcggc gaagggaaat ggcagcgcat cagctttgag caacttattg aagaagtcgt 4860
ggaaggcggc gatctgtttg gcgaaggtca tgtggacgga ctgcgcgcta ttcatgcgcc 4920
ggatacgcca attgacgcaa agcaccccag tttcgggccc aaaaccaatc agttactggt 4980
cacgaatacc agcgacgaag gccgcgatgc gtttctgcgt cgttttgcgc taaatagctt 5040
cggcagcaag aatttcggcg cgcatggcgc ctactgtgga ctggcttacc gggccggctc 5100
cggggcattg atgggcgatc tggataaaaa cccgcatgtc aaacccgact gggaaaacgt 5160
ggagtttgcg ctctttatgg gcacctcccc ggcacagtcc ggcaatccgt ttaaacgcca 5220
ggcacgtcag ttggcgagcg cccgactgcg tgagaatttt caatacgtcg tggtcgcccc 5280

```
cgccctcccc ttatcaacgg tgctcgccga tcctcgcggt cgctggcaac cggtcatgcc   5340

cggcagtgat tcggcgctgg caatggggat gatccgctgg atcatggata atcaacgtta   5400

taatgctgat tatctggcga ttcccggcgt acaggcgatg cagcaggccg gcgagcaaag   5460

ttggaccaac gccacgcacc tggtcattgc ggatgagctg ccgacgcttg ccggacaaca   5520

cctgacgctg cgccatctta cgcccgatgg cgaagagacc cctgtcgtac tgaataccga   5580

cggcgagttg gtcgatgcgt ccacttgccg acaggcacgg cttttcgtga cgcagtacgt   5640

tacgctcgcc gacggccaac gggtcacggt gaagagcggg ttgcaacgcc tgaaagaggc   5700

ggcagaaaag ctctcgttgg cgcaatacag cgaacagtgc ggcgtgccgg aagcgcaaat   5760

tatcgcgctg gcggaaacct ttaccagtca cggacgtaaa gctgcggtca tcagtcacgg   5820

cggcatgatg gccggcaatg ggttttataa cgcctggtcg gtcatgatgc ttaacgcgct   5880

gatcggcaac ctcagcttgt ccggcggcgt ctttgtcggc ggcggcaaat tcaacggcgt   5940

tagcgacggc cccgctaca acatgaacag ttttgccgga aaagtgaaac cgtccgggtt   6000

aagtattgcc cgtagcaaaa ccgcttatga agcatcggaa gaataccgcg acaaaattgc   6060

cggtgggcaa tcccctatc cagccaaagc gccgtggtat ccctttgtgg caggccagct   6120

taccgaactg ttgacctccg cgctcgaagg ctatccttat ccgcttaaag cctggatttc   6180

caatatgagc aacccgtttt acggtgttcc cggtctacgc gccgtggcgg aagaaaaact   6240

aaaagaccct cgccgactgc cgctctttat cgcgattgac gcctttatga atgaaacgac   6300

ggcgctggcg gattacattg tgccggatac gcacaatttt gagagctggg gctttacggc   6360

gccctggggc ggcgtagcca gtaaagccac taccgcccgc tggccggttg tcgcccccgc   6420

cactcaccgc acggcggacg ggcaacctgt ctcaatggaa gcattttgta ttgcggtagc   6480

aaaacggctc catctgcccg gcttcggcga ccgggcgata accgatccgc agggcaatac   6540

ttttccactg aaccgggcgg aagacttcta tctgcgcgta gccgctaata tcgcctttat   6600

gggcaagacg ccggtcgcgc tggcaaatca ggaagatatt tcgcttaccg gcgtcagccg   6660

cattctgcca gcaattcagc acacgcttaa agctgatgag gtcggtcgcg tggcgtttat   6720

ctactcgcgt ggcggccggt ttgcgcccga ggatagcggc tatacggagc aacggttagg   6780

taacgcgtgg aaaaaaccct tacagatctg gaatgcagat gtcgccgccc accgtcacgc   6840

catcaccggg gagcgcttca gcggttgccc ggtctggtat ccggcgcgtt tgtcagatgg   6900

tcgtgcgatt gacgaccagt ttcccattgg gcaatggccg ctgaaactga tttcatttaa   6960

atcaaatacc atgtccagct caacagccgt catcccgcgc ttacaccatg tgaagccagc   7020

aaacctggtg gcgctgaatc cgcaagacgg cgagcgttat ggactgcaac atggcgatcg   7080

ggtacggatc attacgccgg gcggtcaggt cgtggcgcaa atcagtttgt taaatggcgt   7140

gatgccaggc gtcatcgcca tcgaacacgg atatggccac cgcgagatgg gcgcaacgca   7200

gcactctctg gatggcgtgc ctatgccgta tgatccacaa atcagggcag gcataaatct   7260

taacgatctg ggctttgccg atccgacaag aaccattacc aacacctggc tcgactgggt   7320

ttctggcgcg gcagtacgtc aggggctgcc ggcaaaaatc gagcgtatat aac          7373
```

<210> SEQ ID NO 26
<211> LENGTH: 1458
<212> TYPE: DNA
<213> ORGANISM: Vibrio cholerae

<400> SEQUENCE: 26

-continued

```
atgaaaaaac aacctaaaat gaccgctatt gccctgatcc tctctggtat cagtggatta      60

gcgtatggac acggctacgt ttccgcagtg gaaaacggtg tcgccgaagg acgtgtcacc     120

ttgtgtaaat ttgccgctaa cggcactgga gagaaaaaca ctcactgtgg cgcgattcaa     180

tacgaaccac aaagtgtcga aggcccagat ggcttcccgg tcactggccc tcgtgatggc     240

aaaattgcca gtgcggaatc ggcactggcg gcagcgctgg atgagcaaac cgccgaccgt     300

tgggtaaagc gcccaattca agctggccca caaaccttcg agtggacgtt caccgccaac     360

cacgtcacaa aggattggaa atactacatt accaaaccaa actggaaccc aaaccagcca     420

ttgtcgcgtg atgcatttga cctcaatccg ttctgtgtcg ttgaaggaaa tatggtgcag     480

ccaccaaaac gtgtcagcca cgaatgtatc gtgcctgagc gcgaagggta tcaggtcatc     540

ctcgccgtat gggatgttgg cgataccgca gcttccttct acaacgtgat cgacgtgaaa     600

tttgacggta acggcccagt gttacccgat tggaacccag caggtcaaat cattccaagt     660

atggatctca gcattggcga taccgtgtac actcgcgtgt ttgataacga tggggaaaac     720

cctgcttatc gcactgagct aaaaattgac tctgagacgc taaccaaagc caatcaatgg     780

tcttacgctc tggcgactaa aattaaccaa acgcaaaaac agcaacgtgc tggtcagctt     840

aatggcgatc aatttgttcc cgtttacggc accaacccga tttatctgaa agaaggcagt     900

ggcttgaaga gtgttgaaat tggctaccaa attgaagcgc cacagcctga gtattcactg     960

acggtttctg gtctagcgaa agagtatgag attggcgaac aaccgattca gcttgacctg    1020

actttagaag cgcaaggtga aatgagcgca gagctgaccg tgtataacca ccaccaaaaa    1080

ccgctggcaa gttggtcaca agcgatgacg gatggcgagc tgaaatccat cacgctagag    1140

ctgagcgaag ctaaagcggg acatcatatg ttggtttctc gcatcaaaga tcgcgatggc    1200

aatctgcaag atcaacaaac tctcgatttc atgctggttg aaccgcaaac accaccaaca    1260

ccgggtgact acgactttgt gttcccgaat ggcctgaaag agtacgtggc tggcaccaaa    1320

gtgctcgcta gtgatggcgc aatctaccaa tgtaagccat ggccatactc tggctactgc    1380

cagcaatgga caagtaacgc tactcaatac caaccgggta ctggcagtca ttgggaaatg    1440

gcgtgggata aacgttaa                                                  1458
```

<210> SEQ ID NO 27
<211> LENGTH: 540
<212> TYPE: DNA
<213> ORGANISM: Vibrio cholerae

<400> SEQUENCE: 27

```
atgaaaaaac aacctaaaat gaccgctatt gccctgatcc tctctggtat cagtggatta      60

gcgtatggac acggctacgt ttccgcagtg gaaaacggtg tcgccgaagg acgtgtcacc     120

ttgtgtaaat ttgccgctaa cggcactgga gagaaaaaca ctcactgtgg cgcgattcaa     180

tacgaaccac aaagtgtcga aggcccagat ggcttcccgg tcactggccc tcgtgatggc     240

aaaattgcca gtgcggaatc ggcactggcg gcagcgctgg atgagcaaac cgccgaccgt     300

tgggtaaagc gcccaattca agctggccca caaaccttcg agtggacgtt caccgccaac     360

cacgtcacaa aggattggaa atactacatt accaaaccaa actggaaccc aaaccagcca     420

ttgtcgcgtg atgcatttga cctcaatccg ttctgtgtcg ttgaaggaaa tatggtgcag     480

ccaccaaaac gtgtcagcca cgaatgtatc gtgcctgagc gcgaagggta tcaggtcatc     540
```

<210> SEQ ID NO 28
<211> LENGTH: 1222

```
<212> TYPE: PRT
<213> ORGANISM: Lactobacillus reuteri JCM 1112

<400> SEQUENCE: 28

Met Leu Ser Arg Lys Asn Tyr Lys Glu Thr Ile Arg Lys Gln Thr Pro
1               5                   10                  15

Thr Lys Gln Tyr Tyr Thr Ile Lys Lys Leu Thr Val Gly Val Thr Ser
            20                  25                  30

Val Leu Ile Gly Leu Ser Phe Met Gly Glu Leu Glu Gly Asp Ser Val
        35                  40                  45

His Ala Asp Thr Met Thr Ala Ser Ser Glu Ser Thr Ser Val Thr Ser
    50                  55                  60

Thr Thr Ala Gln Asp Gly Leu Lys Lys Ser Pro Gln Leu Tyr Leu Gln
65                  70                  75                  80

Val Thr Asp Thr Asn Asn Pro Ser Thr Pro Leu Ser Ala Ser Ser Thr
                85                  90                  95

Gly Thr Ser Lys Asn Val Thr Ser Ser Ala Ala Val Gln Val Lys Ser
            100                 105                 110

Ala Ser Asp Glu Glu Asp Ser Asp Ser Thr Leu Ala Lys Gly Glu Asn
        115                 120                 125

Lys Phe Ala Arg Ser Ala Val Lys Asp Ser Val Thr Asp Gly Lys Thr
    130                 135                 140

Ser Thr Ala Glu Ile Asn Pro Ala Lys Leu Ser Ser Pro Ala Leu Ile
145                 150                 155                 160

Thr Gln Leu Asn Gln Ser Leu Ala Lys Ser Ser Thr Ser Asp Ala Ala
                165                 170                 175

Lys Ala Asn Asp Glu Leu Glu Ile Lys Ala Thr Asp Pro Thr Asn Tyr
            180                 185                 190

Pro Asn Cys Gly Asp Val Tyr Gly Pro Leu Phe Glu Leu Asp Ala Ser
        195                 200                 205

Gly Gln Leu Val Asn Lys Asp Glu Val Ile Ser Leu Lys Asp Met Tyr
    210                 215                 220

Ile Phe Gln Ile Leu Lys Leu Val Asn Thr Lys Asp Ser Asp Phe Gln
225                 230                 235                 240

Tyr Val Ile Leu Thr Met Asn Arg Lys Asp Thr Ala Asp Arg Ser Val
                245                 250                 255

Tyr Leu Phe Val Thr Gly Ser Asn Tyr Ser Asn Ala Val Val Val Lys
            260                 265                 270

Val Lys Pro Asn Asp Thr Tyr Glu Leu Ser Lys Thr Gly Tyr Ser Val
        275                 280                 285

Thr Tyr Thr Glu Pro Thr Thr Ile Asn Gly His Tyr Val Asp Gly Thr
    290                 295                 300

Phe Tyr Val Thr Gly Ser Thr Tyr Asp Asp Gly Phe Ile Met Pro Asp
305                 310                 315                 320

Trp Gln Leu Gln His Leu Gln Ile Ile Tyr Ser Leu Gly Asn Tyr Asp
                325                 330                 335

Pro Ser Asn Thr Asp Ala Thr Ser Val Cys Glu Ile Met Pro Ser Tyr
            340                 345                 350

Glu Lys Val Pro Val Ile Lys Tyr Ser Gly Val Pro Ser Asn Ile Ser
        355                 360                 365

Gln Pro Lys Val Tyr Ile Thr Gly Phe Thr Gly Gln Glu Phe Asn Val
    370                 375                 380

Thr Asp Ile Ile Asn Asn Tyr Lys Lys Val Phe Lys Gly Tyr Tyr Leu
385                 390                 395                 400
```

-continued

```
Gln Asn Pro Asn Val Ala Ser Met Gly Thr Leu Ser Gln Phe Glu Asn
                405                 410                 415

Gly Gly Tyr Tyr Leu Lys Thr Tyr Tyr Asp Asn Asp Gly Asn Val Asp
            420                 425                 430

Phe Lys Gly Leu Tyr His Gln Ile Asp Asp Gln Gly Thr Met Ser Val
        435                 440                 445

Ser Val Leu Asn Ala Asp Asn Lys Thr Ile Val Gly Pro Glu Asn Ile
    450                 455                 460

Leu Ala Gly Lys Ser His Asn Phe Asn Phe Asn Gly His Asn Trp Ile
465                 470                 475                 480

Ala Arg Asn Pro Tyr Val Thr Ser Ser Ala His Glu Val Ile Leu Lys
                485                 490                 495

Tyr Ala Lys Leu Gly Ser Val Ile Pro Val Asp Glu Asn Gly Asn Lys
            500                 505                 510

Ile Asn Asp Gly Trp Gln Tyr Val Asn Asp Pro Asp Asp Ala Ser Lys
        515                 520                 525

Ala Thr Ser Pro Tyr Glu Lys Ala Pro Val Ile Asp Gly Tyr Val Ala
    530                 535                 540

Val Asn Pro Asp Glu Thr Ile Val Leu Pro His Asn Leu Ser Ser Asp
545                 550                 555                 560

Thr Lys Ile Tyr Tyr Arg Lys Arg Ile Lys Val Thr Tyr Ser Gly Ser
                565                 570                 575

Asp Ser Lys Thr Tyr Asp Gly Asn Pro Ala Asn Phe Glu Pro Thr Thr
            580                 585                 590

Val Gln Trp Ser Gly Leu Lys Gly Leu Asn Thr Ser Thr Leu Thr Ser
        595                 600                 605

Ala Asp Phe Thr Trp Asn Thr Ala Asp Lys Lys Ala Pro Thr Asp Ala
    610                 615                 620

Gly Lys Tyr Thr Leu Ser Leu Asn Thr Thr Gly Glu Ala Ala Leu Arg
625                 630                 635                 640

Lys Ala Asn Pro Asn Tyr Asp Leu Lys Thr Ile Ser Gly Ser Tyr Thr
                645                 650                 655

Tyr Thr Ile Asn Pro Leu Gly Ile Asp Lys Val Thr Tyr Ser Gly Ser
            660                 665                 670

Asp Ser Lys Thr Tyr Asp Gly Asn Pro Ala Asn Phe Glu Pro Thr Thr
        675                 680                 685

Val Gln Trp Ser Gly Leu Lys Gly Leu Asn Thr Ser Thr Leu Thr Ser
    690                 695                 700

Ala Asp Phe Thr Trp Asn Thr Ala Asp Lys Lys Ala Pro Thr Asp Ala
705                 710                 715                 720

Gly Lys Tyr Thr Leu Ser Leu Asn Thr Thr Gly Glu Ala Ala Leu Arg
                725                 730                 735

Lys Ala Asn Pro Asn Tyr Asp Leu Lys Thr Ile Ser Gly Ser Tyr Thr
            740                 745                 750

Tyr Thr Ile Asn Pro Leu Gly Ile Asp Lys Val Thr Tyr Ser Gly Ser
        755                 760                 765

Asp Ser Lys Thr Tyr Asp Gly Asn Pro Ala Asn Phe Glu Pro Thr Thr
    770                 775                 780

Val Gln Trp Ser Gly Leu Lys Gly Leu Asn Thr Ser Thr Leu Thr Ser
785                 790                 795                 800

Ala Asp Phe Thr Trp Asn Thr Ala Asp Lys Lys Ala Pro Thr Asp Ala
                805                 810                 815
```

-continued

```
Gly Lys Tyr Thr Leu Ser Leu Asn Thr Thr Gly Glu Ala Ala Leu Arg
            820                 825                 830

Lys Ala Asn Pro Asn Tyr Asp Leu Lys Thr Ile Ser Gly Ser Tyr Thr
        835                 840                 845

Tyr Thr Ile Asn Pro Leu Gly Ile Asp Lys Val Thr Tyr Ser Gly Ser
    850                 855                 860

Asp Ser Lys Thr Tyr Asp Gly Asn Pro Ala Asn Phe Glu Pro Thr Thr
865                 870                 875                 880

Val Gln Trp Ser Gly Leu Lys Gly Leu Asn Thr Ser Thr Leu Thr Ser
                885                 890                 895

Ala Asp Phe Thr Trp Asn Thr Ala Asp Lys Lys Ala Pro Thr Asp Ala
            900                 905                 910

Gly Lys Tyr Thr Leu Ser Leu Asn Thr Thr Gly Glu Ala Ala Leu Arg
        915                 920                 925

Lys Ala Asn Pro Asn Tyr Asp Leu Lys Thr Ile Ser Gly Ser Tyr Thr
    930                 935                 940

Tyr Thr Ile Asn Pro Leu Gly Ile Asp Lys Val Thr Tyr Ser Gly Ser
945                 950                 955                 960

Asp Ser Lys Thr Tyr Asp Gly Asn Pro Ala Asn Phe Glu Pro Thr Thr
                965                 970                 975

Val Gln Trp Ser Gly Leu Lys Gly Leu Asn Thr Ser Thr Leu Thr Ser
            980                 985                 990

Ala Asp Phe Thr Trp Asn Thr Ala  Asp Lys Lys Ala Pro  Thr Asp Ala
        995                 1000                1005

Gly Lys  Tyr Thr Leu Ser Leu  Asn Thr Thr Gly Glu  Ala Ala Leu
    1010                1015                1020

Arg Lys  Ala Asn Pro Asn Tyr  Asp Leu Lys Thr Ile  Ser Gly Ser
    1025                1030                1035

Tyr Thr  Tyr Thr Ile Asn Pro  Leu Gly Ile Val Thr  Val Asn Tyr
    1040                1045                1050

Lys Gly  Tyr Asp Lys Lys Val  Tyr Asp Gly Gln Pro  Gly Thr Ile
    1055                1060                1065

Asn Pro  Gly Lys Leu Thr Trp  Ser Lys Leu Pro Asp  Gly Thr Ser
    1070                1075                1080

Leu Lys  Met Pro Thr Trp Ser  Ile Asp Asp Phe Ala  Trp Glu Thr
    1085                1090                1095

Ala Asp  Gly Leu Ala Pro Thr  Ala Val Gly Thr Tyr  Arg Ile Ile
    1100                1105                1110

Leu Thr  Asp Ala Gly Lys Ala  Ala Leu Lys Lys Ile  Asn Pro Asn
    1115                1120                1125

Tyr Asp  Leu Ser Ser Ile Thr  Gly Val Phe Thr Tyr  Glu Ile Lys
    1130                1135                1140

Pro Ala  Gln Thr Pro Glu Ile  Leu Gly Gln Thr Pro  Glu Gln Gln
    1145                1150                1155

Pro Gly  Gln Asn Thr Asn Gln  Ser Gly Ala Glu Asn  Gly Phe Gly
    1160                1165                1170

Ser Ser  Thr Arg Pro Asn Ala  Ser Thr Asn Ser Asn  Leu Asn Gln
    1175                1180                1185

Leu Pro  Gln Thr Gly Asn Glu  His Ser Asn Thr Ala  Leu Ala Gly
    1190                1195                1200

Leu Ala  Leu Ala Phe Leu Thr  Ala Met Leu Gly Leu  Gly Lys Lys
    1205                1210                1215

Arg Lys  His Asp
```

1220

<210> SEQ ID NO 29
<211> LENGTH: 1442
<212> TYPE: PRT
<213> ORGANISM: Artificial Sequence
<220> FEATURE:
<223> OTHER INFORMATION: GbpA-MBP Chimeric Sequence

<400> SEQUENCE: 29

Met Leu Ser Arg Lys Asn Tyr Lys Glu Thr Ile Arg Lys Gln Thr Pro
1 5 10 15

Thr Lys Gln Tyr Tyr Thr Ile Lys Lys Leu Thr Val Gly Val Thr Ser
20 25 30

Val Leu Ile Gly Leu Ser Phe Met Gly Glu Leu Glu Gly Asp Ser Val
35 40 45

His Ala Asp Thr Met Thr Ala Ser Ser Glu Ser Thr Ser Val Thr Ser
50 55 60

Thr Thr Ala Gln Asp Gly Leu Lys Lys Ser Pro Gln Leu Tyr Leu Gln
65 70 75 80

Val Thr Asp Thr Asn Asn Pro Ser Thr Pro Leu Ser Ala Ser Ser Thr
85 90 95

Gly Thr Ser Lys Asn Val Thr Ser Ser Ala Ala Val Gln Val Lys Ser
100 105 110

Ala Ser Asp Glu Glu Asp Ser Asp Ser Thr Leu Ala Lys Gly Glu Asn
115 120 125

Lys Phe Ala Arg Ser Ala Val Lys Asp Ser Val Thr Asp Gly Lys Thr
130 135 140

Ser Thr Ala Glu Ile Asn Pro Ala Lys Leu Ser Ser Pro Ala Leu Ile
145 150 155 160

Thr Gln Leu Asn Gln Ser Leu Ala Lys Ser Ser Thr Ser Asp Ala Ala
165 170 175

Lys Ala Asn Asp Glu Leu Glu Ile Lys Ala Thr Asp Pro Thr Asn Tyr
180 185 190

Pro Asn Cys Gly Asp Val Tyr Gly Pro Leu Phe Glu Leu Asp Ala Ser
195 200 205

Gly Gln Leu Val Asn Lys Asp Glu Val Ile Ser Leu Lys Asp Met Tyr
210 215 220

Ile Phe Gln Ile Leu Lys Leu Val Asn Thr Lys Asp Ser Asp Phe Gln
225 230 235 240

Tyr Val Ile Leu Thr Met Asn Arg Lys Asp Thr Ala Asp Arg Ser Val
245 250 255

Tyr Leu Phe Val Thr Gly Ser Asn Tyr Ser Asn Ala Val Val Val Lys
260 265 270

Val Lys Pro Asn Asp Thr Tyr Glu Leu Ser Lys Thr Gly Tyr Ser Val
275 280 285

Thr Tyr Thr Glu Pro Thr Thr Ile Asn Gly His Tyr Val Asp Gly Thr
290 295 300

Phe Tyr Val Thr Gly Ser Thr Tyr Asp Asp Gly Phe Ile Met Pro Asp
305 310 315 320

Trp Gln Leu Gln His Leu Gln Ile Ile Tyr Ser Leu Gly Asn Tyr Asp
325 330 335

Pro Ser Asn Thr Asp Ala Thr Ser Val Cys Glu Ile Met Pro Ser Tyr
340 345 350

Glu Lys Val Pro Val Ile Lys Tyr Ser Gly Val Pro Ser Asn Ile Ser

```
        355                 360                 365

Gln Pro Lys Val Tyr Ile Thr Gly Phe Thr Gly Gln Glu Phe Asn Val
    370                 375                 380

Thr Asp Ile Ile Asn Asn Tyr Lys Lys Val Phe Lys Gly Tyr Tyr Leu
385                 390                 395                 400

Gln Asn Pro Asn Val Ala Ser Met Gly Thr Leu Ser Gln Phe Glu Asn
                405                 410                 415

Gly Gly Tyr Tyr Leu Lys Thr Tyr Tyr Asp Asn Asp Gly Asn Val Asp
            420                 425                 430

Phe Lys Gly Leu Tyr His Gln Ile Asp Asp Gln Gly Thr Met Ser Val
        435                 440                 445

Ser Val Leu Asn Ala Asp Asn Lys Thr Ile Val Gly Pro Glu Asn Ile
    450                 455                 460

Leu Ala Gly Lys Ser His Asn Phe Asn Phe Asn Gly His Asn Trp Ile
465                 470                 475                 480

Ala Arg Asn Pro Tyr Val Thr Ser Ser Ala His Glu Val Ile Leu Lys
                485                 490                 495

Tyr Ala Lys Leu Gly Ser Val Ile Pro Val Asp Glu Asn Gly Asn Lys
            500                 505                 510

Ile Asn Asp Gly Trp Gln Tyr Val Asn Asp Pro Asp Asp Ala Ser Lys
        515                 520                 525

Ala Thr Ser Pro Tyr Glu Lys Ala Pro Val Ile Asp Gly Tyr Val Ala
    530                 535                 540

Val Asn Pro Asp Glu Thr Ile Val Leu Pro His Asn Leu Ser Ser Asp
545                 550                 555                 560

Thr Lys Ile Tyr Tyr Arg Lys Arg Ile Gly Ser Ala Gly Ser Ala Glu
                565                 570                 575

Ala Gly Ser Asn Trp Ser His Pro Gln Phe Glu Lys Gly Ser Ala Gly
            580                 585                 590

Ser Ala Ala Gly Ser His Gly Tyr Val Ser Ala Val Glu Asn Gly Val
        595                 600                 605

Ala Glu Gly Arg Val Thr Leu Cys Lys Phe Ala Ala Asn Gly Thr Gly
    610                 615                 620

Glu Lys Asn Thr His Cys Gly Ala Ile Gln Tyr Glu Pro Gln Ser Val
625                 630                 635                 640

Glu Gly Pro Asp Gly Phe Pro Val Thr Gly Pro Arg Asp Gly Lys Ile
                645                 650                 655

Ala Ser Ala Glu Ser Ala Leu Ala Ala Ala Leu Asp Glu Gln Thr Ala
            660                 665                 670

Asp Arg Trp Val Lys Arg Pro Ile Gln Ala Gly Pro Gln Thr Phe Glu
        675                 680                 685

Trp Thr Phe Thr Ala Asn His Val Thr Lys Asp Trp Lys Tyr Tyr Ile
    690                 695                 700

Thr Lys Pro Asn Trp Asn Pro Asn Gln Pro Leu Ser Arg Asp Ala Phe
705                 710                 715                 720

Asp Leu Asn Pro Phe Cys Val Val Glu Gly Asn Met Val Gln Pro Pro
                725                 730                 735

Lys Arg Val Ser His Glu Cys Ile Val Pro Glu Arg Glu Gly Tyr Gln
            740                 745                 750

Val Ile Leu Ala Val Trp Asp Val Gly Asp Thr Ala Ala Ser Phe Tyr
        755                 760                 765

Asn Val Ile Asp Val Lys Phe Asp Gly Gly Ser Ala Gly Ser Ala Ala
    770                 775                 780
```

```
Gly Ser Gly Glu Phe Lys Val Thr Tyr Ser Gly Ser Asp Ser Lys Thr
785                 790                 795                 800

Tyr Asp Gly Asn Pro Ala Asn Phe Glu Pro Thr Thr Val Gln Trp Ser
                805                 810                 815

Gly Leu Lys Gly Leu Asn Thr Ser Thr Leu Thr Ser Ala Asp Phe Thr
            820                 825                 830

Trp Asn Thr Ala Asp Lys Lys Ala Pro Thr Asp Ala Gly Lys Tyr Thr
        835                 840                 845

Leu Ser Leu Asn Thr Thr Gly Glu Ala Ala Leu Arg Lys Ala Asn Pro
    850                 855                 860

Asn Tyr Asp Leu Lys Thr Ile Ser Gly Ser Tyr Thr Tyr Thr Ile Asn
865                 870                 875                 880

Pro Leu Gly Ile Asp Lys Val Thr Tyr Ser Gly Ser Asp Ser Lys Thr
                885                 890                 895

Tyr Asp Gly Asn Pro Ala Asn Phe Glu Pro Thr Thr Val Gln Trp Ser
            900                 905                 910

Gly Leu Lys Gly Leu Asn Thr Ser Thr Leu Thr Ser Ala Asp Phe Thr
        915                 920                 925

Trp Asn Thr Ala Asp Lys Lys Ala Pro Thr Asp Ala Gly Lys Tyr Thr
    930                 935                 940

Leu Ser Leu Asn Thr Thr Gly Glu Ala Ala Leu Arg Lys Ala Asn Pro
945                 950                 955                 960

Asn Tyr Asp Leu Lys Thr Ile Ser Gly Ser Tyr Thr Tyr Thr Ile Asn
                965                 970                 975

Pro Leu Gly Ile Asp Lys Val Thr Tyr Ser Gly Ser Asp Ser Lys Thr
            980                 985                 990

Tyr Asp Gly Asn Pro Ala Asn Phe  Glu Pro Thr Thr Val  Gln Trp Ser
        995                 1000                1005

Gly Leu  Lys Gly Leu Asn Thr  Ser Thr Leu Thr Ser  Ala Asp Phe
    1010                 1015                 1020

Thr Trp  Asn Thr Ala Asp Lys  Lys Ala Pro Thr Asp  Ala Gly Lys
    1025                 1030                 1035

Tyr Thr  Leu Ser Leu Asn Thr  Thr Gly Glu Ala Ala  Leu Arg Lys
    1040                 1045                 1050

Ala Asn  Pro Asn Tyr Asp Leu  Lys Thr Ile Ser Gly  Ser Tyr Thr
    1055                 1060                 1065

Tyr Thr  Ile Asn Pro Leu Gly  Ile Asp Lys Val Thr  Tyr Ser Gly
    1070                 1075                 1080

Ser Asp  Ser Lys Thr Tyr Asp  Gly Asn Pro Ala Asn  Phe Glu Pro
    1085                 1090                 1095

Thr Thr  Val Gln Trp Ser Gly  Leu Lys Gly Leu Asn  Thr Ser Thr
    1100                 1105                 1110

Leu Thr  Ser Ala Asp Phe Thr  Trp Asn Thr Ala Asp  Lys Lys Ala
    1115                 1120                 1125

Pro Thr  Asp Ala Gly Lys Tyr  Thr Leu Ser Leu Asn  Thr Thr Gly
    1130                 1135                 1140

Glu Ala  Ala Leu Arg Lys Ala  Asn Pro Asn Tyr Asp  Leu Lys Thr
    1145                 1150                 1155

Ile Ser  Gly Ser Tyr Thr Tyr  Thr Ile Asn Pro Leu  Gly Ile Asp
    1160                 1165                 1170

Lys Val  Thr Tyr Ser Gly Ser  Asp Ser Lys Thr Tyr  Asp Gly Asn
    1175                 1180                 1185
```

```
Pro Ala  Asn Phe Glu Pro Thr  Thr Val Gln Trp Ser  Gly Leu Lys
    1190                 1195                 1200

Gly Leu  Asn Thr Ser Thr Leu  Thr Ser Ala Asp Phe  Thr Trp Asn
    1205                 1210                 1215

Thr Ala  Asp Lys Lys Ala Pro  Thr Asp Ala Gly Lys  Tyr Thr Leu
    1220                 1225                 1230

Ser Leu  Asn Thr Thr Gly Glu  Ala Ala Leu Arg Lys  Ala Asn Pro
    1235                 1240                 1245

Asn Tyr  Asp Leu Lys Thr Ile  Ser Gly Ser Tyr Thr  Tyr Thr Ile
    1250                 1255                 1260

Asn Pro  Leu Gly Ile Val Thr  Val Asn Tyr Lys Gly  Tyr Asp Lys
    1265                 1270                 1275

Lys Val  Tyr Asp Gly Gln Pro  Gly Thr Ile Asn Pro  Gly Lys Leu
    1280                 1285                 1290

Thr Trp  Ser Lys Leu Pro Asp  Gly Thr Ser Leu Lys  Met Pro Thr
    1295                 1300                 1305

Trp Ser  Ile Asp Asp Phe Ala  Trp Glu Thr Ala Asp  Gly Leu Ala
    1310                 1315                 1320

Pro Thr  Ala Val Gly Thr Tyr  Arg Ile Ile Leu Thr  Asp Ala Gly
    1325                 1330                 1335

Lys Ala  Ala Leu Lys Lys Ile  Asn Pro Asn Tyr Asp  Leu Ser Ser
    1340                 1345                 1350

Ile Thr  Gly Val Phe Thr Tyr  Glu Ile Lys Pro Ala  Gln Thr Pro
    1355                 1360                 1365

Glu Ile  Leu Gly Gln Thr Pro  Glu Gln Gln Pro Gly  Gln Asn Thr
    1370                 1375                 1380

Asn Gln  Ser Gly Ala Glu Asn  Gly Phe Gly Ser Ser  Thr Arg Pro
    1385                 1390                 1395

Asn Ala  Ser Thr Asn Ser Asn  Leu Asn Gln Leu Pro  Gln Thr Gly
    1400                 1405                 1410

Asn Glu  His Ser Asn Thr Ala  Leu Ala Gly Leu Ala  Leu Ala Phe
    1415                 1420                 1425

Leu Thr  Ala Met Leu Gly Leu  Gly Lys Lys Arg Lys  His Asp
    1430                 1435                 1440
```

<210> SEQ ID NO 30
<211> LENGTH: 4329
<212> TYPE: DNA
<213> ORGANISM: Artificial Sequence
<220> FEATURE:
<223> OTHER INFORMATION: GbpA-MBP Chimeric Sequence

<400> SEQUENCE: 30

```
atgctatcaa gaaaaaatta taaggaaact atacgaaaac agacacctac aaaacagtac     60

tatactatta agaaattaac tgttggggtt acttcggtat taattggtct atcctttatg    120

ggagaactag aaggggatag cgttcatgcg gacacgatga cagcaagcag tgagtcaaca    180

agtgttacgt cgacgactgc tcaggatggt ttaaaaaaat ctccacaact ctatttgcaa    240

gttactgata caaataaccc aagtacacca ttaagtgctt catccacagg gactagtaag    300

aatgttacct catcagctgc ggtacaagtg aagtccgcta gtgatgaaga agatagtgat    360

tctacactag ctaagggaga aaataaattt gctcggtcag cagtaaaaga ttcagtcact    420

gatgggaaaa caagtacagc agaaattaat ccggcaaaat taagcagtcc tgctttaata    480

acgcaactca accaatcctt agctaagagc agtacgagtg atgcagcaaa agctaatgat    540
```

-continued

```
gagttagaaa ttaaagcaac agatccgact aattatccaa actgtggcga tgtgtatggg    600
ccattatttg aattggatgc tagcggacag cttgttaata aagatgaagt tatatctctt    660
aaagatatgt atattttcca aatattgaaa ttagtaaata caaaagatag tgactttcaa    720
tatgtaatat taacaatgaa tcgtaaagat actgcagata ggtctgtata tctttttgta    780
actggaagca attatagtaa tgctgttgtt gttaaagtaa agccaaatga tacttatgaa    840
ttaagtaaaa ctggatatag tgttacttat acagaaccaa caactataaa tggacattat    900
gttgatggaa ctttttatgt tacaggaagt acttacgatg atggttttat aatgccagat    960
tggcaactgc agcaccttca gattatatat agtttaggaa attatgatcc aagcaatact   1020
gacgcaacat cagtttgtga aataatgcca agttatgaaa aggtaccggt aattaaatat   1080
agtggagtac cttcaaatat tagccaacct aaggtttaca ttaccgggtt tacgggtcaa   1140
gagtttaacg ttacagatat tattaacaat tataagaaag tttttaaggg ctactatctt   1200
caaaatccta atgtggcgtc catgggaact ctttcccaat ttgagaatgg tggttattac   1260
ttaaagacat attatgataa tgatggtaat gttgacttta agggcttgta tcatcaaatt   1320
gatgatcagg gaacaatgag tgtgagtgtt cttaatgcag ataataaaac aattgttgga   1380
cctgaaaata ttcttgctgg taaatcgcat aactttaact ttaatggtca taactggatt   1440
gcgcggaatc cttatgtcac tagttcagct cacgaagtca tattaaagta tgctaagtta   1500
ggttcagtta ttcctgttga tgaaaacgga aataaaataa acgatggatg gcaatatgtt   1560
aatgatccag atgatgcttc caaagccact agcccatatg aaaaagcgcc agttatcgat   1620
ggttatgtag ctgtaaatcc agatgaaacg atcgttcttc ctcataactt aagtagtgac   1680
acaaagattt attaccgaaa gaggattggt agtgctggta gtgctgaagc tggtagtaat   1740
tggagtcatc cacaatttga aaaaggtagt gctggtagtg ctgctggtag tcacggttac   1800
gtatcggcag ttgaaaacgg tgtagccgaa gggcgtgtaa ctctttgtaa atttgcagcc   1860
aacggtacag gggagaaaaa cacacactgt ggtgcaattc aatatgaacc tcaatctgta   1920
gaaggtcctg atggtttccc tgtaacaggt cctcgtgatg gtaaaattgc ctctgcagaa   1980
tctgcccttg cagccgcact tgatgaacaa actgcagacc gttgggtcaa gcgtcctatt   2040
caagcaggtc ctcaaacttt cgagtggacc ttcactgcaa accacgtaac gaaggattgg   2100
aagtactaca ttactaagcc aaactggaac ccaaaccagc ctcttagccg tgatgcattt   2160
gacttgaacc ctttctgtgt cgtagaaggg aacatggttc agcctcctaa gcgtgtatct   2220
cacgaatgta ttgttcctga acgtgaaggg taccaggtaa tcctagcagt ctgggatgta   2280
ggtgatactg cagcctcgtt ctacaacgtt attgacgtta agtttgacgg tggtagtgct   2340
ggtagtgctg ctggtagtgg tgaatttaaa gttacctata gtggtagtga cagcaagacc   2400
tacgatggta acccagctaa cttcgagcca acgacagttc agtggagtgg cttgaaagga   2460
ctgaacactt caaccttaac gtccgctgac ttcacgtgga atactgcgga taagaaggca   2520
ccaacggatg ccggtaagta cacacttagt ttgaatacga ccggagaagc agccttacgt   2580
aaggctaacc cgaactatga tctcaagaca attagcggta gttacaccta cacgattaat   2640
ccactaggga ttgataaagt tacctatagt ggtagtgaca gcaagaccta cgatggtaac   2700
ccagctaact tcgagccaac gacagttcag tggagtggct tgaaaggact gaacacttca   2760
accttaacgt ccgctgactt cacgtggaat actgcggata agaaggcacc aacggatgcc   2820
ggtaagtaca cacttagttt gaatacgacc ggagaagcag ccttacgtaa ggctaacccg   2880
aactatgatc tcaagacaat tagcggtagt tacacctaca cgattaatcc actagggatt   2940
```

gataaagtta cctatagtgg tagtgacagc aagacctacg atggtaaccc agctaacttc 3000
gagccaacga cagttcagtg gagtggcttg aaaggactga acacttcaac cttaacgtcc 3060
gctgacttca cgtggaatac tgcggataag aaggcaccaa cggatgccgg taagtacaca 3120
cttagtttga atacgaccgg agaagcagcc ttacgtaagg ctaacccgaa ctatgatctc 3180
aagacaatta gcggtagtta cacctacacg attaatccac tagggattga taaagttacc 3240
tatagtggta gtgacagcaa gacctacgat ggtaacccag ctaacttcga gccaacgaca 3300
gttcagtgga gtggcttgaa aggactgaac acttcaacct taacgtccgc tgacttcacg 3360
tggaatactg cggataagaa ggcaccaacg gatgccggta agtacacact tagtttgaat 3420
acgaccggag aagcagcctt acgtaaggct aacccgaact atgatctcaa gacaattagc 3480
ggtagttaca cctacacgat taatccacta gggattgata aagttaccta tagtggtagt 3540
gacagcaaga cctacgatgg taacccagct aacttcgagc caacgacagt tcagtggagt 3600
ggcttgaaag gactgaacac ttcaacctta acgtccgctg acttcacgtg gaatactgcg 3660
gataagaagg caccaacgga tgccggtaag tacacactta gtttgaatac gaccggagaa 3720
gcagccttac gtaaggctaa cccgaactat gatctcaaga caattagcgg tagttacacc 3780
tacacgatta atccactagg gattgtgact gtaaattaca agggctatga taagaaagtc 3840
tatgatggtc aacctggaac gattaatccg ggtaaattaa cgtggagtaa gttgccagat 3900
ggtacttcat tgaagatgcc aacatggagt atagatgatt tcgcttggga aacagctgat 3960
ggcttagcac caacggcagt aggaacttat cggattatct tgacggatgc tggtaaggct 4020
gcactaaaga agattaatcc aaattatgac ttaagcagta ttactggtgt ctttacttat 4080
gaaattaagc cagcacagac accagaaatc ttaggccaaa cacctgagca acaaccaggc 4140
caaaatacta atcaatcagg agctgaaaac ggctttggtt cttctacaag gcctaatgca 4200
tcaactaact ccaatcttaa tcaacttcca cagactggta atgagcattc taatactgca 4260
cttgctggtc tagcattggc tttcttgact gctatgcttg gtttgggcaa gaagcgtaaa 4320
catgattag 4329

<210> SEQ ID NO 31
<211> LENGTH: 4991
<212> TYPE: DNA
<213> ORGANISM: Salmonella enterica

<400> SEQUENCE: 31
cccaatatcc ctgtcaatta tgttgtttta gatcaacaac aagccgggta tgtggttaac 60
cacaatagag cgcaccccgc ctcgattttt acactgtaaa tcatcgacat tttttattca 120
ttacacatga accaacatcg tgacaaatgt ttcattgttg gcaatgtgga cgggagtcaa 180
tatggacagc agtaaacggc aatttctcca gcagcttggc gtcctgaccg ctggcgcctc 240
gctggttccg ctggctgaag cgaaatttcc tttttcgccg gagcggcatg aaggctctcc 300
ccgacaccgt tacgccatgc ttatcgatct gcggcgttgt atcggctgtc agtcctgtac 360
cgtaagttgc actattgaaa accaaacgcc gcaaggcgcg tttcgtacga cggtgaacca 420
ataccaggtc cagcgtgaag gtagtcagga agtcacgaat gtgctgttgc cgcgtctgtg 480
caaccattgc gataaccccc cctgtgtgcc ggtctgcccg gtacaagcca cctttcagcg 540
ggaagatggc attgtggtgg tggataacaa acgctgcgtc ggctgcgcct attgtgtcca 600
ggcgtgtcct tacgacgccc gatttatcaa tcatgaaacg caaactgccg ataaatgcac 660
gttttgcgtc catcgtctgg aagccggact gttacccgct tgcgtagagt cctgcgtcgg 720
cggcgcgcgt attattggcg atatcaaaga tccccatagc cgcatcgcca ccatgcttca 780
tcagcatcgc gacgctatca aggtattaaa gccggaaaac ggcacgtcgc cccatgtttt 840
ctacctgggt ctggacgacg cctttgtcac cccattaatg ggccgtgcgc agcccgcgct 900
ttggcaggag gtctgaatga cgcattcact catcattgaa gaagtgctgg ctcacccgca 960
ggacattagc tggctgccgt gggcggtaca atatttcttt tttattggca ttgccgcctg 1020
cgccgcactg tttgcctgtt atcttcactg gcggaaaaaa gacgccgcaa cagaagaaaa 1080
tcgggcatta ctgattgcca ttacctgtgc gattaccgca ccgctggcgc tgacggcgga 1140
tctgcaccag accgcccgcg tctggcattt ctatgcctgg ccgacgccct ggtcgtggat 1200
gccctgggga gcgttattcc tgccgctgtt taccggattt ctcgctctgt ggttcctggc 1260
gcagcagatt aaacgattat tcaataaaag ttacaacgtc actaaatggt tggcgttagc 1320
cagcgcgctt tgcgcggtgg gcctgttgat ttataccggc cgcgaagtct ccgttgtgct 1380
ggcgcgccca atctggttta gctacgcctt ccccgtggcg atgtttctta gcgccttaca 1440
ggcgttcttc gcgctgatga ttgtcgccgc ccgacgcgac tcggtaaggc tgccaaaaat 1500
attgtgggga caaatctgga cgctggcggc gctggggctg gttgtggcca tgtgggttag 1560
cggcgatacg ctttccggca cggcaatccg tcagtggatt accgtcgccc tgtcagccaa 1620
atattacgct gtcggctggg tagcgctgtg ggtatgcaca ctgctgttct gtagcctggc 1680
gctacgccat ccgttatcac agctaagacg cgtcctgctg gttctcagcg cgctggcgct 1740
atgttggctg atgcgctgga cattgttgat tcaggtacaa accgtcccca agttcaacgc 1800
gcaatttaac ccttactcgt taccaggcgg aacggatggc tggctggcta ttctcggcac 1860
cttcggcctg tggatagcgc tactgattat tattcgtgaa acgctgaacg gactcaccag 1920
gagattacaa catggctaat ttaacccgtc gtcagtggct aaaagtcggt ctcgccgtcg 1980
gtgggatggt cacttttggt ctgagctacc gtgatgtggc gaaacgcgca attgatggcc 2040
tgttaaacgg gacgtccggc aaggtaacgc gcgaccgcat ctttggcaat gcgttaattc 2100
cggaggcgca ggcgcaaaca cactggcagc aaaatccaca acaaaccatc gccatgacgc 2160
aatgcttcgg ctgttggaca cagtgcggta tccgcgcccg ggttaatgcc gatggcaaag 2220
tgatacgcat cgccggcaat ccctatcacc ccttgtcgca ggaacacccg attgactcgt 2280
ccgtcccttt tagcgaagcc atggagcaac tggcgggaga aagcggtctt gacgcccgct 2340
caaccgcctg cgcgcgcggc gccacgctgc tggaaagcct gtacagtccg ctacgactgc 2400
ttgaaccgat gaaacgcgtg ggtaaacgcg gcgaagggaa atggcagcgc atcagctttg 2460
agcaacttat tgaagaagtc gtggaaggcg gcgatctgtt tggcgaaggt catgtggacg 2520
gactgcgcgc tattcatgcg ccggatacgc caattgacgc aaagcacccc agtttcgggc 2580
ccaaaaccaa tcagttactg gtcacgaata ccagcgacga aggccgcgat gcgtttctgc 2640
gtcgttttgc gctaaatagc ttcggcagca agaatttcgg cgcgcatggc gcctactgtg 2700
gactggctta ccgggccggc tccggggcat tgatgggcga tctggataaa aacccgcatg 2760
tcaaacccga ctgggaaaac gtggagtttg cgctctttat gggcacctcc ccggcacagt 2820
ccggcaatcc gtttaaacgc caggcacgtc agttggcgag cgcccgactg cgtgagaatt 2880
ttcaatacgt cgtggtcgcc cccgccctcc ccttatcaac ggtgctcgcc gatcctcgcg 2940
gtcgctggca accggtcatg cccggcagtg attcggcgct ggcaatgggg atgatccgct 3000
ggatcatgga taatcaacgt tataatgctg attatctggc gattcccggc gtacaggcga 3060

```
tgcagcaggc cggcgagcaa agttggacca acgccacgca cctggtcatt gcggatgagc   3120
tgccgacgct tgccggacaa cacctgacgc tgcgccatct tacgcccgat ggcgaagaga   3180
cccctgtcgt actgaatacc gacggcgagt tggtcgatgc gtccacttgc cgacaggcac   3240
ggcttttcgt gacgcagtac gttacgctcg ccgacggcca acgggtcacg gtgaagagcg   3300
ggttgcaacg cctgaaagag gcggcagaaa agctctcgtt ggcgcaatac agcgaacagt   3360
gcggcgtgcc ggaagcgcaa attatcgcgc tggcggaaac ctttaccagt cacggacgta   3420
aagctgcggt catcagtcac ggcggcatga tggccggcaa tgggttttat aacgcctggt   3480
cggtcatgat gcttaacgcg ctgatcggca acctcagctt gtccggcggc gtctttgtcg   3540
gcggcggcaa attcaacggc gttagcgacg gcccccgcta caacatgaac agttttgccg   3600
gaaaagtgaa accgtccggg ttaagtattg cccgtagcaa aaccgcttat gaagcatcgg   3660
aagaataccg cgacaaaatt gccggtgggc aatcccctta tccagccaaa gcgccgtggt   3720
atccctttgt ggcaggccag cttaccgaac tgttgacctc cgcgctcgaa ggctatcctt   3780
atccgcttaa agcctggatt tccaatatga gcaacccgtt ttacggtgtt cccggtctac   3840
gcgccgtggc ggaagaaaaa ctaaaagacc ctcgccgact gccgctcttt atcgcgattg   3900
acgcctttat gaatgaaacg acggcgctgg cggattacat tgtgccggat acgcacaatt   3960
ttgagagctg gggctttacg gcgccctggg gcggcgtagc cagtaaagcc actaccgccc   4020
gctggccggt tgtcgccccc gccactcacc gcacggcgga cgggcaacct gtctcaatgg   4080
aagcattttg tattgcggta gcaaaacggc tccatctgcc cggcttcggc gaccgggcga   4140
taaccgatcc gcagggcaat acttttccac tgaaccgggc ggaagacttc tatctgcgcg   4200
tagccgctaa tatcgccttt atgggcaaga cgccggtcgc gctggcaaat caggaagata   4260
tttcgcttac cggcgtcagc cgcattctgc cagcaattca gcacacgctt aaagctgatg   4320
aggtcggtcg cgtggcgttt atctactcgc gtggcggccg gtttgcgccc gaggatagcg   4380
gctatacgga gcaacggtta ggtaacgcgt ggaaaaaacc cttacagatc tggaatgcag   4440
atgtcgccgc ccaccgtcac gccatcaccg gggagcgctt cagcggttgc ccggtctggt   4500
atccggcgcg tttgtcagat ggtcgtgcga ttgacgacca gtttcccatt gggcaatggc   4560
cgctgaaact gatttcattt aaatcaaata ccatgtccag ctcaacagcc gtcatcccgc   4620
gcttacacca tgtgaagcca gcaaacctgg tggcgctgaa tccgcaagac ggcgagcgtt   4680
atggactgca acatggcgat cgggtacgga tcattacgcc gggcggtcag gtcgtggcgc   4740
aaatcagttt gttaaatggc gtgatgccag gcgtcatcgc catcgaacac ggatatggcc   4800
accgcgagat gggcgcaacg cagcactctc tggatggcgt gcctatgccg tatgatccac   4860
aaatcagggc aggcataaat cttaacgatc tgggctttgc cgatccgaca agaaccatta   4920
ccaacacctg gctcgactgg gtttctggcg cggcagtacg tcaggggctg ccggcaaaaa   4980
tcgagcgtat a                                                        4991
```

<210> SEQ ID NO 32
<211> LENGTH: 2374
<212> TYPE: DNA
<213> ORGANISM: Salmonella enterica

<400> SEQUENCE: 32

```
tcatggctca tacgttgttc gtattctggt ctctggcgag gccatttttt cgaaacgcct     60
aatcagttcc gccaggctac cggcctgcat tttttccatg actctggcgc ggtgcacctc    120
```

-continued

```
tacggtacgc accgcgatat tcatcgcttc cgcaatttca cggttcataa atccttttgc    180
caccaggctg gccagctcac gctctttcgg cgtcaactgc tggtaacaca gtataatctc    240
acgacgcgcc accgctgccg atgaaaccgt cagcgcacgc tccagcgccg cctgtagcgg    300
ttttaccgat accggttttt gcagaaaatc gacggcgccg cgtttcatct gctccacggc    360
catcggtaca tcgccatgcc cggtaagaaa aacaaccgcc agggtacttc cgcactggcg    420
caacgcatca tgaacgccct gcccatccag taccggcatt cgcatatcca gtaatacgac    480
cccggcctga tacagactgg cctgcgccaa aaaatccgcc ccctgcgtcc agcattttac    540
gtcatatccc agactttcca gtaaaaacgc gcacgcgtta gtgaccgccg tatcatcatc    600
cagtagatga attgtcgcca tccctgcccc cattttcatg taagaaatgt atcgtaacca    660
ccgttcccga cagaccgtcc ggcgcggtct ggttcctgat gctgatatcg ccccgcccat    720
accgcaccag ccgctggcaa atcgccagcc ctaagcccat cccctcttta cgggtggtca    780
taaacggctg aaacgcctga cgtaatagcg cctcatcgat tcccccggcg ttatcctgta    840
aaacaatact gatgccgttt tcagtgcgtt cagcaacgat ccataaatgg gtggcgcccg    900
cctgagccgc attaagaatg atattcgcca gcacctgttc cagcagcact gacggcagcg    960
ttacgcgcag cgcagcgcta acctcggtat gcagagtcac tgtcggaaac tgttgcgcca   1020
tacgcaacaa ttgccagaca tgatcaatcg cctcgcgaat ggctatggcc ttccacgctt   1080
cggttagcac cgggttgccc tgcgcctggc tgacccagtg acgcaggtta cgcagagtat   1140
ccgcaccgcg ttgcgcctgc tggtcaatct gctccagcgc cggcagcaag ggatgctgtt   1200
catctgcagc gcgcagtcga atcaggcacc cctgggcata atgtcgaatc gcggaaagcg   1260
gctgattaag ctcatgggca aacccggagg tcatttcacc caacacgctc atttgccggg   1320
cggtttccag cgcccgctca tgctgatgaa gaactacgct attacgttcc agttgctttc   1380
cacgtcgacg caccagcagc atgacccaaa tataattgag cgtgagcaac aagaacgcca   1440
gaatcacgcc gccgaccatt agctggtgct ggattaacca acttttgaca tccagccaca   1500
gtcgacgctg ctgagggtgc tgacgaacat cacgcagcaa ggcttccacc tgactggtgg   1560
acgcaggcgc gccccagtga aatgacgcgg cggcgggcgc gttgaatagc gctcgcgtta   1620
cgcgatccgc cagcgcatcg cttaccgcag gtagcgccgc gaacgaccag tcaggatata   1680
acggcgtact ggttaagcaa ggcaggggcg tcggtcggga aagcagcgcg ataaagtcct   1740
ttttattaat caatccttcc tgatccatat tttctaacag gcacactggc acaattgccg   1800
cctgcaccgc tttttcgcgc agcatataga ctaaggcatc gccaggaaat ccggtaaaac   1860
ggagatgaaa atcgcgctcc gggcgtaagc ccgcgtcgct gagcgcttta tagcctaata   1920
aatagccgcc aaacgcctga gcatcaatcg cgccgacggt cttaccgatg agatcatgcg   1980
ccgtggtgat gccgctatcg cgccgggtca aaatcacgct gccaataaca ttactcaccg   2040
ctttcccatc gcgcgtggag cgcagggaag ctaaccagcg cagcggcgca tggctgttca   2100
gttggacaaa ttgcgccggg ttggttatca caaactgcac ggttccctgg ttaacggcct   2160
cctgcatttg atgcagatcc agcggctgga tgtgaaaggt ttcgcctgga agctgttggc   2220
ttaatgtctt tgccaacggt tgccagtggc tacgcgtaga cgcctcgccg cgcatggcca   2280
aaataccgat attccacgtc cctgcccacg cgccatgaca aagtagccct actgccgcca   2340
acaccgccag gcgccttacg gttttacctc tcac                                2374
```

<210> SEQ ID NO 33
<211> LENGTH: 3060

<212> TYPE: DNA
<213> ORGANISM: Salmonella enterica

<400> SEQUENCE: 33
atggctaatt taacccgtcg tcagtggcta aaagtcggtc tcgccgtcgg tgggatggtc 60
acttttggtc tgagctaccg tgatgtggcg aaacgcgcaa ttgatggcct gttaaacggg 120
acgtccggca aggtaacgcg cgaccgcatc tttggcaatg cgttaattcc ggaggcgcag 180
gcgcaaacac actggcagca aaatccacaa caaaccatcg ccatgacgca atgcttcggc 240
tgttggacac agtgcggtat ccgcgcccgg gttaatgccg atggcaaagt gatacgcatc 300
gccggcaatc cctatcaccc cttgtcgcag gaacacccga ttgactcgtc cgtccctttt 360
agcgaagcca tggagcaact ggcgggagaa agcggtcttg acgcccgctc aaccgcctgc 420
gcgcgcggcg ccacgctgct ggaaagcctg tacagtccgc tacgactgct tgaaccgatg 480
aaacgcgtgg gtaaacgcgg cgaagggaaa tggcagcgca tcagctttga gcaacttatt 540
gaagaagtcg tggaaggcgg cgatctgttt ggcgaaggtc atgtggacgg actgcgcgct 600
attcatgcgc cggatacgcc aattgacgca aagcacccca gtttcgggcc caaaaccaat 660
cagttactgg tcacgaatac cagcgacgaa ggccgcgatg cgtttctgcg tcgttttgcg 720
ctaaatagct tcggcagcaa gaatttcggc gcgcatggcg cctactgtgg actggcttac 780
cgggccggct ccggggcatt gatgggcgat ctggataaaa acccgcatgt caaacccgac 840
tgggaaaacg tggagtttgc gctctttatg ggcacctccc cggcacagtc cggcaatccg 900
tttaaacgcc aggcacgtca gttggcgagc gcccgactgc gtgagaattt tcaatacgtc 960
gtggtcgccc ccgccctccc cttatcaacg gtgctcgccg atcctcgcgg tcgctggcaa 1020
ccggtcatgc ccggcagtga ttcggcgctg gcaatgggga tgatccgctg gatcatggat 1080
aatcaacgtt ataatgctga ttatctggcg attcccggcg tacaggcgat gcagcaggcc 1140
ggcgagcaaa gttggaccaa cgccacgcac ctggtcattg cggatgagct gccgacgctt 1200
gccggacaac acctgacgct gcgccatctt acgcccgatg gcgaagagac ccctgtcgta 1260
ctgaataccg acggcgagtt ggtcgatgcg tccacttgcc gacaggcacg gcttttcgtg 1320
acgcagtacg ttacgctcgc cgacggccaa cgggtcacgg tgaagagcgg gttgcaacgc 1380
ctgaaagagg cggcagaaaa gctctcgttg gcgcaataca gcgaacagtg cggcgtgccg 1440
gaagcgcaaa ttatcgcgct ggcggaaacc tttaccagtc acggacgtaa agctgcggtc 1500
atcagtcacg gcggcatgat ggccggcaat gggttttata acgcctggtc ggtcatgatg 1560
cttaacgcgc tgatcggcaa cctcagcttg tccggcggcg tctttgtcgg cggcggcaaa 1620
ttcaacggcg ttagcgacgg cccccgctac aacatgaaca gttttgccgg aaaagtgaaa 1680
ccgtccgggt taagtattgc ccgtagcaaa accgcttatg aagcatcgga agaataccgc 1740
gacaaaattg ccggtgggca atccccttat ccagccaaag cgccgtggta tccctttgtg 1800
gcaggccagc ttaccgaact gttgacctcc gcgctcgaag gctatcctta tccgcttaaa 1860
gcctggattt ccaatatgag caacccgttt tacggtgttc ccggtctacg cgccgtggcg 1920
gaagaaaaac taaaagaccc tcgccgactg ccgctcttta tcgcgattga cgcctttatg 1980
aatgaaacga cggcgctggc ggattacatt gtgccggata cgcacaattt tgagagctgg 2040
ggctttacgg cgccctgggg cggcgtagcc agtaaagcca ctaccgcccg ctggccggtt 2100
gtcgcccccg ccactcaccg cacggcggac gggcaacctg tctcaatgga agcattttgt 2160
attgcggtag caaaacggct ccatctgccc ggcttcggcg accgggcgat aaccgatccg 2220

-continued

```
cagggcaata cttttccact gaaccgggcg gaagacttct atctgcgcgt agccgctaat   2280

atcgccttta tgggcaagac gccggtcgcg ctggcaaatc aggaagatat ttcgcttacc   2340

ggcgtcagcc gcattctgcc agcaattcag cacacgctta aagctgatga ggtcggtcgc   2400

gtggcgttta tctactcgcg tggcggccgg tttgcgcccg aggatagcgg ctatacggag   2460

caacggttag gtaacgcgtg gaaaaaaccc ttacagatct ggaatgcaga tgtcgccgcc   2520

caccgtcacg ccatcaccgg ggagcgcttc agcggttgcc cggtctggta tccggcgcgt   2580

ttgtcagatg gtcgtgcgat tgacgaccag tttcccattg ggcaatggcc gctgaaactg   2640

atttcattta aatcaaatac catgtccagc tcaacagccg tcatcccgcg cttacaccat   2700

gtgaagccag caaacctggt ggcgctgaat ccgcaagacg gcgagcgtta tggactgcaa   2760

catggcgatc gggtacggat cattacgccg ggcggtcagg tcgtggcgca aatcagtttg   2820

ttaaatggcg tgatgccagg cgtcatcgcc atcgaacacg gatatggcca ccgcgagatg   2880

ggcgcaacgc agcactctct ggatggcgtg cctatgccgt atgatccaca aatcagggca   2940

ggcataaatc ttaacgatct gggctttgcc gatccgacaa gaaccattac caacacctgg   3000

ctcgactggg tttctggcgc ggcagtacgt caggggctgc cggcaaaaat cgagcgtata   3060
```

<210> SEQ ID NO 34
<211> LENGTH: 1020
<212> TYPE: PRT
<213> ORGANISM: Salmonella enterica

<400> SEQUENCE: 34

```
Met Ala Asn Leu Thr Arg Arg Gln Trp Leu Lys Val Gly Leu Ala Val
1               5                   10                  15

Gly Gly Met Val Thr Phe Gly Leu Ser Tyr Arg Asp Val Ala Lys Arg
            20                  25                  30

Ala Ile Asp Gly Leu Leu Asn Gly Thr Ser Gly Lys Val Thr Arg Asp
        35                  40                  45

Arg Ile Phe Gly Asn Ala Leu Ile Pro Glu Ala Gln Ala Gln Thr His
    50                  55                  60

Trp Gln Gln Asn Pro Gln Gln Thr Ile Ala Met Thr Gln Cys Phe Gly
65                  70                  75                  80

Cys Trp Thr Gln Cys Gly Ile Arg Ala Arg Val Asn Ala Asp Gly Lys
                85                  90                  95

Val Ile Arg Ile Ala Gly Asn Pro Tyr His Pro Leu Ser Gln Glu His
            100                 105                 110

Pro Ile Asp Ser Ser Val Pro Phe Ser Glu Ala Met Glu Gln Leu Ala
        115                 120                 125

Gly Glu Ser Gly Leu Asp Ala Arg Ser Thr Ala Cys Ala Arg Gly Ala
    130                 135                 140

Thr Leu Leu Glu Ser Leu Tyr Ser Pro Leu Arg Leu Leu Glu Pro Met
145                 150                 155                 160

Lys Arg Val Gly Lys Arg Gly Glu Gly Lys Trp Gln Arg Ile Ser Phe
                165                 170                 175

Glu Gln Leu Ile Glu Glu Val Val Glu Gly Gly Asp Leu Phe Gly Glu
            180                 185                 190

Gly His Val Asp Gly Leu Arg Ala Ile His Ala Pro Asp Thr Pro Ile
        195                 200                 205

Asp Ala Lys His Pro Ser Phe Gly Pro Lys Thr Asn Gln Leu Leu Val
    210                 215                 220

Thr Asn Thr Ser Asp Glu Gly Arg Asp Ala Phe Leu Arg Arg Phe Ala
```

-continued

```
225                 230                 235                 240

Leu Asn Ser Phe Gly Ser Lys Asn Phe Gly Ala His Gly Ala Tyr Cys
                245                 250                 255

Gly Leu Ala Tyr Arg Ala Gly Ser Gly Ala Leu Met Gly Asp Leu Asp
            260                 265                 270

Lys Asn Pro His Val Lys Pro Asp Trp Glu Asn Val Glu Phe Ala Leu
        275                 280                 285

Phe Met Gly Thr Ser Pro Ala Gln Ser Gly Asn Pro Phe Lys Arg Gln
    290                 295                 300

Ala Arg Gln Leu Ala Ser Ala Arg Leu Arg Glu Asn Phe Gln Tyr Val
305                 310                 315                 320

Val Val Ala Pro Ala Leu Pro Leu Ser Thr Val Leu Ala Asp Pro Arg
                325                 330                 335

Gly Arg Trp Gln Pro Val Met Pro Gly Ser Asp Ser Ala Leu Ala Met
            340                 345                 350

Gly Met Ile Arg Trp Ile Met Asp Asn Gln Arg Tyr Asn Ala Asp Tyr
        355                 360                 365

Leu Ala Ile Pro Gly Val Gln Ala Met Gln Gln Ala Gly Glu Gln Ser
    370                 375                 380

Trp Thr Asn Ala Thr His Leu Val Ile Ala Asp Glu Leu Pro Thr Leu
385                 390                 395                 400

Ala Gly Gln His Leu Thr Leu Arg His Leu Thr Pro Asp Gly Glu Glu
                405                 410                 415

Thr Pro Val Val Leu Asn Thr Asp Gly Glu Leu Val Asp Ala Ser Thr
            420                 425                 430

Cys Arg Gln Ala Arg Leu Phe Val Thr Gln Tyr Val Thr Leu Ala Asp
        435                 440                 445

Gly Gln Arg Val Thr Val Lys Ser Gly Leu Gln Arg Leu Lys Glu Ala
    450                 455                 460

Ala Glu Lys Leu Ser Leu Ala Gln Tyr Ser Glu Gln Cys Gly Val Pro
465                 470                 475                 480

Glu Ala Gln Ile Ile Ala Leu Ala Glu Thr Phe Thr Ser His Gly Arg
                485                 490                 495

Lys Ala Ala Val Ile Ser His Gly Gly Met Met Ala Gly Asn Gly Phe
            500                 505                 510

Tyr Asn Ala Trp Ser Val Met Met Leu Asn Ala Leu Ile Gly Asn Leu
        515                 520                 525

Ser Leu Ser Gly Gly Val Phe Val Gly Gly Gly Lys Phe Asn Gly Val
    530                 535                 540

Ser Asp Gly Pro Arg Tyr Asn Met Asn Ser Phe Ala Gly Lys Val Lys
545                 550                 555                 560

Pro Ser Gly Leu Ser Ile Ala Arg Ser Lys Thr Ala Tyr Glu Ala Ser
                565                 570                 575

Glu Glu Tyr Arg Asp Lys Ile Ala Gly Gly Gln Ser Pro Tyr Pro Ala
            580                 585                 590

Lys Ala Pro Trp Tyr Pro Phe Val Ala Gly Gln Leu Thr Glu Leu Leu
        595                 600                 605

Thr Ser Ala Leu Glu Gly Tyr Pro Tyr Pro Leu Lys Ala Trp Ile Ser
    610                 615                 620

Asn Met Ser Asn Pro Phe Tyr Gly Val Pro Gly Leu Arg Ala Val Ala
625                 630                 635                 640

Glu Glu Lys Leu Lys Asp Pro Arg Arg Leu Pro Leu Phe Ile Ala Ile
                645                 650                 655
```

```
Asp Ala Phe Met Asn Glu Thr Thr Ala Leu Ala Asp Tyr Ile Val Pro
            660                 665                 670

Asp Thr His Asn Phe Glu Ser Trp Gly Phe Thr Ala Pro Trp Gly Gly
        675                 680                 685

Val Ala Ser Lys Ala Thr Thr Ala Arg Trp Pro Val Val Ala Pro Ala
    690                 695                 700

Thr His Arg Thr Ala Asp Gly Gln Pro Val Ser Met Glu Ala Phe Cys
705                 710                 715                 720

Ile Ala Val Ala Lys Arg Leu His Leu Pro Gly Phe Gly Asp Arg Ala
                725                 730                 735

Ile Thr Asp Pro Gln Gly Asn Thr Phe Pro Leu Asn Arg Ala Glu Asp
            740                 745                 750

Phe Tyr Leu Arg Val Ala Ala Asn Ile Ala Phe Met Gly Lys Thr Pro
        755                 760                 765

Val Ala Leu Ala Asn Gln Glu Asp Ile Ser Leu Thr Gly Val Ser Arg
    770                 775                 780

Ile Leu Pro Ala Ile Gln His Thr Leu Lys Ala Asp Glu Val Gly Arg
785                 790                 795                 800

Val Ala Phe Ile Tyr Ser Arg Gly Gly Arg Phe Ala Pro Glu Asp Ser
                805                 810                 815

Gly Tyr Thr Glu Gln Arg Leu Gly Asn Ala Trp Lys Lys Pro Leu Gln
            820                 825                 830

Ile Trp Asn Ala Asp Val Ala Ala His Arg His Ala Ile Thr Gly Glu
        835                 840                 845

Arg Phe Ser Gly Cys Pro Val Trp Tyr Pro Ala Arg Leu Ser Asp Gly
    850                 855                 860

Arg Ala Ile Asp Asp Gln Phe Pro Ile Gly Gln Trp Pro Leu Lys Leu
865                 870                 875                 880

Ile Ser Phe Lys Ser Asn Thr Met Ser Ser Ser Thr Ala Val Ile Pro
                885                 890                 895

Arg Leu His His Val Lys Pro Ala Asn Leu Val Ala Leu Asn Pro Gln
            900                 905                 910

Asp Gly Glu Arg Tyr Gly Leu Gln His Gly Asp Arg Val Arg Ile Ile
        915                 920                 925

Thr Pro Gly Gly Gln Val Val Ala Gln Ile Ser Leu Leu Asn Gly Val
    930                 935                 940

Met Pro Gly Val Ile Ala Ile Glu His Gly Tyr Gly His Arg Glu Met
945                 950                 955                 960

Gly Ala Thr Gln His Ser Leu Asp Gly Val Pro Met Pro Tyr Asp Pro
                965                 970                 975

Gln Ile Arg Ala Gly Ile Asn Leu Asn Asp Leu Gly Phe Ala Asp Pro
            980                 985                 990

Thr Arg Thr Ile Thr Asn Thr Trp  Leu Asp Trp Val Ser  Gly Ala Ala
        995                 1000                1005

Val Arg  Gln Gly Leu Pro Ala  Lys Ile Glu Arg Ile
    1010                1015                1020
```

<210> SEQ ID NO 35
<211> LENGTH: 752
<212> TYPE: DNA
<213> ORGANISM: Salmonella enterica

<400> SEQUENCE: 35

```
atgtggacgg gagtcaatat ggacagcagt aaacggcaat ttctccagca gcttggcgtc     60
```

```
ctgaccgctg gcgcctcgct ggttccgctg gctgaagcga aatttccttt ttcgccggag      120

cggcatgaag gctctccccg acaccgttac gccatgctta tcgatctgcg gcgttgtatc      180

ggctgtcagt cctgtaccgt aagttgcact attgaaaacc aaacgccgca aggcgcgttt      240

cgtacgacgg tgaaccaata ccaggtccag cgtgaaggta gtcaggaagt cacgaatgtg      300

ctgttgccgc gtctgtgcaa ccattgcgat aaccccccct gtgtgccggt ctgcccggta      360

caagccacct ttcagcggga agatggcatt gtggtggtgg ataacaaacg ctgcgtcggc      420

tgcgcctatt gtgtccaggc gtgtccttac gacgcccgat ttatcaatca tgaaacgcaa      480

actgccgata aatgcacgtt ttgcgtccat cgtctggaag ccggactgtt acccgcttgc      540

gtagagtcct gcgtcggcgg cgcgcgtatt attggcgata tcaaagatcc ccatagccgc      600

atcgccacca tgcttcatca gcatcgcgac gctatcaagg tattaaagcc ggaaaacggc      660

acgtcgcccc atgttttcta cctgggtctg gacgacgcct ttgtcacccc attaatgggc      720

cgtgcgcagc ccgcgctttg gcaggaggtc tg                                   752
```

<210> SEQ ID NO 36
<211> LENGTH: 250
<212> TYPE: PRT
<213> ORGANISM: Salmonella enterica

<400> SEQUENCE: 36

```
Met Trp Thr Gly Val Asn Met Asp Ser Ser Lys Arg Gln Phe Leu Gln
1               5                   10                  15

Gln Leu Gly Val Leu Thr Ala Gly Ala Ser Leu Val Pro Leu Ala Glu
            20                  25                  30

Ala Lys Phe Pro Phe Ser Pro Glu Arg His Glu Gly Ser Pro Arg His
        35                  40                  45

Arg Tyr Ala Met Leu Ile Asp Leu Arg Arg Cys Ile Gly Cys Gln Ser
    50                  55                  60

Cys Thr Val Ser Cys Thr Ile Glu Asn Gln Thr Pro Gln Gly Ala Phe
65                  70                  75                  80

Arg Thr Thr Val Asn Gln Tyr Gln Val Gln Arg Glu Gly Ser Gln Glu
                85                  90                  95

Val Thr Asn Val Leu Leu Pro Arg Leu Cys Asn His Cys Asp Asn Pro
            100                 105                 110

Pro Cys Val Pro Val Cys Pro Val Gln Ala Thr Phe Gln Arg Glu Asp
        115                 120                 125

Gly Ile Val Val Val Asp Asn Lys Arg Cys Val Gly Cys Ala Tyr Cys
    130                 135                 140

Val Gln Ala Cys Pro Tyr Asp Ala Arg Phe Ile Asn His Glu Thr Gln
145                 150                 155                 160

Thr Ala Asp Lys Cys Thr Phe Cys Val His Arg Leu Glu Ala Gly Leu
                165                 170                 175

Leu Pro Ala Cys Val Glu Ser Cys Val Gly Gly Ala Arg Ile Ile Gly
            180                 185                 190

Asp Ile Lys Asp Pro His Ser Arg Ile Ala Thr Met Leu His Gln His
        195                 200                 205

Arg Asp Ala Ile Lys Val Leu Lys Pro Glu Asn Gly Thr Ser Pro His
    210                 215                 220

Val Phe Tyr Leu Gly Leu Asp Asp Ala Phe Val Thr Pro Leu Met Gly
225                 230                 235                 240

Arg Ala Gln Pro Ala Leu Trp Gln Glu Val
                245                 250
```

245 250

<210> SEQ ID NO 37
<211> LENGTH: 1019
<212> TYPE: DNA
<213> ORGANISM: Salmonella enterica

<400> SEQUENCE: 37
atgacgcatt cactcatcat tgaagaagtg ctggctcacc cgcaggacat tagctggctg 60
ccgtgggcgg tacaatattt ctttttttatt ggcattgccg cctgcgccgc actgtttgcc 120
tgttatcttc actggcggaa aaaagacgcc gcaacagaag aaaatcgggc attactgatt 180
gccattacct gtgcgattac cgcaccgctg gcgctgacgg cggatctgca ccagaccgcc 240
cgcgtctggc atttctatgc ctggccgacg ccctggtcgt ggatgccctg gggagcgtta 300
ttcctgccgc tgtttaccgg atttctcgct ctgtggttcc tggcgcagca gattaaacga 360
ttattcaata aaagttacaa cgtcactaaa tggttggcgt tagccagcgc gctttgcgcg 420
gtgggcctgt tgatttatac cggccgcgaa gtctccgttg tgctggcgcg cccaatctgg 480
tttagctacg ccttccccgt ggcgatgttt cttagcgcct tacaggcgtt cttcgcgctg 540
atgattgtcg ccgcccgacg cgactcggta aggctgccaa aaatattgtg gggacaaatc 600
tggacgctgg cggcgctggg gctggttgtg gccatgtggg ttagcggcga tacgctttcc 660
ggcacggcaa tccgtcagtg gattaccgtc gccctgtcag ccaaatatta cgctgtcggc 720
tgggtagcgc tgtgggtatg cacactgctg ttctgtagcc tggcgctacg ccatccgtta 780
tcacagctaa gacgcgtcct gctggttctc agcgcgctgg cgctatgttg gctgatgcgc 840
tggacattgt tgattcaggt acaaaccgtc cccaagttca acgcgcaatt taacccttac 900
tcgttaccag gcggaacgga tggctggctg gctattctcg gcaccttcgg cctgtggata 960
gcgctactga ttattattcg tgaaacgctg aacggactca ccaggagatt acaacatgg 1019

<210> SEQ ID NO 38
<211> LENGTH: 340
<212> TYPE: PRT
<213> ORGANISM: Salmonella enterica

<400> SEQUENCE: 38

Met Thr His Ser Leu Ile Ile Glu Glu Val Leu Ala His Pro Gln Asp
1 5 10 15

Ile Ser Trp Leu Pro Trp Ala Val Gln Tyr Phe Phe Phe Ile Gly Ile
20 25 30

Ala Ala Cys Ala Ala Leu Phe Ala Cys Tyr Leu His Trp Arg Lys Lys
35 40 45

Asp Ala Ala Thr Glu Glu Asn Arg Ala Leu Leu Ile Ala Ile Thr Cys
50 55 60

Ala Ile Thr Ala Pro Leu Ala Leu Thr Ala Asp Leu His Gln Thr Ala
65 70 75 80

Arg Val Trp His Phe Tyr Ala Trp Pro Thr Pro Trp Ser Trp Met Pro
85 90 95

Trp Gly Ala Leu Phe Leu Pro Leu Phe Thr Gly Phe Leu Ala Leu Trp
100 105 110

Phe Leu Ala Gln Gln Ile Lys Arg Leu Phe Asn Lys Ser Tyr Asn Val
115 120 125

Thr Lys Trp Leu Ala Leu Ala Ser Ala Leu Cys Ala Val Gly Leu Leu
130 135 140

-continued

```
Ile Tyr Thr Gly Arg Glu Val Ser Val Val Leu Ala Arg Pro Ile Trp
145                 150                 155                 160

Phe Ser Tyr Ala Phe Pro Val Ala Met Phe Leu Ser Ala Leu Gln Ala
                165                 170                 175

Phe Phe Ala Leu Met Ile Val Ala Ala Arg His Asp Ser Val Arg Leu
            180                 185                 190

Pro Lys Ile Leu Trp Gly Gln Ile Trp Thr Leu Ala Ala Leu Gly Leu
        195                 200                 205

Val Val Ala Met Trp Val Ser Gly Asp Thr Leu Ser Gly Thr Ala Ile
    210                 215                 220

Arg Gln Trp Ile Thr Val Ala Leu Ser Ala Lys Tyr Tyr Ala Val Gly
225                 230                 235                 240

Trp Val Ala Leu Trp Val Cys Thr Leu Leu Phe Cys Ser Leu Ala Leu
                245                 250                 255

Arg His Pro Leu Ser Gln Leu Arg Arg Val Leu Leu Val Leu Ser Ala
            260                 265                 270

Leu Ala Leu Cys Trp Leu Met Arg Trp Thr Leu Leu Ile Gln Val Gln
        275                 280                 285

Thr Val Pro Lys Phe Asn Ala Gln Phe Asn Pro Tyr Ser Leu Pro Gly
    290                 295                 300

Gly Thr Asp Gly Trp Leu Ala Ile Leu Gly Thr Phe Gly Leu Trp Ile
305                 310                 315                 320

Ala Leu Leu Ile Ile Ile Arg Glu Thr Leu Asn Gly Leu Thr Arg Arg
                325                 330                 335

Leu Gln His Gly
            340


<210> SEQ ID NO 39
<211> LENGTH: 639
<212> TYPE: DNA
<213> ORGANISM: Salmonella enterica

<400> SEQUENCE: 39

atgaaaatgg gggcagggat ggcgacaatt catctactgg atgatgatac ggcggtcact      60

aacgcgtgcg cgtttttact ggaaagtctg ggatatgacg taaaatgctg gacgcagggg     120

gcggattttt tggcgcaggc cagtctgtat caggccgggg tcgtattact ggatatgcga     180

atgccggtac tggatgggca gggcgttcat gatgcgttgc gccagtgcgg aagtaccctg     240

gcggttgttt ttcttaccgg gcatggcgat gtaccgatgg ccgtggagca gatgaaacgc     300

ggcgccgtcg attttctgca aaaaccggta tcggtaaaac cgctacaggc ggcgctggag     360

cgtgcgctga cggtttcatc ggcagcggtg gcgcgtcgtg agattatact gtgttaccag     420

cagttgacgc cgaaagagcg tgagctggcc agcctggtgg caaaaggatt tatgaaccgt     480

gaaattgcgg aagcgatgaa tatcgcggtg cgtaccgtag aggtgcaccg cgccagagtc     540

atggaaaaaa tgcaggccgg tagcctggcg gaactgatta ggcgtttcga aaaaatggcc     600

tcgccagaga ccagaatacg aacaacgtat gagccatga                            639


<210> SEQ ID NO 40
<211> LENGTH: 212
<212> TYPE: PRT
<213> ORGANISM: Salmonella enterica

<400> SEQUENCE: 40

Met Lys Met Gly Ala Gly Met Ala Thr Ile His Leu Leu Asp Asp Asp
1               5                   10                  15
```

```
Thr Ala Val Thr Asn Ala Cys Ala Phe Leu Leu Glu Ser Leu Gly Tyr
            20                  25                  30

Asp Val Lys Cys Trp Thr Gln Gly Ala Asp Phe Leu Ala Gln Ala Ser
        35                  40                  45

Leu Tyr Gln Ala Gly Val Val Leu Leu Asp Met Arg Met Pro Val Leu
    50                  55                  60

Asp Gly Gln Gly Val His Asp Ala Leu Arg Gln Cys Gly Ser Thr Leu
65                  70                  75                  80

Ala Val Val Phe Leu Thr Gly His Gly Asp Val Pro Met Ala Val Glu
                85                  90                  95

Gln Met Lys Arg Gly Ala Val Asp Phe Leu Gln Lys Pro Val Ser Val
            100                 105                 110

Lys Pro Leu Gln Ala Ala Leu Glu Arg Ala Leu Thr Val Ser Ser Ala
        115                 120                 125

Ala Val Ala Arg Arg Glu Ile Ile Leu Cys Tyr Gln Gln Leu Thr Pro
    130                 135                 140

Lys Glu Arg Glu Leu Ala Ser Leu Val Ala Lys Gly Phe Met Asn Arg
145                 150                 155                 160

Glu Ile Ala Glu Ala Met Asn Ile Ala Val Arg Thr Val Glu Val His
                165                 170                 175

Arg Ala Arg Val Met Glu Lys Met Gln Ala Gly Ser Leu Ala Glu Leu
            180                 185                 190

Ile Arg Arg Phe Glu Lys Met Ala Ser Pro Glu Thr Arg Ile Arg Thr
        195                 200                 205

Thr Tyr Glu Pro
    210
```

<210> SEQ ID NO 41
<211> LENGTH: 1779
<212> TYPE: DNA
<213> ORGANISM: Salmonella enterica

<400> SEQUENCE: 41

```
gtgagaggta aaaccgtaag gcgcctggcg gtgttggcgg cagtagggct actttgtcat     60

ggcgcgtggg cagggacgtg gaatatcggt attttggcca tgcgcggcga ggcgtctacg    120

cgtagccact ggcaaccgtt ggcaaagaca ttaagccaac agcttccagg cgaaaccttt    180

cacatccagc cgctggatct gcatcaaatg caggaggccg ttaaccaggg aaccgtgcag    240

tttgtgataa ccaacccggc gcaatttgtc caactgaaca gccatgcgcc gctgcgctgg    300

ttagcttccc tgcgctccac gcgcgatggg aaagcggtga gtaatgttat tggcagcgtg    360

attttgaccc ggcgcgatag cggcatcacc acggcgcatg atctcatcgg taagaccgtc    420

ggcgcgattg atgctcaggc gtttggcggc tatttattag gctataaagc gctcagcgac    480

gcgggcttac gcccggagcg cgattttcat ctccgtttta ccggatttcc tggcgatgcc    540

ttagtctata tgctgcgcga aaaagcggtg caggcggcaa ttgtgccagt gtgcctgtta    600

gaaaatatgg atcaggaagg attgattaat aaaaaggact ttatcgcgct gctttcccga    660

ccgacgcccc tgccttgctt aaccagtacg ccgttatatc ctgactggtc gttcgcggcg    720

ctacctgcgg taagcgatgc gctggcggat cgcgtaacgc gagcgctatt caacgcgccc    780

gccgccgcgt catttcactg gggcgcgcct gcgtccacca gtcaggtgga agccttgctg    840

cgtgatgttc gtcagcaccc tcagcagcgt cgactgtggc tggatgtcaa aagttggtta    900

atccagcacc agctaatggt cggcggcgtg attctggcgt tcttgttgct cacgctcaat    960
```

```
tatatttggg tcatgctgct ggtgcgtcga cgtggaaagc aactggaacg taatagcgta   1020

gttcttcatc agcatgagcg ggcgctggaa accgcccggc aaatgagcgt gttgggtgaa   1080

atgacctccg ggtttgccca tgagcttaat cagccgcttt ccgcgattcg acattatgcc   1140

caggggtgcc tgattcgact gcgcgctgca gatgaacagc atcccttgct gccggcgctg   1200

gagcagattg accagcaggc gcaacgcggt gcggatactc tgcgtaacct gcgtcactgg   1260

gtcagccagg cgcagggcaa cccggtgcta accgaagcgt ggaaggccat agccattcgc   1320

gaggcgattg atcatgtctg gcaattgttg cgtatggcgc aacagtttcc gacagtgact   1380

ctgcataccg aggttagcgc tgcgctgcgc gtaacgctgc cgtcagtgct gctggaacag   1440

gtgctggcga atatcattct taatgcggct caggcgggcg ccacccattt atggatcgtt   1500

gctgaacgca ctgaaaacgg catcagtatt gttttacagg ataacgccgg gggaatcgat   1560

gaggcgctat tacgtcaggc gtttcagccg tttatgacca cccgtaaaga ggggatgggc   1620

ttagggctgg cgatttgcca gcggctggtg cggtatgggc ggggcgatat cagcatcagg   1680

aaccagaccg cgccggacgg tctgtcggga acggtggtta cgatacattt cttacatgaa   1740

aatgggggca gggatggcga caattcatct actggatga                           1779


<210> SEQ ID NO 42
<211> LENGTH: 592
<212> TYPE: PRT
<213> ORGANISM: Salmonella enterica

<400> SEQUENCE: 42

Met Arg Gly Lys Thr Val Arg Arg Leu Ala Val Leu Ala Ala Val Gly
1               5                   10                  15

Leu Leu Cys His Gly Ala Trp Ala Gly Thr Trp Asn Ile Gly Ile Leu
            20                  25                  30

Ala Met Arg Gly Glu Ala Ser Thr Arg Ser His Trp Gln Pro Leu Ala
        35                  40                  45

Lys Thr Leu Ser Gln Gln Leu Pro Gly Glu Thr Phe His Ile Gln Pro
    50                  55                  60

Leu Asp Leu His Gln Met Gln Glu Ala Val Asn Gln Gly Thr Val Gln
65                  70                  75                  80

Phe Val Ile Thr Asn Pro Ala Gln Phe Val Gln Leu Asn Ser His Ala
                85                  90                  95

Pro Leu Arg Trp Leu Ala Ser Leu Arg Ser Thr Arg Asp Gly Lys Ala
            100                 105                 110

Val Ser Asn Val Ile Gly Ser Val Ile Leu Thr Arg Arg Asp Ser Gly
        115                 120                 125

Ile Thr Thr Ala His Asp Leu Ile Gly Lys Thr Val Gly Ala Ile Asp
    130                 135                 140

Ala Gln Ala Phe Gly Gly Tyr Leu Leu Gly Tyr Lys Ala Leu Ser Asp
145                 150                 155                 160

Ala Gly Leu Arg Pro Glu Arg Asp Phe His Leu Arg Phe Thr Gly Phe
                165                 170                 175

Pro Gly Asp Ala Leu Val Tyr Met Leu Arg Glu Lys Ala Val Gln Ala
            180                 185                 190

Ala Ile Val Pro Val Cys Leu Leu Glu Asn Met Asp Gln Glu Gly Leu
        195                 200                 205

Ile Asn Lys Lys Asp Phe Ile Ala Leu Leu Ser Arg Pro Thr Pro Leu
    210                 215                 220
```

```
Pro Cys Leu Thr Ser Thr Pro Leu Tyr Pro Asp Trp Ser Phe Ala Ala
225                 230                 235                 240

Leu Pro Ala Val Ser Asp Ala Leu Ala Asp Arg Val Thr Arg Ala Leu
                245                 250                 255

Phe Asn Ala Pro Ala Ala Ala Ser Phe His Trp Gly Ala Pro Ala Ser
            260                 265                 270

Thr Ser Gln Val Glu Ala Leu Leu Arg Asp Val Arg Gln His Pro Gln
        275                 280                 285

Gln Arg Arg Leu Trp Leu Asp Val Lys Ser Trp Leu Ile Gln His Gln
    290                 295                 300

Leu Met Val Gly Gly Val Ile Leu Ala Phe Leu Leu Leu Thr Leu Asn
305                 310                 315                 320

Tyr Ile Trp Val Met Leu Leu Val Arg Arg Arg Gly Lys Gln Leu Glu
                325                 330                 335

Arg Asn Ser Val Val Leu His Gln His Glu Arg Ala Leu Glu Thr Ala
            340                 345                 350

Arg Gln Met Ser Val Leu Gly Glu Met Thr Ser Gly Phe Ala His Glu
        355                 360                 365

Leu Asn Gln Pro Leu Ser Ala Ile Arg His Tyr Ala Gln Gly Cys Leu
    370                 375                 380

Ile Arg Leu Arg Ala Ala Asp Glu Gln His Pro Leu Leu Pro Ala Leu
385                 390                 395                 400

Glu Gln Ile Asp Gln Gln Ala Gln Arg Gly Ala Asp Thr Leu Arg Asn
                405                 410                 415

Leu Arg His Trp Val Ser Gln Ala Gln Gly Asn Pro Val Leu Thr Glu
            420                 425                 430

Ala Trp Lys Ala Ile Ala Ile Arg Glu Ala Ile Asp His Val Trp Gln
        435                 440                 445

Leu Leu Arg Met Ala Gln Gln Phe Pro Thr Val Thr Leu His Thr Glu
    450                 455                 460

Val Ser Ala Ala Leu Arg Val Thr Leu Pro Ser Val Leu Leu Glu Gln
465                 470                 475                 480

Val Leu Ala Asn Ile Ile Leu Asn Ala Ala Gln Ala Gly Ala Thr His
                485                 490                 495

Leu Trp Ile Val Ala Glu Arg Thr Glu Asn Gly Ile Ser Ile Val Leu
            500                 505                 510

Gln Asp Asn Ala Gly Gly Ile Asp Glu Ala Leu Leu Arg Gln Ala Phe
        515                 520                 525

Gln Pro Phe Met Thr Thr Arg Lys Glu Gly Met Gly Leu Gly Leu Ala
    530                 535                 540

Ile Cys Gln Arg Leu Val Arg Tyr Gly Arg Gly Asp Ile Ser Ile Arg
545                 550                 555                 560

Asn Gln Thr Ala Pro Asp Gly Leu Ser Gly Thr Val Val Thr Ile His
                565                 570                 575

Phe Leu His Glu Asn Gly Gly Arg Asp Gly Asp Asn Ser Ser Thr Gly
            580                 585                 590
```

<210> SEQ ID NO 43
<211> LENGTH: 5234
<212> TYPE: DNA
<213> ORGANISM: Artificial Sequence
<220> FEATURE:
<223> OTHER INFORMATION: vector

<400> SEQUENCE: 43

-continued

```
aggcacacga aaaacaagtt aagggatgca gtttatcggg cagcgttggg tcctggccac     60
gggtgcgcat gatcgtgctc ctgtcgttga ggacccggct aggctggcgg ggttgcctta    120
ctggttagca gaatgaatca ccgatacgcg agcgaacgtg aagcgactgc tgctgcaaaa    180
cgtctgcgac ctgagcaaca acatgaatgg tcttcggttt ccgtgtttcg taaagtctgg    240
aaacgcggaa gtcagcgccc tgcaccatta tgttccggat ctgcatcgca ggatgctgct    300
ggctaccctg tggaacacct acatctgtat taacgaagcg ctggcattga ccctgagtga    360
tttttctctg gtcccgccgc atccataccg ccagttgttt accctcacaa cgttccagta    420
accgggcatg ttcatcatca gtaacccgta tcgtgagcat cctctctcgt ttcatcggta    480
tcattacccc catgaacaga aatccccctt acacggaggc atcagtgacc aaacaggaaa    540
aaaccgccct taacatggcc cgctttatca gaagccagac attaacgctt ctggagaaac    600
tcaacgagct ggacgcggat gaacaggcag acatctgtga atcgcttcac gaccacgctg    660
atgagcttta ccgcagctgc ctcgcgcgtt tcggtgatga cggtgaaaac ctctgacaca    720
tgcagctccc ggagacggtc acagcttgtc tgtaagcgga tgccgggagc agacaagccc    780
gtcagggcgc gtcagcgggt gttggcgggt gtcggggcgc agccatgacc cagtcacgta    840
gcgatagcgg agtgtatact ggcttaacta tgcggcatca gagcagattg tactgagagt    900
gcaccatatg cggtgtgaaa taccgcacag atgcgtaagg agaaaatacc gcatcaggcg    960
ctcttccgct tcctcgctca ctgactcgct gcgctcggtc gttcggctgc ggcgagcggt   1020
atcagctcac tcaaaggcgg taatacggtt atccacagaa tcaggggata acgcaggaaa   1080
gaacatgtga gcaaaaggcc agcaaaaggc caggaaccgt aaaaaggccg cgttgctggc   1140
gtttttccat aggctccgcc cccctgacga gcatcacaaa aatcgacgct caagtcagag   1200
gtggcgaaac ccgacaggac tataaagata ccaggcgttt ccccctggaa gctccctcgt   1260
gcgctctcct gttccgaccc tgccgcttac cggatacctg tccgcctttc tcccttcggg   1320
aagcgtggcg ctttctcata gctcacgctg taggtatctc agttcggtgt aggtcgttcg   1380
ctccaagctg ggctgtgtgc acgaaccccc cgttcagccc gaccgctgcg ccttatccgg   1440
taactatcgt cttgagtcca acccggtaag acacgactta tcgccactgg cagcagtccc   1500
ttaacttact tattaaataa tttatagcta ttgaaaagag ataagaattg ttcaaagcta   1560
atattgttta aatcgtcaat tcctgcatgt tttaaggaat tgttaaattg atttttgta    1620
aatattttct tgtattcttt gttaacccat ttcataacga aataattata cttttgttta   1680
tctttgtgtg atattcttga tttttttcta cttaatctga taagtgagct attcacttta   1740
ggtttaggat gaaaatattc tcttggaacc atacttaata tagaaatatc aacttctgcc   1800
attaaaagta atgccaatga gcgttttgta tttaataatc ttttagcaaa cccgtattcc   1860
acgattaaat aaatctcatt agctatacta tcaaaaacaa ttttgcgtat tatatccgta   1920
cttatgttat aaggtatatt accatatatt ttataggatt ggtttttagg aaatttaaac   1980
tgcaatatat ccttgtttaa aacttggaaa ttatcgtgat caacaagttt attttctgta   2040
gttttgcata atttatggtc tatttcaatg gcagttacga aattacacct ctttactaat   2100
tcaagggtaa aatggccttt tcctgagccg atttcaaaga tattatcatg ttcatttaat   2160
cttatatttg tcattatttt atctatatta tgttttgaag taataaagtt ttgactgtgt   2220
tttatatttt tctcgttcat tataaccctc tttaatttgg ttatatgaat tttgcttatt   2280
aacgattcat tataaccact tattttttgt ttggttgata atgaactgtg ctgattacaa   2340
aaatactaaa aatgcccata ttttttcctc cttataaaat tagtataatt atagcacgag   2400
```

```
ctctgataaa tatgaacatg atgagtgatc gttaaattta tactgcaatc ggatgcgatt   2460
attgaataaa agatatgaga gatttatcta atttcttttt tcttgtaaaa aaagaaagtt   2520
cttaaaggtt ttatagtttt ggtcgtagag cacacggttt aacgacttaa ttacgaagta   2580
aataagtcta gtgtgttaga ctttatgaaa tctatatacg tttatatata tttattatcc   2640
gatttttat taaaacgtct caaaatcgtt tctgagacgt tttagcgttt atttcgttta   2700
gttatcggca taatcgttaa aacaggcgtt atcgtagcgt aaaagccctt gagcgtagcg   2760
tggctttgca gcgaagatgt tgtctgttag attatgaaag ccgatgactg aatgaaataa   2820
taagcgcagc gcccttctat ttcggttgga ggaggctcaa gggagtatga gggaatgaaa   2880
ttccctcatg ggtttgattt taaaaattgc ttgcaatttt gccgagcggt agcgctggaa   2940
aatttttgaa aaaaatttgg aatttggaaa aaaatggggg gaaaggaagc gaattttgct   3000
tccgtactac gaccccccat taagtgccga gtgccaattt ttgtgccaaa aacgctctat   3060
cccaactggc tcaagggttt aaggggtttt tcaatcgcca acgaatcgcc aacgttttcg   3120
ccaacgtttt ttataaatct atatttaagt agctttattg ttgtttttat gattacaaag   3180
tgatacacta actttataaa attatttgat tggagttttt taaatggtga tttcagaatc   3240
gaaaaaaaga gttatgattt ctctgacaaa agagcaagat aaaaaattaa cagatatggc   3300
gaaacaaaaa ggtttttcaa aatctgcggt tgcggcgtta gctatagaag aatatgcaag   3360
aaaggaatca gaacaaaaaa aataagcgaa agctcgcgtt tttagaagga tacgagtttt   3420
cgctacttgt ttttgataag gtaattatat catggctatt aaaaatacta aagctagaaa   3480
ttttggattt ttattatatc ctgactcaat tcctaatgat tggaaagaaa aattagagag   3540
tttgggcgta tctatggctg tcagtccttt acacgatatg gacgaaaaaa aagataaaga   3600
tacatggaat aatagtaata ttatacaaaa tggaaagcac tataaaaaac cacactatca   3660
cgttatatat attgcacgaa atcctgtaac aatagaaagc gttaggaaca agattaagcg   3720
aaaattgggg aatagttcag ttgctcatgt tgagatactt gattatatca aaggttcata   3780
tgaatatttg actcatgaat caaaggacgc tattgctaag aataaacata tatacgacaa   3840
aaaagatatt ttgaacatta atgattttga tattgaccgc tatataacac ttgatgaaag   3900
ccaaaaaaga gaattgaaga atttactttt agatatagtg gatgactata atttggtaaa   3960
tacaaaagat ttaatggctt ttattcgcct taggggagcg gagtttggaa ttttaaatac   4020
aaagatattg tttcaacaaa gaatgatgta ctctagcgcc tttagattat ggtttgaggg   4080
caattatcag tgtggatata gagcaagtta tgcaaaggtt cttgatgctg aaacggggga   4140
aataaaatga caaacaaaga aaaagagtta tttgctgaaa atgaggaatt aaaaaaagaa   4200
attaaggact taaaagagcg tattgaaaga tacagagaaa tggaagttga attaagtaca   4260
acaatagatt tattgagagg agggattatt gaataaataa aagccccctg acgaaagtcg   4320
aaggggggttt ttattttggt ttgatgttgc gattaatagc aatacaattg caataaacaa   4380
aatgatcttc cttcaggtta tgaccatctg tgccagttcg taatgtctgg tcaactttcc   4440
gactctgaga aacttctgga atcgctagag aatttctgga atgggattca ggagtggaca   4500
gaacgacacg gatatatagt ggatgtgtca aaacgcatac cattttgaac gatgacctct   4560
aataattgtt aatcatgttg gttacgtatt tattaacttc tcctagtatt agtaattatc   4620
atggctgtca tggcgcatta acggaataaa gggtgtgctt aaatcgggcc attttgcgta   4680
ataagaaaaa ggattaatta tgagcgaatt gaattaataa taaggtaata gatttacatt   4740
```

agaaaatgaa aggggatttt atgcgtgaga atgttacagt ctatccctgg cgaaaggggg 4800
atgtgctgca aggcgattaa gttgggtaac gccagggttt tcccagtcac gacgttgtaa 4860
aacgacggcc agtgagcgcg cgtaatacga ctcactatag ggcgaattgg gtaccgggcc 4920 cccctcgag gtcgacggta tcgataagct tgatatcgaa ttcctgcagc ccgggggatc 4980
cactagttct agagcggccg ccaccgcggt ggagctccag cttttgttcc ctttagtgag 5040
ggttaattgc gcgcttggcg taatcatggt catagctgtt tcctgtgtga aattgttatc 5100
cgctcacaat tccacacaac atacgagccg gaagcataaa gtgtaaagcc tggggtgcct 5160
aatgagtgag ctaactcaca ttaattgcgt tgcgctcact gcccgctttc cagtcgggaa 5220
acctgtcgtg ccag 5234

<210> SEQ ID NO 44
<211> LENGTH: 5234
<212> TYPE: DNA
<213> ORGANISM: Artificial Sequence
<220> FEATURE:
<223> OTHER INFORMATION: vector

<400> SEQUENCE: 44
aggcacacga aaaacaagtt aagggatgca gtttatcggg cagcgttggg tcctggccac 60
gggtgcgcat gatcgtgctc ctgtcgttga ggacccggct aggctggcgg ggttgcctta 120
ctggttagca gaatgaatca ccgatacgcg agcgaacgtg aagcgactgc tgctgcaaaa 180
cgtctgcgac ctgagcaaca acatgaatgg tcttcggttt ccgtgtttcg taaagtctgg 240
aaacgcggaa gtcagcgccc tgcaccatta tgttccggat ctgcatcgca ggatgctgct 300
ggctaccctg tggaacacct acatctgtat taacgaagcg ctggcattga ccctgagtga 360
tttttctctg gtcccgccgc atccataccg ccagttgttt accctcacaa cgttccagta 420
accgggcatg ttcatcatca gtaacccgta tcgtgagcat cctctctcgt ttcatcggta 480
tcattacccc catgaacaga aatccccctt acacggaggc atcagtgacc aaacaggaaa 540
aaaccgccct taacatggcc cgctttatca gaagccagac attaacgctt ctggagaaac 600
tcaacgagct ggacgcggat gaacaggcag acatctgtga atcgcttcac gaccacgctg 660
atgagcttta ccgcagctgc ctcgcgcgtt tcggtgatga cggtgaaaac ctctgacaca 720
tgcagctccc ggagacggtc acagcttgtc tgtaagcgga tgccgggagc agacaagccc 780
gtcagggcgc gtcagcgggt gttggcgggt gtcggggcgc agccatgacc cagtcacgta 840
gcgatagcgg agtgtatact ggcttaacta tgcggcatca gagcagattg tactgagagt 900
gcaccatatg cggtgtgaaa taccgcacag atgcgtaagg agaaaatacc gcatcaggcg 960
ctcttccgct tcctcgctca ctgactcgct gcgctcggtc gttcggctgc ggcgagcggt 1020
atcagctcac tcaaaggcgg taatacggtt atccacagaa tcaggggata acgcaggaaa 1080
gaacatgtga gcaaaaggcc agcaaaaggc caggaaccgt aaaaaggccg cgttgctggc 1140
gtttttccat aggctccgcc cccctgacga gcatcacaaa aatcgacgct caagtcagag 1200
gtggcgaaac ccgacaggac tataaagata ccaggcgttt ccccctggaa gctccctcgt 1260
gcgctctcct gttccgaccc tgccgcttac cggatacctg tccgcctttc tcccttcggg 1320
aagcgtggcg ctttctcata gctcacgctg taggtatctc agttcggtgt aggtcgttcg 1380
ctccaagctg ggctgtgtgc acgaaccccc cgttcagccc gaccgctgcg ccttatccgg 1440
taactatcgt cttgagtcca acccggtaag acacgactta tcgccactgg cagcagtccc 1500
ttaacttact tattaaataa tttatagcta ttgaaaagag ataagaattg ttcaaagcta 1560

```
atattgttta aatcgtcaat tcctgcatgt tttaaggaat tgttaaattg attttttgta   1620
aatattttct tgtattcttt gttaacccat ttcataacga aataattata cttttgttta   1680
tctttgtgtg atattcttga tttttttcta cttaatctga taagtgagct attcacttta   1740
ggtttaggat gaaaatattc tcttggaacc atacttaata tagaaatatc aacttctgcc   1800
attaaaagta atgccaatga gcgttttgta tttaataatc ttttagcaaa cccgtattcc   1860
acgattaaat aaatctcatt agctatacta tcaaaaacaa ttttgcgtat tatatccgta   1920
cttatgttat aaggtatatt accatatatt ttataggatt ggtttttagg aaatttaaac   1980
tgcaatatat ccttgtttaa aacttggaaa ttatcgtgat caacaagttt attttctgta   2040
gttttgcata atttatggtc tatttcaatg gcagttacga aattacacct ctttactaat   2100
tcaagggtaa aatggccttt tcctgagccg atttcaaaga tattatcatg ttcatttaat   2160
cttatatttg tcattatttt atctatatta tgttttgaag taataaagtt ttgactgtgt   2220
tttatatttt tctcgttcat tataaccctc tttaatttgg ttatatgaat tttgcttatt   2280
aacgattcat tataaccact tattttttgt ttggttgata atgaactgtg ctgattacaa   2340
aaatactaaa aatgcccata tttttcctc cttataaaat tagtataatt atagcacgag   2400
ctctgataaa tatgaacatg atgagtgatc gttaaattta tactgcaatc ggatgcgatt   2460
attgaataaa agatatgaga gatttatcta atttcttttt tcttgtaaaa aaagaaagtt   2520
cttaaaggtt ttatagtttt ggtcgtagag cacacggttt aacgacttaa ttacgaagta   2580
aataagtcta gtgtgttaga ctttatgaaa tctatatacg tttatatata tttattatcc   2640
gatttttat taaaacgtct caaaatcgtt tctgagacgt tttagcgttt atttcgttta   2700
gttatcggca taatcgttaa aacaggcgtt atcgtagcgt aaaagccctt gagcgtagcg   2760
tggctttgca gcgaagatgt tgtctgttag attatgaaag ccgatgactg aatgaaataa   2820
taagcgcagc gcccttctat ttcggttgga ggaggctcaa gggagtatga gggaatgaaa   2880
ttccctcatg ggtttgattt taaaaattgc ttgcaatttt gccgagcggt agcgctggaa   2940
aatttttgaa aaaaatttgg aatttggaaa aaaatggggg gaaaggaagc gaattttgct   3000
tccgtactac gaccccccat taagtgccga gtgccaattt ttgtgccaaa aacgctctat   3060
cccaactggc tcaagggttt aaggggtttt tcaatcgcca acgaatcgcc aacgttttcg   3120
ccaacgtttt ttataaatct atatttaagt agctttattg ttgtttttat gattacaaag   3180
tgatacacta actttataaa attatttgat tggagttttt taaatggtga tttcagaatc   3240
gaaaaaaaga gttatgattt ctctgacaaa agagcaagat aaaaaattaa cagatatggc   3300
gaaacaaaaa ggtttttcaa aatctgcggt tgcggcgtta gctatagaag aatatgcaag   3360
aaaggaatca gaacaaaaaa aataagcgaa agctcgcgtt tttagaagga tacgagtttt   3420
cgctacttgt ttttgataag gtaattatat catggctatt aaaaatacta aagctagaaa   3480
ttttggattt ttattatatc ctgactcaat tcctaatgat tggaaagaaa aattagagag   3540
tttgggcgta tctatggctg tcagtccttt acacgatatg gacgaaaaaa aagataaaga   3600
tacatggaat aatagtaata ttatacaaaa tggaaagcac tataaaaaac cacactatca   3660
cgttatatat attgcacgaa atcctgtaac aatagaaagc gttaggaaca agattaagcg   3720
aaaattgggg aatagttcag ttgctcatgt tgagatactt gattatatca aaggttcata   3780
tgaatatttg actcatgaat caaaggacgc tattgctaag aataaacata tatacgacaa   3840
aaaagatatt ttgaacatta atgattttga tattgaccgc tatataacac ttgatgaaag   3900
```

```
ccaaaaaaga gaattgaaga atttactttt agatatagtg gatgactata atttggtaaa   3960

tacaaaagat ttaatggctt ttattcgcct taggggagcg gagtttggaa ttttaaatac   4020

aaagatattg tttcaacaaa gaatgatgta ctctagcgcc tttagattat ggtttgaggg   4080

caattatcag tgtggatata gagcaagtta tgcaaaggtt cttgatgctg aaacggggga   4140

aataaaatga caaacaaaga aaaagagtta tttgctgaaa atgaggaatt aaaaaaagaa   4200

attaaggact taaaagagcg tattgaaaga tacagagaaa tggaagttga attaagtaca   4260

acaatagatt tattgagagg agggattatt gaataaataa aagccccctg acgaaagtcg   4320

aagggggttt ttattttggt ttgatgttgc gattaatagc aatacaattg caataaacaa   4380

aatgatcttc cttcaggtta tgaccatctg tgccagttcg taatgtctgg tcaactttcc   4440

gactctgaga aacttctgga atcgctagag aatttctgga atgggattca ggagtggaca   4500

gaacgacacg gatatatagt ggatgtgtca aaacgcatac cattttgaac gatgacctct   4560

aataattgtt aatcatgttg gttacgtatt tattaacttc tcctagtatt agtaattatc   4620

atggctgtca tggcgcatta acggaataaa gggtgtgctt aaatcgggcc attttgcgta   4680

ataagaaaaa ggattaatta tgagcgaatt gaattaataa taaggtaata gatttacatt   4740

agaaaatgaa aggggatttt atgcgtgaga atgttacagt ctatccctgg cgaaaggggg   4800

atgtgctgca aggcgattaa gttgggtaac gccagggttt tcccagtcac gacgttgtaa   4860

aacgacggcc agtgagcgcg cgtaatacga ctcactatag ggcgaattgg gtaccgggcc   4920

ccccctcgag gtcgacggta tcgataagct tgatatcgaa ttcctgcagc ccgggggatc   4980

cactagttct agagcggccg ccaccgcggt ggagctccag cttttgttcc ctttagtgag   5040

ggttaattgc gcgcttggcg taatcatggt catagctgtt tcctgtgtga aattgttatc   5100

cgctcacaat tccacacaac atacgagccg gaagcataaa gtgtaaagcc tggggtgcct   5160

aatgagtgag ctaactcaca ttaattgcgt tgcgctcact gcccgctttc cagtcgggaa   5220

acctgtcgtg ccag                                                     5234
```

<210> SEQ ID NO 45
<211> LENGTH: 4500
<212> TYPE: DNA
<213> ORGANISM: Artificial Sequence
<220> FEATURE:
<223> OTHER INFORMATION: vector

<400> SEQUENCE: 45

```
ttccccttct ctgaaaatca acgggcaggt cactgacttg cccgtttttt tatcccttct     60

ccacaccgtt gagctcgaat tctcatgttt gacagcttat cactgatcag tgaattaatg    120

gcgatgacgc atcctcacga taatatccgg gtaggcgcaa tcactttcgt ctctactccg    180

ttacaaagcg aggctgggta tttcccggcc tttctgttat ccgaaatcca ctgaaagcac    240

agcggctggc tgaggagata aataataaac gaggggctgt atgcacaaag catcttctgt    300

tgagttaaga acgagtatcg agatggcaca tagccttgct caaattggaa tcaggtttgt    360

gccaatacca gtagaaacag acgaagaagc tagaggtgaa tcacgacaaa gcgtatcaaa    420

aacgtatgga gtagggctct aaactctgta taaaaagttt ccagctagct gataacggga    480

aagaaacaga gaagggcaca aatattgtgt actttaatgt gccctttaat ttattgattg    540

gtggttgaat tgtccgtaac tttttgattt aagtgcaaat ttctaataaa ttagaacact    600

ttcttaaatt gtcatttggc atattacgaa caattccgcg taaaaacgtt ctgttacgct    660

aaacccttat ccagcaggct ttcaaggatg taaaccataa cactctgcga actagtgtta    720
```

```
cattgcgtgt agctttgagt gggcaacttt gtgtacactt ttgtgtaccc aaaaacaaaa    780
atgtgtaccc attcaatgat caccgacaca aagctcagga aggcgctcgg caagaaaaga    840
gatgatatcg agattatttc tgattcgcac gagctttcta gacgctcaag ttagtataaa    900
aaagctgaac gagaaacgta aaatgatata aatatcaata tattaaatta gattttgcat    960
aaaaaacaga ctacataata ctgtaaaaca caacatatgc agtcactatg aatcaactac   1020
ttagatggta ttagtgacct gtaacagact gcgggcccag gttatgctgc ttttaagacc   1080
cactttcaca tttaagttgt ttttctaatc cgcatatgat caattcaagg ccgaataaga   1140
aggctggctc tgcaccttgg tgatcaaata attcgatagc ttgtcgtaat aatggcggca   1200
tactatcagt agtaggtgtt tccctttctt ctttagcgac ttgatgctct tgatcttcca   1260
atacgcaacc taaagtaaaa tgccccacag cgctgagtgc atataatgca ttctctagtg   1320
aaaaaccttg ttggcataaa aaggctaatt gattttcgag agtttcatac tgtttttctg   1380
taggccgtgt acctaaatgt acttttgctc catcgcgatg acttagtaaa gcacatctaa   1440
aacttttagc gttattacgt aaaaaatctt gccagctttc cccttctaaa gggcaaaagt   1500
gagtatggtg cctatctaac atctcaatgg ctaaggcgtc gagcaaagcc cgcttatttt   1560
ttacatgcca atacaatgta ggctgctcta cacctagctt ctgggcgagt ttacgggttg   1620
ttaaaccttc gattccgacc tcattaagca gctctaatgc gctgttaatc actttacttt   1680
tatctaatct agacatcatt aattcctaat ttttgttgac actctatcat tgatagagtt   1740
attttaccac tccctatcag tgatagagaa aagtgaaatg aatagttcga caaagatcgc   1800
attggtaatt acgttactcg atgccatggg gattggcctt atcatgccag tcttgccaac   1860
gttattacgt gaatttattg cttcggaaga tatcgctaac cactttggcg tattgcttgc   1920
actttatgcg ttaatgcagg ttatctttgc tccttggctt ggaaaaatgt ctgaccgatt   1980
tggtcggcgc ccagtgctgt tgttgtcatt aataggcgca tcgctggatt acttattgct   2040
ggctttttca agtgcgcttt ggatgctgta tttaggccgt ttgctttcag ggatcacagg   2100
agctactggg gctgtcgcgg catcggtcat tgccgatacc acctcagctt ctcaacgcgt   2160
gaagtggttc ggttggttag ggcaagtttt tgggcttggt ttaatagcgg ggcctattat   2220
tggtggtttt gcaggagaga tttcaccgca tagtcccttt tttatcgctg cgttgctaaa   2280
tattgtcact ttccttgtgg ttatgttttg gttccgtgaa accaaaaata cacgtgataa   2340
tacagatacc gaagtagggg ttgagacgca atcgaattcg gtatacatca ctttatttaa   2400
aacgatgccc attttgttga ttatttattt ttcagcgcaa ttgataggcc aaattcccgc   2460
aacggtgtgg gtgctattta ccgaaaatcg ttttggatgg aatagcatga tggttggctt   2520
ttcattagcg ggtcttggtc ttttacactc agtattccaa gcctttgtgg caggaagaat   2580
agccactaaa tggggcgaaa aaacggcagt actgctcgaa tttattgcag atagtagtgc   2640
atttgccttt ttagcgttta tatctgaagg ttggttagat ttccctgttt taattttatt   2700
ggctggtggt gggatcgctt tacctgcatt acagggagtg atgtctatcc aaacaaagag   2760
tcatgagcaa ggtgctttac agggattatt ggtgagcctt accaatgcaa ccggtgttat   2820
tggcccatta ctgtttactg ttatttataa tcattcacta ccaatttggg atggctggat   2880
ttggattatt ggtttagcgt tttactgtat tattatcctg ctatcgatga ccttcatgtt   2940
aacccctcaa gctcagggga gtaaacagga gacaagtgct tagttatttc gtcaccaaat   3000
gatgttattc cgcgaaatat aatgaccctc ttgataaccc aagagggcat tttttacgag   3060
```

```
acgtcctaat tcccatgtca gccgttaagt gttcctgtgt cactgaaaat tgctttgaga    3120

ggctctaagg gcttctcagt gcgttacatc cctggcttgt tgtccacaac cgttaaacct    3180

taaaagcttt aaaagcctta tatattcttt tttttcttat aaaacttaaa accttagagg    3240

ctatttaagt tgctgattta tattaatttt attgttcaaa catgagagct tagtacgtga    3300

aacatgagag cttagtacgt tagccatgag agcttagtac gttagccatg agggtttagt    3360

tcgttaaaca tgagagctta gtacgttaaa catgagagct tagtacgtga aacatgagag    3420

cttagtacgt actatcaaca ggttgaactg ctgatcttca gatcctctac gccggacgca    3480

tcgtggccgg atcttgcggc cgcaaaaatt aaaaatgaag ttttggaggc ctcatttggt    3540

gacgaaataa ctaagcactt gtctcctgtt tactcccctg agcttgaggg gtcaacatga    3600

aggtcattga tagcaggata ataatacagt aaaacgctaa accaataatc caaatccagc    3660

catcccaaat tggtagtgaa tgattataaa taacagtaaa cagtaatggg ccaataacac    3720

cggttgcatt ggtaaggctc accaataatc cctgtaaagc accttgctca tgactctttg    3780

tttggataga catcactccc tgtaatgcag gtaaagcgat cccaccacca gccaataaaa    3840

ttaaaacagg gaaatctaac caaccttcag atataaacgc taaaaaggca aatgcactac    3900

tatctgcaat aaattcgagc agtactgccg ttttttcgcc ccatttagtg gctattcttc    3960

ctgccacaaa ggcttggaat actgagtgta aaagaccaag acccgctaat gaaaagccaa    4020

ccatcatgct attccatcca aaacgatttt cggtaaatag cacccacacc gttgcgggaa    4080

tttggcctat caattcgaaa tcaaataatg attttatttt gactgatagt gacctgttcg    4140

ttgcaacaaa ttgataagca atgcttttt ataatgccaa cttagtataa aaaagcaggc    4200

ttcagagcga tggcccccga tggtagtgtg gggtctcccc atgcgagagt agggaactgc    4260

caggcatcaa ataaaacgaa aggctcagtc gaaagactgg gcctttcgtt ttatctgttg    4320

tttgtcggtg aacgctctcc tgagtaggac aaatccgccg ggagcggatt tgaacgttgc    4380

gaagcaacgg cccggagggt ggcgggcagg acgcccgcca taaactgcca ggcatcaaat    4440

taagcagaag gccatcctga cggatggcct ttttgcgtgg ccagtgccaa gcttgcatgc    4500
```

<210> SEQ ID NO 46  
<211> LENGTH: 10255  
<212> TYPE: DNA  
<213> ORGANISM: Artificial Sequence  
<220> FEATURE:  
<223> OTHER INFORMATION: vector

<400> SEQUENCE: 46

```
ctgcaggtcg actctagagg atccgttata tacgctcgat ttttgccggc agcccctgac      60

gtactgccgc gccagaaacc cagtcgagcc aggtgttggt aatggttctt gtcggatcgg     120

caaagcccag atcgttaaga tttatgcctg ccctgatttg tggatcatac ggcataggca     180

cgccatccag agagtgctgc gttgcgccca tctcgcggtg gccatatccg tgttcgatgg     240

cgatgacgcc tggcatcacg ccatttaaca aactgatttg cgccacgacc tgaccgcccg     300

gcgtaatgat ccgtacccga tcgccatgtt gcagtccata cgctcgccg tcttgcggat     360

tcagcgccac caggtttgct ggcttcacat ggtgtaagcg cgggatgacg gctgttgagc     420

tggacatggt atttgattta aatgaaatca gtttcagcgg ccattgccca atgggaaact     480

ggtcgtcaat cgcacgacca tctgacaaac gcgccggata ccagaccggg caaccgctga     540

agcgctcccc ggtgatggcg tgacggtggg cggcgacatc tgcattccag atctgtaagg    600

gttttttcca cgcgttacct aaccgttgct ccgtatagcc gctatcctcg ggcgcaaacc    660
```

ggccgccacg cgagtagata aacgccacgc gaccgacctc atcagcttta agcgtgtgct 720
gaattgctgg cagaatgcgg ctgacgccgg taagcgaaat atcttcctga tttgccagcg 780
cgaccggcgt cttgcccata aaggcgatat tagcggctac gcgcagatag aagtcttccg 840
cccggttcag tggaaaagta ttgccctgcg gatcggttat cgcccggtcg ccgaagccgg 900
gcagatggag ccgttttgct accgcaatac aaaatgcttc cattgagaca ggttgcccgt 960
ccgccgtgcg gtgagtggcg ggggcgacaa ccggccagcg ggcggtagtg gctttactgg 1020
ctacgccgcc ccagggcgcc gtaaagcccc agctctcaaa attgtgcgta tccggcacaa 1080
tgtaatccgc cagcgccgtc gtttcattca taaaggcgtc aatcgcgata aagagcggca 1140
gtcggcgagg gtcttttagt tttcttccg ccacggcgcg tagaccggga acaccgtaaa 1200
acgggttgct catattggaa atccaggctt taagcggata aggatagcct tcgagcgcgg 1260
aggtcaacag ttcggtaagc tggcctgcca caaagggata ccacggcgct ttggctggat 1320
aaggggattg cccaccggca attttgtcgc ggtattcttc cgatgcttca taagcggttt 1380
tgctacgggc aatacttaac ccggacggtt tcacttttcc ggcaaaactg ttcatgttgt 1440
agcgggggcc gtcgctaacg ccgttgaatt tgccgccgcc gacaaagacg ccgccggaca 1500
agctgaggtt gccgatcagc gcgttaagca tcatgaccga ccaggcgtta taaaacccat 1560
tgccggccat catgccgccg tgactgatga ccgcagcttt acgtccgtga ctggtaaagg 1620
tttccgccag cgcgataatt tgcgcttccg gcacgccgca ctgttcgctg tattgcgcca 1680
acgagagctt ttctgccgcc tctttcaggc gttgcaaccc gctcttcacc gtgacccgtt 1740
ggccgtcggc gagcgtaacg tactgcgtca cgaaaagccg tgcctgtcgg caagtggacg 1800
catcgaccaa ctcgccgtcg gtattcagta cgacaggggt ctcttcgcca tcgggcgtaa 1860
gatggcgcag cgtcaggtgt tgtccggcaa gcgtcggcag ctcatccgca atgaccaggt 1920
gcgtggcgtt ggtccaactt tgctcgccgg cctgctgcat cgcctgtacg ccgggaatcg 1980
ccagataatc agcattataa cgttgattat ccatgatcca gcggatcatc cccattgcca 2040
gcgccgaatc actgccgggc atgaccggtt gccagcgacc gcgaggatcg gcgagcaccg 2100
ttgataaggg gagggcgggg gcgaccacga cgtattgaaa attctcacgc agtcgggcgc 2160
tcgccaactg acgtgcctgg cgtttaaacg gattgccgga ctgtgccggg gaggtgccca 2220
taaagagcgc aaactccacg ttttcccagt cgggtttgac atgcgggttt ttatccagat 2280
cgcccatcaa tgccccggag ccggcccggt aagccagtcc acagtaggcg ccatgcgcgc 2340
cgaaattctt gctgccgaag ctatttagcg caaaacgacg cagaaacgca tcgcggcctt 2400
cgtcgctggt attcgtgacc agtaactgat tggttttggg cccgaaactg gggtgctttg 2460
cgtcaattgg cgtatccggc gcatgaatag cgcgcagtcc gtccacatga ccttcgccaa 2520
acagatcgcc gccttccacg acttcttcaa taagttgctc aaagctgatg cgctgccatt 2580
tcccttcgcc gcgtttaccc acgcgtttca tcggttcaag cagtcgtagc ggactgtaca 2640
ggctttccag cagcgtggcg ccgcgcgcgc aggcggttga gcgggcgtca agaccgcttt 2700
ctcccgccag ttgctccatg gcttcgctaa aagggacgga cgagtcaatc gggtgttcct 2760
gcgacaaggg gtgataggga ttgccggcga tgcgtatcac tttgccatcg gcattaaccc 2820
gggcgcggat accgcactgt gtccaacagc cgaagcattg cgtcatggcg atggtttgtt 2880
gtggattttg ctgccagtgt gtttgcgcct gcgcctccgg aattaacgca ttgccaaaga 2940
tgcggtcgcg cgttaccttg ccggacgtcc cgtttaacag gccatcaatt gcgcgtttcg 3000

-continued

```
ccacatcacg gtagctcaga ccaaaagtga ccatcccacc gacggcgaga ccgactttta   3060
gccactgacg acgggttaaa ttagccatgt tgtaatctcc tggtgagtcc gttcagcgtt   3120
tcacgaataa taatcagtag cgctatccac aggccgaagg tgccgagaat agccagccag   3180
ccatccgttc cgcctggtaa cgagtaaggg ttaaattgcg cgttgaactt ggggacggtt   3240
tgtacctgaa tcaacaatgt ccagcgcatc agccaacata gcgccagcgc gctgagaacc   3300
agcaggacgc gtcttagctg tgataacgga tggcgtagcg ccaggctaca gaacagcagt   3360
gtgcataccc acagcgctac ccagccgaca gcgtaatatt tggctgacag ggcgacggta   3420
atccactgac ggattgccgt gccggaaagc gtatcgccgc taacccacat ggccacaacc   3480
agccccagcg ccgccagcgt ccagatttgt ccccacaata tttttggcag ccttaccgag   3540
tcgcgtcggg cggcgacaat catcagcgcg aagaacgcct gtaaggcgct aagaaacatc   3600
gccacgggga aggcgtagct aaaccagatt gggcgcgcca gcacaacgga gacttcgcgg   3660
ccggtataaa tcaacaggcc caccgcgcaa agcgcgctgg ctaacgccaa ccatttagtg   3720
acgttgtaac ttttattgaa taatcgttta atctgctgcg ccaggaacca cagagcgaga   3780
aatccggtaa acagcggcag gaataacgct ccccagggca tccacgacca gggcgtcggc   3840
caggcataga aatgccagac gcgggcggtc tggtgcagat ccgccgtcag cgccagcggt   3900
gcggtaatcg cacaggtaat ggcaatcagt aatgcccgat tttcttctgt tgcggcgtct   3960
tttttccgcc agtgaagata acaggcaaac agtgcggcgc aggcggcaat gccaataaaa   4020
aagaaatatt gtaccgccca cggcagccag ctaatgtcct gcgggtgagc cagcacttct   4080
tcaatgatga gtgaatgcgt cattcagacc tcctgccaaa gcgcgggctg cgcacggccc   4140
attaatgggg tgacaaaggc gtcgtccaga cccaggtaga aaacatgggg cgacgtgccg   4200
ttttccggct ttaatacctt gatagcgtcg cgatgctgat gaagcatggt ggcgatgcgg   4260
ctatggggat ctttgatatc gccaataata cgcgcgccgc cgacgcagga ctctacgcaa   4320
gcgggtaaca gtccggcttc cagacgatgg acgcaaaacg tgcatttatc ggcagtttgc   4380
gtttcatgat tgataaatcg ggcgtcgtaa ggacacgcct ggacacaata ggcgcagccg   4440
acgcagcgtt tgttatccac caccacaatg ccatcttccc gctgaaaggt ggcttgtacc   4500
gggcagaccg gcacacaggg ggggttatcg caatggttgc acagacgcgg caacagcaca   4560
ttcgtgactt cctgactacc ttcacgctgg acctggtatt ggttcaccgt cgtacgaaac   4620
gcgccttgcg gcgtttggtt ttcaatagtg caacttacgg tacaggactg acagccgata   4680
caacgccgca gatcgataag catggcgtaa cggtgtcggg gagagccttc atgccgctcc   4740
ggcgaaaaag gaaatttcgc ttcagccagc ggaaccagcg aggcgccagc ggtcaggacg   4800
ccaagctgct ggagaaattg ccgtttactg ctgtccatat tgactcccgt ccacattgcc   4860
aacaatgaaa catttgtcac gatgttggtt catgtgtaat gaataaaaaa tgtcgatgat   4920
ttacagtgta aaaatcgagg cggggtgcgc tctattgtgg ttaaccacat acccggcttg   4980
ttgttgatct aaaacaacat aattgacagg gatattgggg tgagaggtaa aaccgtaagg   5040
cgcctggcgg tgttggcggc agtagggcta ctttgtcatg gcgcgtgggc agggacgtgg   5100
aatatcggta ttttggccat gcgcggcgag gcgtctacgc gtagccactg gcaaccgttg   5160
gcaaagacat taagccaaca gcttccaggc gaaacctttc acatccagcc gctggatctg   5220
catcaaatgc aggaggccgt taaccaggga accgtgcagt ttgtgataac caacccggcg   5280
caatttgtcc aactgaacag ccatgcgccg ctgcgctggt tagcttccct gcgctccacg   5340
cgcgatggga aagcggtgag taatgttatt ggcagcgtga ttttgacccg gcgcgatagc   5400
```

-continued

```
ggcatcacca cggcgcatga tctcatcggt aagaccgtcg gcgcgattga tgctcaggcg   5460
tttggcggct atttattagg ctataaagcg ctcagcgacg cgggcttacg cccggagcgc   5520
gattttcatc tccgttttac cggatttcct ggcgatgcct tagtctatat gctgcgcgaa   5580
aaagcggtgc aggcggcaat tgtgccagtg tgcctgttag aaaatatgga tcaggaagga   5640
ttgattaata aaaaggactt tatcgcgctg ctttcccgac cgacgcccct gccttgctta   5700
accagtacgc cgttatatcc tgactggtcg ttcgcggcgc tacctgcggt aagcgatgcg   5760
ctggcggatc gcgtaacgcg agcgctattc aacgcgcccg ccgccgcgtc atttcactgg   5820
ggcgcgcctg cgtccaccag tcaggtggaa gccttgctgc gtgatgttcg tcagcaccct   5880
cagcagcgtc gactgtggct ggatgtcaaa agttggttaa tccagcacca gctaatggtc   5940
ggcggcgtga ttctggcgtt cttgttgctc acgctcaatt atatttgggt catgctgctg   6000
gtgcgtcgac gtggaaagca actggaacgt aatagcgtag ttcttcatca gcatgagcgg   6060
gcgctggaaa ccgcccggca aatgagcgtg ttgggtgaaa tgacctccgg gtttgcccat   6120
gagcttaatc agccgctttc cgcgattcga cattatgccc aggggtgcct gattcgactg   6180
cgcgctgcag atgaacagca tcccttgctg ccggcgctgg agcagattga ccagcaggcg   6240
caacgcggtg cggatactct gcgtaacctg cgtcactggg tcagccaggc gcagggcaac   6300
ccggtgctaa ccgaagcgtg gaaggccata gccattcgcg aggcgattga tcatgtctgg   6360
caattgttgc gtatggcgca acagtttccg acagtgactc tgcataccga ggttagcgct   6420
gcgctgcgcg taacgctgcc gtcagtgctg ctggaacagg tgctggcgaa tatcattctt   6480
aatgcggctc aggcgggcgc cacccattta tggatcgttg ctgaacgcac tgaaaacggc   6540
atcagtattg ttttacagga taacgccggg ggaatcgatg aggcgctatt acgtcaggcg   6600
tttcagccgt ttatgaccac ccgtaaagag ggatgggct tagggctggc gatttgccag   6660
cggctggtgc ggtatgggcg gggcgatatc agcatcagga accagaccgc gccggacggt   6720
ctgtcgggaa cggtggttac gatacatttc ttacatgaaa atgggggcag ggatggcgac   6780
aattcatcta ctggatgatg atacggcggt cactaacgcg tgcgcgtttt tactggaaag   6840
tctgggatat gacgtaaaat gctggacgca gggggcggat tttttggcgc aggccagtct   6900
gtatcaggcc ggggtcgtat tactggatat gcgaatgccg gtactggatg ggcagggcgt   6960
tcatgatgcg ttgcgccagt gcggaagtac cctggcggtt gtttttctta ccgggcatgg   7020
cgatgtaccg atggccgtgg agcagatgaa acgcggcgcc gtcgattttc tgcaaaaacc   7080
ggtatcggta aaaccgctac aggcggcgct ggagcgtgcg ctgacggttt catcggcagc   7140
ggtggcgcgt cgtgagatta tactgtgtta ccagcagttg acgccgaaag agcgtgagct   7200
ggccagcctg gtggcaaaag gatttatgaa ccgtgaaatt gcggaagcga tgaatatcgc   7260
ggtgcgtacc gtagaggtgc accgcgccag agtcatggaa aaaatgcagg ccggtagcct   7320
ggcggaactg attaggcgtt tcgaaaaaat ggcctcgcca gagaccagaa tacgaacaac   7380
gtatgagcca tgaataagag ctcgaattct catgtttgac agcttatcac tgatcagtga   7440
attaatggcg atgacgcatc ctcacgataa tatccgggta ggcgcaatca ctttcgtctc   7500
tactccgtta caaagcgagg ctgggtattt cccggccttt ctgttatccg aaatccactg   7560
aaagcacagc ggctggctga ggagataaat aataaacgag ggctgtatg cacaaagcat   7620
cttctgttga gttaagaacg agtatcgaga tggcacatag ccttgctcaa attggaatca   7680
ggtttgtgcc aataccagta gaaacagacg aagaagctag aggtgaatca cgacaaagcg   7740
```

```
tatcaaaaac gtatggagta gggctctaaa ctctgtataa aaagtttcca gctagctgat   7800
aacgggaaag aaacagagaa gggcacaaat attgtgtact ttaatgtgcc ctttaattta   7860
ttgattggtg gttgaattgt ccgtaacttt ttgatttaag tgcaaatttc taataaatta   7920
gaacactttc ttaaattgtc atttggcata ttacgaacaa ttccgcgtaa aaacgttctg   7980
ttacgctaaa cccttatcca gcaggctttc aaggatgtaa accataacac tctgcgaact   8040
agtgttacat tgcgtgtagc tttgagtggg caactttgtg tacacttttg tgtacccaaa   8100
aacaaaaatg tgtacccatt caatgatcac cgacacaaag ctcaggaagg cgctcggcaa   8160
gaaaagagat gatatcgaga ttatttctga ttcgcacggg cccatggcta attcccatgt   8220
cagccgttaa gtgttcctgt gtcactgaaa attgctttga gaggctctaa gggcttctca   8280
gtgcgttaca tccctggctt gttgtccaca accgttaaac cttaaaagct ttaaaagcct   8340
tatatattct ttttttcttt ataaaactta aaaccttaga ggctatttaa gttgctgatt   8400
tatattaatt ttattgttca aacatgagag cttagtacgt gaaacatgag agcttagtac   8460
gttagccatg agagcttagt acgttagcca tgagggttta gttcgttaaa catgagagct   8520
tagtacgtta aacatgagag cttagtacgt gaaacatgag agcttagtac gtactatcaa   8580
caggttgaac tgctgatctt cagatcctct acgccggacg catcgtggcc ggatcttgcg   8640
gccgcaaaaa ttaaaaatga agttttggag gcctcatttg gtgacgaaat aactaagcac   8700
ttgtctcctg tttactcccc tgagcttgag ggtcaacat gaaggtcatt gatagcagga    8760
taataataca gtaaaacgct aaaccaataa tccaaatcca gccatcccaa attggtagtg   8820
aatgattata aataacagta aacagtaatg ggccaataac accggttgca ttggtaaggc   8880
tcaccaataa tccctgtaaa gcaccttgct catgactctt tgtttggata gacatcactc   8940
cctgtaatgc aggtaaagcg atcccaccac cagccaataa aattaaaaca gggaaatcta   9000
accaaccttc agatataaac gctaaaaagg caaatgcact actatctgca ataaattcga   9060
gcagtactgc cgtttttttcg ccccatttag tggctattct tcctgccaca aaggcttgga  9120
atactgagtg taaaagacca agacccgcta atgaaaagcc aaccatcatg ctattccatc   9180
caaaacgatt ttcggtaaat agcacccaca ccgttgcggg aatttggcct atcaattgcg   9240
ctgaaaaata aataatcaac aaaatgggca tcgttttaaa taaagtgatg tacaccgaat   9300
ttgattgcgt ctcaacccct acttcggtat ctgtattatc acgtgtattt ttggtttcac   9360
ggaaccaaaa cataaccaca aggaaagtga caatatttag caacgcagcg ataaaaaagg   9420
gactatgcgg tgaaatctct cctgcaaaac caccaataat aggccccgct attaaaccaa   9480
gcccaaaact tgcccctaac caaccgaacc acttcacgcg ttgagaagct gaggtggtat   9540
cggcaatgac cgatgccgcg acagccccag tagctcctgt gatccctgaa agcaaacggc   9600
ctaaatacag catccaaagc gcacttgaaa aagccagcaa taagtaatcc agcgatgcgc   9660
ctattaatga caacaacagc actgggcgcc gaccaaatcg gtcagacatt tttccaagcc   9720
aaggagcaaa gataacctgc attaacgcat aaagtgcaag caatacgcca aagtggttag   9780
cgatatcttc cgaagcaata aattcacgta ataacgttgg caagactggc atgataaggc   9840
caatccccat ggcatcgagt aacgtaatta ccaatgcgat ctttgtcgaa ctattcattt   9900
cacttttctc tatcactgat agggagtggg aaaataactc tatcaatgat agggtgtcaa   9960
atcgatggcc cccgatggta gtgtggggtc tccccatgcg agagtaggga actgccaggc  10020
atcaaataaa acgaaaggct cagtcgaaag actgggcctt tcgttttatc tgttgtttgt  10080
cggtgaacgc tctcctgagt aggacaaatc cgccgggagc ggatttgaac gttgcgaagc  10140
```

aacggcccgg agggtggcgg gcaggacgcc cgccataaac tgccaggcat caaattaagc 10200
agaaggccat cctgacggat ggcctttttg cgtggccagt gccaagcttg catgc 10255

<210> SEQ ID NO 47
<211> LENGTH: 10465
<212> TYPE: DNA
<213> ORGANISM: Artificial Sequence
<220> FEATURE:
<223> OTHER INFORMATION: vector

<400> SEQUENCE: 47
gacctataag gaaaggccaa acaagaacac ggttgcaaaa accgtgccct taaatattga 60
atttctattc agaacacttt cttaaattgt catttggcat attacgaaca attccgcgta 120
aaaacgttct gttacgctaa acccttatcc agcaggcttt caaggatgta aaccataaca 180
ctctgcgaac tagtgttaca ttgcgtgtag ctttgagtgg gcaactttgt gtacactttt 240
gtgtacccaa aaacaaaaat gtgtacccat tcaatgatca ccgacacaaa gctcaggaag 300
gcgctcggca agaaaagaga tgatatcgag attatttctg attcgcacgg gcccatggct 360
aattcccatg tcagccgtta agtgttcctg tgtcactgaa aattgctttg agaggctcta 420
agggcttctc agtgcgttac atccctggct tgttgtccac aaccgttaaa ccttaaaagc 480
tttaaaagcc ttatatattc tttttttct tataaaactt aaaaccttag aggctattta 540
agttgctgat ttatattaat tttattgttc aaacatgaga gcttagtacg tgaaacatga 600
gagcttagta cgttagccat gagagcttag tacgttagcc atgagggttt agttcgttaa 660
acatgagagc ttagtacgtt aaacatgaga gcttagtacg tgaaacatga gagcttagta 720
cgtactatca acaggttgaa ctgctgatct tcagatcctc tacgccggac gcatcgtggc 780
cggatcttgc ggccgcaaaa attaaaaatg aagttttgga ggcctcattt ggtgacgaaa 840
taactaagca cttgtctcct gtttactccc ctgagcttga ggggtcaaca tgaaggtcat 900
tgatagcagg ataataatac agtaaaacgc taaaccaata atccaaatcc agccatccca 960
aattggtagt gaatgattat aaataacagt aaacagtaat gggccaataa caccggttgc 1020
attggtaagg ctcaccaata atccctgtaa agcaccttgc tcatgactct ttgtttggat 1080
agacatcact ccctgtaatg caggtaaagc gatcccacca ccagccaata aaattaaaac 1140
agggaaatct aaccaacctt cagatataaa cgctaaaaag gcaaatgcac tactatctgc 1200
aataaattcg agcagtactg ccgtttttc gccccattta gtggctattc ttcctgccac 1260
aaaggcttgg aatactgagt gtaaaagacc aagacccgct aatgaaaagc caaccatcat 1320
gctattccat ccaaaacgat ttcggtaaa tagcacccac accgttgcgg gaatttggcc 1380
tatcaattgc gctgaaaaat aaataatcaa caaaatgggc atcgttttaa ataaagtgat 1440
gtacaccgaa tttgattgcg tctcaacccc tacttcggta tctgtattat cacgtgtatt 1500
tttggtttca cggaaccaaa acataaccac aaggaaagtg acaatattta gcaacgcagc 1560
gataaaaaag ggactatgcg gtgaaatctc tcctgcaaaa ccaccaataa taggccccgc 1620
tattaaacca agcccaaaac ttgcccctaa ccaaccgaac cacttcacgc gttgagaagc 1680
tgaggtggta tcggcaatga ccgatgccgc gacagcccca gtagctcctg tgatccctga 1740
aagcaaacgg cctaaataca gcatccaaag cgcacttgaa aaagccagca ataagtaatc 1800
cagcgatgcg cctattaatg acaacaacag cactgggcgc cgaccaaatc ggtcagacat 1860
ttttccaagc caaggagcaa agataacctg cattaacgca taaagtgcaa gcaatacgcc 1920

-continued

```
aaagtggtta gcgatatctt ccgaagcaat aaattcacgt aataacgttg gcaagactgg   1980
catgataagg ccaatcccca tggcatcgag taacgtaatt accaatgcga tctttgtcga   2040
actattcatt tcacttttct ctatcactga tagggagtgg gaaaataact ctatcaatga   2100
tagggtgtca aatcgatggc ccccgatggt agtgtggggt ctccccatgc gagagtaggg   2160
aactgccagg catcaaataa aacgaaaggc tcagtcgaaa gactgggcct ttcgttttat   2220
ctgttgtttg tcggtgaacg ctctcctgag taggacaaat ccgccgggag cggatttgaa   2280
cgttgcgaag caacggcccg gagggtggcg ggcaggacgc ccgccataaa ctgccaggca   2340
tcaaattaag cagaaggcca tcctgacgga tggccttttt gcgtggccag tgccaagctt   2400
gcatgcctgc aggtcgactc tagaggatcc gttatatacg ctcgattttt gccggcagcc   2460
cctgacgtac tgccgcgcca gaaacccagt cgagccaggt gttggtaatg gttcttgtcg   2520
gatcggcaaa gcccagatcg ttaagattta tgcctgccct gatttgtgga tcatacggca   2580
taggcacgcc atccagagag tgctgcgttg cgcccatctc gcggtggcca tatccgtgtt   2640
cgatggcgat gacgcctggc atcacgccat ttaacaaact gatttgcgcc acgacctgac   2700
cgcccggcgt aatgatccgt acccgatcgc catgttgcag tccataacgc tcgccgtctt   2760
gcggattcag cgccaccagg tttgctggct tcacatggtg taagcgcggg atgacggctg   2820
ttgagctgga catggtattt gatttaaatg aaatcagttt cagcggccat tgcccaatgg   2880
gaaactggtc gtcaatcgca cgaccatctg acaaacgcgc cggataccag accgggcaac   2940
cgctgaagcg ctccccggtg atggcgtgac ggtgggcggc gacatctgca ttccagatct   3000
gtaagggttt tttccacgcg ttacctaacc gttgctccgt atagccgcta tcctcgggcg   3060
caaaccggcc gccacgcgag tagataaacg ccacgcgacc gacctcatca gctttaagcg   3120
tgtgctgaat tgctggcaga atgcggctga cgccggtaag cgaaatatct tcctgatttg   3180
ccagcgcgac cggcgtcttg cccataaagg cgatattagc ggctacgcgc agatagaagt   3240
cttccgcccg gttcagtgga aaagtattgc cctgcggatc ggttatcgcc cggtcgccga   3300
agccgggcag atggagccgt tttgctaccg caatacaaaa tgcttccatt gagacaggtt   3360
gcccgtccgc cgtgcggtga gtggcggggg cgacaaccgg ccagcgggcg gtagtggctt   3420
tactggctac gccgccccag ggcgccgtaa agccccagct ctcaaaattg tgcgtatccg   3480
gcacaatgta atccgccagc gccgtcgttt cattcataaa ggcgtcaatc gcgataaaga   3540
gcggcagtcg gcgagggtct tttagttttt cttccgccac ggcgcgtaga ccgggaacac   3600
cgtaaaacgg gttgctcata ttggaaatcc aggctttaag cggataagga tagccttcga   3660
gcgcggaggt caacagttcg gtaagctggc ctgccacaaa gggataccac ggcgctttgg   3720
ctggataagg ggattgccca ccggcaattt tgtcgcggta ttcttccgat gcttcataag   3780
cggttttgct acgggcaata cttaacccgg acggtttcac ttttccggca aaactgttca   3840
tgttgtagcg gggccgtcg ctaacgccgt tgaatttgcc gccgccgaca aagacgccgc   3900
cggacaagct gaggttgccg atcagcgcgt taagcatcat gaccgaccag gcgttataaa   3960
acccattgcc ggccatcatg ccgccgtgac tgatgaccgc agctttacgt ccgtgactgg   4020
taaaggtttc cgccagcgcg ataatttgcg cttccggcac gccgcactgt tcgctgtatt   4080
gcgccaacga gagcttttct gccgcctctt tcaggcgttg caacccgctc ttcaccgtga   4140
cccgttggcc gtcggcgagc gtaacgtact gcgtcacgaa aagccgtgcc tgtcggcaag   4200
tggacgcatc gaccaactcg ccgtcggtat tcagtacgac aggggtctct tcgccatcgg   4260
gcgtaagatg gcgcagcgtc aggtgttgtc cggcaagcgt cggcagctca tccgcaatga   4320
```

ccaggtgcgt ggcgttggtc caactttgct cgccggcctg ctgcatcgcc tgtacgccgg 4380
gaatcgccag ataatcagca ttataacgtt gattatccat gatccagcgg atcatcccca 4440
ttgccagcgc cgaatcactg ccgggcatga ccggttgcca gcgaccgcga ggatcggcga 4500
gcaccgttga taaggggagg gcggggggcga ccacgacgta ttgaaaattc tcacgcagtc 4560
gggcgctcgc caactgacgt gcctggcgtt taaacggatt gccggactgt gccggggagg 4620
tgcccataaa gagcgcaaac tccacgtttt cccagtcggg tttgacatgc gggtttttat 4680
ccagatcgcc catcaatgcc ccggagccgg cccggtaagc cagtccacag taggcgccat 4740
gcgcgccgaa attcttgctg ccgaagctat ttagcgcaaa acgacgcaga aacgcatcgc 4800
ggccttcgtc gctggtattc gtgaccagta actgattggt tttgggcccg aaactggggt 4860
gctttgcgtc aattggcgta tccggcgcat gaatagcgcg cagtccgtcc acatgacctt 4920
cgccaaacag atcgccgcct tccacgactt cttcaataag ttgctcaaag ctgatgcgct 4980
gccatttccc ttcgccgcgt ttacccacgc gtttcatcgg ttcaagcagt cgtagcggac 5040
tgtacaggct ttccagcagc gtggcgccgc gcgcgcaggc ggttgagcgg gcgtcaagac 5100
cgctttctcc cgccagttgc tccatggctt cgctaaaagg gacggacgag tcaatcgggt 5160
gttcctgcga caaggggtga tagggattgc cggcgatgcg tatcactttg ccatcggcat 5220
taacccgggc gcggataccg cactgtgtcc aacagccgaa gcattgcgtc atggcgatgg 5280
tttgttgtgg attttgctgc cagtgtgttt gcgcctgcgc ctccggaatt aacgcattgc 5340
caaagatgcg gtcgcgcgtt accttgccgg acgtcccgtt taacaggcca tcaattgcgc 5400
gtttcgccac atcacggtag ctcagaccaa aagtgaccat cccaccgacg gcgagaccga 5460
cttttagcca ctgacgacgg gttaaattag ccatgttgta atctcctggt gagtccgttc 5520
agcgtttcac gaataataat cagtagcgct atccacaggc cgaaggtgcc gagaatagcc 5580
agccagccat ccgttccgcc tggtaacgag taagggttaa attgcgcgtt gaacttgggg 5640
acggtttgta cctgaatcaa caatgtccag cgcatcagcc aacatagcgc cagcgcgctg 5700
agaaccagca ggacgcgtct tagctgtgat aacggatggc gtagcgccag gctacagaac 5760
agcagtgtgc atacccacag cgctacccag ccgacagcgt aatatttggc tgacagggcg 5820
acggtaatcc actgacggat tgccgtgccg gaaagcgtat cgccgctaac ccacatggcc 5880
acaaccagcc ccagcgccgc cagcgtccag atttgtcccc acaatatttt tggcagcctt 5940
accgagtcgc gtcgggcggc gacaatcatc agcgcgaaga acgcctgtaa ggcgctaaga 6000
aacatcgcca cggggaaggc gtagctaaac cagattgggc gcgccagcac aacggagact 6060
tcgcggccgg tataaatcaa caggcccacc gcgcaaagcg cgctggctaa cgccaaccat 6120
ttagtgacgt tgtaactttt attgaataat cgtttaatct gctgcgccag gaaccacaga 6180
gcgagaaatc cggtaaacag cggcaggaat aacgctcccc agggcatcca cgaccagggc 6240
gtcggccagg catagaaatg ccagacgcgg gcggtctggt gcagatccgc cgtcagcgcc 6300
agcggtgcgg taatcgcaca ggtaatggca atcagtaatg cccgattttc ttctgttgcg 6360
gcgtcttttt tccgccagtg aagataacag gcaaacagtg cggcgcaggc ggcaatgcca 6420
ataaaaaaga aatattgtac cgcccacggc agccagctaa tgtcctgcgg gtgagccagc 6480
acttcttcaa tgatgagtga atgcgtcatt cagacctcct gccaaagcgc gggctgcgca 6540
cggcccatta atggggtgac aaaggcgtcg tccagaccca ggtagaaaac atggggcgac 6600
gtgccgtttt ccggctttaa taccttgata gcgtcgcgat gctgatgaag catggtggcg 6660

-continued

```
atgcggctat ggggatcttt gatatcgcca ataatacgcg cgccgccgac gcaggactct   6720
acgcaagcgg gtaacagtcc ggcttccaga cgatggacgc aaaacgtgca tttatcggca   6780
gtttgcgttt catgattgat aaatcgggcg tcgtaaggac acgcctggac acaataggcg   6840
cagccgacgc agcgtttgtt atccaccacc acaatgccat cttcccgctg aaaggtggct   6900
tgtaccgggc agaccggcac acaggggggg ttatcgcaat ggttgcacag acgcggcaac   6960
agcacattcg tgacttcctg actaccttca cgctggacct ggtattggtt caccgtcgta   7020
cgaaacgcgc cttgcggcgt ttggttttca atagtgcaac ttacggtaca ggactgacag   7080
ccgatacaac gccgcagatc gataagcatg gcgtaacggt gtcggggaga gccttcatgc   7140
cgctccggcg aaaaaggaaa tttcgcttca gccagcggaa ccagcgaggc gccagcggtc   7200
aggacgccaa gctgctggag aaattgccgt ttactgctgt ccatattgac tcccgtccac   7260
attgccaaca atgaaacatt tgtcacgatg ttggttcatg tgtaatgaat aaaaaatgtc   7320
gatgatttac agtgtaaaaa tcgaggcggg gtgcgctcta ttgtggttaa ccacataccc   7380
ggcttgttgt tgatctaaaa caacataatt gacagggata ttggggtgag aggtaaaacc   7440
gtaaggcgcc tggcggtgtt ggcggcagta gggctacttt gtcatggcgc gtgggcaggg   7500
acgtggaata tcggtatttt ggccatgcgc ggcgaggcgt ctacgcgtag ccactggcaa   7560
ccgttggcaa agacattaag ccaacagctt ccaggcgaaa cctttcacat ccagccgctg   7620
gatctgcatc aaatgcagga ggccgttaac cagggaaccg tgcagtttgt gataaccaac   7680
ccggcgcaat ttgtccaact gaacagccat gcgccgctgc gctggttagc ttccctgcgc   7740
tccacgcgcg atgggaaagc ggtgagtaat gttattggca gcgtgatttt gacccggcgc   7800
gatagcggca tcaccacggc gcatgatctc atcggtaaga ccgtcggcgc gattgatgct   7860
caggcgtttg gcggctattt attaggctat aaagcgctca gcgacgcggg cttacgcccg   7920
gagcgcgatt ttcatctccg ttttaccgga tttcctggcg atgccttagt ctatatgctg   7980
cgcgaaaaag cggtgcaggc ggcaattgtg ccagtgtgcc tgttagaaaa tatggatcag   8040
gaaggattga ttaataaaaa ggactttatc gcgctgcttt cccgaccgac gcccctgcct   8100
tgcttaacca gtacgccgtt atatcctgac tggtcgttcg cggcgctacc tgcggtaagc   8160
gatgcgctgg cggatcgcgt aacgcgagcg ctattcaacg cgcccgccgc cgcgtcattt   8220
cactggggcg cgcctgcgtc caccagtcag gtggaagcct tgctgcgtga tgttcgtcag   8280
caccctcagc agcgtcgact gtggctggat gtcaaaagtt ggttaatcca gcaccagcta   8340
atggtcggcg gcgtgattct ggcgttcttg ttgctcacgc tcaattatat ttgggtcatg   8400
ctgctggtgc gtcgacgtgg aaagcaactg gaacgtaata gcgtagttct tcatcagcat   8460
gagcgggcgc tggaaaccgc ccggcaaatg agcgtgttgg gtgaaatgac ctccgggttt   8520
gcccatgagc ttaatcagcc gctttccgcg attcgacatt atgcccaggg gtgcctgatt   8580
cgactgcgcg ctgcagatga acagcatccc ttgctgccgg cgctggagca gattgaccag   8640
caggcgcaac gcggtgcgga tactctgcgt aacctgcgtc actgggtcag ccaggcgcag   8700
ggcaacccgg tgctaaccga agcgtggaag gccatagcca ttcgcgaggc gattgatcat   8760
gtctggcaat tgttgcgtat ggcgcaacag tttccgacag tgactctgca taccgaggtt   8820
agcgctgcgc tgcgcgtaac gctgccgtca gtgctgctgg aacaggtgct ggcgaatatc   8880
attcttaatg cggctcaggc gggcgccacc catttatgga tcgttgctga acgcactgaa   8940
aacggcatca gtattgtttt acaggataac gccgggggaa tcgatgaggc gctattacgt   9000
caggcgtttc agccgtttat gaccacccgt aaagagggga tgggcttagg gctggcgatt   9060
```

```
tgccagcggc tggtgcggta tgggcggggc gatatcagca tcaggaacca gaccgcgccg   9120
gacggtctgt cgggaacggt ggttacgata catttcttac atgaaaatgg gggcagggat   9180
ggcgacaatt catctactgg atgatgatac ggcggtcact aacgcgtgcg cgtttttact   9240
ggaaagtctg ggatatgacg taaaatgctg gacgcagggg gcggattttt tggcgcaggc   9300
cagtctgtat caggccgggg tcgtattact ggatatgcga atgccggtac tggatgggca   9360
gggcgttcat gatgcgttgc gccagtgcgg aagtaccctg gcggttgttt ttcttaccgg   9420
gcatggcgat gtaccgatgg ccgtggagca gatgaaacgc ggcgccgtcg attttctgca   9480
aaaaccggta tcggtaaaac cgctacaggc ggcgctggag cgtgcgctga cggtttcatc   9540
ggcagcggtg gcgcgtcgtg agattatact gtgttaccag cagttgacgc cgaaagagcg   9600
tgagctggcc agcctggtgg caaaaggatt tatgaaccgt gaaattgcgg aagcgatgaa   9660
tatcgcggtg cgtaccgtag aggtgcaccg cgccagagtc atggaaaaaa tgcaggccgg   9720
tagcctggcg gaactgatta ggcgtttcga aaaaatggcc tcgccagaga ccagaatacg   9780
aacaacgtat gagccatgaa taagagctcg aattctcatg tttgacagct tatcactgat   9840
cagtgaatta atggcgatga cgcatcctca cgataatatc cgggtaggcg caatcacttt   9900
cgtctctact ccgttacaaa gcgaggctgg gtatttcccg gcctttctgt tatccgaaat   9960
ccactgaaag cacagcggct ggctgaggag ataaataata aacgaggggc tgtatgcaca  10020
aagcatcttc tgttgagtta agaacgagta tcgagatggc acatagcctt gctcaaattg  10080
gaatcaggtt tgtgccaata ccagtagaaa cagacgaaga agctagaggt gaatcacgac  10140
aaagcgtatc aaaaacgtat ggagtagggc tctaaactct gtataaaaag tttccagcta  10200
gctgataacg ggaaagaaac agagaagggc acaaatattg tgtactttaa tgtgcccttt  10260
aatttattga ttggtggttg aattgtccgt aactttttga tttaagtgca aatttctaat  10320
aaattagaac actttcttaa atggtttcac tgaaacgtgt tcatagactc ctgccgctac  10380
gtacgggtca gcatcggccc aagcctgagc tgcttccagc gactcaaatt cagcaataac  10440
ggttgagcca gtaaatcccg cagcc                                         10465
```

<210> SEQ ID NO 48
<211> LENGTH: 4395
<212> TYPE: DNA
<213> ORGANISM: Artificial Sequence
<220> FEATURE:
<223> OTHER INFORMATION: vector

<400> SEQUENCE: 48

```
gacctataag gaaaggccaa acaagaacac ggttgcaaaa accgtgccct taaatattga     60
atttctattc agaacacttt cttaaattgt catttggcat attacgaaca attccgcgta    120
aaaacgttct gttacgctaa acccttatcc agcaggcttt caaggatgta aaccataaca    180
ctctgcgaac tagtgttaca ttgcgtgtag ctttgagtgg gcaactttgt gtacactttt    240
gtgtacccaa aaacaaaaat gtgtacccat tcaatgatca ccgacacaaa gctcaggaag    300
gcgctcggca agaaaagaga tgatatcgag attatttctg attcgcacgg gcccatggct    360
aattcccatg tcagccgtta agtgttcctg tgtcactgaa aattgctttg agaggctcta    420
agggcttctc agtgcgttac atccctggct tgttgtccac aaccgttaaa ccttaaaagc    480
tttaaaagcc ttatatattc tttttttttct tataaaactt aaaaccttag aggctattta    540
agttgctgat ttatattaat tttattgttc aaacatgaga gcttagtacg tgaaacatga    600
```

-continued

```
gagcttagta cgttagccat gagagcttag tacgttagcc atgagggttt agttcgttaa    660
acatgagagc ttagtacgtt aaacatgaga gcttagtacg tgaaacatga gagcttagta    720
cgtactatca acaggttgaa ctgctgatct tcagatcctc tacgccggac gcatcgtggc    780
cggatcttgc ggccgcaaaa attaaaaatg aagttttgga ggcctcattt ggtgacgaaa    840
taactaagca cttgtctcct gtttactccc ctgagcttga ggggtcaaca tgaaggtcat    900
tgatagcagg ataataatac agtaaaacgc taaaccaata atccaaatcc agccatccca    960
aattggtagt gaatgattat aaataacagt aaacagtaat gggccaataa caccggttgc   1020
attggtaagg ctcaccaata atccctgtaa agcaccttgc tcatgactct ttgtttggat   1080
agacatcact ccctgtaatg caggtaaagc gatcccacca ccagccaata aaattaaaac   1140
agggaaatct aaccaacctt cagatataaa cgctaaaaag gcaaatgcac tactatctgc   1200
aataaattcg agcagtactg ccgttttttc gccccattta gtggctattc ttcctgccac   1260
aaaggcttgg aatactgagt gtaaaagacc aagacccgct aatgaaaagc caaccatcat   1320
gctattccat ccaaaacgat ttcggtaaa tagcacccac accgttgcgg gaatttggcc   1380
tatcaattgc gctgaaaaat aaataatcaa caaaatgggc atcgttttaa ataaagtgat   1440
gtacaccgaa tttgattgcg tctcaacccc tacttcggta tctgtattat cacgtgtatt   1500
tttggtttca cggaaccaaa acataaccac aaggaaagtg acaatattta gcaacgcagc   1560
gataaaaaag ggactatgcg gtgaaatctc tcctgcaaaa ccaccaataa taggccccgc   1620
tattaaacca agcccaaaac ttgcccctaa ccaaccgaac cacttcacgc gttgagaagc   1680
tgaggtggta tcggcaatga ccgatgccgc gacagcccca gtagctcctg tgatccctga   1740
aagcaaacgg cctaaataca gcatccaaag cgcacttgaa aaagccagca ataagtaatc   1800
cagcgatgcg cctattaatg acaacaacag cactgggcgc cgaccaaatc ggtcagacat   1860
ttttccaagc caaggagcaa agataacctg cattaacgca taaagtgcaa gcaatacgcc   1920
aaagtggtta gcgatatctt ccgaagcaat aaattcacgt aataacgttg gcaagactgg   1980
catgataagg ccaatcccca tggcatcgag taacgtaatt accaatgcga tctttgtcga   2040
actattcatt tcacttttct ctatcactga tagggagtgg gaaaataact ctatcaatga   2100
tagggtgtca aatcgatggc cccgatggt agtgtggggt ctccccatgc gagagtaggg   2160
aactgccagg catcaaataa aacgaaaggc tcagtcgaaa gactgggcct ttcgttttat   2220
ctgttgtttg tcggtgaacg ctctcctgag taggacaaat ccgccgggag cggatttgaa   2280
cgttgcgaag caacggcccg gagggtggcg ggcaggacgc ccgccataaa ctgccaggca   2340
tcaaattaag cagaaggcca tcctgacgga tggccttttt gcgtggccag tgccaagctt   2400
gcatgcctgc aggtcgactc tagaggatcc attccgggga tccgtcgacc tgcagttcga   2460
agttcctatt ctctagaaag tataggaact tcagagcgct tttgaagctc acgctgccgc   2520
aagcactcag ggcgcaaggg ctgctaaagg aagcggaaca cgtagaaagc cagtccgcag   2580
aaacggtgct gaccccggat gaatgtcagc tactgggcta tctggacaag ggaaaacgca   2640
agcgcaaaga gaaagcaggt agcttgcagt gggcttacat ggcgatagct agactgggcg   2700
gttttatgga cagcaagcga accggaattg ccagctgggg cgccctctgg taaggttggg   2760
aagccctgca aagtaaactg gatggctttc ttgccgccaa ggatctgatg gcgcagggga   2820
tcaagatctg atcaagagac aggatgagga tcgtttcgca tgattgaaca agatggattg   2880
cacgcaggtt ctccggccgc ttgggtggag aggctattcg gctatgactg ggcacaacag   2940
acaatcggct gctctgatgc cgccgtgttc cggctgtcag cgcaggggcg cccggttctt   3000
```

```
tttgtcaaga ccgacctgtc cggtgccctg aatgaactgc aggacgaggc agcgcggcta   3060

tcgtggctgg ccacgacggg cgttccttgc gcagctgtgc tcgacgttgt cactgaagcg   3120

ggaagggact ggctgctatt gggcgaagtg ccggggcagg atctcctgtc atctcacctt   3180

gctcctgccg agaaagtatc catcatggct gatgcaatgc ggcggctgca tacgcttgat   3240

ccggctacct gcccattcga ccaccaagcg aaacatcgca tcgagcgagc acgtactcgg   3300

atggaagccg gtcttgtcga tcaggatgat ctggacgaag agcatcaggg gctcgcgcca   3360

gccgaactgt tcgccaggct caaggcgcgc atgcccgacg gcgaggatct cgtcgtgacc   3420

catggcgatg cctgcttgcc gaatatcatg gtggaaaatg gccgcttttc tggattcatc   3480

gactgtggcc ggctgggtgt ggcggaccgc tatcaggaca tagcgttggc tacccgtgat   3540

attgctgaag agcttggcgg cgaatgggct gaccgcttcc tcgtgcttta cggtatcgcc   3600

gctcccgatt cgcagcgcat cgccttctat cgccttcttg acgagttctt ctaataaggg   3660

gatcttgaag ttcctattcc gaagttccta ttctctagaa agtataggaa cttcgaagca   3720

gctccagcct acagagctcg aattctcatg tttgacagct tatcactgat cagtgaatta   3780

atggcgatga cgcatcctca cgataatatc cgggtaggcg caatcacttt cgtctctact   3840

ccgttacaaa gcgaggctgg gtatttcccg gcctttctgt tatccgaaat ccactgaaag   3900

cacagcggct ggctgaggag ataaataata aacgaggggc tgtatgcaca aagcatcttc   3960

tgttgagtta agaacgagta tcgagatggc acatagcctt gctcaaattg gaatcaggtt   4020

tgtgccaata ccagtagaaa cagacgaaga agctagaggt gaatcacgac aaagcgtatc   4080

aaaaacgtat ggagtagggc tctaaactct gtataaaaag tttccagcta gctgataacg   4140

ggaaagaaac agagaagggc acaaatattg tgtactttaa tgtgcccttt aatttattga   4200

ttggtggttg aattgtccgt aactttttga tttaagtgca aatttctaat aaattagaac   4260

actttcttaa atggtttcac tgaaacgtgt tcatagactc ctgccgctac gtacgggtca   4320

gcatcggccc aagcctgagc tgcttccagc gactcaaatt cagcaataac ggttgagcca   4380

gtaaatcccg cagcc                                                    4395
```

<210> SEQ ID NO 49
<211> LENGTH: 28
<212> TYPE: PRT
<213> ORGANISM: Artificial Sequence
<220> FEATURE:
<223> OTHER INFORMATION: linker

<400> SEQUENCE: 49

```
Gly Ser Ala Gly Ser Ala Glu Ala Gly Ser Asn Trp Ser His Pro Gln
1               5                   10                  15

Phe Glu Lys Gly Ser Ala Gly Ser Ala Ala Gly Ser
            20                  25
```

<210> SEQ ID NO 50
<211> LENGTH: 12
<212> TYPE: PRT
<213> ORGANISM: Artificial Sequence
<220> FEATURE:
<223> OTHER INFORMATION: linker

<400> SEQUENCE: 50

```
Gly Ser Ala Gly Ser Ala Ala Gly Ser Gly Glu Phe
1               5                   10
```

<210> SEQ ID NO 51
<211> LENGTH: 84
<212> TYPE: DNA
<213> ORGANISM: Artificial Sequence
<220> FEATURE:
<223> OTHER INFORMATION: linker

<400> SEQUENCE: 51
ggtagtgctg gtagtgctga agctggtagt aattggagtc atccacaatt tgaaaaaggt 60
agtgctggta gtgctgctgg tagt 84

<210> SEQ ID NO 52
<211> LENGTH: 36
<212> TYPE: DNA
<213> ORGANISM: Artificial Sequence
<220> FEATURE:
<223> OTHER INFORMATION: linker

<400> SEQUENCE: 52
ggtagtgctg gtagtgctgc tggtagtggt gaattt 36

<210> SEQ ID NO 53
<211> LENGTH: 3669
<212> TYPE: DNA
<213> ORGANISM: Lactobacillus reuteri JCM 1112

<400> SEQUENCE: 53
atgctatcaa gaaaaaatta taaggaaact atacgaaaac agacacctac aaaacagtac 60
tatactatta agaaattaac tgttggggtt acttcggtat taattggtct atcctttatg 120
ggagaactag aaggggatag cgttcatgcg gacacgatga cagcaagcag tgagtcaaca 180
agtgttacgt cgacgactgc tcaggatggt ttaaaaaaat ctccacaact ctatttgcaa 240
gttactgata caaataaccc aagtacacca ttaagtgctt catccacagg gactagtaag 300
aatgttacct catcagctgc ggtacaagtg aagtccgcta gtgatgaaga agatagtgat 360
tctacactag ctaagggaga aaataaattt gctcggtcag cagtaaaaga ttcagtcact 420
gatgggaaaa caagtacagc agaaattaat ccggcaaaat taagcagtcc tgctttaata 480
acgcaactca accaatcctt agctaagagc agtacgagtg atgcagcaaa agctaatgat 540
gagttagaaa ttaaagcaac agatccgact aattatccaa actgtggcga tgtgtatggg 600
ccattatttg aattggatgc tagcggacag cttgttaata aagatgaagt tatatctctt 660
aaagatatgt atattttcca aatattgaaa ttagtaaata caaaagatag tgactttcaa 720
tatgtaatat taacaatgaa tcgtaaagat actgcagata ggtctgtata tctttttgta 780
actggaagca attatagtaa tgctgttgtt gttaaagtaa agccaaatga tacttatgaa 840
ttaagtaaaa ctggatatag tgttacttat acagaaccaa caactataaa tggacattat 900
gttgatggaa ctttttatgt tacaggaagt acttacgatg atggttttat aatgccagat 960
tggcaactgc agcaccttca gattatatat agtttaggaa attatgatcc aagcaatact 1020
gacgcaacat cagtttgtga aataatgcca agttatgaaa aggtaccggt aattaaatat 1080
agtggagtac cttcaaatat tagccaacct aaggtttaca ttaccgggtt tacgggtcaa 1140
gagtttaacg ttacagatat tattaacaat tataagaaag tttttaaggg ctactatctt 1200
caaaatccta atgtggcgtc catgggaact ctttcccaat ttgagaatgg tggttattac 1260
ttaaagacat attatgataa tgatggtaat gttgacttta agggcttgta tcatcaaatt 1320
gatgatcagg gaacaatgag tgtgagtgtt cttaatgcag ataataaaac aattgttgga 1380

-continued

```
cctgaaaata ttcttgctgg taaatcgcat aactttaact ttaatggtca taactggatt   1440
gcgcggaatc cttatgtcac tagttcagct cacgaagtca tattaaagta tgctaagtta   1500
ggttcagtta ttcctgttga tgaaaacgga aataaaataa acgatggatg gcaatatgtt   1560
aatgatccag atgatgcttc caaagccact agcccatatg aaaaagcgcc agttatcgat   1620
ggttatgtag ctgtaaatcc agatgaaacg atcgttcttc ctcataactt aagtagtgac   1680
acaaagattt attaccgaaa gaggattaaa gttacctata gtggtagtga cagcaagacc   1740
tacgatggta acccagctaa cttcgagcca acgacagttc agtggagtgg cttgaaagga   1800
ctgaacactt caaccttaac gtccgctgac ttcacgtgga atactgcgga taagaaggca   1860
ccaacggatg ccggtaagta cacacttagt ttgaatacga ccggagaagc agccttacgt   1920
aaggctaacc cgaactatga tctcaagaca attagcggta gttacaccta cacgattaat   1980
ccactaggga ttgataaagt tacctatagt ggtagtgaca gcaagaccta cgatggtaac   2040
ccagctaact tcgagccaac gacagttcag tggagtggct tgaaaggact gaacacttca   2100
accttaacgt ccgctgactt cacgtggaat actgcggata agaaggcacc aacggatgcc   2160
ggtaagtaca cacttagttt gaatacgacc ggagaagcag ccttacgtaa ggctaacccg   2220
aactatgatc tcaagacaat tagcggtagt tacacctaca cgattaatcc actagggatt   2280
gataaagtta cctatagtgg tagtgacagc aagacctacg atggtaaccc agctaacttc   2340
gagccaacga cagttcagtg gagtggcttg aaaggactga acacttcaac cttaacgtcc   2400
gctgacttca cgtggaatac tgcggataag aaggcaccaa cggatgccgg taagtacaca   2460
cttagtttga atacgaccgg agaagcagcc ttacgtaagg ctaacccgaa ctatgatctc   2520
aagacaatta gcggtagtta cacctacacg attaatccac tagggattga taaagttacc   2580
tatagtggta gtgacagcaa gacctacgat ggtaacccag ctaacttcga gccaacgaca   2640
gttcagtgga gtggcttgaa aggactgaac acttcaacct taacgtccgc tgacttcacg   2700
tggaatactg cggataagaa ggcaccaacg gatgccggta agtacacact tagtttgaat   2760
acgaccggag aagcagcctt acgtaaggct aacccgaact atgatctcaa gacaattagc   2820
ggtagttaca cctacacgat taatccacta gggattgata aagttaccta tagtggtagt   2880
gacagcaaga cctacgatgg taacccagct aacttcgagc caacgacagt tcagtggagt   2940
ggcttgaaag gactgaacac ttcaacctta acgtccgctg acttcacgtg gaatactgcg   3000
gataagaagg caccaacgga tgccggtaag tacacactta gtttgaatac gaccggagaa   3060
gcagccttac gtaaggctaa cccgaactat gatctcaaga caattagcgg tagttacacc   3120
tacacgatta atccactagg gattgtgact gtaaattaca agggctatga taagaaagtc   3180
tatgatggtc aacctggaac gattaatccg ggtaaattaa cgtggagtaa gttgccagat   3240
ggtacttcat tgaagatgcc aacatggagt atagatgatt tcgcttggga aacagctgat   3300
ggcttagcac caacggcagt aggaacttat cggattatct tgacggatgc tggtaaggct   3360
gcactaaaga agattaatcc aaattatgac ttaagcagta ttactggtgt ctttacttat   3420
gaaattaagc cagcacagac accagaaatc ttaggccaaa cacctgagca acaaccaggc   3480
caaaatacta atcaatcagg agctgaaaac ggctttggtt cttctacaag gcctaatgca   3540
tcaactaact ccaatcttaa tcaacttcca cagactggta atgagcattc taatactgca   3600
cttgctggtc tagcattggc tttcttgact gctatgcttg gtttgggcaa gaagcgtaaa   3660
catgattag                                                           3669
```

<210> SEQ ID NO 54
<211> LENGTH: 18
<212> TYPE: DNA
<213> ORGANISM: Artificial Sequence
<220> FEATURE:
<223> OTHER INFORMATION: Primer

<400> SEQUENCE: 54
cggctaccac ccaaggaa 18

<210> SEQ ID NO 55
<211> LENGTH: 18
<212> TYPE: DNA
<213> ORGANISM: Artificial Sequence
<220> FEATURE:
<223> OTHER INFORMATION: Primer

<400> SEQUENCE: 55
gctggaatta ccgcggct 18

<210> SEQ ID NO 56
<211> LENGTH: 21
<212> TYPE: DNA
<213> ORGANISM: Artificial Sequence
<220> FEATURE:
<223> OTHER INFORMATION: Primer

<400> SEQUENCE: 56
accgtgaatc ttggctgtaa c 21

<210> SEQ ID NO 57
<211> LENGTH: 21
<212> TYPE: DNA
<213> ORGANISM: Artificial Sequence
<220> FEATURE:
<223> OTHER INFORMATION: Primer

<400> SEQUENCE: 57
gcagcaaatc gcttgggatt a 21

<210> SEQ ID NO 58
<211> LENGTH: 20
<212> TYPE: DNA
<213> ORGANISM: Artificial Sequence
<220> FEATURE:
<223> OTHER INFORMATION: Primer

<400> SEQUENCE: 58
tgtcagtcat cgcccatgtg 20

<210> SEQ ID NO 59
<211> LENGTH: 21
<212> TYPE: DNA
<213> ORGANISM: Artificial Sequence
<220> FEATURE:
<223> OTHER INFORMATION: Primer

<400> SEQUENCE: 59
catccttgcg agtgtcagtg a 21

<210> SEQ ID NO 60
<211> LENGTH: 24
<212> TYPE: DNA
<213> ORGANISM: Artificial Sequence
<220> FEATURE:
<223> OTHER INFORMATION: Primer

<400> SEQUENCE: 60
catcttctca aaattcgagt gaca 24

<210> SEQ ID NO 61
<211> LENGTH: 23
<212> TYPE: DNA
<213> ORGANISM: Artificial Sequence
<220> FEATURE:
<223> OTHER INFORMATION: Primer

<400> SEQUENCE: 61
tgggagtaga caaggtacaa ccc 23

<210> SEQ ID NO 62
<211> LENGTH: 23
<212> TYPE: DNA
<213> ORGANISM: Artificial Sequence
<220> FEATURE:
<223> OTHER INFORMATION: Primer

<400> SEQUENCE: 62
tcaagtggca tagatgtgga aga 23

<210> SEQ ID NO 63
<211> LENGTH: 21
<212> TYPE: DNA
<213> ORGANISM: Artificial Sequence
<220> FEATURE:
<223> OTHER INFORMATION: Primer

<400> SEQUENCE: 63
tggctctgca ggattttcat g 21

<210> SEQ ID NO 64
<211> LENGTH: 20
<212> TYPE: DNA
<213> ORGANISM: Artificial Sequence
<220> FEATURE:
<223> OTHER INFORMATION: Primer

<400> SEQUENCE: 64
agggcccttt gctatggtgt 20

<210> SEQ ID NO 65
<211> LENGTH: 20
<212> TYPE: DNA
<213> ORGANISM: Artificial Sequence
<220> FEATURE:
<223> OTHER INFORMATION: Primer

<400> SEQUENCE: 65
tggccacagt tttcagggat 20

<210> SEQ ID NO 66
<211> LENGTH: 20
<212> TYPE: DNA
<213> ORGANISM: Artificial Sequence
<220> FEATURE:
<223> OTHER INFORMATION: Primer

<400> SEQUENCE: 66
agcttccttg tgcaagtgtc 20

<210> SEQ ID NO 67
<211> LENGTH: 20

<212> TYPE: DNA
<213> ORGANISM: Artificial Sequence
<220> FEATURE:
<223> OTHER INFORMATION: Primer

<400> SEQUENCE: 67
cccttcatct tttggggtcc 20

<210> SEQ ID NO 68
<211> LENGTH: 20
<212> TYPE: DNA
<213> ORGANISM: Artificial Sequence
<220> FEATURE:
<223> OTHER INFORMATION: Primer

<400> SEQUENCE: 68
tccctctgtg atctgggaag 20

<210> SEQ ID NO 69
<211> LENGTH: 20
<212> TYPE: DNA
<213> ORGANISM: Artificial Sequence
<220> FEATURE:
<223> OTHER INFORMATION: Primer

<400> SEQUENCE: 69
ctcgaccctg aaagtgaagg 20

<210> SEQ ID NO 70
<211> LENGTH: 22
<212> TYPE: DNA
<213> ORGANISM: Artificial Sequence
<220> FEATURE:
<223> OTHER INFORMATION: Primer

<400> SEQUENCE: 70
cccgtataac catcaccatc at 22

<210> SEQ ID NO 71
<211> LENGTH: 21
<212> TYPE: DNA
<213> ORGANISM: Artificial Sequence
<220> FEATURE:
<223> OTHER INFORMATION: Primer

<400> SEQUENCE: 71
ggcatctttc ttggcaactt c 21

<210> SEQ ID NO 72
<211> LENGTH: 17
<212> TYPE: DNA
<213> ORGANISM: Artificial Sequence
<220> FEATURE:
<223> OTHER INFORMATION: Primer

<400> SEQUENCE: 72
gccagatccc gaaacca 17

<210> SEQ ID NO 73
<211> LENGTH: 20
<212> TYPE: DNA
<213> ORGANISM: Artificial Sequence
<220> FEATURE:
<223> OTHER INFORMATION: Primer -continued

<400> SEQUENCE: 73
tataggagtc tcggcagtca 20

PROBIOTIC COMPOSITIONS AND USES THEREOF

CROSS-REFERENCE TO RELATED APPLICATION(S)

This application is a national phase application under 35 U.S.C. § 371 and claims priority to and the benefit of International Application No. PCT/CA2018/050188 filed Feb. 19, 2018, which claims priority to and the benefit of U.S. Provisional Application No. 62/460,185 filed Feb. 17, 2017, the entire contents of both of which are incorporated herein by reference.

SEQUENCE LISTING

The instant application contains a Sequence Listing submitted in ASCII format via EFS-Web and is incorporated herein by reference in its entirety. The ASCII file, modified on Nov. 6, 2019, is named Amended-SQL-txt and is 161,176 bytes in size.

FIELD OF INVENTION

The present invention relates to probiotic compositions. More specifically, the present invention relates to probiotic compositions that are useful in reducing inflammation.

BACKGROUND OF THE INVENTION

Inflammatory bowel disease (IBD), inclusive of ulcerative colitis and Crohn's disease, is a major health burden in Western countries. A highly oxidized environment is found within the gastrointestinal tract during periods of inflammation. At sites of active inflammation within the gut of IBD patients, enhanced production of reactive oxygen species (ROS) is common. The abundance of these chemically-reactive species results in higher suppression of growth of anaerobic bacteria, compared to aerobic bacteria, because the latter are better adapted to ROS survival. The resulting overabundance of aerobic bacterial species is opposite to a healthy microbial ecosystem. This dysbiosis within the gastrointestinal system can have profound implications on human health. It is known that some aerobic bacteria residing within the gastrointestinal tract, such as *Escherichia coli*, induce damaging inflammation. Pathobiotic aerobic species, such as Adherent Invasive *E. coli* (AIEC), are associated with the mucosa of ulcerative colitis patients in elevated levels and cause damaging pro-inflammatory effects. This inflammation-induced disbalance is believed to further enhance inflammation and production of ROS.

Probiotic therapy, which is the ingestion of non-pathogenic microorganisms to provide health benefits, has been described as a potential treatment option for IBD. Probiotics are considered safe for human consumption, even in the absence of disease, as some have been shown to provide beneficial properties to the host. Various kinds of probiotics have been tested clinically as potential therapeutic agents for gut health. To date, however, many clinical trials have reported low efficacy of tested probiotic strains.

Probiotics face strong competition when trying to colonize the gut and very few studies have shown long-term colonization. Even adherent strains are diluted out by the existing microbiota unless replenished by a fresh inoculum of the strain. They are also not able to outcompete and face strong competition when trying to colonize and establish themselves (Alander M. et al. (1999) Appl Environ Microbiol. 65(1):351-354). Even in the absence of disease, there is a lack of evidence to support colonization of probiotics in healthy individuals.

Many of the commonly used probiotic species have a low tolerance to ROS. Aerobic probiotic species with anti-inflammatory effects (e.g. *E. coli* Nissle), may have additional colonization issues as inflammation sites are already heavily colonized with native gut aerobes and more invasive strains of *E. coli* (the effect commonly known as colonization resistance). The use of recombinant probiotic organisms that express bacterial virulence factors and stress survival genes from pathogenic bacteria (reviewed in Eamonn et al. 2009. Gut Pathogens November 23; 1(1):19) has been explored.

The N-acetyl-glucosamine binding protein (GbpA) from *Vibrio cholerae* is a well-studied adhesin with a modular multi-domain structure and studies have shown that the first N-terminal domain ($GbpA_{DI}$) is required for binding to intestinal epithelial cell (IEC)-associated mucins (Wong E et al. 2012 PLoS Pathog 8:e1002373.5).

Tetrathionate reductase is encoded as a 5-gene operon present in *Salmonella* ssp. and promotes the growth of *Salmonella* in the intestinal lumen during inflammation (Winter et al. (2010) Nature. 467:426-429). Studies have shown that the genes required for tetrathionate utilization can be expressed from a plasmid in *E. coli* giving its host the capacity to utilize tetrathionate (Hensel et al. 1999. Mol Microbiol. 32:275-287).

SUMMARY OF THE INVENTION

The present invention relates, in part, to probiotic compositions.

In one aspect the present invention provides a recombinant probiotic bacterium expressing an N-acetyl-glucosamine binding protein A or fragment or homologue thereof.

In some embodiments, the N-acetyl-glucosamine binding protein A may include an amino acid sequence substantially identical to the sequence set forth in NCBI Accession No. KKP14471.

In some embodiments, the N-acetyl-glucosamine binding protein A may include an amino acid sequence substantially identical to SEQ ID NO: 19.

In some embodiments, the N-acetyl-glucosamine binding protein A may be encoded by a nucleic acid sequence substantially identical to SEQ ID NO: 26.

In some embodiments, the N-acetyl-glucosamine binding protein A fragment may be an N-terminal fragment.

In some embodiments, the N-terminal fragment may include a mucin binding domain.

In some embodiments, the mucin binding domain may be encoded by a nucleic acid sequence substantially identical to SEQ ID NO: 22.

In some embodiments, the N-terminal fragment may include an amino acid sequence substantially identical to SEQ ID NO: 20.

In some embodiments, the N-acetyl-glucosamine binding protein A may be encoded by a nucleic acid sequence substantially identical to SEQ ID NO: 27.

In some embodiments, the N-acetyl-glucosamine binding protein A may be encoded by a nucleic acid sequence harmonized for expression in a host microorganism.

In some embodiments, the N-acetyl-glucosamine binding protein A may be from a bacterium from the phyla Gammaproteobacteria, Enterobacteria or Firmicutes.

In some embodiments, the N-acetyl-glucosamine binding protein A may be from a *Vibrio* spp, *Escherichia* ssp., *Yersinia* ssp., *Shewanella* ssp., *Photobacterium* ssp., *Listeria* ssp., *Enterobacter* ssp., *Aeromonas* ssp., *Klebsiella* ssp. or *Aliivibrio* ssp.

In some embodiments, the N-acetyl-glucosamine binding protein A may be from a *V. cholerae, V. mimicus, V. metoecus, V. vulnificus, V. parahaemolyticus*, or *V. fischeri.*

In some embodiments, the N-acetyl-glucosamine binding protein A or fragment thereof may be co-expressed or recombined with a bacterial surface protein.

In some embodiments, the bacterial surface protein may be a mucus binding protein or a fragment thereof.

In some embodiments, the N-acetyl-glucosamine binding protein may include the mucus binding protein or a fragment thereof.

In some embodiments, the mucus binding protein may include an amino acid sequence substantially identical to SEQ ID NO: 21 or SEQ ID NO: 28.

In some embodiments, the recombined mucus binding protein-N-acetyl-glucosamine binding protein A may include an amino acid sequence substantially identical to SEQ ID NO: 29.

In some embodiments, the recombined mucus binding protein-N-acetyl-glucosamine binding protein A may be encoded by a nucleic acid sequence substantially identical to SEQ ID NO: 24 or SEQ ID NO: 30.

In some embodiments, the bacterial surface protein may be isolated from a non-pathogenic bacterium, such as a probiotic bacterium.

In some embodiments, the bacterial surface protein may be isolated from *Lactobacillus reuteri.*

In another aspect, the present invention provides a recombinant probiotic bacterium expressing a tetrathionate reductase or homologue thereof.

In some embodiments, the tetrathionate reductase may be encoded by the tetrathionate respiratory operon or portion thereof.

In some embodiments, the tetrathionate respiratory operon may include the ttrACBSR operon from *Salmonella enterica.*

In some embodiments, the ttrACBSR operon from *Salmonella enterica* may include a sequence substantially identical to SEQ ID NO: 25.

In some embodiments, the tetrathionate respiratory operon may include the ttrACB operon from *Salmonella enterica.*

In some embodiments, the ttrACB operon from *Salmonella enterica* may include a sequence substantially identical to SEQ ID NO: 31.

In some embodiments, the tetrathionate respiratory operon may further include the ttrSR operon from *Salmonella enterica.*

In some embodiments, the ttrSR operon from *Salmonella enterica* may include a sequence substantially identical to SEQ ID NO: 32.

In some embodiments, the tetrathionate reductase or the tetrathionate respiratory operon may include the ttrA, ttrC and ttrB genes of *Salmonella enterica.*

In some embodiments, the ttrA gene of *Salmonella enterica* may include a nucleic acid sequence substantially identical to SEQ ID NO: 33.

In some embodiments, the ttrA gene of *Salmonella enterica* may encode an amino acid sequence including a sequence substantially identical to SEQ ID NO: 34.

In some embodiments, the ttrB gene of *Salmonella enterica* may include a nucleic acid sequence substantially identical to SEQ ID NO: 35.

In some embodiments, the ttrB gene of *Salmonella enterica* may encode an amino acid sequence including a sequence substantially identical to SEQ ID NO: 36.

In some embodiments, the ttrC gene of *Salmonella enterica* may include a nucleic acid sequence substantially identical to SEQ ID NO: 37.

In some embodiments, the ttrC gene of *Salmonella enterica* may encode an amino acid sequence including a sequence substantially identical to SEQ ID NO: 38.

In some embodiments, the tetrathionate reductase may be encoded by, or the tetrathionate respiratory operon may further include, the ttrS and ttrR genes of *Salmonella enterica.*

In some embodiments, the ttrR gene of *Salmonella enterica* may include a nucleic acid sequence substantially identical to SEQ ID NO: 39.

In some embodiments, the ttrR gene of *Salmonella enterica* may encode an amino acid sequence including a sequence substantially identical to SEQ ID NO: 40.

In some embodiments, the ttrS gene of *Salmonella enterica* may include a nucleic acid sequence substantially identical to SEQ ID NO: 41.

In some embodiments, the ttrS gene of *Salmonella enterica* may encode an amino acid sequence including a sequence substantially identical to SEQ ID NO: 42.

In some embodiments, the ttrA, ttrC and ttrB genes of *Salmonella enterica*, or a tetrathionate respiratory operon including the ttrA, ttrC and ttrB genes of *Salmonella enterica*, may be provided in combination with an oxygen-sensitive promoter-operator.

In some embodiments, the tetrathionate reductase or homologue thereof may be isolated from the Enterobacteriaceae family or the Vibrionaceae family.

In some embodiments, the tetrathionate reductase or the tetrathionate respiratory operon may be isolated from a *Salmonella* ssp., *Yersinia* ssp., *Proteus* ssp., *Citrobacter* ssp., *Klebsiella* sp., *Raoultella* sp., *Escherichia* sp., *Serratia* sp., *Leclercia* sp., *Morganella* sp., *Providencia* sp. *Enterobacter* sp. or *Vibrio* sp.

In some embodiments, the tetrathionate reductase may be encoded by, or the tetrathionate respiratory operon may include, a nucleic acid sequence harmonized for expression in a host microorganism.

In some embodiments, the expression of the N-acetyl-glucosamine binding protein A, the tetrathionate reductase, or both, may be chromosomal or may be plasm id-based.

In some embodiments, the recombinant probiotic bacterium may be a *Lactobacillus, Bifidobacterium, Lactococcus, Enterococcus, Streptococcus, Pediococcus, Leuconostoc, Bacillus*, or *Escherichia.*

In some embodiments, the recombinant probiotic bacterium may be a *Lactobacillus reuteri, Lactobacillus plantarum, Lactobacillus casei, Lactobacillus casei* Shirota, *Lactobacillus salivarius, Lactobacillus paracasei, Lactobacillus lactis, Lactobacillus acidophilus, Lactobacillus sakei, Lactobacillus brevis, Lactobacillus buchneri, Lactobacillus fermentum, Lactobacillus delbrueckii, Lactobacillus delbrueckii* subsp. *bulgaricus, Lactobacillus helveticus, Lactobacillus garvieae, Lactobacillus acetotolerans, Lactobacillus agilis, Lactobacillus algidus, Lactobacillus alimentarius, Lactobacillus amylolyticus, Lactobacillus amylophilus, Lactobacillus amylovorus, Lactobacillus animalis, Lactobacillus aviarus, Lactobacillus bifermentans, Lactobacillus bulgaricus, Lactobacillus camis, Lacto-

*bacillus caternaformis, Lactobacillus cellobiosis, Lactobacillus collinoides, Lactobacillus confuses, Lactobacillus coryniformis, Lactobacillus crispatus, Lactobacillus curvatus, Lactobacillus divergens, Lactobacillus farciminis, Lactobacillus fructivorans, Lactobacillus fructosus, Lactobacillus gallinarum, Lactobacillus gasseri, Lactobacillus graminis, Lactobacillus halotolerans, Lactobacillus hamster, Lactobacillus heterohiochii, Lactobacillus hilgardii, Lactobacillus homohiochii, Lactobacillus iners, Lactobacillus intestinalis, Lactobacillus jensenii, Lactobacillus johnsonii, Lactobacillus kandleri, Lactobacillus kefiri, Lactobacillus kefuranofaciens, Lactobacillus kefirgranum, Lactobacillus kunkeei, Lactobacillus leichmannii, Lactobacillus lindneri, Lactobacillus malefermentans, Lactobacillus mali, Lactobacillus maltaromicus, Lactobacillus manihotivorans, Lactobacillus minor, Lactobacillus minutus, Lactobacillus mucosae, Lactobacillus murinus, Lactobacillus nagelii, Lactobacillus oris, Lactobacillus panis, Lactobacillus parabuchneri, Lactobacillus paracasei, Lactobacillus parakefiri, Lactobacillus paralimentarius, Lactobacillus paraplantarum, Lactobacillus pentosus, Lactobacillus perolens, Lactobacillus piscicola, Lactobacillus plantarum, Lactobacillus pontis, Lactobacillus rhamnosus, Lactobacillus rhamnosus* GG, *Lactobacillus* rimae, *Lactobacillus rogosae, Lactobacillus ruminis, Lactobacillus sanfranciscensis, Lactobacillus sharpeae, Lactobacillus suebicus, Lactobacillus trichodes, Lactobacillus uli, Lactobacillus vaccinostercus, Lactobacillus vaginalis, Lactobacillus viridescens, Lactobacillus vitulinus, Lactobacillus xylosus, Lactobacillus yamanashiensis*, or a *Lactobacillus zeae, Escherichia coli, Bifidobacterium infantis, Bifidobacterium adolescentis, Bifidobacterium animalis* subsp *animalis, Bifidobacterium longum, Bifidobacterium breve, Bifidobacterium bifidum, Bifidobacterium animalis* subsp. *Lactis, Bifidobacterium lactis, Bifidobacterium lactis* DN-173 010, *Bacillus coagulans, Lactococcus lactis* subsp. *Lactis, Lactococcus lactis* subsp. *lactis* CV56, *Enterococcus durans*, or *Streptococcus thermophilus*.

In some embodiments, the recombinant probiotic bacterium may be *E. coli* Nissle 1917 or *L. reuteri* DSM20016.

In some embodiments, the recombinant probiotic bacterium may include an auxotrophic mutation.

In alternative aspects, the present invention provides a nucleic acid molecule including a nucleic acid sequence encoding an N-acetyl-glucosamine binding protein A or fragment or homologue thereof in combination with a bacterial surface protein.

In some embodiments, the N-acetyl-glucosamine binding protein A or fragment or homologue thereof may be encoded by a nucleic acid sequence substantially identical to SEQ ID NO: 22, SEQ ID NO: 26 or SEQ ID NO: 27.

In some embodiments, the nucleic acid molecule may encode a N-acetyl-glucosamine binding protein A or fragment or homologue thereof including an amino acid sequence substantially identical to SEQ ID NO: 19 or SEQ ID NO: 20.

In some embodiments, the bacterial surface protein may be a mucus binding protein or homologue thereof.

In some embodiments, the mucus binding protein may be encoded by a nucleic acid sequence substantially identical to SEQ ID NO: 23 or SEQ ID NO: 53.

In some embodiments, the nucleic acid molecule may encode a mucus binding protein or homologue thereof including an amino acid sequence substantially identical to SEQ ID NO: 21 or SEQ ID NO: 28.

In some embodiments, the nucleic acid molecule may include a sequence substantially identical to SEQ ID NO: 24 or SEQ ID NO: 30.

In alternative aspects, the present invention provides a vector including a nucleic acid sequence as described herein.

In some embodiments, the vector may include a sequence substantially identical to SEQ ID NO: 44.

In alternative aspects, the present invention provides a host cell including a vector as described herein.

In alternative aspects, the present invention provides a method of increasing colonization of a probiotic bacterium in the gastrointestinal tract of a subject in need thereof, by administering a recombinant probiotic bacterium as described herein to the subject.

In alternative aspects, the present invention provides a method of reducing inflammation in the gastrointestinal tract of a subject in need thereof, by administering a recombinant probiotic bacterium as described herein to the subject.

In alternative aspects, the present invention provides a method of treating or preventing irritable bowel disease in a subject in need thereof, by administering a recombinant probiotic bacterium as described herein to the subject.

In alternative aspects, the present invention provides a use of the recombinant probiotic bacterium as described herein, for increasing colonization of a probiotic bacterium in the gastrointestinal tract of a subject in need thereof.

In alternative aspects, the present invention provides a use of the recombinant probiotic bacterium as described herein, for reducing inflammation in the gastrointestinal tract of a subject in need thereof.

In alternative aspects, the present invention provides a use of the recombinant probiotic bacterium as described herein, for treating or preventing irritable bowel disease in a subject in need thereof.

In some embodiments, the subject may be a human.

This summary of the invention does not necessarily describe all features of the invention.

BRIEF DESCRIPTION OF THE DRAWINGS

These and other features of the invention will become more apparent from the following description in which reference is made to the appended drawings.

Figure 27:
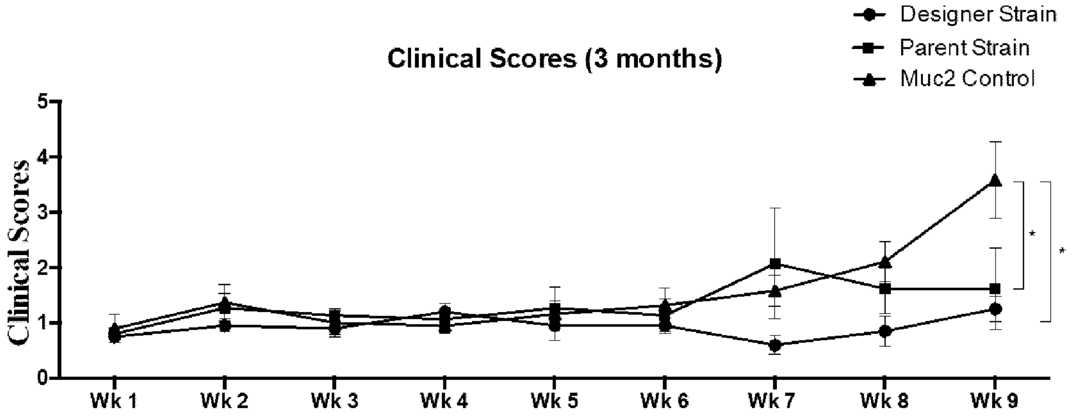

FIG. 27 is a graph showing clinical scores at 3 months of age of *E. coli* designer probiotic supplemented Muc2$^{-/-}$ mice, *E. coli* parent probiotic supplemented Muc2$^{-/-}$ mice or the control Muc2$^{-/-}$ mice. Clinical scores are based on parameters of body movement, rectal bleeding, stool consistency, weight change, and hydration. Circles represent mice treated with the *E. coli* designer strain, squares represent mice treated with the *E. coli* parent strain, and triangles represent Muc2$^{-/-}$ control mice. Values are expressed as mean+/−SEM (n=15-20). Non-parametric one-way ANOVA (Kruskal-Wallis) test was used.

Figure 28A:
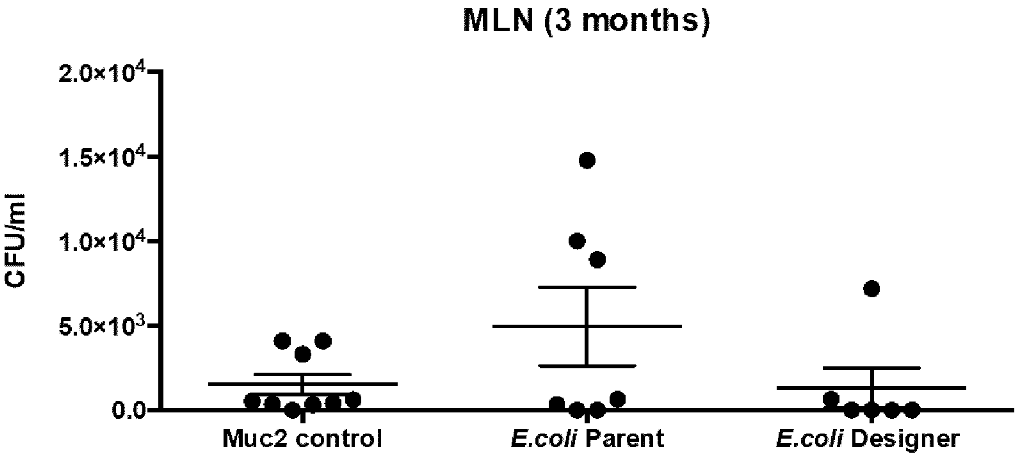

FIG. 28A is a graph showing CFU/mL counts at 3 months of age. CFU/ml calculated from homogenates of mesenteric lymph nodes (MLN) grown on 1.8% LB agar. Values are expressed as mean+/−SEM (n=7-12).

Figure 28B:
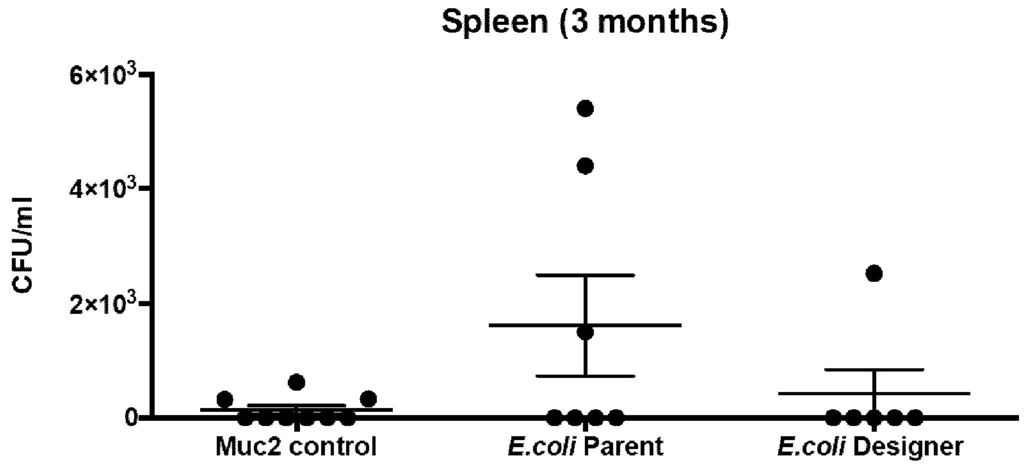

FIG. 28B is a graph showing CFU/mL counts at 3 months of age. CFU/ml calculated from homogenates of spleen grown on 1.8% LB agar. Values are expressed as mean+/−SEM (n=7-12).

Figure 29A:
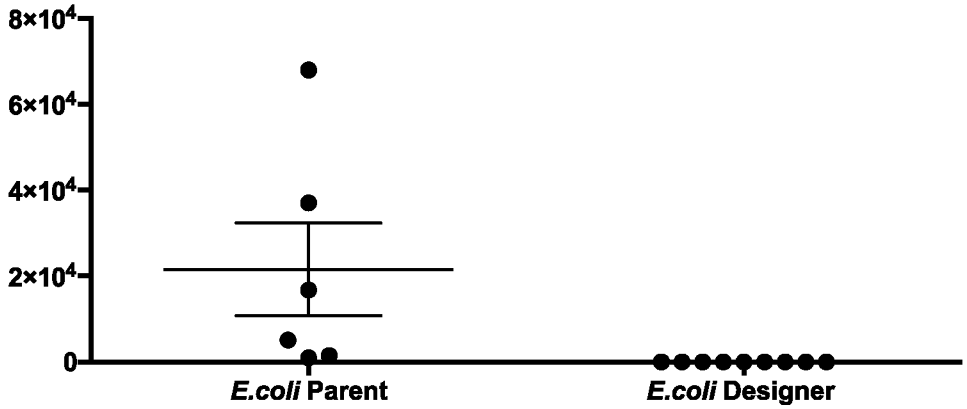

FIG. 29A is a graph showing CFU/mL counts at 4 months of age. CFU/mL calculated from homogenates of MLN grown on 1.8% LB agar. Values are expressed as mean+/−SEM (n=7-12). Non-parametric t-test (Mann-Whitney U test) was used.

Figure 29B:
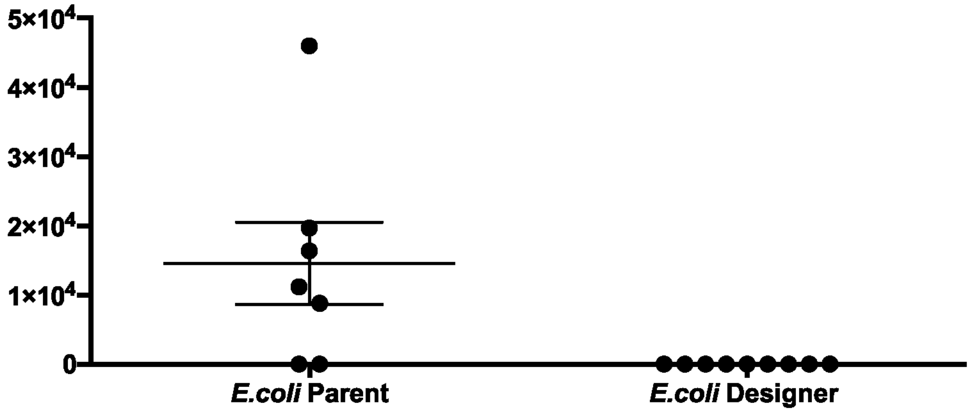

FIG. 29B is a graph showing CFU/mL counts at 4 months of age. CFU/mL calculated from homogenates of spleen grown on 1.8% LB agar. Values are expressed as mean+/−SEM (n=7-12). Non-parametric t-test (Mann-Whitney U test) was used.

FIG. 30A is the amino acid sequence of the N-acetyl-glucosamine binding protein (GbpA) from *Vibrio cholerae*, UniRef100 accession number: UniRef100_Q9KLD5, SEQ ID NO: 19.

FIG. 30B is the nucleic acid sequence encoding the N-acetyl-glucosamine binding protein (GbpA) from *Vibrio cholerae*, SEQ ID NO: 26.

FIG. 31A is the amino acid sequence of the N-terminal mucin binding domain ($GbpA_{DI}$) of GbpA from *Vibrio cholerae*, UniRef100 Accession No: UniRef100_Q9KLD5, SEQ ID NO: 20.

FIG. 31B is a nucleic acid sequence encoding a N-terminal fragment, including the signal peptide, of GbpA from *Vibrio cholerae*, SEQ ID NO: 27.

FIG. 31C is a harmonized nucleic acid sequence encoding the N-terminal mucin binding domain ($GbpA_{DI}$) of GbpA from *Vibrio cholerae* (SEQ ID NO: 22)

FIG. 32A is the amino acid sequence of a mucus binding protein (MBP), SEQ ID NO: 21.

FIG. 32B is the amino acid sequence of a mucus binding protein (MBP), SEQ ID NO: 28.

FIG. 32C is the nucleic acid sequence encoding a mucus binding protein (MBP), SEQ ID NO: 53.

FIG. 32D is the nucleic acid sequence encoding a mucus binding protein (MBP), SEQ ID NO: 23.

FIG. 33A is a nucleic acid sequence encoding a GbpA fragment within a MBP nucleotide sequence (SEQ ID NO: 24).

FIG. 33B is the amino acid sequence of a GbpA-MBP chimeric protein, with the linker sequence indicated in bold and the GbpA fragment underlined, SEQ ID NO: 29.

FIG. 33C is the nucleic acid sequence encoding a GbpA-MBP chimeric protein, with the linker sequence indicated in bold and the GbpA fragment underlined, SEQ ID NO: 30.

FIG. 34A is the nucleic acid sequence of the ttr operon (SEQ ID NO: 25).

FIG. 34B is the nucleic acid sequence of the ttrACB operon (SEQ ID NO: 31).

FIG. 34C is the nucleic acid sequence of the ttrSR operon (SEQ ID NO: 32).

FIG. 34D is the nucleic acid sequence of the ttrA gene (SEQ ID NO: 33).

FIG. 34E is the amino acid sequence of a ttrA protein (SEQ ID NO: 34).

FIG. 34F is the nucleic acid sequence of the ttrB gene (SEQ ID NO: 35).

FIG. 34G is the amino acid sequence of a ttrB protein (SEQ ID NO: 36).

FIG. 34H is the nucleic acid sequence of the ttrC gene (SEQ ID NO: 37).

FIG. 34I is the amino acid sequence of a ttrC protein (SEQ ID NO: 38).

FIG. 34J is the nucleic acid sequence of the ttrR gene (SEQ ID NO: 39).

FIG. 34K is the amino acid sequence of a ttrR protein (SEQ ID NO: 40).

FIG. 34L is the nucleic acid sequence of the ttrS gene (SEQ ID NO: 41).

FIG. 34M is the amino acid sequence of a ttrS protein (SEQ ID NO: 42).

FIG. 35A is the nucleic acid sequence of the pG+host5 empty vector (SEQ ID NO: 43).

FIG. 35B is the nucleic acid sequence of the pG+host5-lar-gbpA vector (SEQ ID NO: 44).

FIG. 36A is the nucleic acid sequence of the pAH162 empty vector (SEQ ID NO: 45).

FIG. 36B is the nucleic acid sequence of the pAH162-ttrACBSR vector (SEQ ID NO: 46).

FIG. 37A is a portion of the nucleic acid sequence of *Escherichia coli* Nissle 1917 (GenBank Accession No. CP007799.1) with the pAH162-ttrACBSR plasmid integrated to the attB-site of phage phi 80 (the integrated plasmid is underlined) (*E. coli* Nissle $attB^{phi80}$::ttrACBSR, (SEQ ID NO: 47).

FIG. 37B is a portion of the nucleic acid sequence of *E. coli* Nissle $attB^{phi80}$::ttrACBSR with the ttrACBSR operon deleted (the integrated plasmid is underlined) (*E. coli* Nissle $attB^{phi80}$::$Km^R$, (SEQ ID NO: 48).

DETAILED DESCRIPTION

The present disclosure relates, in part, to probiotic compositions and uses thereof. In some embodiments, a probiotic composition in accordance with the present disclosure may exhibit increased colonization and persistence in the gastrointestinal tract of a subject. In some embodiments, a probiotic composition in accordance with the present disclosure may prevent, reduce or ameliorate inflammation in the gastrointestinal tract of a subject.

The gastrointestinal tract or "GI" tract is often the site of inflammation. Inflammation of the GI tract has been correlated to several disorders including, but not limited to, ulcers, gastritis, inflammatory bowel disease, etc. The terms "inflammatory bowel disease" (IBD), "irritable bowel syndrome", or "intestinal inflammation," as used herein, refer to or describe a group of physiological conditions that are typically associated with intestinal inflammation, abdominal pain, cramping, constipation or diarrhea. IBD includes ulcerative colitis and Crohn's disease.

The term "probiotic bacteria" refers to live bacteria, which may confer health benefits to their host when administered in sufficient amounts. Probiotic bacteria may be useful in the prophylaxis and/or treatment of undesirable inflammatory activity, especially undesirable gastrointestinal inflammatory activity, such as inflammatory bowel disease, irritable bowel syndrome, or intestinal inflammation. In some embodiments, a probiotic bacterium, as used herein, may be any probiotic bacterium amenable to recombinant techniques. Examples of probiotic bacteria include, but are not limited to, specific probiotic strains of *Lactobacillus, Bifidobacterium, Lactococcus, Enterococcus, Streptococcus, Pediococcus, Leuconostoc, Bacillus*, or *Escherichia coli*. In some embodiments, a probiotic *Lactobacillus* may include, without limitation, a *Lactobacillus reuteri, Lactobacillus plantarum, Lactobacillus casei* (such as *Lactobacillus casei* Shirota), *Lactobacillus salivarius, Lactobacillus paracasei, Lactobacillus lactis, Lactobacillus acidophilus, Lactobacillus sakei, Lactobacillus brevis, Lactobacillus buchneri, Lactobacillus fermentum, Lactobacillus delbrueckii, Lactobacillus delbrueckii* subsp. *bulgaricus, Lactobacillus helveticus, Lactobacillus garvieae, Lactobacillus acetotolerans, Lactobacillus agilis, Lactobacillus algidus, Lactobacillus alimentarius, Lactobacillus amylolyticus, Lactobacillus amylophilus, Lactobacillus amylovorus, Lactobacillus animalis, Lactobacillus aviarus, Lactobacillus bifermentans, Lactobacillus bulgaricus, Lactobacillus camis, Lactobacillus caternaformis, Lactobacillus cellobiosis, Lactobacillus collinoides, Lactobacillus confuses, Lactobacillus coryniformis, Lactobacillus crispatus, Lactobacillus curvatus, Lactobacillus divergens, Lactobacillus farciminis, Lactobacillus fructivorans, Lactobacillus fructosus, Lactobacillus gallinarum, Lactobacillus gasseri, Lactobacillus graminis, Lactobacillus halotolerans, Lactobacillus hamster, Lactobacillus heterohiochii, Lactobacillus hilgardii, Lactobacillus homohiochii, Lactobacillus iners, Lactobacillus intestinalis, Lactobacillus jensenii, Lactobacillus johnsonii, Lactobacillus kandleri, Lactobacillus kefiri, Lactobacillus kefuranofaciens, Lactobacillus kefirgranum, Lactobacillus kunkeei, Lactobacillus leichmannii, Lactobacillus lindneri, Lactobacillus malefermentans, Lactobacillus mali, Lactobacillus maltaromicus, Lactobacillus manihotivorans, Lactobacillus minor, Lactobacillus minutus, Lactobacillus mucosae, Lactobacillus murinus, Lactobacillus nagelii, Lactobacillus oris, Lactobacillus panis, Lactobacillus parabuchneri, Lactobacillus paracasei, Lactobacillus parakefiri, Lactobacillus paralimentarius, Lactobacillus paraplantarum, Lactobacillus pentosus, Lactobacillus perolens, Lactobacillus piscicola, Lactobacillus plantarum, Lactobacillus pontis, Lactobacillus rhamnosus, Lactobacillus rhamnosus* GG, *Lactobacillus rimae, Lactobacillus rogosae, Lactobacillus ruminis, Lactobacillus sanfranciscensis, Lactobacillus sharpeae, Lactobacillus suebicus, Lactobacillus trichodes, Lactobacillus uli, Lactobacillus vaccinostercus, Lactobacillus vaginalis, Lactobacillus viridescens, Lactobacillus vitulinus, Lactobacillus xylosus, Lactobacillus yamanashiensis*, or a *Lactobacillus zeae*. In some embodiments, a probiotic *Escherichia coli* may be *E. coli* Nissle 1917 (complete genome set forth in Accession No. CP007799.1; www[dot]ncbi[dot]nlm[dot]nih[dot]gov/nuccore/CP007799.1?report=fasta) or a subspecies or strain thereof. In some embodiments, a probiotic *Bifidobacterium* may be *Bifidobacterium infantis, Bifidobacterium adolescentis, Bifidobacterium animalis* subsp *animalis, Bifidobacterium longum, Bifidobacterium fidobacterium breve, Bifidobacterium bifidum, Bifidobacterium animalis* subsp. *lactis* or *Bifidobacterium lactis*, such as *Bifidobacterium lactis* DN-173 010. In some embodiments, a probiotic *Bacillus* may be *Bacillus coagulans*. In some embodiments, a probiotic *Lactococcus* may be *Lactococcus lactis* subsp. *Lactis* such as *Lactococcus lactis* subsp. *lactis* CV56. In some embodiments, a probiotic *Enterococcus* may be *Enterococcus durans*. In some embodiments, a probiotic *Streptococcus* may be *Streptococcus thermophilus*. In some embodiments, the probiotic bacterium may be an auxotrophic strain designed, for example, to limit its survival outside of the human or animal intestine, using standard techniques.

The term "recombinant" means that something has been recombined, so that when made in reference to a nucleic acid construct the term refers to a molecule that is comprised of nucleic acid sequences that are joined together or produced by means of molecular biological techniques. The term "recombinant" when made in reference to a protein or a polypeptide refers to a protein or polypeptide molecule which is expressed using a recombinant nucleic acid construct created by means of molecular biological techniques. The term "recombinant" when made in reference to genetic composition refers to a gamete or progeny with new combinations of alleles that did not occur in the parental genomes. Recombinant nucleic acid constructs may include a nucleotide sequence which is ligated to, or is manipulated to become ligated to, a nucleic acid sequence to which it is not ligated in nature, or to which it is ligated at a different location in nature. Referring to a nucleic acid construct as 'recombinant' therefore indicates that the nucleic acid molecule has been manipulated using genetic engineering, i.e. by human intervention. Recombinant nucleic acid constructs may for example be introduced into a host cell, such as a probiotic bacterium, to generate a "recombinant probiotic bacterium." Such recombinant nucleic acid constructs may include sequences derived from the same host cell species or from different host cell species, which have been isolated and reintroduced into cells of the host species. Recombinant nucleic acid construct sequences may become integrated into a host cell genome, either as a result of the original transformation of the host cells, or as the result of subsequent recombination and/or repair events, including the use of integrative vectors, site specific recombination or CRISPR-mediated engineering.

The term "GbpA," as used herein, refers to a N-acetyl glucosamine binding protein A. In some embodiments, a suitable GbpA protein, or homologue thereof, may be isolated from a pathogenic bacterium. In some embodiments, a suitable GbpA protein, or homologue thereof, may be isolated from a bacterial species from the phyla Gammaproteobacteria, Enterobacteria or Firmicutes. In some embodiments, a suitable GbpA protein, or homologue thereof, may be isolated from a bacterium including, but not limited to, *Vibrio* spp, *Escherichia* ssp., *Yersinia* ssp., *Shewanella* ssp., *Photobacterium* ssp., *Listeria* ssp., *Enterobacter* ssp., *Aeromonas* ssp., *Klebsiella* ssp. or *Aliivibrio* ssp. In some embodiments, a GbpA protein, or homologue thereof, may be isolated from *Vibrio* spp, including, but not limited to, *V. cholerae, V. mimicus, V. metoecus, V. vulnificus, V. parahaemolyticus*, or *V. fischeri*. In some embodiments, a GbpA protein, or homologue thereof, may be isolated from *Yersinia* spp, including, but not limited to, *Yersinia enterocolitica*. In some embodiments, a homologue of a GbpA protein may include, without limitation, a sequence as set forth in Accession Nos. YP_001007736.1, WP_057644048.1, WP_049605074.1, WP_053010295.1, WP_050077216.1, AUD62036.1, OXS01804.1, KPN78673.1, KEK29442.1, AAN54144.1, OUM13866.1, WP_011220398.1, OCH04476.1, WP_083198965.1, WP_081091566.1, WP_049940440.1, WP_065604524.1, KRT36821.1, WP_032608383, WP_015455208.1, OUY95058.1, PJI14410.1, OXV29379.1, PJZ14491.1, ATP91661.1, ATY82669.1, OSP53097.1, WP_102803702.1, OLP12672.1, or PDO74205.

In some embodiments, a GbpA protein may have the amino acid sequence set forth in NCBI Accession No. KKP14471. In some embodiments, a GbpA protein may have a sequence substantially identical to the amino acid sequence set forth in SEQ ID NO: 19, for example, at least 30%, 35%, 40%, 45%, 50%, 55%, 60%, 65%, 70%, 75%, 80%, 85%, 90%, 95% or 99% amino acid sequence identity to the amino acid sequence set forth in SEQ ID NO: 19. In some embodiments, a GbpA protein may be encoded by the nucleic acid sequence set forth in SEQ ID NO: 26. In some embodiments, a GbpA protein may include a mucin binding domain, referred to as "$GbpA_{DI}$," from a GbpA protein from *Vibrio cholerae.*

In alternative embodiments, a GbpA protein may include the full-length protein as well as fragments, isoforms or homologue thereof. In some embodiments, a fragment of a GbpA protein may be a non-pathogenic fragment. In some embodiments, a fragment of a GbpA protein may include a fragment including the mucin binding domain or a portion thereof, as long as mucin binding activity is retained. In some embodiments, a fragment of a GbpA protein may include an amino acid sequence substantially identical to SEQ ID NO: 20, for example, at least 30%, 35%, 40%, 45%, 50%, 55%, 60%, 65%, 70%, 75%, 80%, 85%, 90%, 95% or 99% A amino acid sequence identity to the amino acid sequence set forth in SEQ ID NO: 20. In some embodiments, a fragment of a GbpA protein may be encoded by the nucleic acid sequence set forth in SEQ ID NO: 27 or a portion thereof.

In alternative embodiments, a GbpA protein may be harmonized, for example, for expression in a particular host. In some embodiments, a harmonized GbpA protein may include a sequence harmonized for expression in *L. reuterii*, for example, as set forth in SEQ ID NO: 22, or a sequence having substantial identity thereto, for example, at least 30%, 35%, 40%, 45%, 50%, 55%, 60%, 65%, 70%, 75%, 80%, 85%, 90%, 95% or 99% sequence identity to the nucleic acid sequence set forth in SEQ ID NO: 22.

In alternative embodiments, a GbpA protein may include a form that results from processing within a cell, such as truncated forms.

A "bacterial surface protein," as used herein, refers to a protein associated with, or protruding from, the cell wall of a bacterium. Accordingly, in some embodiments, a bacterial surface protein may be anchored to, or embedded in and protruding from, the cell wall of a bacterium or may be associated with such a protein. In some embodiments, a bacterial surface protein may be a mucin binding protein, an S-layer protein (for example, a *Lactobacillus* S-layer protein), an integrin, a G-coupled protein, a mannose-binding lectin (for example, a *Lactobacillus* mannose-binding lectin), fimbria or flagella (for example, from *E. coli*) or any surface projection that may bind with host mucosae. In some embodiments, a bacterial surface protein may include, without limitation, a S-layer protein, such as slpA of *Lactobacillus acidophilus*, UniProt Accession No. P35829 or CbsA of *Lactobacillus* crispatus, UniProt Accession No. 007120; an integrin-binding protein, such as collagen-binding protein cnb *Lactobacillus reuteri*, UniProt Accession No. E2IQ97; a fimbria, such fimA of *E. coli*, UniProt Accession No. Q1R2K0); or a mucus binding protein, such as from *Lactobacillus acidophilus* UniProt Accession No. Q5FJA7.

The term "MBP," as used here, refers to a bacterial surface protein known as "mucus binding protein." The MBP protein may be isolated from various bacteria, including non-pathogenic bacteria including, but not limited to, *Lactobacillus*. In some embodiments, an MBP protein may be isolated from a probiotic bacterium. In some embodiments, an MBP protein may be isolated from *Lactobacillus reuteri.*

In some embodiments, an MBP protein may be the "hypothetical protein LAR_0958" of *Lactobacillus reuteri* JCM 1112. In some embodiments, an MBP protein may have the amino acid sequence set forth in NCBI Accession No. BAG25474.1. In some embodiments, a MBP protein may have an amino acid sequence substantially identical to SEQ ID NO: 21 or SEQ ID NO: 28, for example, at least 30%, 35%, 40%, 45%, 50%, 55%, 60%, 65%, 70%, 75%, 80%, 85%, 90%, 95% or 99% amino acid sequence identity to the amino acid sequence set forth in SEQ ID NO: 21 or SEQ ID NO: 28. In some embodiments, a MBP protein may encompass the full-length protein, as well as isoforms, fragments or homologues thereof. In alternative embodiments, a MBP protein includes a form that results from processing within a cell. In some embodiments, a MBP protein may be encoded by the nucleic acid sequence substantially identical to SEQ ID NO: 23 or SEQ ID NO: 53 or a fragment thereof.

In some embodiments, a GbpA protein or fragment thereof may be co-expressed, for example, as part of a surface protein operon, or recombined with a bacterial surface protein. In some embodiments, multiple copies of a GbpA protein or fragment thereof may be expressed in combination with a repeating surface protein, such as fimbriae. In embodiments where a GbpA protein or fragment thereof is recombined with a bacterial surface protein, it is to be understood that the exact location of the GbpA protein within the bacterial surface protein is not important, as long as the recombined GbpA protein or fragment thereof is expressed on the surface of a host cell, such as a probiotic bacterium, and can bind to an organic surface, such as an intestinal cell surface or a mucin.

In some embodiments, a GbpA protein or fragment thereof may be recombined with a MBP protein or fragment thereof to form a chimeric GbpA-MBP protein. In some embodiments, the GbpA protein fragment may be the mucin binding domain, or a mucin binding portion thereof.

In some embodiments, a chimeric GbpA-MBP protein may have a sequence substantially identical to SEQ ID NO: 29, for example, at least 30%, 35%, 40%, 45%, 50%, 55%, 60%, 65%, 70%, 75%, 80%, 85%, 90%, 95% or 99% amino acid sequence identity to the amino acid sequence set forth in SEQ ID NO: 29. In some embodiments, a chimeric GbpA-MBP protein may be encoded by a nucleic acid sequence substantially identical to SEQ ID NO: 24 or SEQ ID NO: 30.

A "substantially identical" sequence is an amino acid or nucleotide sequence that differs from a reference sequence only by one or more conservative substitutions, as discussed herein, or by one or more non-conservative substitutions, deletions, or insertions located at positions of the sequence that do not destroy the biological function of the amino acid or nucleic acid molecule. Such a sequence can be any value from 30% to 99%, or more generally at least 30%, 40%, 50, 55% or 60%, or at least 65%, 75%, 80%, 85%, 90%, or 95%, or as much as 96%, 97%, 98%, or 99% identical when optimally aligned at the amino acid or nucleotide level to the sequence used for comparison using, for example, the Align Program (Myers and Miller, CABIOS, 1989, 4:11-17) or FASTA. For polypeptides, the length of comparison sequences may be at least 2, 5, 10, or 15 amino acids, or at least 20, 25, or 30 amino acids. In alternate embodiments, the length of comparison sequences may be at least 35, 40, or 50 amino acids, or over 60, 80, or 100 amino acids. For nucleic acid molecules, the length of comparison sequences may be at least 5, 10, 15, 20, or 25 nucleotides, or at least 30, 40, or 50 nucleotides. In alternate embodiments, the length of comparison sequences may be at least 60, 70, 80, or 90 nucleotides, or over 100, 200, or 500 nucleotides. Sequence identity can be readily measured using publicly available sequence analysis software (e.g., Sequence Analysis Software Package of the Genetics Computer Group, University of Wisconsin Biotechnology Center, 1710 University Avenue, Madison, Wis. 53705, or BLAST software available from the National Library of Medicine, or as described herein). Examples of useful software include the programs Pile-up and PrettyBox. Such software matches similar sequences by assigning degrees of homology to various substitutions, deletions, substitutions, and other modifications.

Alternatively, or additionally, two nucleic acid sequences may be "substantially identical" if they hybridize under high stringency conditions. In some embodiments, high stringency conditions are, for example, conditions that allow hybridization comparable with the hybridization that occurs using a DNA probe of at least 500 nucleotides in length, in a buffer containing 0.5 M $NaHPO_4$, pH 7.2, 7% SDS, 1 mM EDTA, and 1% BSA (fraction V), at a temperature of 65° C., or a buffer containing 48% formamide, 4.8×SSC, 0.2 M Tris-Cl, pH 7.6, 1×Denhardt's solution, 10% dextran sulfate, and 0.1% SDS, at a temperature of 42° C. (These are typical conditions for high stringency northern or Southern hybridizations.) Hybridizations may be carried out over a period of about 20 to 30 minutes, or about 2 to 6 hours, or about 10 to 15 hours, or over 24 hours or more. High stringency hybridization is also relied upon for the success of numerous techniques routinely performed by molecular biologists, such as high stringency PCR, DNA sequencing, single strand conformational polymorphism analysis, and in situ hybridization. In contrast to northern and Southern hybridizations, these techniques are usually performed with relatively short probes (e.g., usually about 16 nucleotides or longer for PCR or sequencing and about 40 nucleotides or longer for in situ hybridization). The high stringency conditions used in these techniques are well known to those skilled in the art of molecular biology, and examples of them can be found, for example, in Ausubel et al., Current Protocols in Molecular Biology, John Wiley & Sons, New York, N.Y., 1998.

In some embodiments, a chimeric GbpA-bacterial surface protein, such as a chimeric GbpA-MBP protein, may include flexible linkers between the GbpA and bacterial surface protein components to, for example, facilitate presentation of the GbpA moiety. It is to be understood that the linker may be of any length or composition, as long as the linker facilitates presentation of the GbpA moiety on the bacterial surface. In some embodiments, the linkers may be about 10 to about 30 amino acids in length, for example, 10, 11, 12, 13, 14, 15, 16, 17, 18, 19, 20, 21, 22, 23, 24, 25, 26, 27, 28, 29, or 30 amino acids in length. In alternative embodiments, the linker may be longer or shorter. In some embodiments, the linkers may have the amino acid sequence:

```
                              (SEQ ID NO: 49)
GSAGSAEAGSNWSHPQFEKGSAGSAAGS
or
                              (SEQ ID NO: 50)
GSAGSAAGSGEF,
```

although it is to be understood that any suitable linker sequence may be used.

In some embodiments, the linkers may have the nucleic acid sequence:

```
                                                  (SEQ ID NO: 51)
ggtagtgctggtagtgctgaagctggtagtaattggagtcatccacaa

tttgaaaaaggtagtgctggtagtgctgctggtagt
or
                                                  (SEQ ID NO: 52)
ggtagtgctggtagtgctgctggtagtggtgaattt,
```

although it is to be understood that any suitable linker sequence may be used.

The term "ttr," as used herein, refers to tetrathionate reductase, which is involved in making tetrathionate available as an electron acceptor through the reduction of tetrathionate to thiosulfate.

In some embodiments, genes encoding tetrathionate reductase include the ttrACBSR operon from *Salmonella enterica*; the ttrA, ttrC, ttrB, ttrR and ttrS genes from *Salmonella enterica*; the ttrA, ttrC, and ttrB genes from *Salmonella enterica*, or a homologue, isoform or fragment thereof. In some embodiments, a ttr protein or operon may be isolated from a bacterium of the Enterobacteriaceae family, such as a *Salmonella* ssp., *Yersinia* ssp., *Proteus* ssp., *Citrobacter* ssp., *Klebsiella* sp., *Raoultella* sp., *Escherichia* sp., *Serratia* sp., *Leclercia* sp., *Morganella* sp., *Providencia* sp. or *Enterobacter* sp., or of the Vibrionaceae family, such as a *Vibrio* ssp. In some embodiments, a ttr protein or operon may be isolated from a *Yersinia enterocolitica, Proteus mirabilis, Escherichia coli, Serratia marcescens, Leclerica adecarboxylata, Morganella morganii, Citrobacter freundii, Klebsiella oxytoca, Raoultella ornithinolytica, Vibrio cyclitrophicus, Providencia alcalifaciens* PAL3, or *Enterobacter*sp GN02600. In some embodiments, a ttr protein or operon may be isolated from *Salmonella enterica* subsp. *enterica* (ex Kauffmann and Edwards) Le Minor and Popoff serovar *Typhimurium* (ATCC® 14028™). In some embodiments, a homologue of a tetrationate reducatase may include, without limitation, a molybdopterin oxidoreductase, an octaheme tetrathionate reductase or a bifunctional thiosulfate dehydrogenase/tetrathionate reductase.

In some embodiments, a ttrA protein may include, without limitation, an amino acid sequence as set forth in Accession No. NP_460348 or SEQ ID NO: 34. In some embodiments, a ttrA protein may be encoded by, without limitation, a nucleic acid sequence as set forth in SEQ ID NO: 33. In some embodiments, a ttrA protein may include, without limitation, an amino acid sequence, or be encoded by a nucleic acid sequence, having at least about 36% identity thereto, for example, at least 36%, 40%, 45%, 50%, 55%, 60%, 65%, 70%, 75%, 80%, 85%, 90%, 95% or 99% sequence identity to the sequence set forth in SEQ ID NO: 34 or SEQ ID NO: 33, respectively. In some embodiments, a homologue of a ttrA protein may include, without limitation, a molybdopterin oxidoreductase. In some embodiments, a homologue of a ttrA protein may include, without limitation, a sequence as set forth in GenBank Accession Nos. YP_001005907.1, EEQ20500.1, EEQ14547.1, AKP35086.1, KSW19446.1, OZS67160.1, KZE53847.1, WP_036976853.1, KPR51726.1, WP_044699957.1, AKE58784.1, CEJ67217.1, KHE12612.1, SBL10805.1, OVJ00655.1, AJF72717.1, OMP97259.1, KXQ61755.1, KPO10992.1, KXP28341.1, ALE97083.1, KFF88851.1, ALX93812.1, AKE11813.1, ALZ97153.1, AGG30792.1, WP_067426732.1, or KLQ21159.1.

In some embodiments, a ttrB protein may include, without limitation, an amino acid sequence as set forth in Accession No. NP_460350 or SEQ ID NO: 36. In some embodiments, a ttrB protein may be encoded by, without limitation, a nucleic acid sequence as set forth in SEQ ID NO: 35. In some embodiments, a ttrB protein may include, without limitation, an amino acid sequence, or be encoded by a nucleic acid sequence, having at least about 37% identity thereto, for example, at least 37%, 40%, 45%, 50%, 55%, 60%, 65%, 70%, 75%, 80%, 85%, 90%, 95% or 99% sequence identity to the sequence set forth in SEQ ID NO: 36 or SEQ ID NO: 35, respectively. In some embodiments, a homologue of a ttrB protein may include, without limitation, a 4Fe-4S ferredoxin, for example, from *Vibrio* cyclitrophicus. In some embodiments, a homologue of a ttrB protein may include, without limitation, a sequence as set forth in GenBank Accession Nos. YP_001005905.1, CFQ93022.1, CFQ43076.1, CRY54230.1, CAR43509.1, WP_036971149.1, AVA40532.1, GAL39716.1, GAL44236.1, PKQ50411.1, AMG54481.1, WP_103814386.1, PPA47719.1, WP_094310326.1, WP_041145060 WP_076945285.1 WP_077910396.1 WP_085949444.1, WP_060452523.1, SMZ55374.1, SM 825440.1, AMG99006.1, WP_059308319.1, WP_024473892.1, WP_067402438.1 or WP_019076686.1.

In some embodiments, a ttrC protein may include, without limitation, an amino acid sequence as set forth in Accession No. NP_460349 or SEQ ID NO: 38. In some embodiments, a ttrC protein may be encoded by, without limitation, a nucleic acid sequence as set forth in SEQ ID NO: 37. In some embodiments, a ttrC protein may include, without limitation, an amino acid sequence, or be encoded by a nucleic acid sequence, having at least about 39% identity thereto, for example, at least 39%, 40%, 45%, 50%, 55%, 60%, 65%, 70%, 75%, 80%, 85%, 90%, 95% or 99% sequence identity to the sequence set forth in SEQ ID NO: 38 or SEQ ID NO: 37, respectively. In some embodiments, a homologue of a ttrC protein may include, without limitation, a polysulfide reductase NrfD, for example, from a *Providencia alcalifaciens* PAL-3. In some embodiments, a homologue of a ttrC protein may include, without limitation, a sequence as set forth in GenBank Accession Nos. WP_077173918.1, WP_057615346.1, WP_057646861.1, WP_012368068.1, WP_087802132.1, WP_086551155.1, PKQ50348.1, WP_096757206.1, WP_080858725.1 WP_085521140.1 WP_102802900.1 WP_041145059.1, WP_076945284.1, WP_044864557.1, WP_094461085.1, WP_047730217.1, WP_059308318.1, WP_004236882.1, WP_067426730.1, or WP_047358863.1.

In some embodiments, a ttrR protein may include, without limitation, an amino acid sequence as set forth in Accession No. NP_460352 or SEQ ID NO: 40. In some embodiments, a ttrR protein may be encoded by, without limitation, a nucleic acid sequence as set forth in SEQ ID NO: 39. In some embodiments, a ttrR protein may include, without limitation, an amino acid sequence, or be encoded by a nucleic acid sequence, having at least about 43% identity thereto, for example, at least 43%, 45%, 50%, 55%, 60%, 65%, 70%, 75%, 80%, 85%, 90%, 95% or 99% sequence identity to the sequence set forth in SEQ ID NO: 40 or SEQ ID NO: 39, respectively. In some embodiments, a homologue of a ttrR protein may include, without limitation, a DNA-binding response regulator for example from *Escherichia coli*. In some embodiments, a homologue of a ttrR protein may include, without limitation, a sequence as set forth in GenBank Accession Nos. YP_001005903.1, CRL60521.1, KKJ88792.1, OUE56241.1, AID90294.1, AIE70476.1, AJF75264.1, KPO10996.1, SAY44133.1, KJY05630.1 or KLQ21155.1.

In some embodiments, a ttrS protein may include, without limitation, an amino acid sequence as set forth in Accession No. NP_460351 or SEQ ID NO: 42. In some embodiments, a ttrS protein may be encoded by, without limitation, a nucleic acid sequence as set forth in SEQ ID NO: 41. In some embodiments, a ttrS protein may include, without limitation, an amino acid sequence, or be encoded by a nucleic acid sequence, having at least about 36% identity thereto, for example, at least 36%, 40%, 45%, 50%, 55%, 60%, 65%, 70%, 75%, 80%, 85%, 90%, 95% or 99% sequence identity to the sequence set forth in SEQ ID NO: 42 or SEQ ID NO: 41, respectively. In some embodiments, a homologue of a ttrS protein may include, without limitation, a sensor histidine kinase from Enterobacteriacea. In some embodiments, a homologue of a ttrS protein may include, without limitation, a sequence as set forth in GenBank Accession Nos. YP_001005904.1, CFR17843.1, CNE64519.1, CAR43511.1, EST58419.1 or ALE97086.1.

In some embodiments, the tetrathionate respiratory operon includes the nucleic acid sequence set forth in SEQ ID NO: 25 or a sequence having at least about 40% identity thereto for example, at least 40%, 45%, 50%, 55%, 60%, 65%, 70%, 75%, 80%, 85%, 90%, 95% or 99% sequence identity to the nucleic acid sequence set forth in SEQ ID NO: 25. In some embodiments, the tetrathionate respiratory operon includes the nucleic acid sequence set forth in SEQ ID NO: 31 (ttrACB operon) or a sequence having at least about 40% identity thereto for example, at least 40%, 45%, 50%, 55%, 60%, 65%, 70%, 75%, 80%, 85%, 90%, 95% or 99% sequence identity to the nucleic acid sequence set forth in SEQ ID NO: 31. In some embodiments, the tetrathionate respiratory operon may additionally include the nucleic acid sequence set forth in SEQ ID NO: 32 (ttrSR operon) or a sequence having at least about 40% identity thereto for example, at least 40%, 45%, 50%, 55%, 60%, 65%, 70%, 75%, 80%, 85%, 90%, 95% or 99% sequence identity to the nucleic acid sequence set forth in SEQ ID NO: 32.

A "vector" is a DNA molecule derived, for example, from a plasmid or bacteriophage, into which a nucleic acid molecule, for example, encoding a GbpA protein, a bacterial surface protein or a tetrathionate reductase, or a fragment thereof, may be inserted. A vector may contain one or more unique restriction sites and may be capable of autonomous replication in a defined host or vehicle organism such that the cloned sequence is reproducible. A vector may be a DNA expression vector, i.e, any autonomous element capable of directing the synthesis of a recombinant polypeptide, and thus may be used to express a polypeptide, for example a GbpA protein, a bacterial surface protein or a tetrathionate reductase, or a fragment thereof, in a host cell. DNA expression vectors include bacterial plasmids and phages and mammalian and insect plasmids and viruses. In some embodiments, a vector may integrate into the genome of the host cell, such that any modification introduced into the genome of the host cell by the vector becomes part of the genome of the host cell. In some embodiments, a vector may remain as an autonomously replicating unit, such as a plasmid. Accordingly, the term "expression vector," as used herein, refers to a polynucleotide composition which may be integrating or autonomous, (i.e. self-replicating), and which contains the necessary components to achieve transcription of an expressible sequence in a target cell, when introduced into the target cell. Expression vectors may include plasmids, cosmids, bacterial artificial chromosomes (BACs), viruses, etc. An expression vector optionally contains nucleic acid elements that facilitate replication of the vector, elements that facilitate integration of the vector into the genome of the target host cell, elements which confer properties, for example antibiotic resistance, to the target host cell which allow selection or screening of transformed cells and the like. Techniques and methods for design and construction of expression vectors are described herein and well known in the art.

A vector in accordance with the present disclosure may be used to express a GbpA protein, a bacterial surface protein and/or a tetrathionate reductase, or a fragment thereof, in a prokaryotic host cell, such as a probiotic bacterium.

In some embodiments, a GbpA protein or fragment thereof may be expressed on the surface of a probiotic bacterium. In some embodiments, a GbpA protein or fragment thereof may be expressed on the surface of a probiotic bacterium such that it can bind to an organic surface, such as an intestinal cell surface or a mucin. In some embodiments, the GbpA protein or fragment thereof may be expressed on the surface of a probiotic bacterium as part of a bacterial surface protein as a single repeat or in multiple repeats. In alternative embodiments, the GbpA protein or fragment thereof may be expressed on the surface of a probiotic bacterium as a single, separate protein including a membrane-anchoring sequence and/or signal peptide, and may be integrated into the bacterial chromosome. In alternative embodiments, the GbpA protein or fragment thereof may be expressed on the surface of a probiotic bacterium as part of a complex, multi-domain protein, each domain of which includes a GbpA binding domain, and may be integrated into the bacterial chromosome; the multi-domain protein may include a membrane-anchoring sequence and/or signal peptide. Membrane-anchoring sequences are known in the art and may include, without limitation, a LXPTG-motif cell wall, S-layer homology (SLH) domains, lipoproteins, amino-terminal membrane anchors or transmembrane domains. Signal peptides are known in the art and may include, without limitation, a YSIRK-G/S motif signal peptide or exemplary signal peptides as described in Ivankov D N, Payne S H, Galperin M Y, Bonissone S, Pevzner P A, Frishman D. How many signal peptides are there in bacteria? *Environmental microbiology.* 2013; 15(4):983-990 or Payne S H, Bonissone S, Wu S, Brown R N, Ivankov D N, Frishman D, Pasa-Tolic L, Smith R D, Pevzner P A. Unexpected diversity of signal peptides in prokaryotes. MBio. 2012; 3(6). Pii: e00339-12.

In some embodiments, a tetrathionate reductase, or a fragment thereof, may be expressed in a gram-negative bacterium. In some embodiments, a tetrathionate reductase, or a fragment thereof, may be expressed in a probiotic *Escherichia coli*, such as *E. coli* Nissle 1917 (complete genome set forth in Accession No. CP007799.1; www[dot]ncbi[dot]nlm[dot]nih[dot]gov/nuccore/CP007799.1?report=fasta) or a subspecies or strain thereof. In some embodiments, a tetrathionate reductase, or a fragment thereof, may be may be integrated into the bacterial chromosome. In some embodiments, a tetrathionate reductase may be expressed by expression of the ttrA, ttrB and ttrC genes separately, in combination with an oxygen-sensitive promoter-operator that, for example, includes a binding site for an oxygen-responding transcription factor such as the fumarate-nitrate reduction regulator (FNR) transcription factor or the aerobic respiration control (ArcA) transcription factor. In some embodiments, an oxygen-sensitive promoter-operator may include, without limitation, a fumarate-nitrate reduction regulator (FNR) transcription factor, aerobic respiration control (ArcA) transcription factor, FixL-FixJ system of *Sinorhizobium meliloti*, DosT/DevS system found in *Mycobacterium tuberculosis*, nar operon of *Escherichia coli*, vgb operon of *Vitreoscilla* hemoglobin, arc operon of *Staphylococcus aureus*, etc. In some embodiments, a tetrathionate reductase may be expressed by an operon including the ttrA, ttrB and ttrC genes, in combination with an oxygen-sensitive promoter-operator. In some embodiments, a tetrathionate reductase may be expressed by expression of the ttrA, ttrB, ttrC, ttrR and ttrS genes separately. In some embodiments, a tetrathionate reductase may be expressed by an operon including the ttrA, ttrB, ttrC, ttrR and ttrS genes.

In some embodiments, nucleic acid sequences encoding a GbpA protein, a bacterial surface protein and/or a tetrathionate reductase, or a fragment thereof, may be harmonized for expression in a host microorganism, such as a probiotic bacterium. Techniques for harmonization of a sequence to account for differences in codon usage across species in order to improve the level of protein expression are described herein or known in the art.

Recombinant probiotic bacteria, as described herein, may be provided alone or in combination with other compounds or probiotic bacteria, in any pharmaceutically acceptable carrier, in a form suitable for administration to a subject, to increase colonization of the probiotic bacterium in the gastrointestinal tract of a subject, reduce inflammation in the gastrointestinal tract of a subject and/or treat or prevent irritable bowel disease in a subject in need thereof. In some embodiments, a recombinant probiotic bacterium expressing a GbpA protein, as described herein, may be administered in combination with a recombinant probiotic bacterium expressing a tetrathionate reductase, as described herein. In some embodiments, a recombinant probiotic bacterium expressing a GbpA protein, as described herein, and a tetrathionate reductase, as described herein, may be administered to a subject in need thereof. If desired, treatment with a recombinant probiotic bacterium according to the present disclosure may be combined with more traditional and existing therapies for gastrointestinal inflammation or irritable bowel disease. A recombinant probiotic bacterium according to the present disclosure may be provided chronically or intermittently. "Chronic" administration refers to administration of the agent(s) in a continuous mode as opposed to an acute mode, so as to maintain the initial therapeutic effect (activity) for an extended period of time. "Intermittent" administration is treatment that is not consecutively done without interruption, but rather is cyclic in nature.

Conventional pharmaceutical practice may be employed to provide suitable formulations or compositions to administer a recombinant probiotic bacterium according to the present disclosure to a subject suffering from or presymptomatic for gastrointestinal inflammation or irritable bowel disease. Any appropriate route of administration may be employed, for example, oral administration. For oral administration, formulations may be in the form of tablets or capsules. Methods well known in the art for making formulations are found in, for example, "Remington's Pharmaceutical Sciences" (19th edition), ed. A. Gennaro, 1995, Mack Publishing Company, Easton, Pa.

For therapeutic or prophylactic compositions, a recombinant probiotic bacterium according to the present disclosure may be administered to an individual in an amount sufficient to stop or slow gastrointestinal inflammation or irritable bowel disease. An "effective amount" of a compound according to the invention includes a therapeutically effective amount or a prophylactically effective amount. A "therapeutically effective amount" refers to an amount effective, at dosages and for periods of time necessary, to achieve the desired therapeutic result, such as amelioration of gastrointestinal inflammation or irritable bowel disease. A therapeutically effective amount of a recombinant probiotic bacterium according to the present disclosure may vary according to factors such as the disease state, age, sex, and weight of the individual, and the ability of the compound to elicit a desired response in the individual. Dosage regimens may be adjusted to provide the optimum therapeutic response. A therapeutically effective amount is also one in which any detrimental or side effects of the recombinant probiotic bacterium according to the present disclosure are outweighed by the therapeutically beneficial effects. A "prophylactically effective amount" refers to an amount effective, at dosages and for periods of time necessary, to achieve the desired prophylactic result, such as amelioration of gastrointestinal inflammation or irritable bowel disease. Typically, a prophylactic dose is used in subjects prior to or at an earlier stage of disease, so that a prophylactically effective amount may be less than a therapeutically effective amount.

It is to be noted that dosage values may vary with the severity of the condition to be alleviated. For any particular subject, specific dosage regimens may be adjusted over time according to the individual need and the professional judgement of the person administering or supervising the administration of the compositions. Dosage ranges set forth herein are exemplary only and do not limit the dosage ranges that may be selected by medical practitioners. The amount of a recombinant probiotic bacterium according to the present disclosure in a composition may vary according to factors such as the disease state, age, sex, and weight of the individual. Dosage regimens may be adjusted to provide the optimum therapeutic response. For example, a single bolus may be administered, several divided doses may be administered over time or the dose may be proportionally reduced or increased as indicated by the exigencies of the therapeutic situation. It may be advantageous to formulate parenteral compositions in dosage unit form for ease of administration and uniformity of dosage.

As used herein, a subject may be a human, non-human primate, rat, mouse, cow, horse, pig, sheep, goat, dog, cat, etc. The subject may be a clinical patient, a clinical trial volunteer, an experimental animal, etc. The subject may be suspected of having or at risk for having gastrointestinal inflammation or irritable bowel disease, be diagnosed with gastrointestinal inflammation or irritable bowel disease, or be a control subject that is confirmed to not have gastrointestinal inflammation or irritable bowel disease. Diagnostic methods for gastrointestinal inflammation or irritable bowel disease and the clinical delineation of such diagnoses are known to those of ordinary skill in the art.

In some embodiments, the subject may be benefited by increased colonization and/or persistence of a recombinant probiotic bacterium in the gastrointestinal tract. Determination and monitoring of colonization and/or persistence of a recombinant probiotic bacterium in the gastrointestinal tract may be done using standard techniques, such as by obtaining a sample (such as a stool sample) from a subject and determining the presence, absence or amount of a recombinant probiotic bacterium by amplification of a nucleic acid sequence unique to the recombinant probiotic bacterium.

The present invention will be further illustrated in the following examples.

Materials and Methods

Bacterial Strains and Growth Conditions

*E. coli* strains and *S. typhimurium* SL1344 were routinely cultivated in liquid Luria-Bertani-Miller (LB) media or plates with 1.8% w/w agar. For some experiments, strains were cultivated in minimal M9 medium (64 g/L $Na_2HPO_4.7H_2O$, 15 g/L $KH_2PO_4$, 2.5 g/L NaCl, 5 g/L $NH_4C$, 2 mM $MgSO_4$, 0.1 mM $CaCl_2$)). Media were supplied with ampicillin (Ap; 100 ug/ml), tetracycline (Tc; 12.5 ug/ml for all of the strains, except 4 ug/ml for *E. coli* Nissle attB$^{phi80}$::ttrACBSR), Kanamycin (Km; 40 ug/ml). Strains, plasmids and primers used in the construction of the *E. coli* Nissle attB$^{phi80}$::ttrACBSR strain are described in Table 1.

TABLE 1

Strains, plasmids and primers used in the construction of *E. coli* Nissle attB$^{phi80}$::ttrACBSR

| Name | Description | Source/SEQ ID NO |
|---|---|---|
| Strains | | |
| *Salmonella enteric*a subsp. *enterica* serovar Typhimurium SL1344 | Wild-type | Gibson laboratory |
| *Escherichia coli* Nissle 1917 | Wild-type | Mutaflor |
| *E. coli* Nissle attB$^{phi80}$::ttrACBSR | Derivative of *Escherichia coli* Nissle 1917 with pAH162-ttrACBSR plasmid integrated to attB-site of phage phi 80 | SEQ ID NO: 47 |
| *E. coli* Nissle attB$^{phi80}$::$Km^R$ | Derivative of *E. coli* Nissle attB$^{phi80}$::ttrACBSR with deletion of ttrACBSR operon | SEQ ID NO: 48 |
| BW23473 | $Pir^+$ strain, required for propagation of CRIM pAH162 plasmid and its derivatives (Haldimann et al. (2001) *J. +iBacteriol.* 183:6384-93) | CGSC |

TABLE 1-continued

Strains, plasmids and primers used in the construction of *E. coli* Nissle attB$^{phi80}$::ttrACBSR

| Name | Description | Source/SEQ ID NO |
|---|---|---|
| Plasmids | | |
| pAH162 | conditional replication, integration and modular (CRIM) plasmid, carries phage phi 80 attP-site and Tc-resistance cassette (Haldimann et al. (2001) *J. Bacteriol.* 183:6384-93) | isolated from CGSC 7873 strain |
| pAH123 | thermo sensitive helper plasmid, carrying phage phi 80 int gene behind phage Lambda Pr promoter under c1857 control; required for integration of pAH162 (Haldimann et al. (2001) *J. Bacteriol.* 183:6384-93) | isolated from CGSC 7861 strain |
| pAH162-ttrACBSR | pAH162 with ttrACBSR operon cloned | SEQ ID NO: 46 |
| pKD46 | thermo sensitive, carries the λ red genes behind the araBAD promoter | isolated from CGSC 7669 strain |
| Primers | | |
| | | SEQ ID NO: |
| ga1 (Primer to amplify the pAH162 plasmid backbone) | **gagctcgaattctcatgtttg** | 1 |
| ga2 (Primer to amplify the pAH162 plasmid backbone) | **ggatcctctagagtcgacctg** | 2 |
| ga3 (Primer to amplify ttrACBSR from *S. Typhimurium* SL1344 (bold font denotes region of primer binding to ttr) | gcatgcctgcaggtcgactctagaggatcc**gttatatacgctcga tttttgc** | 3 |
| ga4 (Primer to amplify ttrACBSR from *S. Typhimurium* SL1344 (bold font denotes region of primer binding to ttr) | ataagctgtcaaacatgagaattcgagctc**ttattcatggctcata cgttg** | 4 |
| ga5 (Primer to confirm ttr integration into pAH162 plasmid) | cgttatggactgcaacatgg | 5 |
| ga6 (Primer to confirm ttr integration into pAH162 plasmid) | gcaaacggcctaaatacagc | 6 |
| ga7 (Primer to amplify Kanamycin-resistance cassette) | tgccaagcttgcatgcctgcaggtcgactctagaggatcc**attcc ggggatccgtcgacc** | 7 |
| ga8 (Primer to amplify Kanamycin-resistance cassette) | ctgatcagtgataagctgtcaaacatgagaattcgagctc**tgtag gctggagctgcttcg** | 8 |

*L. reuteri* DSM20016 strain and its derivatives were routinely cultivated in liquid MRS media without agitation or plates with the same media supplemented with 1.8% w/w agar in anoxic conditions of anaerobic jar. *E. coli* DH5α strain was cultivated in LB, SOB or SOC media. Media was supplied with Erythromycin (Erm; 5 ug/ml for *L. reuteri,* 150 ug/ml for *E. coli*).

Molecular Biology Techniques

PCR fragments for cloning were generated using Q5 High Fidelity DNA polymerase (NEB) unless otherwise noted and oligonucleotide primers were from IDT Inc., Vancouver, BC. Qiagen (Hilden, Germany) products were used for the isolation of plasmid or chromosome DNA and purification of PCR fragments.

Strain construction of *E. coli* Nissle $attB^{phi80}$::ttrACBSR

The ttrACBSR operon (SEQ ID NO: 25) of *S. typhimurium* SL1344 was cloned to CRIM plasmid pAH162 (SEQ ID NO: 45) by Polymerase Incomplete Primer Extension technique (Klock H E et al. 2008 Proteins 71:982-994) and the plasmid was subsequently integrated into phi80-phage attachment site on the chromosome of *E. coli* Nissle as described (Haldimann A and Wanner B L 2001 J Bacteriol 183:6384-6393). Briefly, ttrACBSR was amplified with ga3/ga4 primers (SEQ ID NO: 3 and 4) and pAH162 plasmid backbone was amplified with ga1/ga2 (SEQ ID NO: 1 and 2) primers using Q5 High-Fidelity polymerase (New-England Biolabs) according to the manufacturer's instructions with chromosomal DNA as a template. The obtained PCR products were combined and transformed into *E. coli* BW23473. Several resulting plasm ids were tested for functionality in growth competition assays and one plasmid was selected. *E. coli* Nissle/pAH123, cultivated at 30° C., was transformed with the selected plasm id and outgrowth continued at 37° C. The resulting chromosomal integration of the plasmid was confirmed by PCR.

For construction of the control *E. coli* Nissle $attB^{phi80}$::$Km^R$ strain, the phage-Lambda Red recombinase-mediated recombination-based method was employed as described (Datsenko K A and Wanner B L 2000 Proc Nat Acad Sci USA 97:6640-6645). A Kanamycin-resistance cassette was amplified with ga7/ga8 (SEQ ID NO: 7 and 8) primers using the chromosome of *E. coli* JW4283-3 as a template. The resulting PCR-fragment was introduced into *E. coli* Nissle $attB^{phi80}$::ttrACBSR/pKD46 and the resulting strain cultivated in the presence of L-arabinose (Datsenko K A and Wanner B L 2000 Proc Nat Acad Sci USA 97:6640-6645). The structure of the resulting *E. coli* Nissle $attB^{phi80}$::$Km^R$ strain was confirmed by PCR with ga7/ga8 (SEQ ID NO: 7 and 8) primers by the presence of amplification of the corresponding fragment.

Growth Characteristics of the *E. coli* Nissle $attB^{phi80}$::ttrACBSR Strain

Growth Competition Assay

Cultures of tested strains (*E. coli* Nissle and *E. coli* Nissle $attB^{phi80}$::ttrACBSR, or *E. coli* BW23473 and *E. coli* BW23473/pAH162-ttr) were inoculated with overnight cultures of the corresponding strain (1/50) and incubated until they reached $OD_{600}$=0.55-0.7. The subcultures were dissolved to similar optical densities, mixed and then dissolved to $OD_{600}$=0.05 with media, which did or did not contain potassium tetrathionate (30 mM). Mixed cultures were incubated without agitation in media-filled capped tubes overnight. The next day, cultures were dissolved and plated onto selective (Tc) and non-selective plates to count modified/unmodified colonies.

Tetrathionate Reduction Assay

M9 media (+0.2% w/w glycerol, 30 mM potassium tetrathionate) was inoculated with fresh cultures of modified or wild-type strains in the same media (1/100) and incubated overnight with agitation or in media-filled closed test tubes with no agitation. The next day, cultures were centrifuged (12000 g, 2 min) and thiosulfate concentration in the supernatant was estimated by neutral iodimetric titration. Concentration of consumed tetrathionate was estimated based on the fact that one molecule of tetrationate is converted into two thiosulfate molecules by ttr operon enzyme activity (Hensel et al. 1999 Mol Microbiol 32:275-287).

*L. reuteri* Strain Construction

The *L. reuteri* lar_0958::$gbpA_{24-203}$ strain, also referred to herein as. *L. reuteri*::GbpA, was constructed as follows.

Construction of pG+host-MBP-gbpA plasmid was performed using Gibson Assembly Master Mix (NEB) and Q5 High Fidelity DNA polymerase (NEB). pG+host5 plasmid (SEQ ID NO: 43) was kindly provided by Dr. John K. McCormick (Lia et al. (2011) PNAS 108:3360-3365). GbpA N-terminal domain coding sequence was synthesized by IDT DNA with sequence optimization for expression in *L. reuteri* (SEQ ID NO: 22) by harmonization algorithm (as described by Angov et al. (2011) Mol Microbiol 705(1):1-13). Table 2 shows the primers used in the construction of the recombinant probiotic strain expressing a fragment of the GbpA protein. The fragment encoding N-terminal part of *L. reuteri* mucus-binding protein (MBP) was amplified with primers 1 and 2 (SEQ ID NO: 9 and 10), fragment encoding N-terminal domain of *Vibrio cholerae* GbpA protein was amplified with primers 3 and 4 (SEQ ID NO: 11 and 12), fragment encoding C-terminal part of *L. reuteri* MBP was amplified with primers 5 and 6 (SEQ ID NO: 13 and 14), plasmid backbone of pG+host5 was amplified with primers 7 and 8 (SEQ ID NO: 15 and 16). All the amplified fragments were mixed and Gibson Assembly reaction was performed according to the manufacturer's instruction. After reaction was performed, the mix was transformed to *E. coli* DH5α strain by electroporation. The structure of resulting plasmid was confirmed by PCR with several sets of primers, flanking each region, and sequencing.

pG+host-MBP-gbpA was electroporated to *L. reuteri* DSM20016 strain. Strain was cultivated at 30 C to enable plasmid replication, then diluted and cultivated at 37 C overnight to obtain population of single-crossover integrants. Integration was confirmed by PCR and sequencing. Integrants had $Erm^R$ phenotype with no mutations found in pG+host-MBP-gbpA ori found by sequencing. The single crossover integrants were cultivated at 30 C overnight without antibiotic to obtain double-crossover integrants, then plated on non-selective plates to single colonies. Several colonies were transferred by toothpicks to Erm-agar plate and Erm-sensitive clones were isolated. Double-crossover integrants were found by PCR, the sequence was confirmed by sequencing.

Double crossover homologous integration technique was employed for strain construction. First pG+host-LAR-gbpA plasmid (SEQ ID NO: 44) was extracted from *E. coli* strain and transformed to *L. reuteri*. An electroporation protocol with modifications was used. Briefly, 1/20 inoculum of overnight culture of *L. reuteri* was inoculated in MRS broth+1% glycine as described in Wei et al. (Wei et al. (1995) J. Microbiol Methods. 21:97-109). Once $OD_{600}$ reached 0.2-0.3, bacteria were left on ice for 10 minutes to stop growth. Bacteria were then washed twice with ice-cold water, once in ice-cold 0.3M sucrose, and then re-suspended in 1/50 volume of 0.3M sucrose. Electroporation was performed on ice using a 1 mm electroporation cuvette with a BTX ECM 399 electroporation system. 4 ul of extracted pG+host-LAR-gbpA plasmid with 16 ul electrocompetent *L. reuteri* cells and 20 ul of electroporation buffer (0.3M sucrose) was electroporated at 1290V. Cell and plasmid mixture was immediately transferred to 2 mL pre-warmed 37° C. MRS broth and incubated for 2 hours under anaerobic conditions. 70 ul of cells were plated on 1.8% MRS agar plates supplemented with 5 ug/ml Erm. After 62 hours of anaerobic incubation, 3 colonies resulted. Colonies were selected and plated on 1.8% MRS agar plates supplemented with 5 ug/ml Erm. Integration of plasmid was confirmed using primers 9 and 10 (SEQ ID NO: 17 and 18) for *L. reuteri* backbone and primers 3 and 4 (SEQ ID NO: 11 and 12) for N-terminal domain of *Vibrio cholerae* gbpA protein.

TABLE 2

Primers used in the construction of the recombinant *L. reuteri*::GbpA

| Primer name | Sequence | SEQ ID NO: |
|---|---|---|
| Primer 1 (Primer to amplify DNA fragment encoding the N-terminal region of *L. reuteri* mucus-binding protein (MBP) (italicized sequence encodes flexible peptide linkers added between MBP and GbpA) | ccaattactaccagcttcagcactacc<br>agcactaccaatcctctttcggtaata<br>aatctt | 9 |
| Primer 2 (Primer to amplify the DNA fragment encoding the N-terminal region of *L. reuteri* mucus-binding protein (MBP)) | gtgagcgcgcgtaatacgactcacta<br>tagggcggatccggtctatcctttatgg<br>gagaac | 10 |
| Primer 3 (Primer to amplify the DNA fragment encoding the N-terminal domain of *Vibrio cholera* GbpA protein (italicized sequence encodes flexible peptide linkers added between MBP and GbpA; underlined sequence denotes strep-tag II)) | *gtgctgaagctggtagt*aattggagtc<br>atccacaatttgaaaaa*ggtagtgct*<br>*ggtagtgct*<br>*gctggtagt*cacggttacgtatcggca<br>g | 11 |
| Primer 4 (Primer to amplify the DNA fragment encoding the N-terminal domain of Vibrio cholera GbpA protein (italicized sequence encodes flexible peptide linkers added between MBP and GbpA)) | *aattcaccactaccagcagcactacc*<br>agcactaccaccgtcaaacttaacgt<br>caataacg | 12 |
| Primer 5 (Primer to amplify the DNA fragment encoding the C-terminal region of *L. reuteri* MBP (italicized sequence encodes flexible peptide linkers added between MBP and GbpA)) | *agtgctggtagtgctgctggtagtggt*<br>*gaatttaaagttacctatagtggtagtg*<br>acagc | 13 |
| Primer 6 (Primer to amplify the DNA fragment encoding the C-terminal region of *L. reuteri* MBP) | cgatatcaagcttatcgataccgtcga<br>cctcgagaattcccgtcaagataatc<br>cgataag | 14 |
| Primer 7 (Primer to amplify the plasmid backbone of pG+host5) | gaattgggtaccgggccccccctcg<br>agg | 15 |
| Primer 8 (Primer to amplify the plasmid backbone of pG+host5) | gccctatagtgagtcgtattacgcgcg<br>c | 16 |
| Primer 9 (Primer to confirm integration of pG+host-LAR-gbpA plasmid into *L. reuteri* backbone) | aactgttggggttacttcggta | 17 |
| Primer 10 (Primer to confirm integration of pG+host-LAR-gbpA plasmid into *L. reuteri* backbone) | ctggttgttgctcaggtgttt | 18 |

Colitis Animal Trials

C57BL/6 female mice (Jackson Laboratories, Bar Harbor, Me.) were maintained in pathogen free conditions at the Bioscience Facility at the University of British Columbia Okanagan (UBCO), Kelowna, BC. They were bred in house and caged in a temperature controlled (22±2° C.) room with 12-hour light/dark cycle. They were fed irradiated food and sterile tap water. Post-weaned female offspring were weaned at 4 weeks and then assigned of three groups: no probiotic, modified designer probiotic, or unmodified parent probiotic. Probiotic groups received 100 μL ($3\times10^{12}$ CFU/mL when testing the parental and recombinant strain expressing the ttr operon and $2\times10^{9}$ cfu/mL when testing the parental and recombinant strain expressing the GbpA fragment) of the probiotic via oral gavage administered once per day for a period of three days for the *E. coli* strains and one gavage for the *L. reuteri* strains. The third treatment group served as the control group and received no oral gavage or probiotic supplementation.

Mice were then exposed to 3.5% DSS via drinking water and monitored throughout the 7-day exposure for mortality/morbidity Mice were immediately euthanized if they showed signs of distress due to gavage such as: lethargy, hunched posture, difficulty breathing, blood emerging from the mouth and/or nose or a loss in total body weight≥20%. Mice were sacrificed at day 7. Body weight was measured every day during the 7 day DSS exposure. Body weight data is presented as percentage of the initial body weight. Probiotic supplemented groups were exposed to DSS and no DSS. A DSS control with no supplementation was also used to provide a control for the DSS-induced colitis.

In a second set of trials, C57BL/6 (Jackson Laboratories, Bar Harbor, Me.) and Muc2$^{-/-}$ male and female mice (Morampudi V, et al. Mucosal Immunology. 2016:1-16) were maintained in pathogen free conditions at the Bioscience Facility at the University of British Columbia Okanagan (UBCO), Kelowna, BC. They were bred in house and caged in a temperature controlled (22±2° C.) room with 12-hour light/dark cycles, fed irradiated food, and sterile tap water. The protocols used were approved by the University of British Columbia's Animal Care Committee and in direct accordance with guidelines drafted by the Canadian Council on the Use of Laboratory Animals. C57BL/6 offspring were weaned at 19-21 days of age and Muc2$^{-/-}$ offspring were weaned at 28-30 days of age. Mice were then assigned one of three groups: no probiotic, modified designer probiotic, or unmodified parent probiotic. Probiotic groups received 100 μL ($3\times10^{12}$ CFU/mL when testing the parental and recombinant strain expressing the ttr operon and $2\times10^{9}$ cfu/mL when testing the parental and recombinant strain expressing the GbpA fragment) of the probiotic. For Muc2$^{-/-}$ spontaneous colitis, mice were gavaged once weekly for 4 consecutive weeks. Since Muc2$^{-/-}$ spontaneous colitis progresses with age, 2 time points were used when testing the *E. coli* strains and for the Muc2$^{-/-}$ control. One cohort of the mice was taken out to 3 months of age and then sacrificed and a second cohort was taken out to 4 months of age and then sacrificed. Mice were monitored daily and weighed weekly to score and check for colitis disease progression. Mice were immediately euthanized if they developed rectal prolapse or total clinical score of 11 or greater.

In the second set of trials, for DSS-induced colitis, mice were administered probiotics via oral gavage once per day for a period of three days for testing parental and recombinant strain expressing ttr operon. Mice were administered probiotics only once for testing the parental and recombinant strain expressing GbpA. The third treatment group served as the control group and received no oral gavage or probiotic supplementation. Mice were then exposed to 3.5% DSS via drinking water and monitored throughout the 7-day exposure for mortality/morbidity. Mice were immediately euthanized if they showed signs of distress due to gavage such as: lethargy, hunched posture, difficulty breathing, blood emerging from the mouth and/or nose or a loss in total body weight≥20%. Mice were sacrificed at day 7. Body weight was measured every day during the 7 day DSS exposure. Probiotic supplemented groups were exposed to DSS and no DSS. A DSS control with no supplementation was also used to provide a control for the DSS-induced colitis.

Body Weight and Clinical Scores

In the second set of trials, for DSS-induced colitis, body weight data is presented as percentage of weight change of the initial body weight. For Muc2$^{-/-}$ spontaneous colitis, body weight data is presented as a percentage of weight change from each consecutive week.

Mice were scored based on their body movement, rectal bleeding, stool consistency, weight change, and hydration. For DSS-induced colitis; for body movement, a score of 2 was given for piloerection and a 2 for reduced movement, a score of 3 for hunched posture and a 3 for inactive, and a score of 5 was given for shaking. For rectal bleeding, a score of 1 was given for a positive fecal occult blood test, 2 for blood in the stool, 3 for large amount, and 4 for extensive blood in stool and visible blood at anus. For stool consistency, a score of 1 was given for loose stool, 2 for watery stool, 3 for diarrhea, and a 4 for no formed stool. For weight, a score of 1 was given for loss of 5-10% of initial weight, a 2 for 10-15%, and weight loss of more than 15% was given a 3. For hydration, a score of 1 was given for slight sunken eyes, 3 for dehydrated eyes, and a 4 for a skin tent. All scores from each category were tallied and a final clinical score per day for each mouse was given during the DSS treatment. Higher clinical scores correlated with increased intestinal inflammation.

For Muc2$^{-/-}$, for body movement, a score of 2 was given for piloerection and a 2 for reduced movement, a score of 3 for hunched posture and a 3 for inactive, and a score of 5 was given for shaking. For rectal bleeding, a score of 1 was given for rectal swelling, a score of 2 for visible blood in the stool, a score of 3 for large amount of blood in stool and/or cage, a score of 4 for blood in stool and anus, and a score of 4 for rectal prolapse. For stool consistency, a score of 1 was given for soft stool, and a score of 2 for diarrhea. For weight loss, a score of 1 was given for loss of up to 5%, a score of 2 for 5-10%, a score of 3 for loss of 10-19%, and a score of 5 for loss of more than 20%. For hydration, a score of 1 was given for slight sunken eyes, 3 for dehydrated eyes, and a 4 for a skin tent. All scores from each category were tallied and a final clinical score per week for each mouse was given during the Muc2$^{-/-}$ spontaneous colitis. A total clinical score of 11 or greater or rectal prolapse indicated immediate euthanization.

Tissue Collection

Mice were first anesthetized with isofluorane and then euthanized by asphyxiation by $CO_2$ and then cervical dislocation; the distal colon, ileum, and cecum were removed and immersed in 1 mL of RNA-later (Qiagen) and stored at −80° C. for RNA extractions and quantitative polymerase chain reaction (qPCR) cytokine analysis or immersed in 1 mL of 10% neutral buffered formalin (Thermo Fisher Scientific) at 4° C. for histological analyses and immunofluorescence.

In the second set of trials, for DSS-induced colitis, mice were first anesthetized with isofluorane, sacrificed by asphyxiation by $CO_2$, and then followed by cervical dislocation. For Muc2$^{-/-}$ spontaneous colitis, mice were first anesthetized with isofluorane, and then blood was withdrawn using intracardiac puncture and then cervical dislocation. Cardiac puncture was used a terminal end-point.

The distal colon, ileum, and cecum were removed and sectioned into 3 pieces. One section was immersed in 1 mL of RNAlater (Qiagen) and stored at −80° C. for RNA extractions and quantitative polymerase chain reaction (qPCR) cytokine analysis, second section was immersed in 1 mL of 10% neutral buffered formalin (Thermo Fisher Scientific) at 4° C. for histological analyses and immunofluorescence, and the third section was flash frozen in LN2 (liquid nitrogen) for microbial analysis. For Muc2$^{-/-}$ colitis, the mesenteric lymph nodes (MLN) and spleen were collected and stored in 1 mL of sterile 1×PBS (Lonza).

Histopathological Scoring

In the second set of trials, for histology, tissue sections were placed in 10% neutral-buffered formalin, left overnight at 4° C., and then transferred into 70% ethanol after 2 1×PBS washes. These sections were paraffin embedded and cut into 5 μm sections onto slides. A slide was stained for Hematoxylin and eosin stain (H&E) staining for histopathological scoring. Paraffin-embedded colon cross sections were stained using H&E staining and damage scores measured. The histopathology scores were based on 4 parameters. Scores were determined as: crypt damage (0=intact, 1=loss of ⅓ basal, 2=loss of ⅔ basal, 3=entire crypt loss, 4=change of epithelial surface with erosion, 5=confluent erosion); ulceration (0=absence of ulcers, 1=1 or 2 foci of ulcerations, 2=3 or 4 foci of ulcerations, 3=confluent or extensive ulcerations); inflammation (0=normal, 0.5=very minimal, 1=minimal, 2=mild, 3=moderate, 4=marked, 5=severe); and goblet cell depletion (0=>50, 1=25-50, 2=10-25, 3=<10). Scores in each category were added up and a total histopathological score was given. Slides were viewed on an Olympus IX81 fluorescent microscope at 200× magnification. Histopathological images were taken on MetaMorph software.

Immunoflourescence

For the second set of trials, paraffin-embedded tissue sections were deparaffinized and antigen retrieval of rehydrated tissues was performed using 1 mg/ml trypsin (Sigma Aldrich) followed by incubation with primary antibodies. Slides were incubated with either rat monoclonal $IgG_{2a}$ antibody raised against F4/80 (Cedarlane) to examine macrophages or rabbit polyclonal antibody IgG raised against MPO-1 (Thermo Fisher Scientific) to examine polymorphonuclear leukocytes. This was followed by secondary antibodies of goat anti-rabbit IgG ALEXA FLUOR-conjugated 594-red antibody (Invitrogen) or goat anti-rabbit IgG ALEXA FLUOR-conjugated 488-green antibody (Invitrogen). Tissue sections were mounted using DAPI (Sigma Aldrich) and viewed on an Olympus IX81 fluorescent microscope at 200× magnification. For inflammatory cell counts, positive cells were quantified in the sub-mucosal region by a blinded observer and verified by another from a stitched image using METAMORPH software. The total number of positive cells in all sub-mucosal regions per mouse tissue were tallied.

mRNA Extraction, cDNA Synthesis, and Cytokine Analysis

Total RNA was purified using Qiagen RNEASY kits (Qiagen) according to the manufacturer's instructions. Extracted RNA was purified using Oligo (dT) purification of mRNA using DYNABEADS mRNA purification kit (Invitrogen). 5-10 μg of DSS-exposed total RNA (estimated to contain 5000 ng of mRNA) was used with 0.25 mg of DYNABEADS Oligo (dT)25 in a total volume of 200 μl (including buffers). The beads were washed with buffers according to the manufacturer's instructions. This was eluted in 20 μl of Tris-HCl and 7.5 μl of this elute was used for cDNA synthesis. DNA was synthesized with ISCRIPT cDNA Synthesis Kit (Bio-rad Laboratories). Quantitative PCR (qPCR) was performed in duplicates in a volume of 10 μl with SSO FAST EVA GREEN Supermix (Bio-rad Laboratories) on the Biorad CFX 96 real time PCR detection system with cycling conditions previously described (Baker J et al. 2012 Am J Physiol Gastrintest Liver Physiol 303(7): G825-G836). All primers were synthesized by the Integrated DNA Technology (IDT), Canada. Primer efficiencies were verified according to the Minimum Information for Publication of Quantitative Real-Time PCR Experiments guidelines. The specificity of the primers was verified by using Bio-rad CFX software and efficiencies were determined using standard curves. Expression of 18S and GAPDH were used as reference genes for gene expression analysis carried out using CFX manager software version 1.6.541.1028 (Bio-rad Laboratories).

For the second set of trials, total RNA was purified using Qiagen RNEASY kits (Qiagen) according to the manufacturer's instructions. Extracted RNA was purified using Oligo (dT) purification of mRNA using DYNABEADS mRNA purification kit (Invitrogen). 5-10 μg of DSS-exposed total RNA (estimated to contain 5000 ng of mRNA) was used with 0.25 mg of DYNABEADS Oligo (dT)25 in a total volume of 200 μl (including buffers). The beads were washed with buffers according to the manufacturer's instructions. This was eluted in 20 μl of Tris-HCl and 7.5 μl of this elute was used for cDNA synthesis. DNA was synthesized with ISCRIPT cDNA Synthesis Kit (Bio-rad Laboratories). Quantitative PCR (qPCR) was performed in duplicates in a volume of 10 μl with SSO FAST EVA GREEN Supermix (Bio-rad Laboratories) on the Biorad CFX 96 real time PCR detection system with cycling conditions previously described (Baker J et al. 2012 Am J Physiol Gastrintest Liver Physiol 303(7):G825-G836). All primers were synthesized by the Integrated DNA Technology (IDT), Canada. Primer efficiencies were verified according to the Minimum Information for Publication of Quantitative Real-Time PCR Experiments guidelines. The specificity of the primers was verified by using Bio-rad CFX software and efficiencies were determined using standard curves. Expression of 18S, TATA-binding protein (TBP), and eukaryotic elongation factor 2 (EEF2) were used as reference genes for gene expression analysis carried out using CFX manager software version 1.6.541.1028 (Bio-rad Laboratories). Table 3 includes a list of primer sequences used for qPCR.

TABLE 3

Primers used for mRNA cytokine analysis for qPCR

| Primer | Forward Primer | Reverse Primer |
|---|---|---|
| 18S | CGGCTACCACCCAAGGAA (SEQ ID NO: 54) | GCTGGAATTACCGCGGCT (SEQ ID NO: 55) |
| TBP | ACCGTGAATCTTGGCTG TAAC (SEQ ID NO: 56) | GCAGCAAATCGCTTGGG ATTA (SEQ ID NO: 57) |
| EEF2 | TGTCAGTCATCGCCCA TGTG (SEQ ID NO: 58) | CATCCTTGCGAGTGTCA GTGA (SEQ ID NO: 59) |

TABLE 3-continued

Primers used for mRNA cytokine analysis for qPCR

| Primer | Forward Primer | Reverse Primer |
|---|---|---|
| TNF-α | CATCTTCTCAAAATTCGAGT GACA (SEQ ID NO: 60) | TGGGAGTAGACAAGGTACA ACCC (SEQ ID NO: 61) |
| IFN-γ | TCAAGTGGCATAGATGTGG AAGA (SEQ ID NO: 62) | TGGCTCTGCAGGATTTT CATG (SEQ ID NO: 63) |
| IL-10 | AGGGCCCTTTGCTATGGTGT (SEQ ID NO: 64) | TGGCCACAGTTTTCAGGGAT (SEQ ID NO: 65) |
| IL-1β | AGCTTCCTTGTGCAAGTGTC (SEQ ID NO: 66) | CCCTTCATCTTTTGGGGTCC (SEQ ID NO: 67) |
| IL-17a | TCCCTCTGTGATCTGGGAAG (SEQ ID NO: 68) | CTCGACCCTGAAAGTGAAGG (SEQ ID NO: 69) |
| Reg3γ | CCCGTATAACCATCACCAT CAT (SEQ ID NO: 70) | GGCATCTTTCTTGGCAAC TTC (SEQ ID NO: 71) |
| Muc2 | GCCAGATCCCGAAACCA (SEQ ID NO: 72) | TATAGGAGTCTCGGCAG TCA (SEQ ID NO: 73) |

SCFA Analysis

The amount of short chain fatty acids (SCFA) were analyzed in cecal samples by gas chromatography (with modifications) Zhao G, et al. Biomedical Chromatography. 2006; 20(8):674-682. Cecal tissue samples were homogenized with 700 μl isopropyl alcohol, containing 2-ethylbutiric acid at 0.01% v/v as internal standard at 30 Hz for 13 minutes in a homogenizer (Retsch Metal Beads MixerMill MM 400) with stainless steel metal beads. Samples were kept at room temperature for 15 minutes and then centrifuged in a MEGAFUGE 40R (Thermo Fisher) at 15,100×g for 10 minutes at 4° C. Resulting supernatant was collected and the procedure was repeated for a second time on the leftover pellet to confirm complete extraction. 0.9 μl of the cleared supernatant was directly injected to a Trace 1300 Gas Chromatograph in splitless mode, that is equipped with a Flame-ionization detector, and an AI1310 auto sampler (Thermo Fisher Scientific). A fused silica FAMEWAX (Restek Cat #12498) column 30 m×0.32 mm i.d. coated with 0.25 μm film thickness was used. Helium was supplied as the carrier gas at a flow rate of 1.8 mL/min. The initial oven temperature was 80° C., maintained for 5 minutes, rose to 90° C. at 5° C./min, then increased to 105° C. at 0.9° C./min, and finally increased to 240° C. at 20° C./min and held for 5 minutes. The temperature of the FID and the injection port was 240 and 230° C., respectively. The flow rates of hydrogen, air and nitrogen as makeup gas were 30, 300 and 20 mL/min, respectively. Data analysis was carried out with CHROMELEON 7 software. Peaks were analyzed on software and the area under peaks for acetic, propionic, and butyric acid data was represented as weight percentage of the total cecal tissue.

Figure 8:
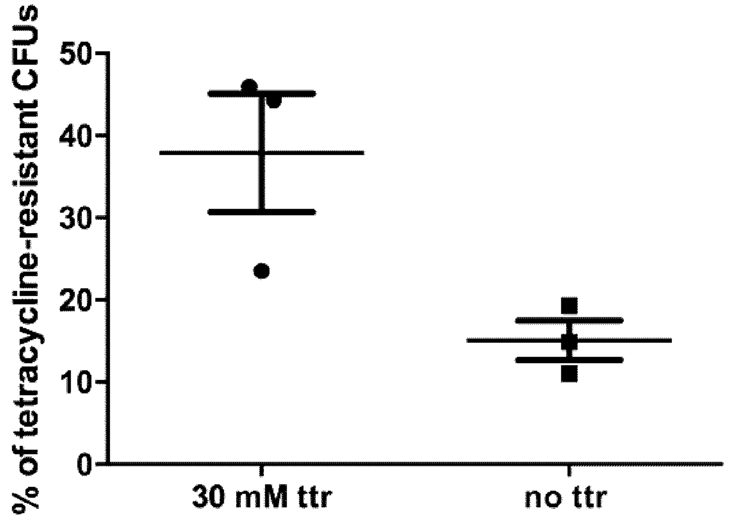
FIG. 8 is a graph showing the growth advantage of *E. coli* Nissle attB$^{phi80}$::ttrACBSR in growth competition with wild type *E. coli* Nissle in the presence of tetrathionate. Difference in the percent of tetracycline resistant colony forming units (CFUs) is related to growth advantage of *E. coli* Nissle attB$^{phi80}$::ttrACBSR in the presence of tetrathionate.

Example 1— Construction of a Recombinant Probiotic Strain Expressing the Ttr Operon and Analysis of Growth In Vitro A recombinant probiotic strain of *E. coli* Nissle was genetically engineered to express the tetrathionate respiratory operon as described herein. The PCR amplification of the long ttr operon (7.4 kb) (Gene ID: 1252901 in NCBI Gene), even with a high-fidelity polymerase, might result in random mutations possibly interfering with the proper function of the enzymes. To select for the best pAH162-ttr plasmid for subsequent chromosomal integration, a growth competition assay and a thiosulfate production assay were performed. During the growth competition assay, a strain bearing ttr operon (on plasmid or integrated into the chromosome) and its parental strain were incubated simultaneously in the same liquid culture without aeration. After the inoculation of the culture with the mixture of tested strains, tetrathionate solution or water (as a control) were added to determine whether the ttr-bearing strain had a growth advantage in the presence of tetrathionate and if this advantage is enough to outcompete the parental strain. Resistance of the ttr-bearing strain to Tc was employed to estimate its numbers. FIG. 8 shows that the percentage of Tc-resistant colonies (*E. coli* Nissle attB$^{phi80}$::ttrACBSR) in mixed culture is higher in the presence of tetrathionate and that the ttr operon integration resulted in a growth advantage during simultaneous cultivation. The competition coefficients (percent of Tc-resistant colonies in the presence of tetrathionate divided by the percent of Tc-resistant colonies in the absence of tetrathionate) for the mixture of *E. coli* BW23473, bearing pAH162-ttr plasmid, with wild type strain and for the mixture of *E. coli* Nissle with chromosome-integrated ttr operon mixed with the wild type strain were similar. This shows that a single copy of the ttr operon is sufficient to induce the same effect as several copies in the case of plasmid-based expression.

Figure 9:
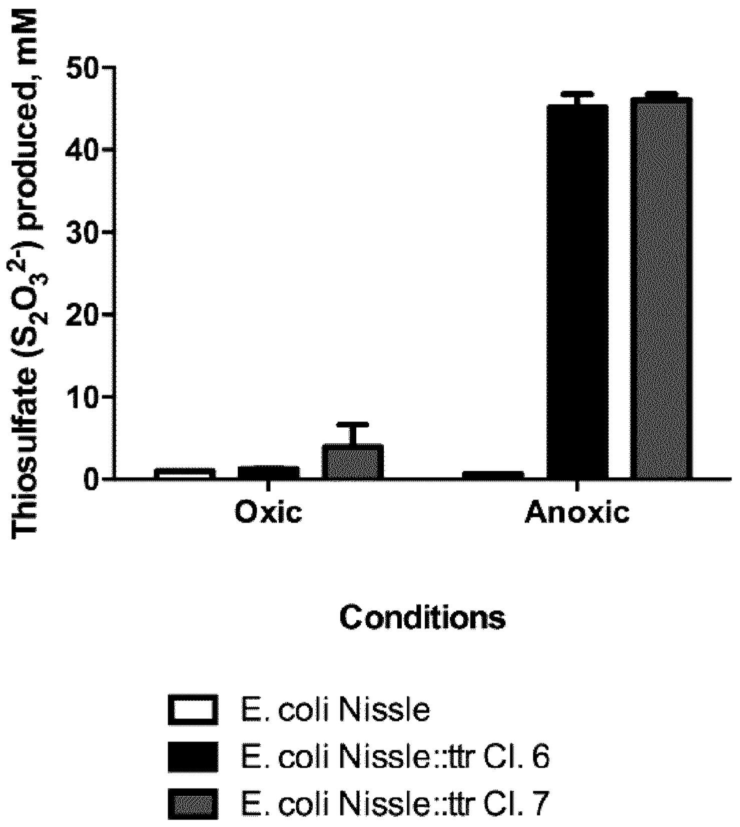
FIG. 9 is a graph showing thiosulfate production by wild type *E. coli* Nissle or the designer *E. coli* Nissle attB$^{phi80}$::ttrACBSR strain under oxic or anoxic conditions. All strains were grown in tetrathionate-containing media and consumption of tetrathionate was estimated based on conversion of tetrationate to thiosulfate.

To determine if *E. coli* Nissle strain with the integrated ttr operon is capable of reducing tetrathionate, a thiosulfate production assay was performed. This assay is based on the colorimetric estimation of the concentration of thiosulfate—a product of tetrathionate reduction. Wild type *E. coli* Nissle and modified *E. coli* Nissle attB$^{phi80}$::ttrACBSR were grown in media containing 30 mM potassium tetrathionate under oxic or anoxic conditions. The consumption of tetrathionate in each condition was estimated based on the amount of thiosulfate produced using a conversion factor of one molecule of tetrationate converts to two thiosulfate molecules (described herein). FIG. 9 shows that modified *E. coli* Nissle attB$^{phi80}$::ttrACBSR consumed more tetrathionate than wild type *E. coli* Nissle as evidenced by increased production of thiosulfate. FIG. 9 further shows that the tetrathionate reducing enzymes (encoded by ttrACB genes) work and that transcription factors, regulating the expression of the ttr operon (encoded by ttrSR genes), perform regulation correctly—in oxic conditions tetrathionate oxidation is less effective. It may therefore be concluded that ttr operon integration with the native promoter region results in the proper functioning of the operon and its activity results in the growth advantage of *E. coli* Nissle strain in the presence of tetrathionate.

Figure 1:
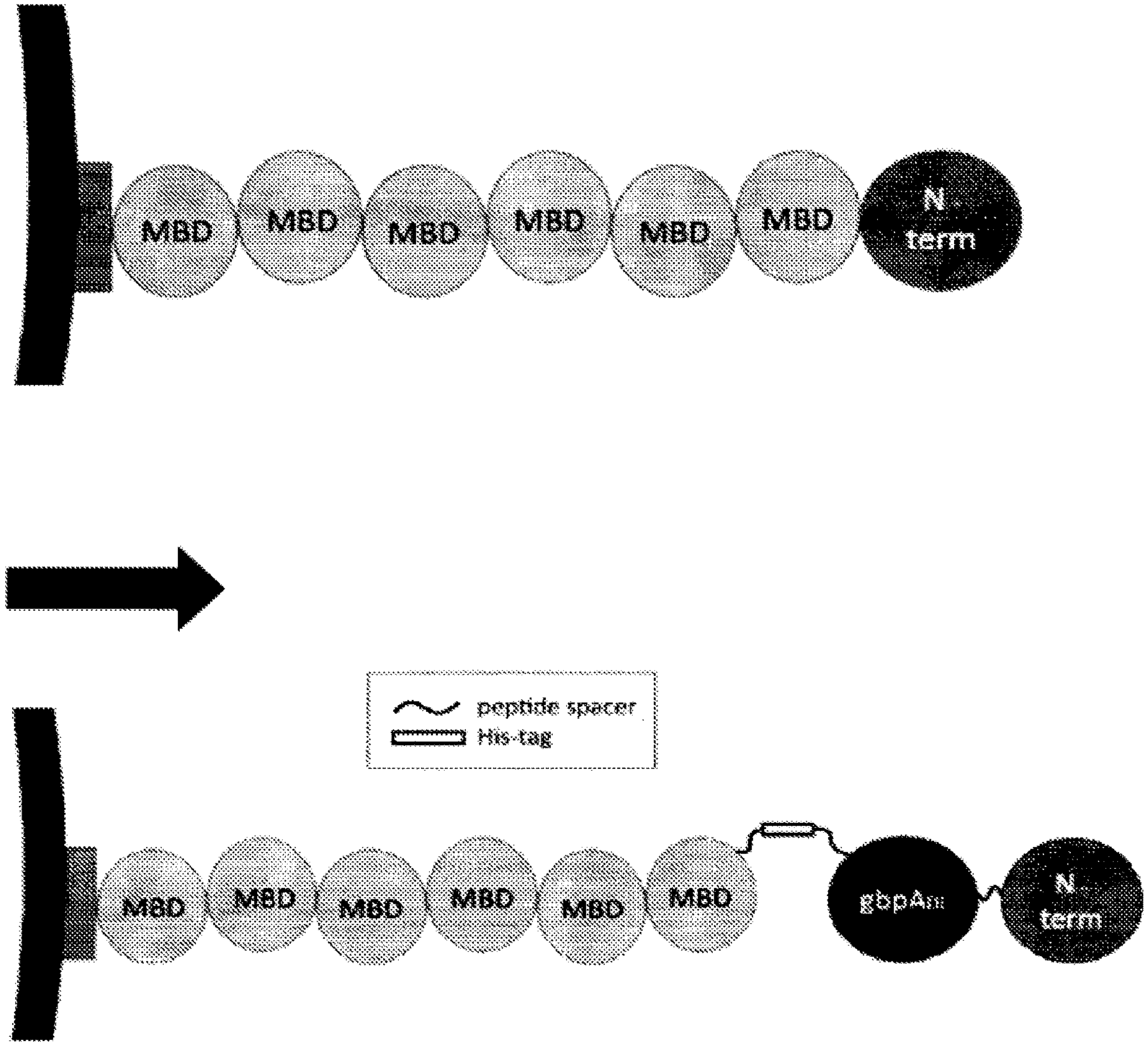
FIG. 1 is a schematic representation of the multi-domain structure of Mucus Binding Protein of *Lactobacillus reuteri* DSM20016, consisting of several Mucus Binding Domains (MBD) before and after proposed modification.
Figure 2:
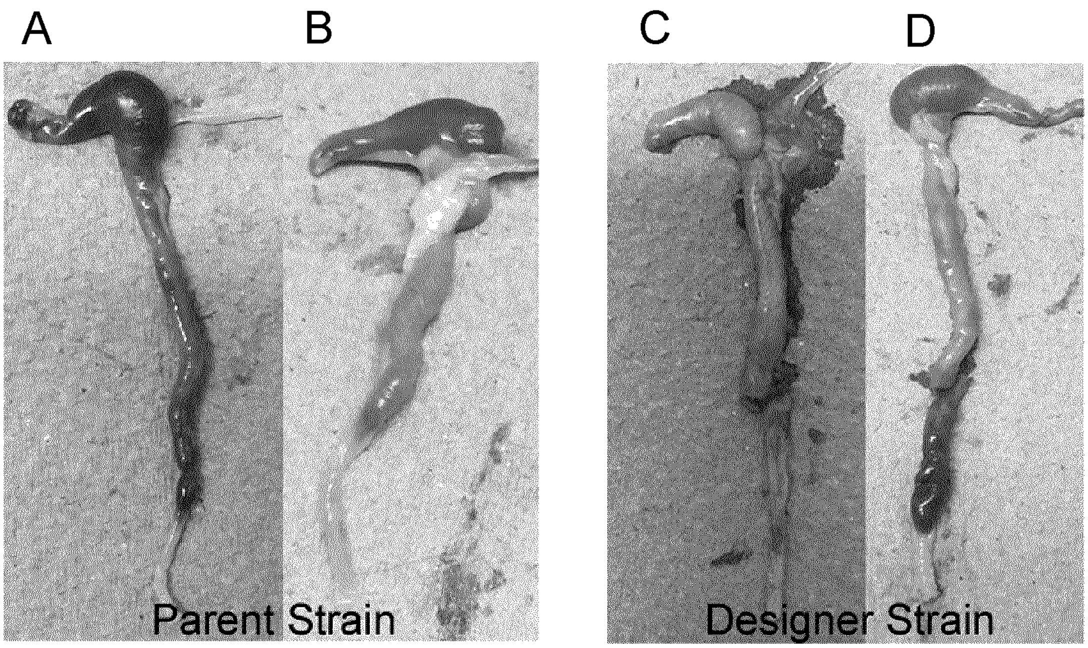
FIG. 2A is a photograph showing the macroscopic examination of cecum and colon from a mouse treated with a parental probiotic strain (*E. coli* Nissle attB$^{phi80}$::Km$^{R}$) followed by exposure to 3.5% DSS to induce colitis.
FIG. 2B is a second photograph showing the macroscopic examination of cecum and colon from a mouse treated with a parental probiotic strain (*E. coli* Nissle attB$^{phi80}$::Km$^{R}$) followed by exposure to 3.5% DSS to induce colitis.
FIG. 2C is a photograph showing the macroscopic examination of cecum and colon from a mouse treated with a recombinant probiotic strain expressing the ttr operon (*E. coli* Nissle attB$^{phi80}$::ttrACBSR) followed by exposure to 3.5% DSS to induce colitis.
FIG. 2D is a second photograph showing the macroscopic examination of cecum and colon from a mouse treated with a recombinant probiotic strain expressing the ttr operon (*E. coli* Nissle attB$^{phi80}$::ttrACBSR) followed by exposure to 3.5% DSS to induce colitis.
Figure 3:
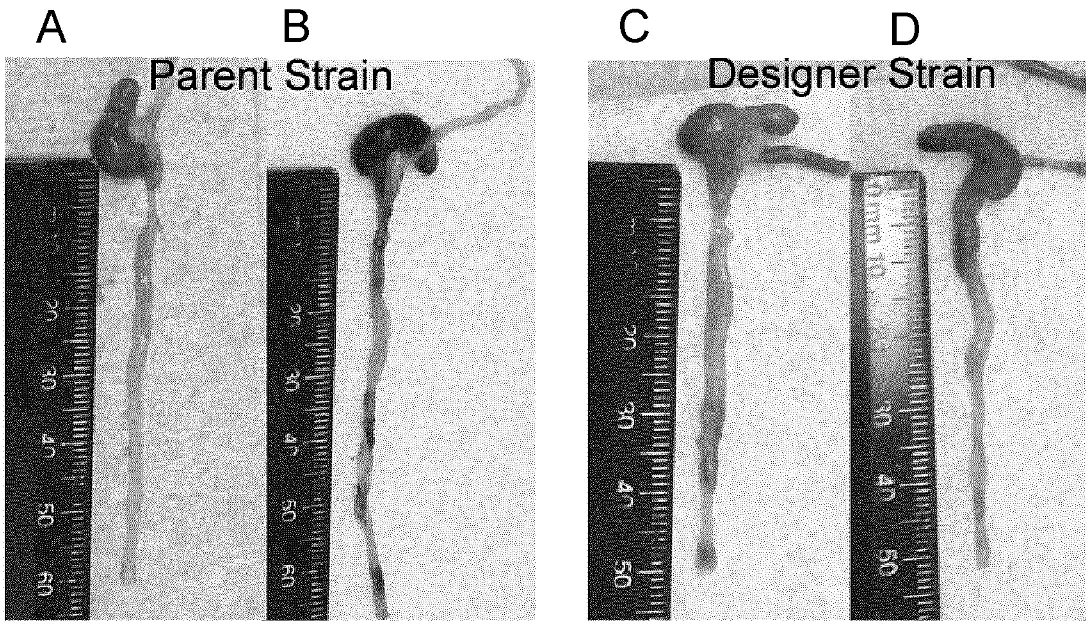
FIG. 3A is a photograph showing the macroscopic examination of cecum and colon from a mouse treated with a parental probiotic strain (*L. reuteri*) followed by exposure to 3.5% DSS to induce colitis.
FIG. 3B is a second photograph showing the macroscopic examination of cecum and colon from a mouse treated with a parental probiotic strain (*L. reuteri*) followed by exposure to 3.5% DSS to induce colitis.
FIG. 3C is a photograph showing the macroscopic examination of cecum and colon from a mouse treated with a recombinant probiotic strain expressing the recombinant probiotic (*L. reuteri*::GbpA) followed by exposure to 3.5% DSS to induce colitis.
FIG. 3D is a second photograph showing the macroscopic examination of cecum and colon from a mouse treated with a recombinant probiotic strain expressing the recombinant probiotic (*L. reuteri*::GbpA) followed by exposure to 3.5% DSS to induce colitis.

Example 2—Construction of a Recombinant Probiotic Strain Expressing a Fragment of the GbpA Protein A recombinant probiotic strain of *L. reuteri* was genetically engineered to express a fragment of the GbpA protein as described herein. In a constructed strain, the isolated fragment of the gbpA gene (SEQ ID NO: 23) encoding the N-terminal (binding) domain is inserted between the mucus-binding domain and the N-terminal domain of MBP from *L. reuteri* (FIG. 1). Flexible peptide linkers were added between the MBP part of the construction and gbpA part, to make N-terminal domain of GbpA accessible for interaction (see sequences in italics in Table 2). A STREP-TAG II was inserted in spacer between N-terminal part of MBP and N-terminal domain of GbpA to make the construction possible to be detected on cell surface with anti-strep-tag II antibodies (see underlined sequence in primer 3 in Table 2 (SEQ ID NO: 11)). The final nucleotide sequence of the combined construct containing the insertion of the gbpA fragment within the MBP nucleotide sequence is provided as SEQ ID NO: 30.

Example 3— Testing the Recombinant Probiotic Strains in the Murine IBD Model

Mice were given probiotic supplementation once daily for three days for testing of *E. coli* strains and once for testing of *L. reuteri* strains and then given 3.5% DSS in drinking water for 7 days. All mice were weighed before probiotic administration. All mice across all groups had relatively the same weights and any differences were not significant. Intake of 3.5% DSS drinking water was measured to ensure mice in all groups were being exposed to the same amount of DSS. All mice across all groups had relatively the same water intake and any differences were not significant. Upon sacrifice on day 7, tissues were harvested and examined macroscopically.

FIGS. 2A-D are a comparison of the ilea, ceca, and colons of mice who were administered either the parent probiotic (*E. coli* Nissle 1917) or the recombinant probiotic (*E. coli* Nissle attB$^{phi80}$::ttrACBSR). FIGS. 3A-D are a comparison of the ilea, ceca, and colons of mice who were administered either the parent probiotic (*L. reuteri*) or the designer probiotic (*L. reuteri*::GbpA). In both cases, mice who were administered the parental probiotic strain had very dark loose, rather than formed stool, with blood primarily located in the ceca. Additionally, the colons of these mice also appeared to have loose bloody diarrhoea in lumps still present within the colon and some ulceration mainly near the distal colon (FIGS. 2A, 2B and 3A, 3B). In contrast, mice who were administered the recombinant probiotic strains had less bloody diarrhoea in their ceca and distal colons compared to controls (FIGS. 2C, 2D and 3C, 3D).

As DSS-induced colitis was allowed to progress, mice were given daily clinical scores to score and assess the visual clinical symptoms observed. Mice were scored based on their body movement, rectal bleeding, stool consistency, weight change, and hydration. For body movement, a score of 2 was given for piloerection and a 2 for reduced movement, a score of 3 for hunched posture and a 3 for inactive, and a score of 5 was given for shaking. For rectal bleeding, a score of 1 was given for a positive fecal occult blood test, 2 for blood in the stool, 3 for large amount, and 4 for extensive blood in stool and visible blood at anus. For stool consistency, a score of 1 was given for loose stool, 2 for watery stool, 3 for diarrhoea, and a 4 for no formed stool. For weight, a score of 1 was given for loss of 5-10% of initial weight, a 2 for 10-15%, and weight loss of more than 15% was given a 3. For hydration, a score of 1 was given for slight sunken eyes, 3 for dehydrated eyes, and a 4 for a skin tent. All scores from each category were tallied and a final clinical score per day for each mouse was given during the DSS treatment. Higher clinical scores correlated with increased intestinal inflammation.

Figure 5A:
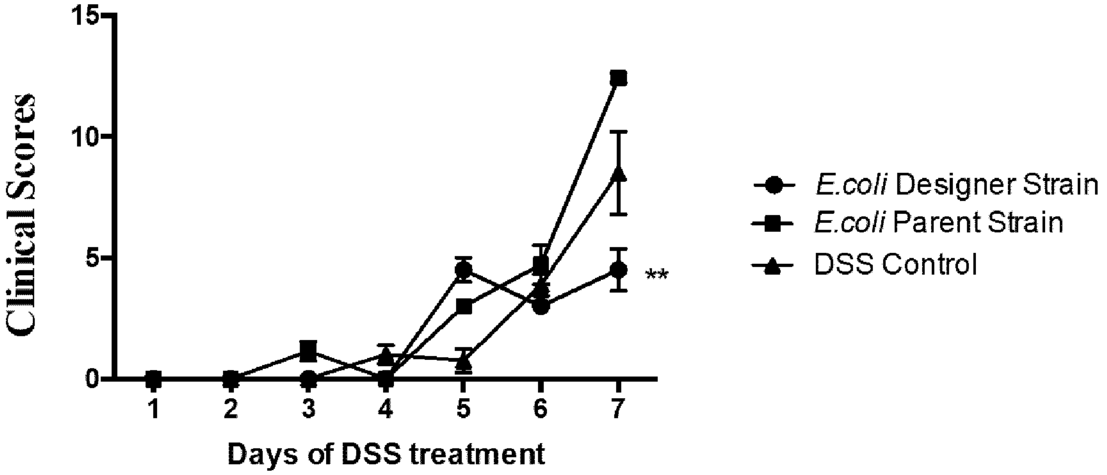
FIG. 5A is a graph showing clinical scores following DSS-induced colitis in mice pre-treated with the parental probiotic strain (*E. coli* Nissle), labelled as Parent Strain (Squares). Circles represent the group of mice treated with the recombinant probiotic strain, labelled as the Designer Strain (*E. coli* Nissle attB$^{phi80}$::ttrACBSR). Triangles represent the no probiotic DSS control. Movement, rectal bleeding, stool consistency, weight loss, and hydration were used to calculate clinical scores. Values expressed as mean+/−SEM (n=4-8). Non-parametric one-way ANOVA (Kruskal-Wallis) was used.
Figure 10A:
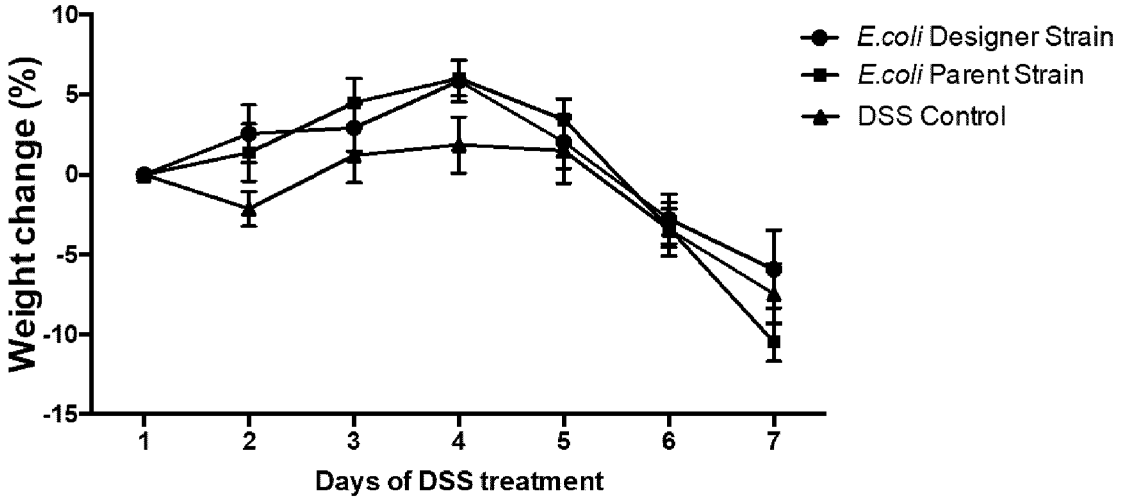
FIG. 10A is a graph showing weight loss during DSS treatment period for mice treated with the parental probiotic strain (*E. coli* Nissle), labelled as Parent Strain (Squares). Circles represent the group of mice treated with the recombinant probiotic strain, labelled as the Designer Strain (*E. coli* Nissle attB$^{phi80}$::ttrACBSR). Triangles represent the no probiotic DSS control. Weight loss was calculated as percentage of weight loss from starting body weight prior to DSS exposure. Values are expressed as mean+/−SEM (n=10-12).
Figure 10B:
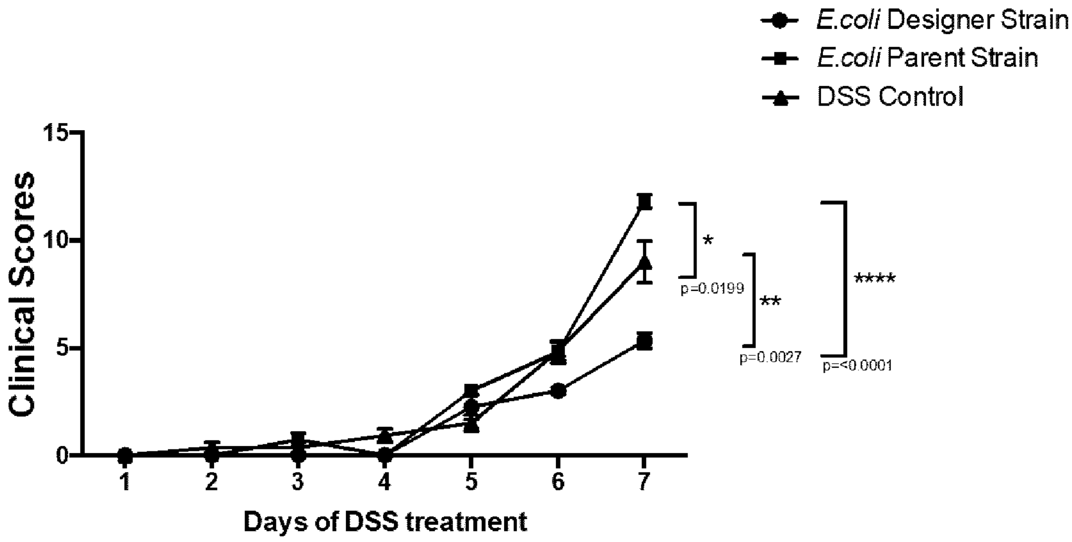
FIG. 10B is a graph showing clinical scores following DSS-induced colitis in mice pre-treated with the parental probiotic strain (*E. coli* Nissle), labelled as Parent Strain (Squares). Circles represent the group of mice treated with the recombinant probiotic strain, labelled as the Designer Strain (*E. coli* Nissle attB$^{phi80}$::ttrACBSR). Triangles represent the no probiotic DSS control. Movement, rectal bleeding, stool consistency, weight loss, and hydration were used to calculate clinical scores. Values expressed as mean+/−SEM (n=10-12). Non-parametric one-way ANOVA (Kruskal-Wallis) was used.

FIGS. 5A and 10B show clinical scores on days 1-7 of DSS treatment for mice who were administered either the parent probiotic (*E. coli* Nissle 1917) or the recombinant probiotic (*E. coli* Nissle attB$^{phi80}$::ttrACBSR). The recombinant probiotic-treated mice displayed reduced clinical scores throughout DSS treatment and shows that administration of the recombinant strain may have improved therapeutic properties over the parent strain. By day 7, the day with the clinically most relevant scores, the parent probiotic reached close to a score of 15 (FIGS. 5A and 10B). The recombinant probiotic had a significantly reduced score of fewer than 5. This further confirms that administration of the designer strain is beneficial over the parent strain.

Figure 5B:
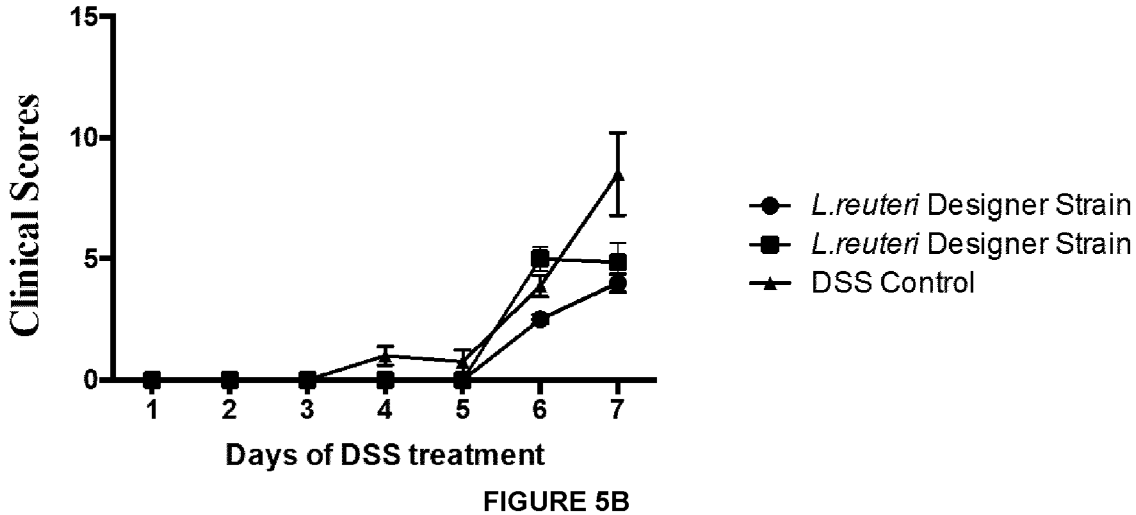
FIG. 5B is a graph showing clinical scores following DSS-induced colitis in mice pre-treated with the parental probiotic strain (*L. reuteri*), labelled as Parent Strain (Squares). Circles represent the group of mice treated with the recombinant probiotic strain, labelled as the Designer Strain (*L. reuteri*::GbpA). Triangles represent the no probiotic DSS control. Movement, rectal bleeding, stool consistency, weight loss, and hydration were used to calculate clinical scores. Values expressed as mean+/−SEM (n=4-8).
Figure 6A:
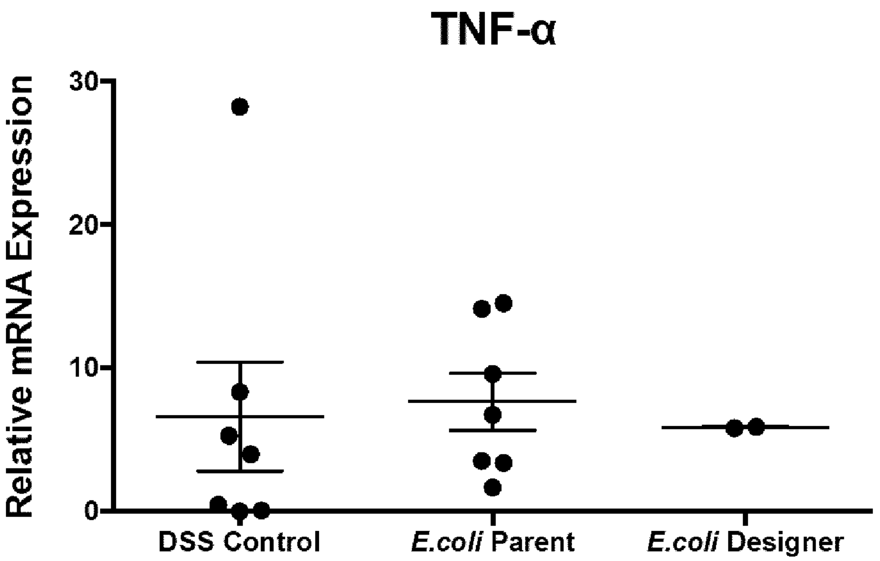
FIG. 6A is a graph showing the inflammatory cytokine TNF-α profile after DSS exposure for mice pre-treated with either the parental probiotic strain (*E. coli* Nissle 1917), labelled as Parent Strain, the recombinant probiotic strain (*E. coli* Nissle attB$^{phi80}$::ttrACBSR) labelled as Designer Strain, or a no-probiotic DSS control. Non-parametric one-way ANOVA (Kruskal-Wallis) was used.
Figure 6B:
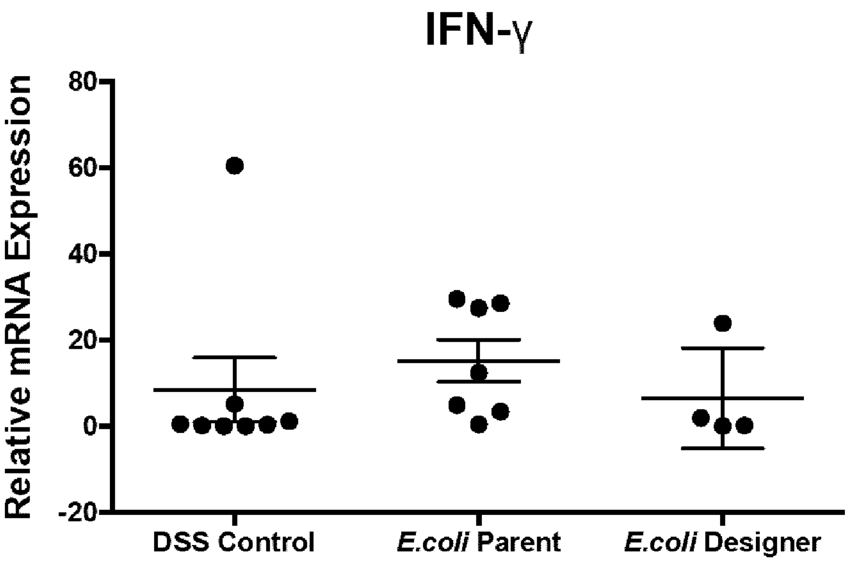
FIG. 6B is a graph showing the inflammatory cytokine IFN-γ profile after DSS exposure for mice pre-treated with either the parental probiotic strain (*E. coli* Nissle 1917), labelled as Parent Strain, the recombinant probiotic strain (*E. coli* Nissle attB$^{phi80}$::ttrACBSR) labelled as Designer Strain, or a no-probiotic DSS control. Non-parametric one-way ANOVA (Kruskal-Wallis) was used.
Figure 6C:
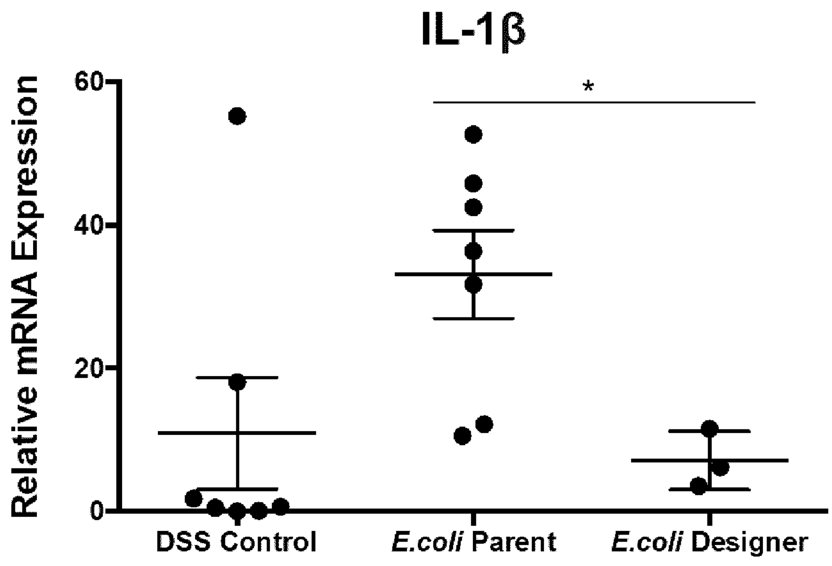
FIG. 6C is a graph showing the inflammatory cytokine IL-1β profile after DSS exposure for mice pre-treated with either the parental probiotic strain (*E. coli* Nissle 1917), labelled as Parent Strain, the recombinant probiotic strain (*E. coli* Nissle attB$^{phi80}$::ttrACBSR) labelled as Designer Strain, or a no-probiotic DSS control. Non-parametric one-way ANOVA (Kruskal-Wallis) was used.
Figure 6D:
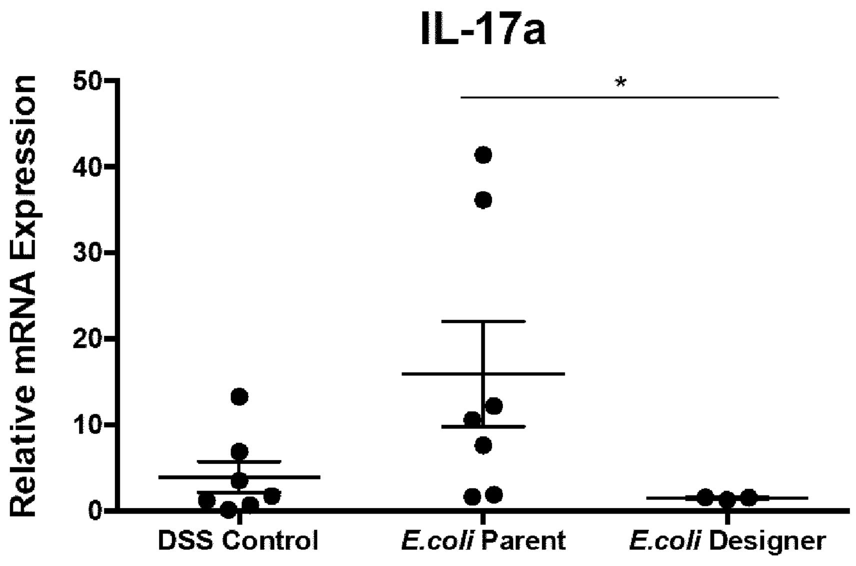
FIG. 6D is a graph showing the inflammatory cytokine IL-17a profile after DSS exposure for mice pre-treated with either the parental probiotic strain (*E. coli* Nissle 1917), labelled as Parent Strain, the recombinant probiotic strain (*E. coli* Nissle attB$^{phi80}$::ttrACBSR) labelled as Designer Strain, or a no-probiotic DSS control. Non-parametric one-way ANOVA (Kruskal-Wallis) was used.
Figure 7A:
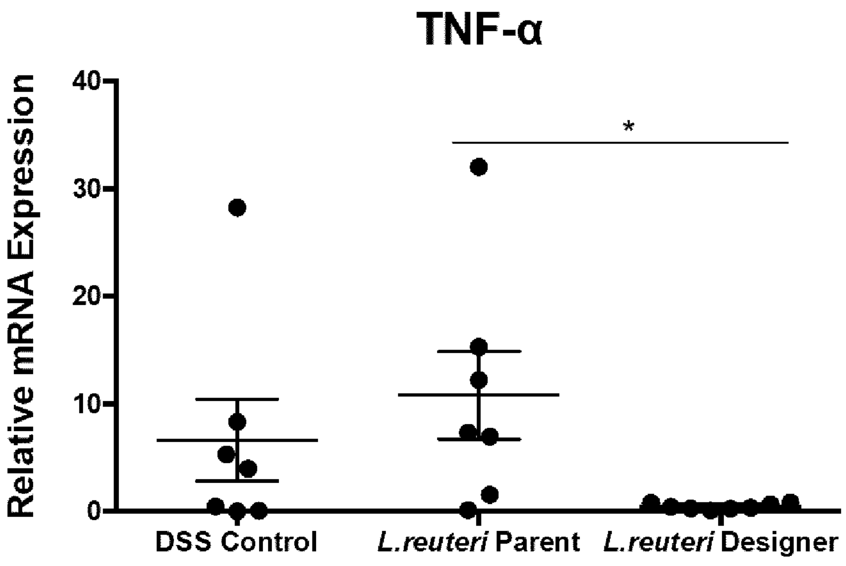
FIG. 7A is a graph showing the inflammatory cytokine TNF-α profile after DSS exposure for mice pre-treated with either the parental probiotic strain (*L. reuteri*), labelled as Parent Strain, the recombinant probiotic strain (*L. reuteri*::GbpA) labelled as Designer Strain, or the no probiotic DSS control. Non-parametric one-way ANOVA (Kruskal-Wallis) was used.
Figure 7B:
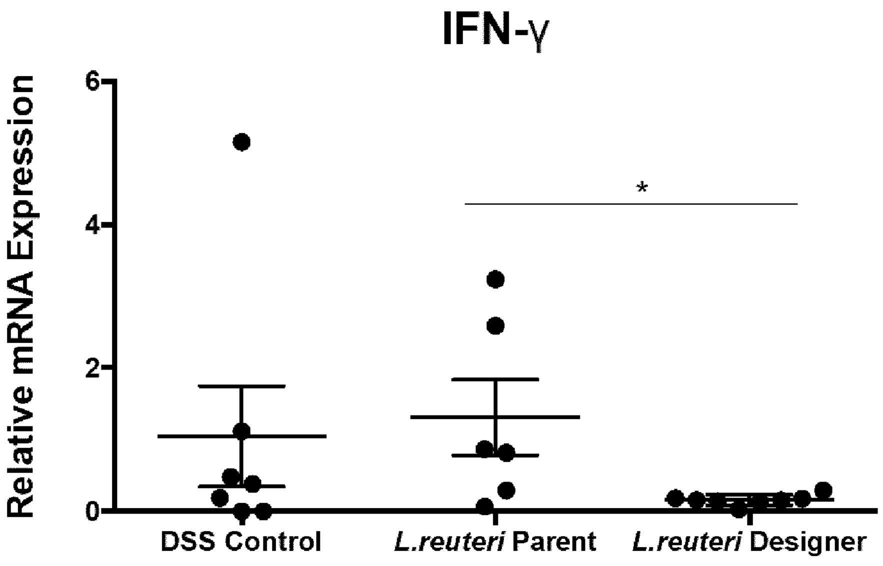
FIG. 7B is a graph showing the inflammatory cytokine IFN-γ profile after DSS exposure for mice pre-treated with either the parental probiotic strain (*L. reuteri*), labelled as Parent Strain, the recombinant probiotic strain (*L. reuteri*::GbpA) labelled as Designer Strain, or the no probiotic DSS control. Non-parametric one-way ANOVA (Kruskal-Wallis) was used.
Figure 7C:
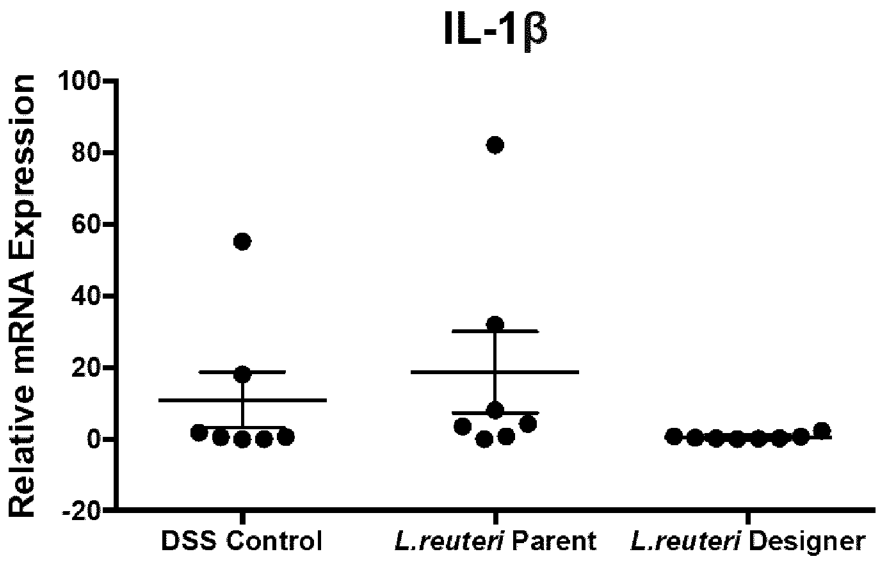
FIG. 7C is a graph showing the inflammatory cytokine IL-1β profile after DSS exposure for mice pre-treated with either the parental probiotic strain (*L. reuteri*), labelled as Parent Strain, the recombinant probiotic strain (*L. reuteri*::GbpA) labelled as Designer Strain, or the no probiotic DSS control. Non-parametric one-way ANOVA (Kruskal-Wallis) was used.
Figure 7D:
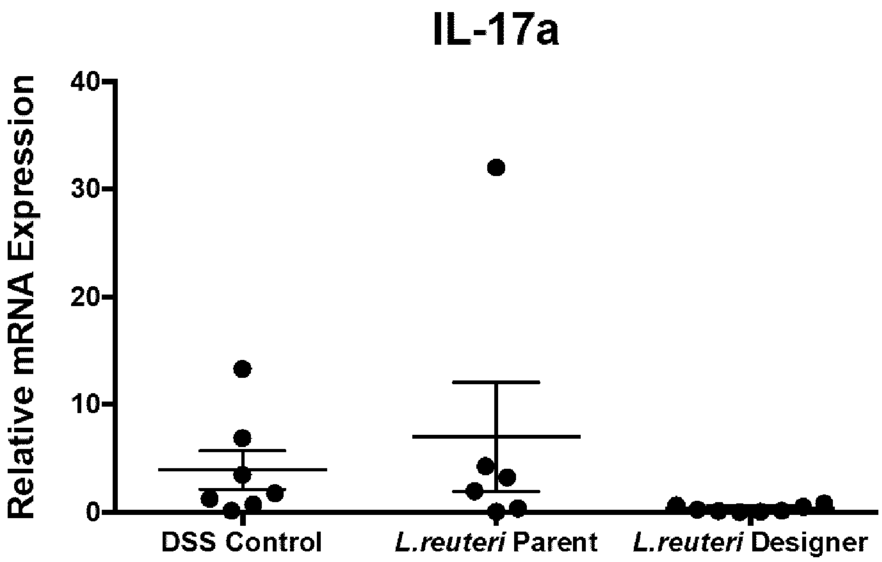
FIG. 7D is a graph showing the inflammatory cytokine IL-17a profile after DSS exposure for mice pre-treated with either the parental probiotic strain (*L. reuteri*), labelled as Parent Strain, the recombinant probiotic strain (*L. reuteri*::GbpA) labelled as Designer Strain, or the no probiotic DSS control. Non-parametric one-way ANOVA (Kruskal-Wallis) was used.
Figure 11A:
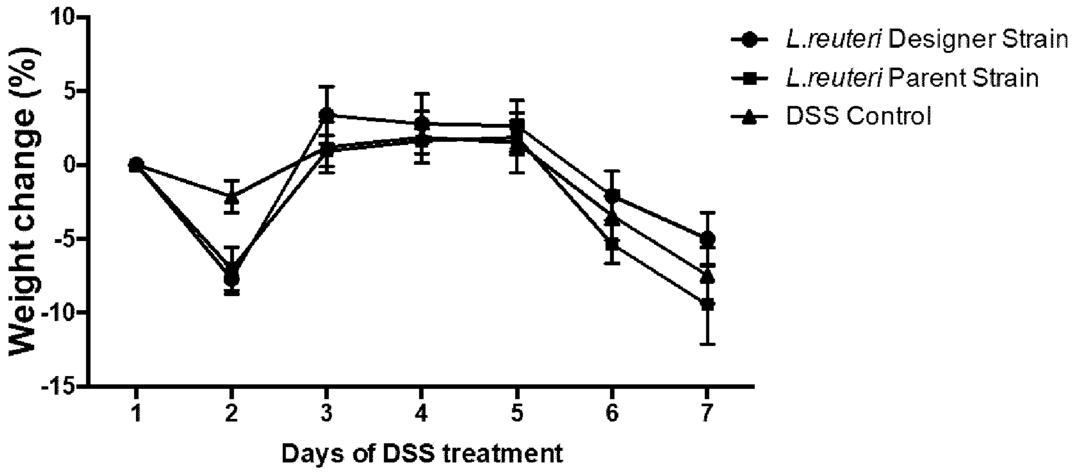
FIG. 11A is a graph showing the weight loss during the DSS treatment period for mice treated with parental probiotic (*L. reuteri*), labeled as Parent Strain (Squares). Circles represent the group of mice treated with the recombinant probiotic strain, labeled as the Designer Strain (*L. reuteri*::GbpA). Triangles represent the no probiotic DSS control Weight loss calculated as percentage of weight loss from starting body weight. Values are expressed as mean+/−SEM (n=10-12).
Figure 11B:
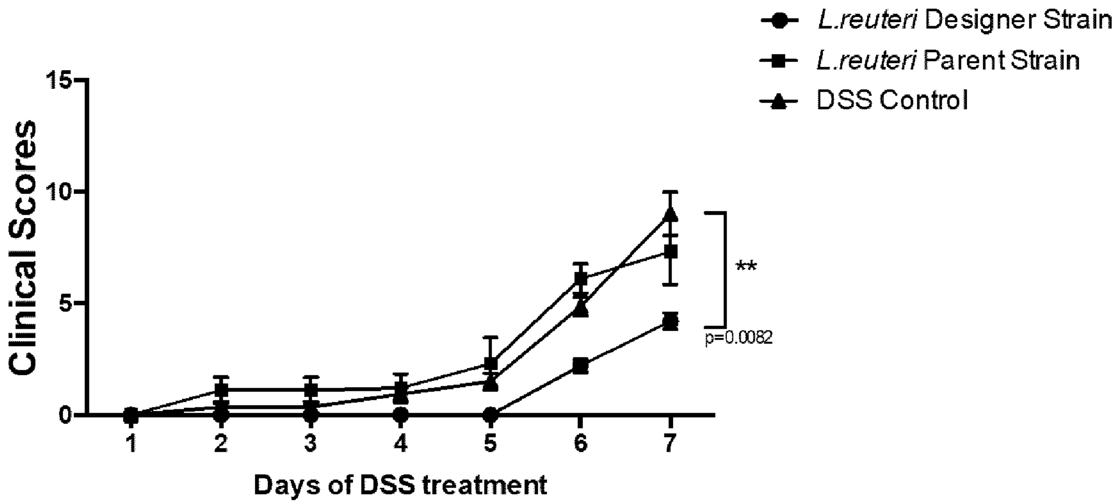
FIG. 11B is a graph showing clinical scores following DSS-induced colitis in mice pre-treated with the parental probiotic strain (*L. reuteri*), labelled as Parent Strain (Squares). Circles represent the group of mice treated with the recombinant probiotic strain, labeled as the Designer Strain (*L. reuteri*::GbpA). Triangles represent the no probiotic DSS control. Movement, rectal bleeding, stool consistency, weight loss, and hydration were used to calculate clinical scores. Values expressed as mean+/−SEM (n=10-12). Non-parametric one-way ANOVA (Kruskal-Wallis) was used.
Figure 12A:
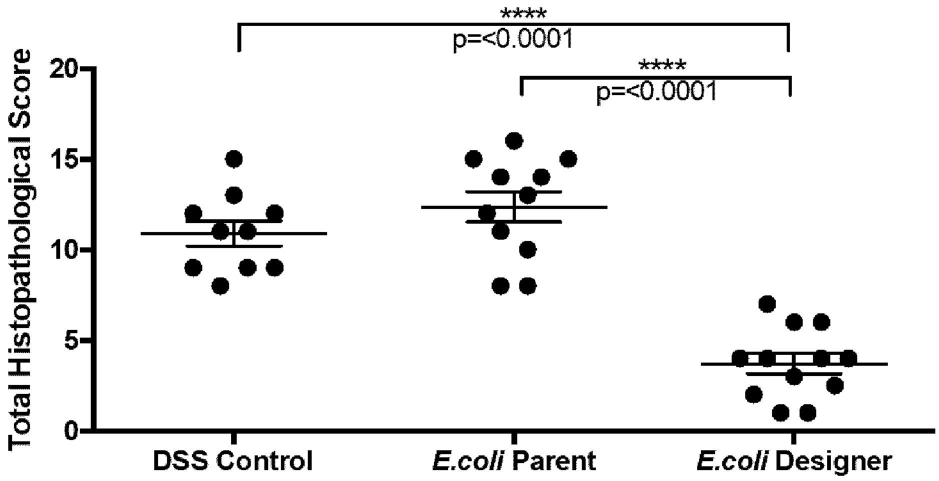
FIG. 12A is a graph showing the total histopathological scores of the DSS control, *E. coli* parent, and *E. coli* designer strains. H&E stained slides of cross sections of the distal colon were used to calculate histopathological scores. Epithelial integrity, immune cell infiltration, ulceration, and goblet cell depletion were used to calculate histopathological scores in cross sections of the distal colon. Values are expressed as mean+/−SEM (n=10-12). Non-parametric one-way ANOVA (Kruskal-Wallis) test was used.
Figure 12:
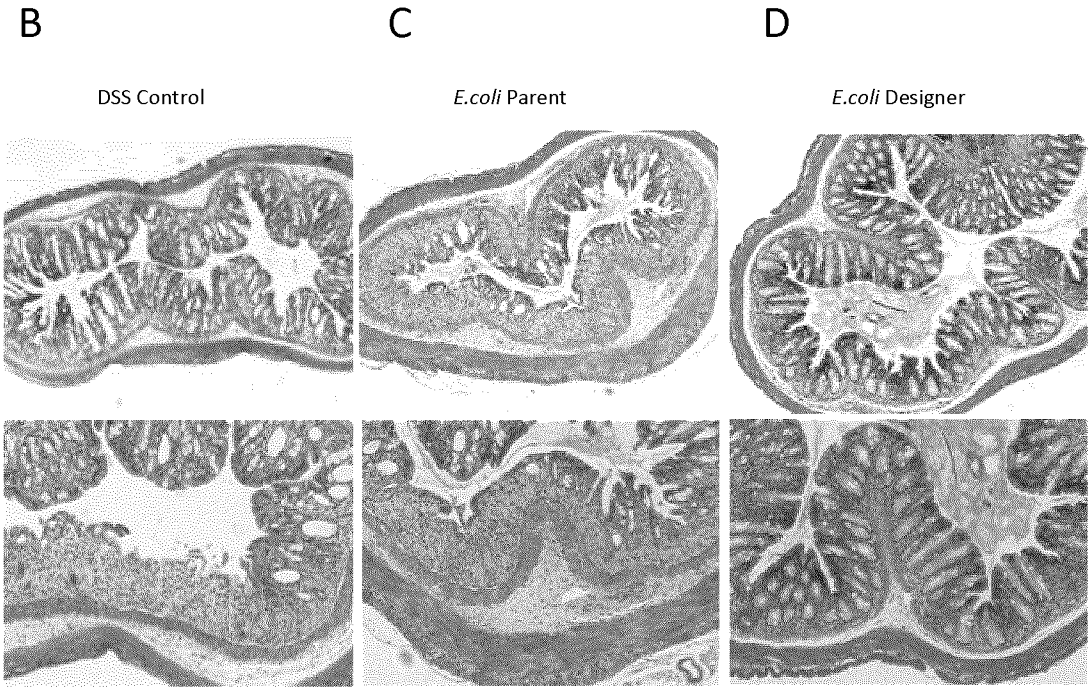
FIG. 12B shows representative images of H&E stained slides of cross sections of the distal colon of DSS-induced colitis mice used to calculate histopathological scores of the DSS control. H&E stained slides of cross sections of the distal colon were used to calculate histopathological scores. Epithelial integrity, immune cell infiltration, ulceration, and goblet cell depletion were used to calculate histopathological scores in cross sections of the distal colon. Values are expressed as mean+/−SEM (n=10-12). Non-parametric one-way ANOVA (Kruskal-Wallis) test was used.
FIG. 12C shows representative images of H&E stained slides of cross sections of the distal colon of *E. coli* DSS-induced colitis mice used to calculate histopathological scores of the *E. coli* parent strain. H&E stained slides of cross sections of the distal colon were used to calculate histopathological scores. Epithelial integrity, immune cell infiltration, ulceration, and goblet cell depletion were used to calculate histopathological scores in cross sections of the distal colon. Values are expressed as mean+/−SEM (n=10-12). Non-parametric one-way ANOVA (Kruskal-Wallis) test was used.
FIG. 12D shows representative images of H&E stained slides of cross sections of the distal colon of *E. coli* DSS-induced colitis mice used to calculate histopathological scores of the *E. coli* designer strain. H&E stained slides of cross sections of the distal colon were used to calculate histopathological scores. Epithelial integrity, immune cell infiltration, ulceration, and goblet cell depletion were used to calculate histopathological scores in cross sections of the distal colon. Values are expressed as mean+/−SEM (n=10-12). Non-parametric one-way ANOVA (Kruskal-Wallis) test was used.
Figure 13A:
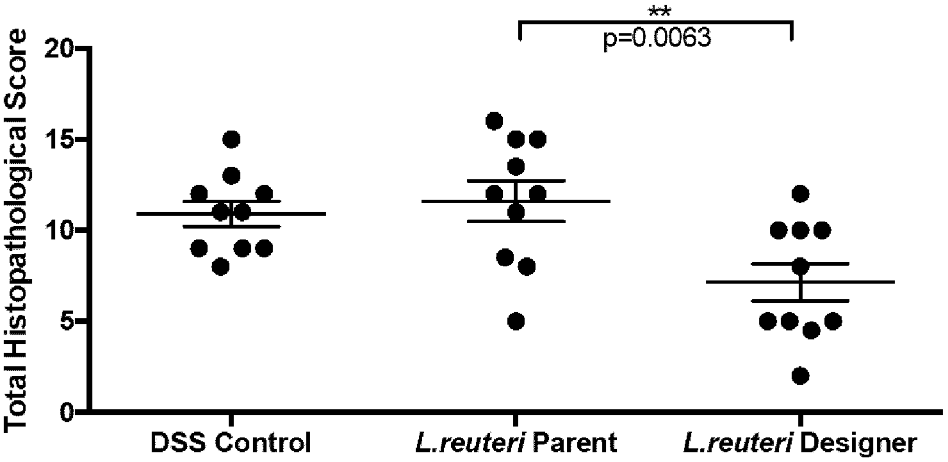
FIG. 13A is a graph showing the total histopathological of the DSS control, *L. reuteri* parent, and *L. reuteri* designer strains. H&E stained slides of cross sections of the distal colon were used to calculate histopathological scores. Epithelial integrity, immune cell infiltration, ulceration, and goblet cell depletion were used to calculate histopathological scores. Values are expressed as mean+/−SEM (n=10-12). Non-parametric one-way ANOVA (Kruskal-Wallis) test was used.
Figure 13:
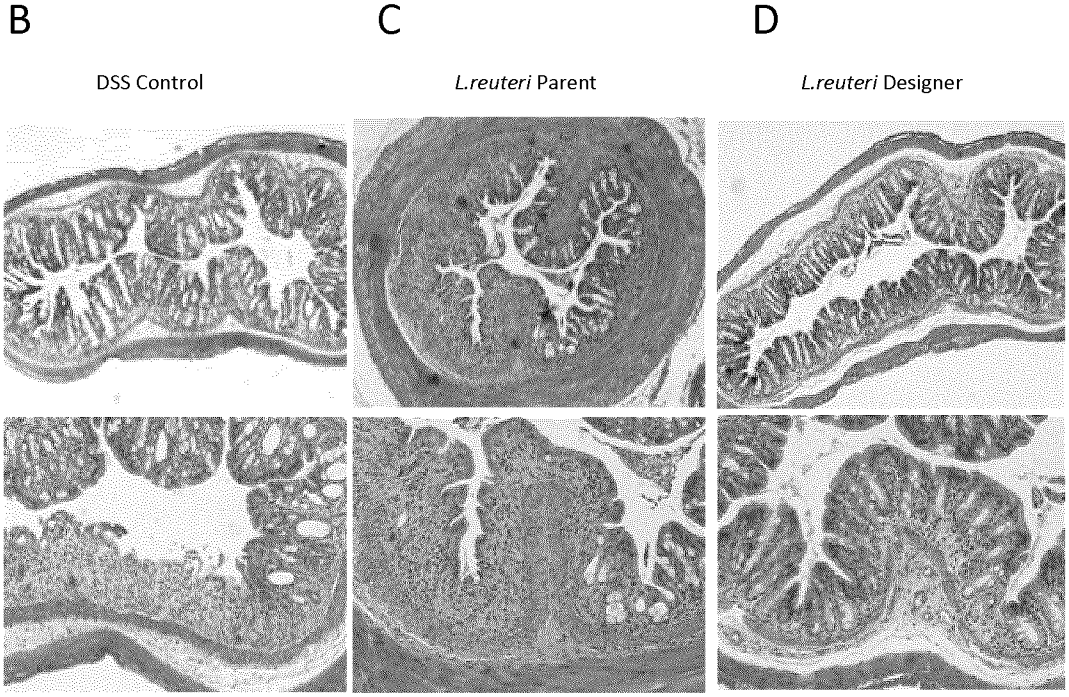
FIG. 13B shows representative images of H&E stained slides of cross sections of the distal colon of DSS-induced colitis mice used to calculate histopathological scores of the DSS control. H&E stained slides of cross sections of the distal colon were used to calculate histopathological scores. Epithelial integrity, immune cell infiltration, ulceration, and goblet cell depletion were used to calculate histopathological scores. Values are expressed as mean+/−SEM (n=10-12). Non-parametric one-way ANOVA (Kruskal-Wallis) test was used.
FIG. 13C shows representative images of H&E stained slides of cross sections of the distal colon of *L. reuteri* DSS-induced colitis mice used to calculate histopathological scores of the *L. reuteri* parent strain. H&E stained slides of cross sections of the distal colon were used to calculate histopathological scores. Epithelial integrity, immune cell infiltration, ulceration, and goblet cell depletion were used to calculate histopathological scores. Values are expressed as mean+/−SEM (n=10-12). Non-parametric one-way ANOVA (Kruskal-Wallis) test was used.
FIG. 13D shows representative images of H&E stained slides of cross sections of the distal colon of *L. reuteri* DSS-induced colitis mice used to calculate histopathological scores of the *L. reuteri* designer strain. H&E stained slides of cross sections of the distal colon were used to calculate histopathological scores. Epithelial integrity, immune cell infiltration, ulceration, and goblet cell depletion were used to calculate histopathological scores. Values are expressed as mean+/−SEM (n=10-12). Non-parametric one-way ANOVA (Kruskal-Wallis) test was used.
Figure 14A:
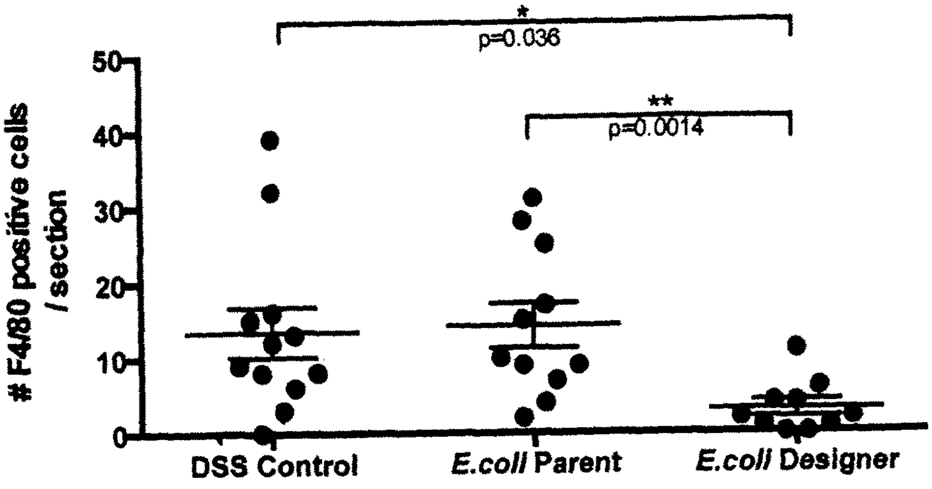
FIG. 14A is a graph showing macrophage colonic cell infiltration (F4/80 positive cells per mouse tissue section) in DSS-induced colitis mice pre-treated with either the *E. coli* Parent strain, *E. coli* Designer strain or the DSS control. Positive cells were quantified in the sub-mucosal lamina propria region on stained tissues via immunofluorescence. Values are expressed as mean+/−SEM (n=10-12). Non-parametric one-way ANOVA (Kruskal-Wallis) test was used.
Figure 14:
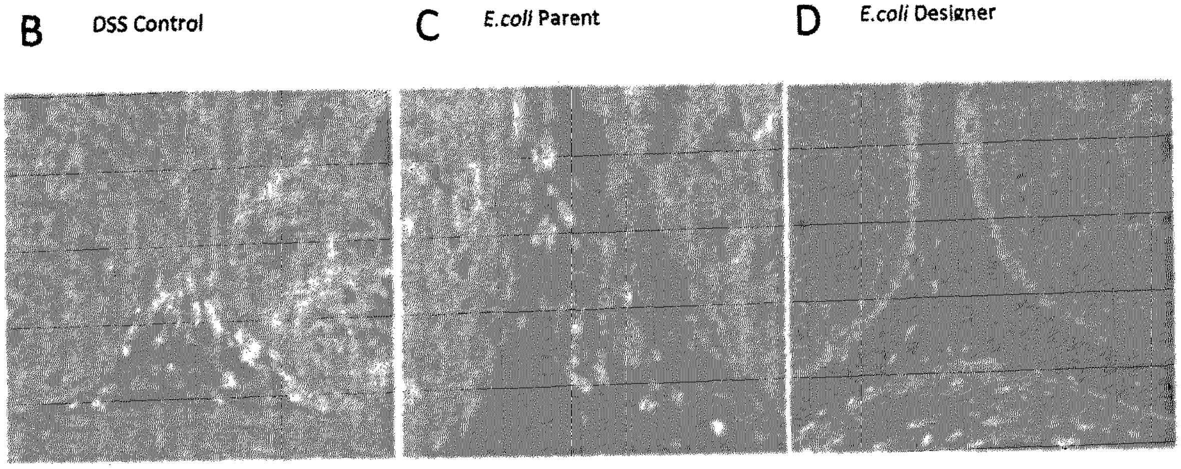
FIG. 14B is an immunofluorescence stained slide of the distal colon of DSS-induced colitis mice, showing a representative image of colonic cell infiltration in the sub-mucosal region on a cross sectional cut slide of the distal colon of the DSS control. Positive cells were quantified in the sub-mucosal lamina propria region on stained tissues via immunofluorescence. Values are expressed as mean+/−SEM (n=10-12). Non-parametric one-way ANOVA (Kruskal-Wallis) test was used.
FIG. 14C is an immunofluorescence stained slide of the distal colon of *E. coli* DSS-induced colitis mice, showing a representative image of colonic cell infiltration in the sub-mucosal region on a cross sectional cut slide of the distal colon of the *E. coli* parent strain. Positive cells were quantified in the sub-mucosal lamina propria region on stained tissues via immunofluorescence. Values are expressed as mean+/−SEM (n=10-12). Non-parametric one-way ANOVA (Kruskal-Wallis) test was used.
FIG. 14D is an immunofluorescence stained slide of the distal colon of *E. coli* DSS-induced colitis mice, showing a representative image of colonic cell infiltration in the sub-mucosal region on a cross sectional cut slide of the distal colon of the *E. coli* designer strain. Positive cells were quantified in the sub-mucosal lamina propria region on stained tissues via immunofluorescence. Values are expressed as mean+/−SEM (n=10-12). Non-parametric one-way ANOVA (Kruskal-Wallis) test was used.
Figure 15A:
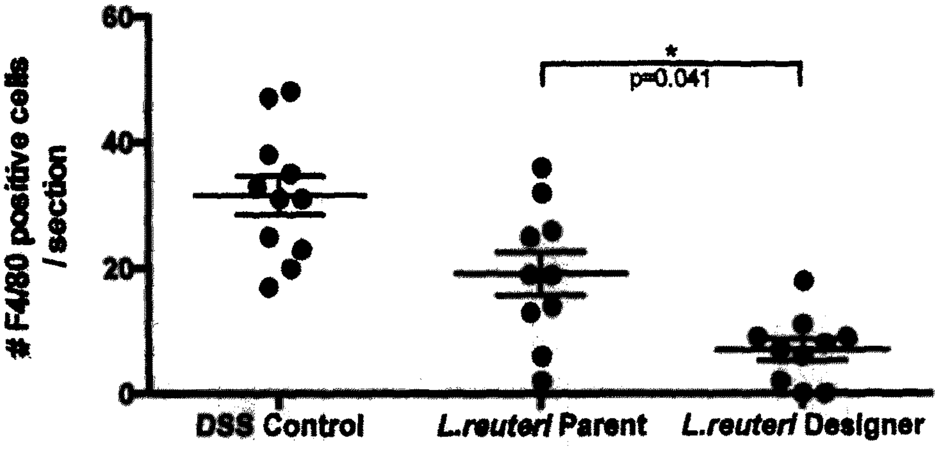
FIG. 15A is a graph showing macrophage colonic cell infiltration (F4/80 positive cells per mouse tissue section) in DSS-induced colitis mice that were administered either the *L. reuteri* Parent strain, *L. reuteri* Designer strain or the DSS control. Positive cells were quantified in the sub-mucosal lamina propria region on stained tissues via immunofluorescence. Values are expressed as mean+/−SEM (n=10-12). Non-parametric one-way ANOVA (Kruskal-Wallis) test was used.
Figure 15:
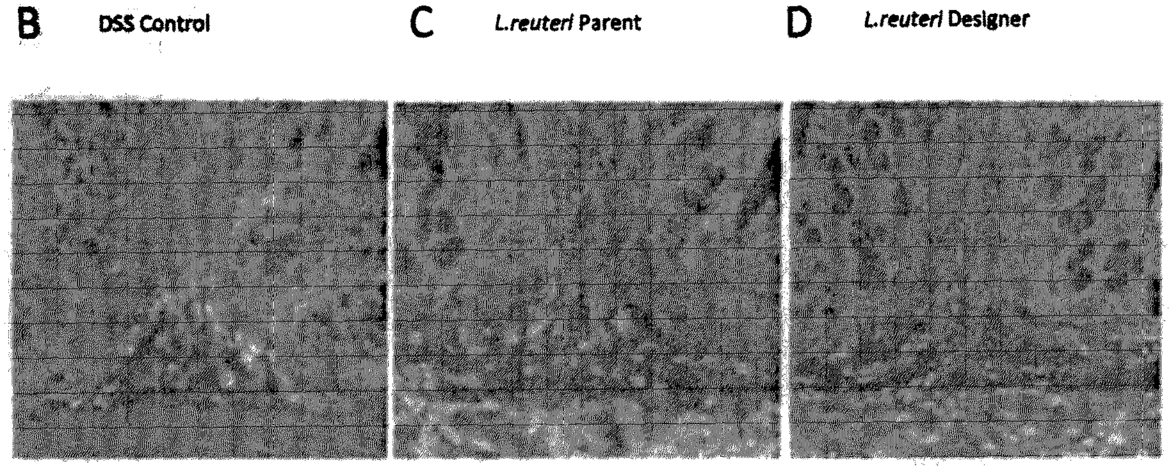
FIG. 15B is an immunofluorescence stained slide of the distal colon of DSS-induced colitis mice, showing a representative image of colonic cell infiltration in the sub-mucosal region on a cross sectional cut slide of the distal colon of the DSS control. Positive cells were quantified in the sub-mucosal lamina propria region on stained tissues via immunofluorescence. Values are expressed as mean+/−SEM (n=10-12). Non-parametric one-way ANOVA (Kruskal-Wallis) test was used.
FIG. 15C is an immunofluorescence stained slide of the distal colon of *L. reuteri* DSS-induced colitis mice, showing a representative image of colonic cell infiltration in the sub-mucosal region on a cross sectional cut slide of the distal colon of the *L. reuteri* parent strain. Positive cells were quantified in the sub-mucosal lamina propria region on stained tissues via immunofluorescence. Values are expressed as mean+/−SEM (n=10-12). Non-parametric one-way ANOVA (Kruskal-Wallis) test was used.
FIG. 15D is an immunofluorescence stained slide of the distal colon of *L. reuteri* DSS-induced colitis mice, showing a representative image of colonic cell infiltration in the sub-mucosal region on a cross sectional cut slide of the distal colon of the *L. reuteri* designer strain. Positive cells were quantified in the sub-mucosal lamina propria region on stained tissues via immunofluorescence. Values are expressed as mean+/−SEM (n=10-12). Non-parametric one-way ANOVA (Kruskal-Wallis) test was used.
Figure 16A:
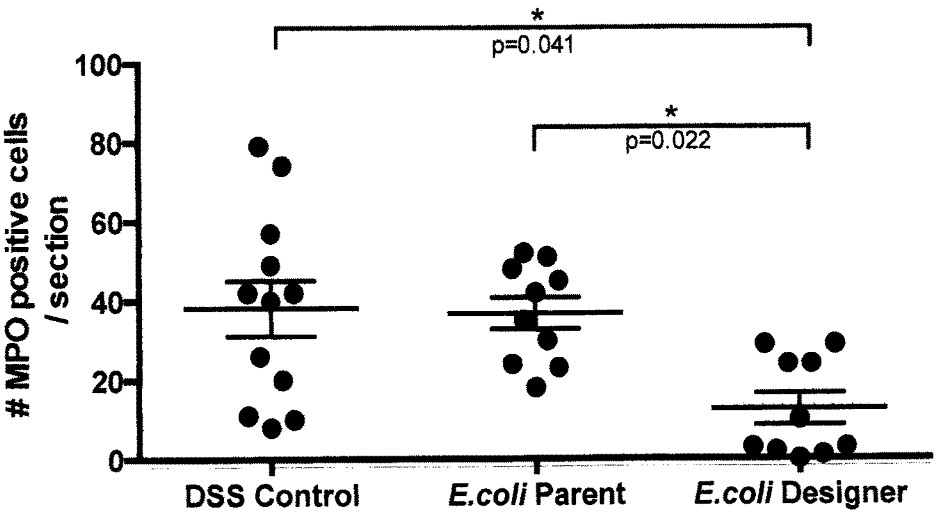
FIG. 16A is a graph showing neutrophil colonic cell infiltration (MPO positive cells per mouse tissue section) in DSS-induced colitis mice that were administered with the *E. coli* Parent strain, *E. coli* Designer strain or the DSS control. Positive cells were quantified in the sub-mucosal lamina propria region on stained tissues via immunofluorescence. Values are expressed as mean+/−SEM (n=10-12). Non-parametric one-way ANOVA (Kruskal-Wallis) test was used.
Figure 16:
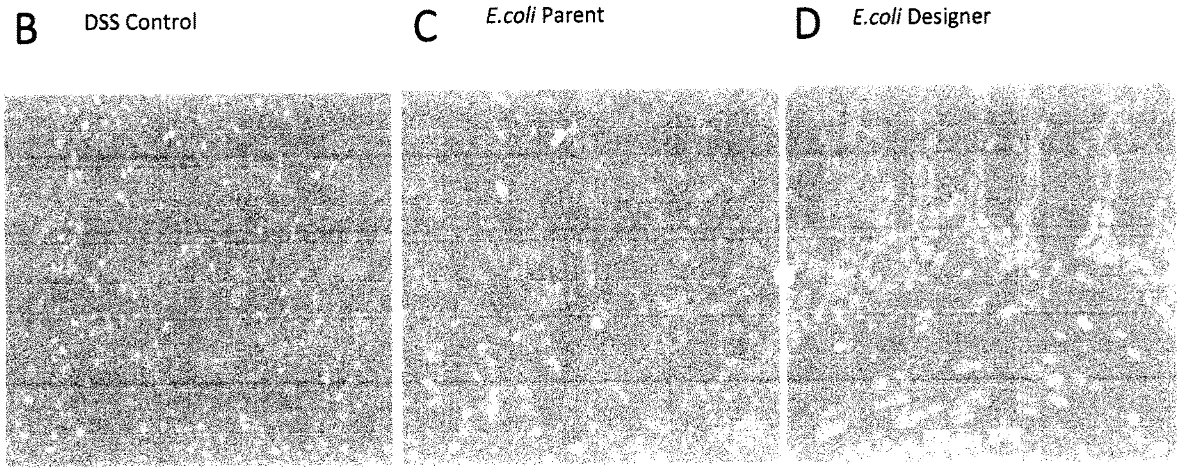
FIG. 16B is an immunofluorescence stained slide of the distal colon of DSS-induced colitis mice showing a representative image of colonic cell infiltration in the sub-mucosal region on a cross sectional cut slide of the distal colon of the DSS control. Positive cells were quantified in the sub-mucosal lamina propria region on stained tissues via immunofluorescence. Values are expressed as mean+/−SEM (n=10-12). Non-parametric one-way ANOVA (Kruskal-Wallis) test was used.
FIG. 16C is an immunofluorescence stained slide of the distal colon of *E. coli* DSS-induced colitis mice showing a representative image of colonic cell infiltration in the sub-mucosal region on a cross sectional cut slide of the distal colon of the *E. coli* parent strain. Positive cells were quantified in the sub-mucosal lamina propria region on stained tissues via immunofluorescence. Values are expressed as mean+/−SEM (n=10-12). Non-parametric one-way ANOVA (Kruskal-Wallis) test was used.
FIG. 16D is an immunofluorescence stained slide of the distal colon of *E. coli* DSS-induced colitis mice showing a representative image of colonic cell infiltration in the sub-mucosal region on a cross sectional cut slide of the distal colon of the *E. coli* designer strain. Positive cells were quantified in the sub-mucosal lamina propria region on stained tissues via immunofluorescence. Values are expressed as mean+/−SEM (n=10-12). Non-parametric one-way ANOVA (Kruskal-Wallis) test was used.
Figure 17A:
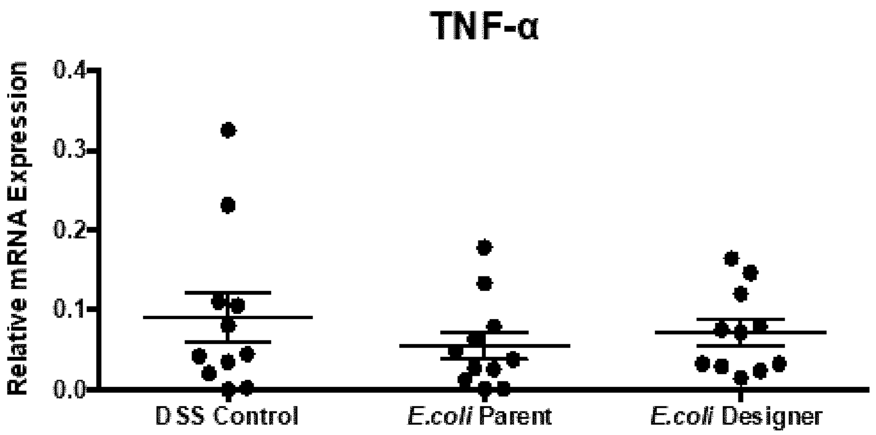
FIG. 17A is a graph showing TNF-α cytokine expression. Designer *E. coli* DSS-induced colitis group shows a general trend in reduction of expression of pro-inflammatory cytokines and increase in expression of anti-inflammatory cytokine. Gene expression of inflammatory cytokines in the colonic tissue of DSS treated probiotic groups performed via qPCR. Values are expressed as mean (n=10-12)+/−SEM.
Figure 17B:
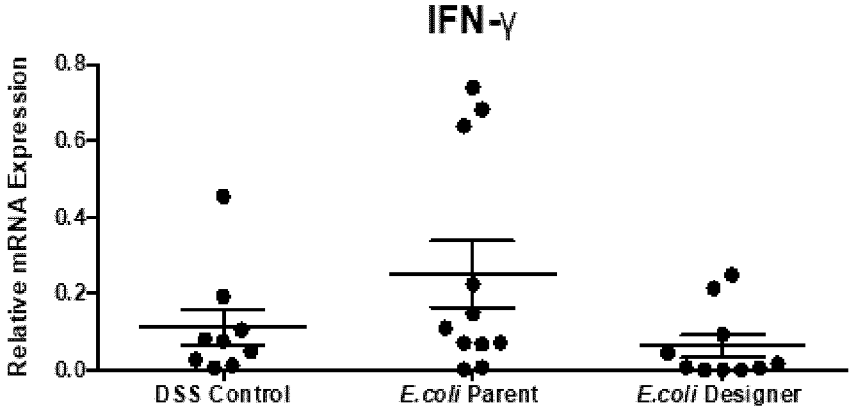
FIG. 17B is a graph showing IFN-γ cytokine expression. Designer *E. coli* DSS-induced colitis group shows a general trend in reduction of expression of pro-inflammatory cytokines and increase in expression of anti-inflammatory cytokine. Gene expression of inflammatory cytokines in the colonic tissue of DSS treated probiotic groups performed via qPCR. Values are expressed as mean (n=10-12)+/−SEM.
Figure 17C:
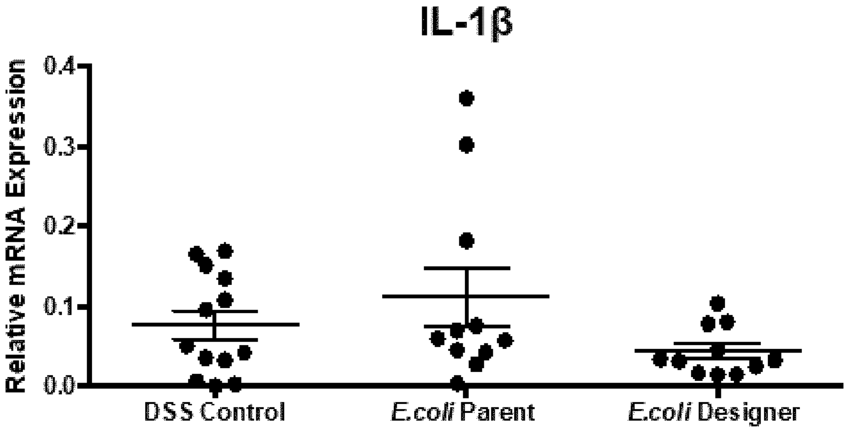
FIG. 17C is a graph showing IL-1β cytokine expression. Designer *E. coli* DSS-induced colitis group shows a general trend in reduction of expression of pro-inflammatory cytokines and increase in expression of anti-inflammatory cytokine. Gene expression of inflammatory cytokines in the colonic tissue of DSS treated probiotic groups performed via qPCR. Values are expressed as mean (n=10-12)+/−SEM.
Figure 17D:
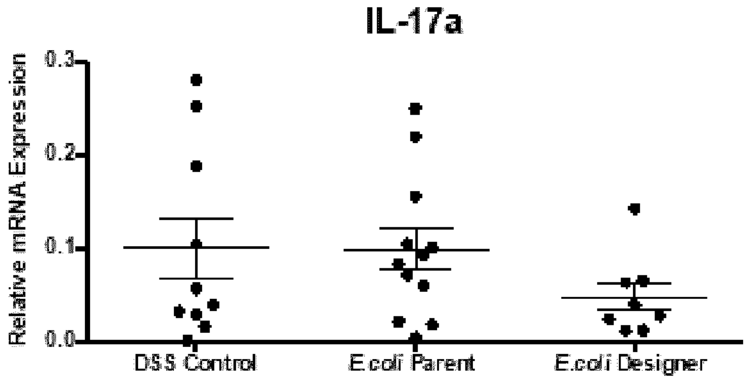
FIG. 17D is a graph showing IL-17a cytokine expression. Designer *E. coli* DSS-induced colitis group shows a general trend in reduction of expression of pro-inflammatory cytokines and increase in expression of anti-inflammatory cytokine. Gene expression of inflammatory cytokines in the colonic tissue of DSS treated probiotic groups performed via qPCR. Values are expressed as mean (n=10-12)+/−SEM.
Figure 17E:
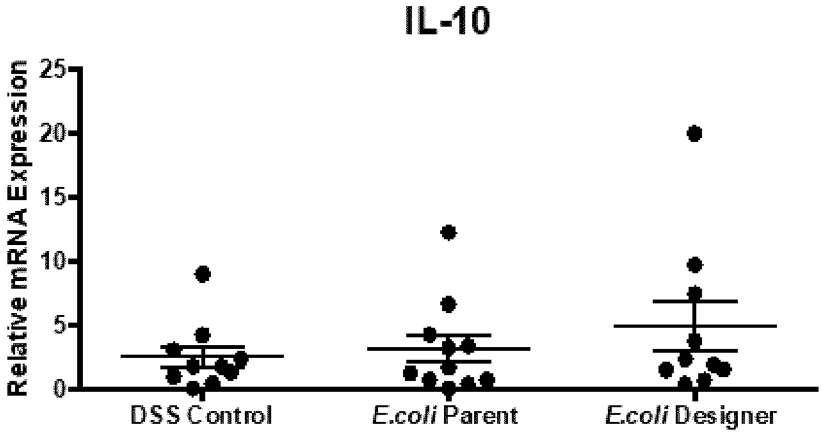
FIG. 17E is a graph showing IL-10 cytokine expression. Designer *E. coli* DSS-induced colitis group shows a general trend in reduction of expression of pro-inflammatory cytokines and increase in expression of anti-inflammatory cytokine. Gene expression of inflammatory cytokines in the colonic tissue of DSS treated probiotic groups performed via qPCR. Values are expressed as mean (n=10-12)+/−SEM.
Figure 18A:
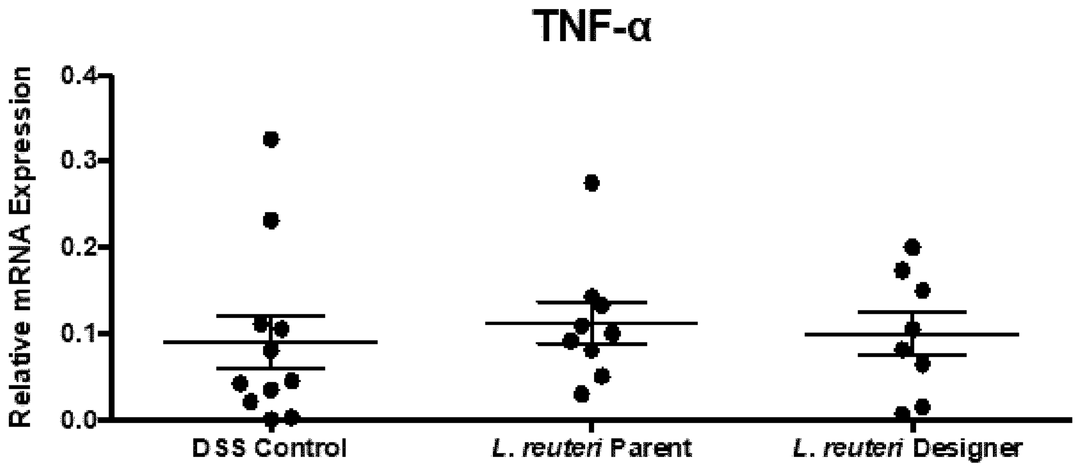
FIG. 18A is a graph showing TNF-α cytokine expression. Designer *L. reuteri* DSS-induced colitis group shows a general trend in reduction of expression of pro-inflammatory cytokines and increase in expression of anti-inflammatory cytokine. Gene expression of inflammatory cytokines in the colonic tissue of DSS treated probiotic groups performed via qPCR. Values are expressed as mean (n=10-12)+/−SEM.
Figure 18B:
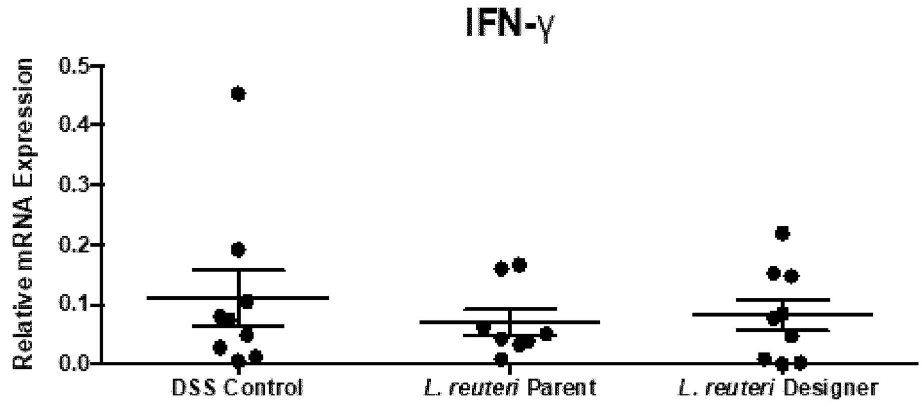
FIG. 18B is a graph showing IFN-γ cytokine expression. Designer *L. reuteri* DSS-induced colitis group shows a general trend in reduction of expression of pro-inflammatory cytokines and increase in expression of anti-inflammatory cytokine. Gene expression of inflammatory cytokines in the colonic tissue of DSS treated probiotic groups performed via qPCR. Values are expressed as mean (n=10-12)+/−SEM
Figure 18C:
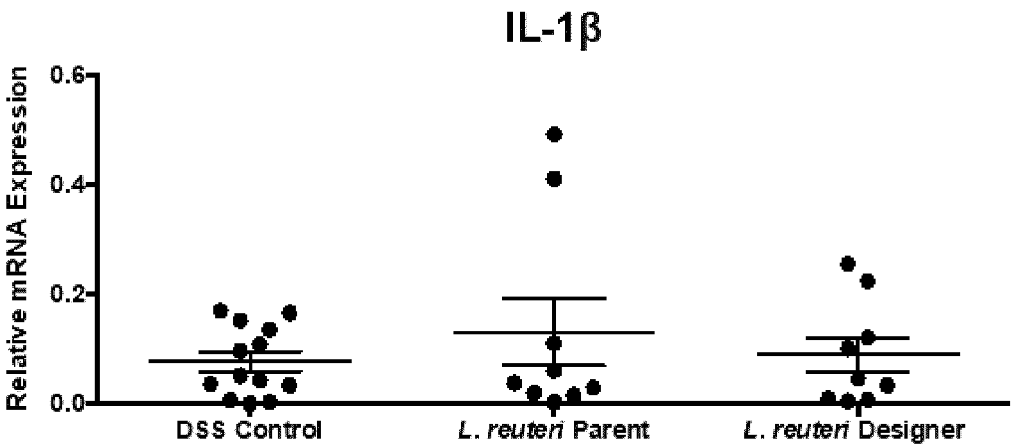
FIG. 18C is a graph showing IL-1β cytokine expression. Designer *L. reuteri* DSS-induced colitis group shows a general trend in reduction of expression of pro-inflammatory cytokines and increase in expression of anti-inflammatory cytokine. Gene expression of inflammatory cytokines in the colonic tissue of DSS treated probiotic groups performed via qPCR. Values are expressed as mean (n=10-12)+/−SEM
Figure 18D:
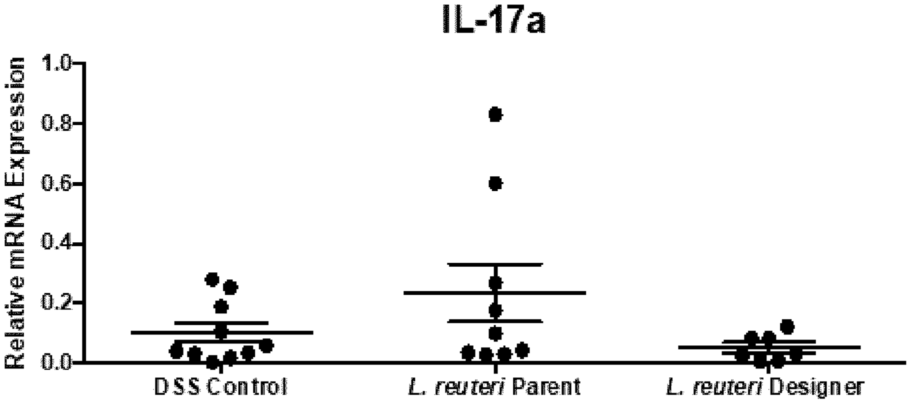
FIG. 18D is a graph showing IL-17a cytokine expression. Designer *L. reuteri* DSS-induced colitis group shows a general trend in reduction of expression of pro-inflammatory cytokines and increase in expression of anti-inflammatory cytokine. Gene expression of inflammatory cytokines in the colonic tissue of DSS treated probiotic groups performed via qPCR. Values are expressed as mean (n=10-12)+/−SEM.
Figure 18E:
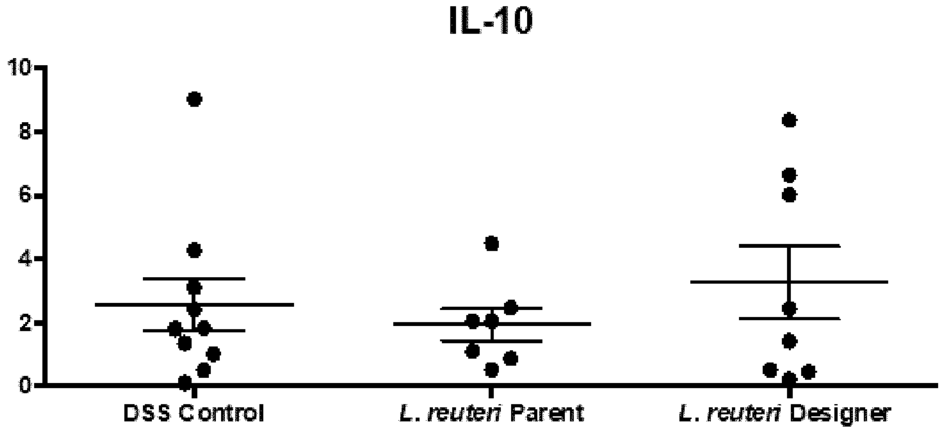
FIG. 18E is a graph showing IL-10 cytokine expression. Designer *L. reuteri* DSS-induced colitis group shows a general trend in reduction of expression of pro-inflammatory cytokines and increase in expression of anti-inflammatory cytokine. Gene expression of inflammatory cytokines in the colonic tissue of DSS treated probiotic groups performed via qPCR. Values are expressed as mean (n=10-12)+/−SEM.

FIGS. 5B and 11B show the clinical scores on days 1-7 of DSS treatment for mice who were administered either the parent probiotic (*L. reuteri*) or the recombinant probiotic strain (*L. reuteri*::GbpA). By day 7, the day with the clinically most relevant scores, shows that the designer strain has a slight advantage over the parent strain in that the clinical score was slightly lower than that of the parent strain (FIGS. 5B and 11B). This again shows that the designer strain does not exert any adverse effect on the host.

Figure 4A:
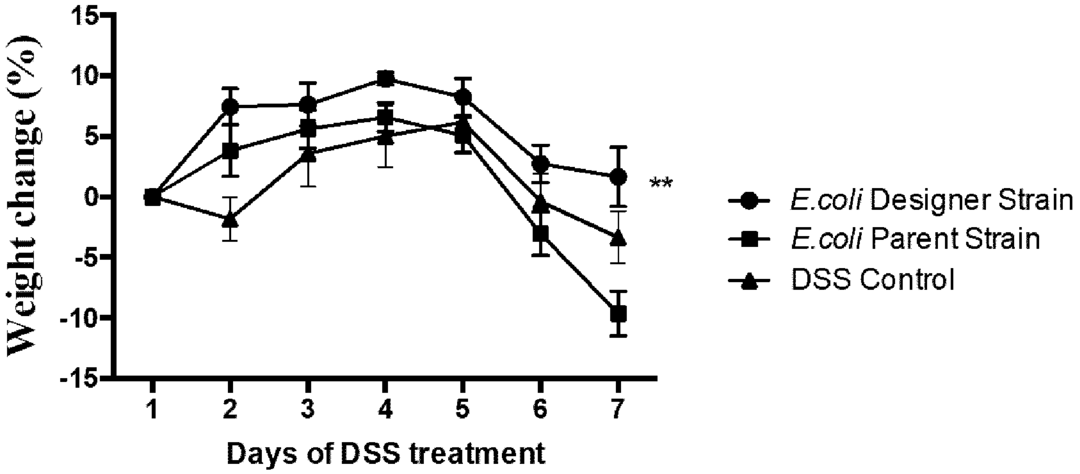
FIG. 4A is a graph showing the weight loss during the DSS treatment period for mice treated with the parental probiotic strain (*E. coli* Nissle), labelled as Parent Strain (Squares). Circles represent the group of mice treated with the recombinant probiotic strain, labelled as the Designer Strain (*E. coli* Nissle attB$^{phi80}$::ttrACBSR). Triangles represent the no probiotic DSS control. Weight loss calculated as percentage of weight loss from starting body weight prior to DSS exposure. Values are expressed as mean+/−SEM (n=4-8). Non-parametric one-way ANOVA (Kruskal-Wallis) was used.
Figure 4B:
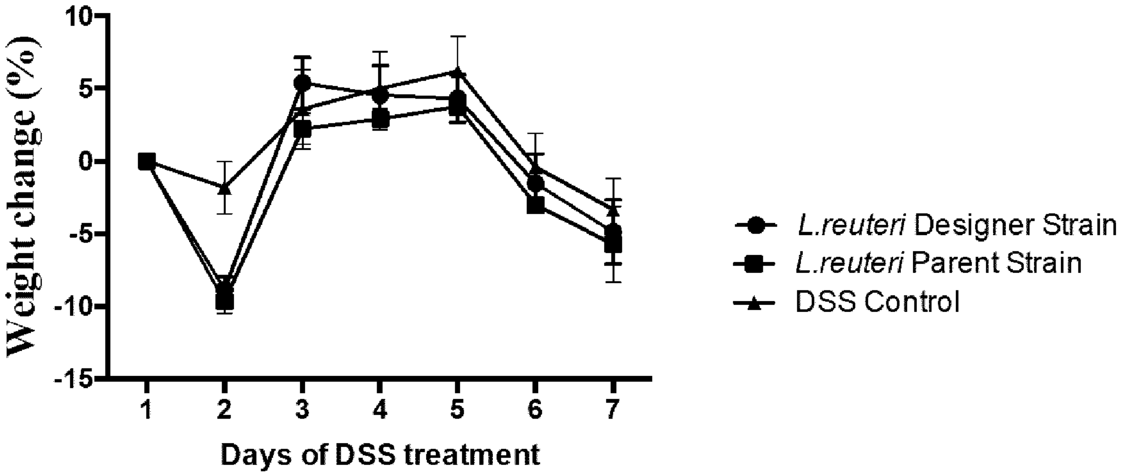
FIG. 4B is a graph showing the weight loss during the DSS treatment period for mice treated with the parental probiotic strain (*L. reuteri*), labelled as Parent Strain (Squares). Circles represent the group of mice treated with the recombinant probiotic strain, labelled as the Designer Strain (*L. reuteri*::GbpA). Triangles represent the no probiotic DSS control. Weight loss calculated as percentage of weight loss from starting body weight prior to DSS exposure. Values are expressed as mean+/−SEM (n=4-8).

During the 7-day DSS treatment, the body weights of mice who had been administered either the parent probiotic (*E. coli* Nissle 1917) or the recombinant strain (*E. coli* Nissle attB$^{phi80}$::ttrACBSR) were measured. FIGS. 4A and 10A show that mice who were administered the recombinant strain displayed a lower % body weight change overall in comparison to the parent strain. Overall, mice administered the recombinant strain maintained their body weight even though they were challenged with DSS. The recombinant probiotic may therefore provide enhanced protection against colitis. FIGS. 4B and 11A show the body weights of mice who had been administered either the parental probiotic strain (*L. reuteri*) or the recombinant strain (*L. reuteri*::GbpA). Both the recombinant and parental strains are shown to have about the same weight change during the course of the DSS treatment. The recombinant strain is shown to have slightly less weight loss over the parent strain. Overall, this shows that the recombinant strain does not have any detrimental effect and is able to provide some protection against the DSS-induced colitis.

In the second set of trials, to assess histopathological damage, tissue sections were scored based on parameters such as crypt damage, epithelial integrity, goblet cell depletion, and ulceration. A higher histopathological score indicates more inflammation and thus more damage as a result from the DSS-induced colitis. The maximum histopathological score is a score of 16. As shown in FIGS. 12A-D and 13A-D, both the designer strains had lower histopathological scores. This indicates that there is less tissue damage seen in the distal colons of these mice. Both the parent and DSS controls show higher histopathological scores with some mice even reaching a score of 15, indicating severe inflammatory conditions. Histopathological damage in active IBD patients is characterized by inflammation in the colonic mucosa. Inflamed tissue as shown in the DSS control, involves infiltration of immune cells (macrophages, neutrophils, lymphocytes etc.) into the sub-mucosal region, destruction or loss of colonic crypts, ulceration present in the crypts, and depletion of mucosal goblet cells. Based on these histopathological scores, the parent strains resemble the DSS control and thus more of an inflamed damage tissue, whereas the designer strains show lower histopathological scores during the DSS-induced colitis.

To assess the role of immune cells in the second set of trials, sections of the distal colon were cut onto slides and stained using immunofluorescence. F4/80 marker was used to stain for macrophages. Positive F4/80 cells that co-localized with DAPI stain, for nuclei, were quantified. As shown in FIGS. 14A-D and 15A-D, the designer strains both showed a reduction in the macrophage colonic infiltration. The DSS control and parent strains both show high levels of macrophage cells in the sub-mucosal region. Based on the previous histopathological scores that looked at immune cell infiltration as a parameter, this confirms the previous finding that both the DSS control and parent strains showed increased immune cell infiltration. Although these immune cells are beneficial by acting as the host's defense; excessive recruitment of these cells is seen in inflammatory states. They work in further recruiting more immune cells and signaling molecules like cytokines to the area of inflammation. In a tissue that is undergoing severe inflammation, further recruitment of cells and molecules may be detrimental. It has been shown that in IBD, these immune cells and molecules can result in uncontrolled activation of the immune system and lead to chronic inflammation (Neurath M F. *Nature Reviews Immunology.* 2014; 14:329-342). Further, looking at MPO marker for neutrophils, a similar pattern is observed in FIGS. 16A-D, that the *E. coli* designer strain has a lower neutrophil infiltration compared to the DSS control and *E. coli* parent strain.

Figure 19:
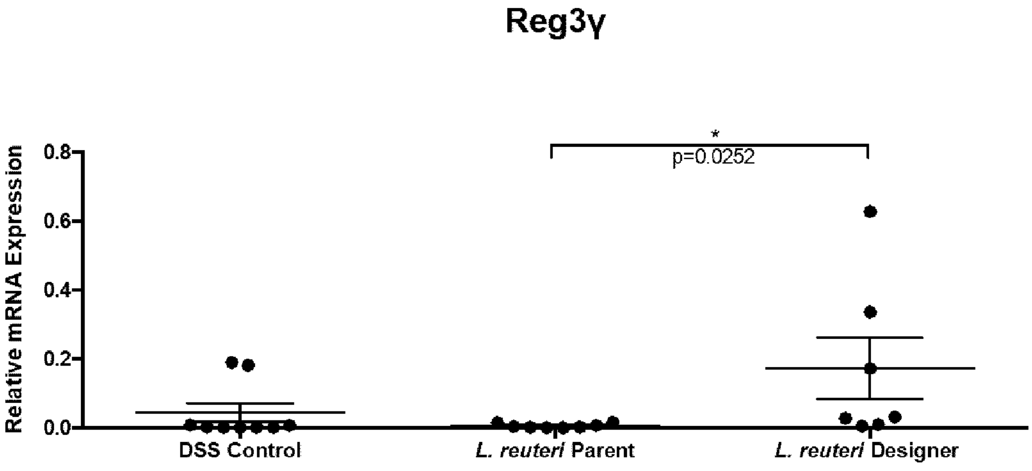
FIG. 19 is a graph showing gene expression of Reg3γ in DSS-induced colitis mice. Gene expression of inflammatory cytokines in the colonic tissue of DSS treated *L. reuteri* probiotic groups performed via qPCR. Values are expressed as mean (n=10-12)+/−SEM. Non-parametric one-way ANOVA (Kruskal-Wallis) test was used.
Figure 20A:
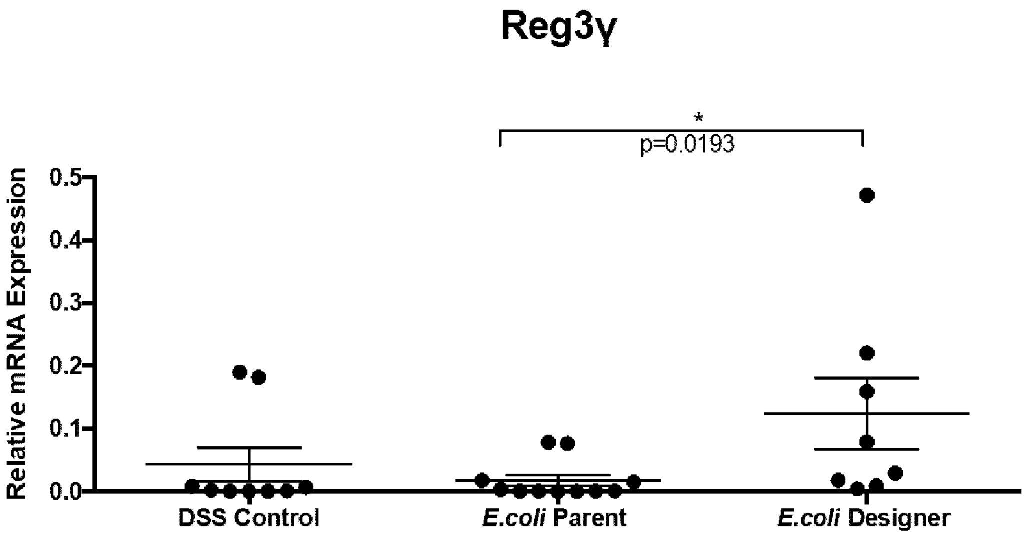
FIG. 20A is a graph showing gene expression of Reg3γ in DSS-induced colitis mice. Gene expression of inflammatory cytokines in the colonic tissue of DSS treated *E. coli* probiotic groups performed via qPCR. Values are expressed as mean (n=10-12)+/−SEM. Non-parametric one-way ANOVA (Kruskal-Wallis) test was used.
Figure 20B:
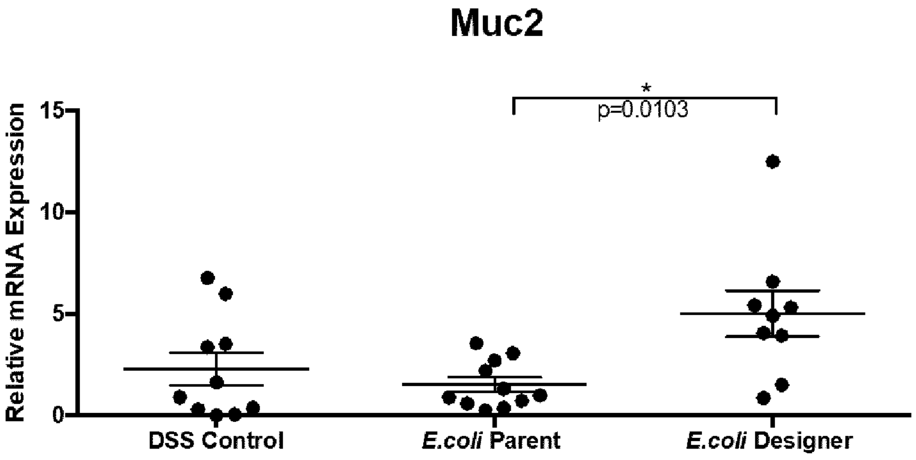
FIG. 20B is a graph showing gene expression of Muc2 in DSS-induced colitis mice. Gene expression of inflammatory cytokines in the colonic tissue of DSS treated *E. coli* probiotic groups performed via qPCR. Values are expressed as mean (n=10-12)+/−SEM. Non-parametric one-way ANOVA (Kruskal-Wallis) test was used.

In the second set of trials, to examine if there were any cytokines that were modulated during DSS-induced colitis, pro-inflammatory cytokines were examined. mRNA was synthesized from extracted host RNA in the distal colon. qPCR was used to look at the relative gene expression. As shown in FIGS. 17A-E and 18A-E, there was an overall pattern in that the pro-inflammatory cytokine gene expression (TNF-α, IFN-γ, IL-1β, and IL-17a) in mice administered the designer strains was lower than the DSS control animals and mice administered the parent strain. Lower expression of these pro-inflammatory cytokines can help reduce some of the uncontrolled activation seen during inflammation and thus can help control some of the symptoms seen during DSS-induced colitis. In contrast, the expression of the anti-inflammatory IL-10 cytokine was shown to be increased in mice administered the designer strains as compared to the parent strain and the DSS control (FIGS. 17E and 18E) This shows that the designer strains are much more protective during inflammation compared to the parent strains. To further look at protective responses, the gene expression of Reg3 and Mucin2 was examined. As shown in FIGS. 19 and 20A-B, the gene expression of these was up-regulated in mice administered the designer probiotic strains as compared to the parent strains and the DSS control. Reg3γ is an anti-microbial peptide that targets gram-positive bacteria by binding to the peptidoglycan layer (Ratsimandresy R A, et al. Cellular & Molecular Immunology. 2017; 14:127-142). The higher expression of this peptide can help in controlling some of the opportunistic bacteria that can populate as a result of the damaged epithelial layer. Following the administration of the *E. coli* designer strain, Muc2 gene expression is higher in mice as compared to animals that received the parent strain. Muc2 is a colonic secretory mucin that is synthesized by goblet cells (Bergstrom K S et al. PLOS Pathogens. 2010; 13(6)). It makes up the mucus layer found in the gut epithelial. Increased expression of this would be beneficial in a tissue undergoing inflammation. With the gene expression of these protective responses, the designer strains are found to be more protective than the parent strains.

Figure 21:
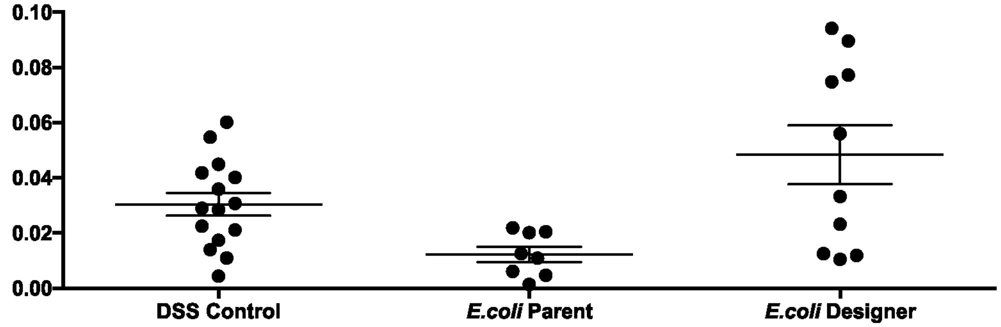
FIG. 21 is a graph showing short chain fatty acid analysis of DSS-induced colitis mice pre-treated with either the *E. coli* Parent strain, *E. coli* Designer strain or the DSS control. Short chain fatty acid analysis performed via gas chromatography on cecal samples of mice from each group. Values are expressed as the amount of butyric acid as a weight percentage of the total cecal tissue and shown as mean+/−SEM (n=10-12). Non-parametric one-way ANOVA (Kruskal-Wallis) test was used.
Figure 22:
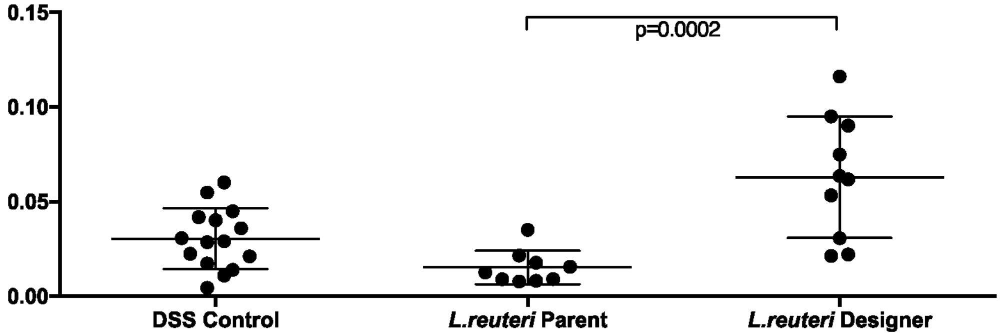
FIG. 22 is a graph showing short chain fatty acid analysis of DSS-induced colitis mice pre-treated with either the *L. reuteri* Parent strain, *L. reuteri* Designer strain or the DSS control. Short chain fatty acid analysis performed via gas chromatography on cecal samples of mice from each group. Values are expressed as the amount of butyric acid as a weight percentage of the total cecal tissue and shown as mean+/−SEM (n=10-12). Non-parametric one-way ANOVA (Kruskal-Wallis) test was used.
Figure 23A:
FIG. 23A is a photograph of the macroscopic examination of cecum and colon from Muc2-deficient mice, showing the $Muc2^{-/-}$ control at 3 months of age at sacrifice. Mice were administered either parent or designer probiotics via oral gavage weekly for 4 weeks. Images were taken to show the colon and ceca of the $Muc2^{-/-}$ colitic mice.
Figure 23B:
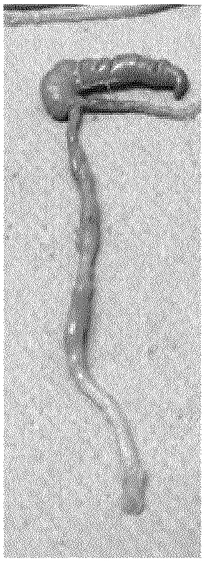
FIG. 23B is a photograph of the macroscopic examination of cecum and colon from Muc2-deficient mice 3 months of age at sacrifice that had been treated with the *E. coli* parent strain. Mice were administered either parent or designer probiotics via oral gavage weekly for 4 weeks.
Figure 23C:
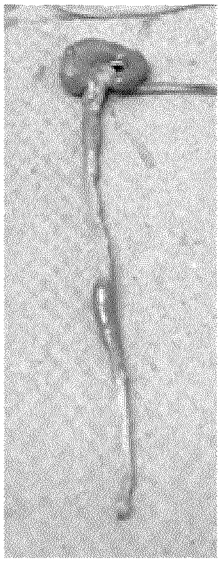
FIG. 23C is a photograph of the macroscopic examination of cecum and colon from Muc2-deficient mice at 3 months of age at sacrifice that had been treated with the designer *E. coli* strain. Mice were administered either parent or designer probiotics via oral gavage weekly for 4 weeks.
Figure 23D:
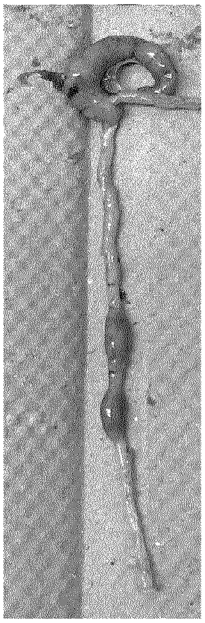
FIG. 23D is a photograph of the macroscopic examination of cecum and colon from Muc2-deficient mice, showing the $Muc2^{-/-}$ control at 4 months of age at sacrifice. Mice were administered either parent or designer probiotics via oral gavage weekly for 4 weeks.
Figure 23E:
FIG. 23E is a photograph of the macroscopic examination of cecum and colon from Muc2-deficient mice at 4 months of age at sacrifice that had been treated with the parent *E. coli* strain. Mice were administered either parent or designer probiotics via oral gavage weekly for 4 weeks.
Figure 23F:
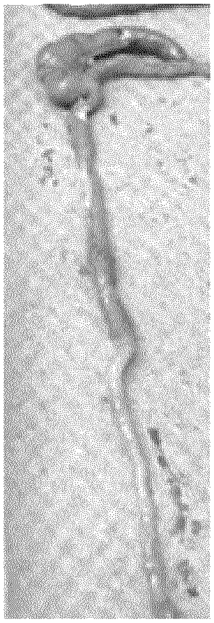
FIG. 23F is a photograph of the macroscopic examination of cecum and colon from Muc2-deficient mice at 4 months of age at sacrifice that had treated with the designer *E. coli* strain. Mice were administered either parent or designer probiotics via oral gavage weekly for 4 weeks.
Figure 24A:
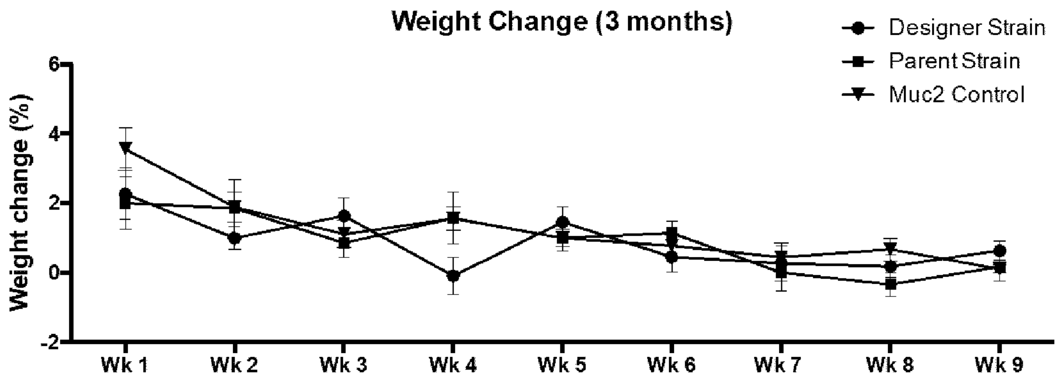
FIG. 24A is a graph showing weight change in Muc2-deficient mice at 3 months for $Muc2^{-/-}$ control, parent *E. coli* strain, and designer *E. coli* strain mice. Weight change calculated as percentage of weight loss from starting body weight. Circles represent *E. coli* designer strain, squares represent *E. coli* parent strain, and triangles represent $Muc2^{-/-}$ control. Values are expressed as mean+/−SEM (n=7-11).
Figure 24B:
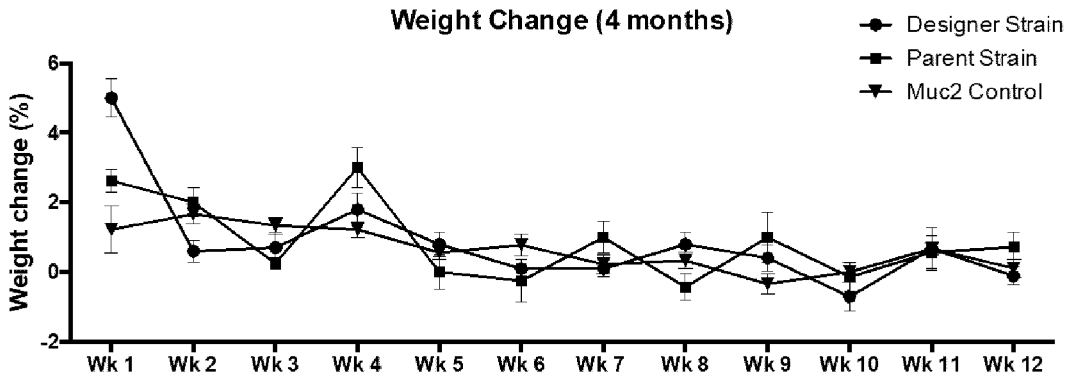
FIG. 24B is a graph showing weight change in Muc2-deficient mice at 4 months for $Muc2^{-/-}$ control, parent *E. coli* strain, and designer *E. coli* strain mice. Weight change calculated as percentage of weight loss from starting body weight. Circles represent *E. coli* designer strain, squares represent *E. coli* parent strain, and triangles represent $Muc2^{-/-}$ control. Values are expressed as mean+/−SEM (n=7-11).
Figure 25A:
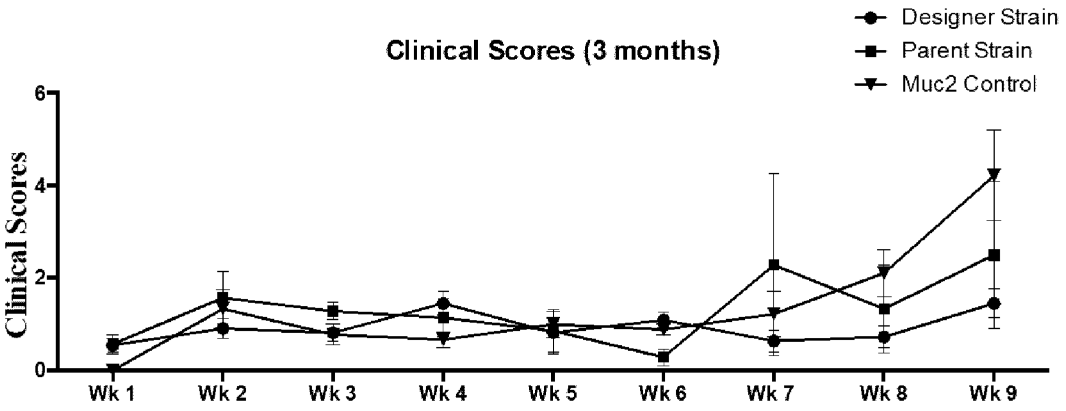
FIG. 25A is a graph showing the clinical scores in Muc2-deficient mice at 3 months that were treated with the parent *E. coli* strain, the designer *E. coli* strain or the untreated $Muc2^{-/-}$ control mice. Clinical scores calculated throughout the study are shown. Scores are based on parameters of body movement, rectal bleeding, stool consistency, weight change, and hydration. Circles represent *E. coli* designer strain, squares represent *E. coli* parent strain, and triangles represent $Muc2^{-/-}$ control. Values are expressed as mean+/−SEM (n=7-11). Non-parametric one-way ANOVA (Kruskal-Wallis) test was used.
Figure 25B:
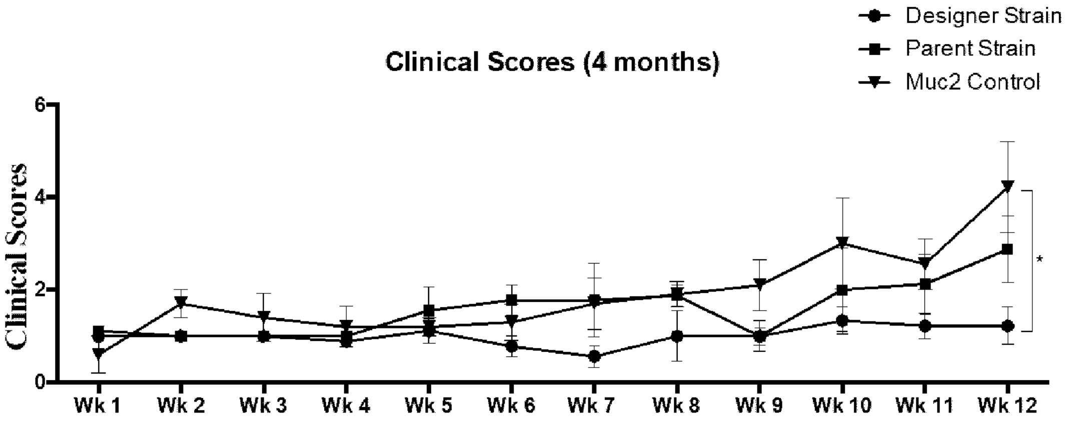
FIG. 25B is a graph showing the clinical scores in Muc2-deficient mice at 4 months that were treated with the parent *E. coli* strain, the designer *E. coli* strain or the untreated $Muc2^{-/-}$ control mice. Clinical scores calculated throughout the study are shown. Scores are based on parameters of body movement, rectal bleeding, stool consistency, weight change, and hydration. Circles represent *E. coli* designer strain, squares represent *E. coli* parent strain, and triangles represent $Muc2^{-/-}$ control. Values are expressed as mean+/−SEM (n=7-11). Non-parametric one-way ANOVA (Kruskal-Wallis) test was used.
Figure 26:
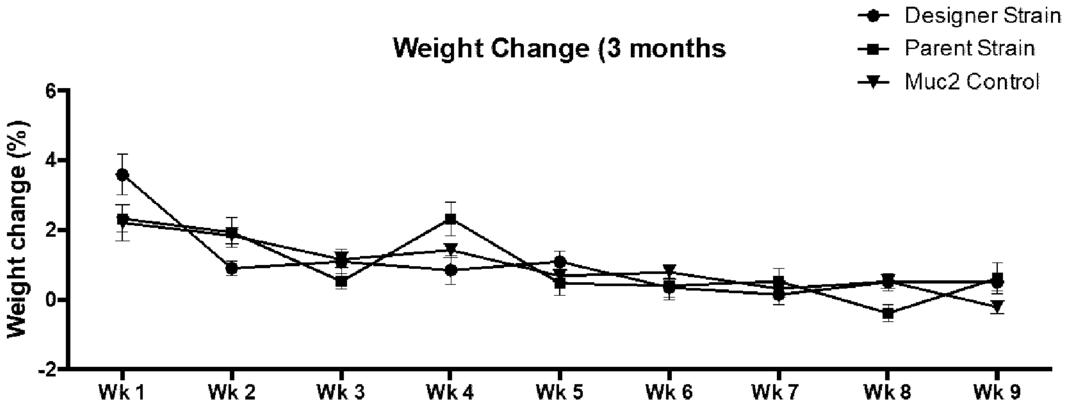
FIG. 26 is a graph showing weight change during duration of colitis in mouse strains, all at 3 months. Weight change calculated as percentage of weight loss from starting body weight. Circles represent mice treated with the *E. coli* designer strain, squares represent mice treated with the *E. coli* parent strain, and triangles represent Muc2$^{-/-}$ control mice. Values are expressed as mean+/−SEM (n=15-20).

To further explore protective responses, the production of short chain fatty acids (SCFAs) was examined. The by-products of fermentation of indigestible dietary residues result in metabolites such as short chain fatty acids (SCFAs). SCFAs have many roles such as nutrients for colonic epithelium, mediating intercellular pH, cell volume, ion transport, and regulation of proliferation, differentiation, and gene expression. Butyric acid not only acts as fuel for colonic epithelial cells but it also regulates cell proliferation and differentiation. Butyric acid is preferred over propionate and acetate in colonocyte metabolism, where butyrate oxidation makes up 70% of the oxygen consumed by colonic tissue (Morrison D J and Preston T. Gut Microbes. 2016; 7(3):189-200). Since, butyric acid is an important regulator of colonic proliferation, increased amounts are beneficial during inflammation. SCFAs were examined using gas chromatography. As shown in FIGS. 21 and 22, butyric acid was found to be more abundant in animals that received the designer stains compared to the parent stains and DSS control. Acetic acid and propionic acid showed no significance differences. This further shows that the designer strains are more protective compared to the parent strains.

Example 4—Pro-Inflammatory Cytokine Expression

In order to investigate the protection seen in the recombinant strain (*E. coli* Nissle attB$^{phi80}$::ttrACBSR), we examined whether there were any cytokines that were modulated during DSS-induced colitis. At day 7 of the DSS treatment, mice were sacrificed and inflammatory cytokine levels in colonic tissues were assessed. FIGS. 6A-D show cytokines levels in colonic tissues of mice who received either the parent probiotic (*E. coli* Nissle 1917) or the recombinant probiotic (*E. coli* Nissle attB$^{phi80}$::ttrACBSR). Overall, mice who received the recombinant strain showed a trend towards lower levels of cytokine expression in comparison to those who received the parent strain. FIGS. 6A-D show the parent strain is associated with higher levels of pro-inflammatory cytokine expression, indicating that the designer probiotic may have an improved protective effect during colitis, compared to the parent probiotic strain. The most drastic and significant differences were seen with the pro-inflammatory cytokines interleukin-1 beta (IL-1β) and interleukin-17a (IL-17a). IL-1β is a mediator of inflammatory responses that are involved in cell proliferation, differentiation, and apoptosis. IL-17a is a signaling molecule secreted mainly by T-helper cells and may be a mediator of inflammatory responses. It induces the activation of certain genes that are associated with inflammation. It further stimulates pro-inflammatory responses, including those induced by IL-1β. The lowered expression of these pro-inflammatory responses, especially during colitis, help to reduce the inflammation and this would be beneficial in controlling the symptoms seen. The parent strain is seen to have highly elevated expression of these pro-inflammatory cytokines, indicating that there are high levels of inflammation undergoing. Therefore, the designer parent is seen to be much more protective during colitis compared to the parent strain probiotic.

FIG. 7A-D show cytokine profiles from colonic tissues of mice treated with either the parental strain (*L. reuteri*) or the recombinant strain (*L. reuteri*::GbpA). Most of the cytokines examined showed a trend in which the recombinant strain had lower expression levels. The most drastic and significant differences were seen with the pro-inflammatory cytokines tumor necrosis factor alpha (TNF-α) and interferon gamma (IFN-γ). TNF-α is a signaling molecule that plays a role in the activation of further inflammatory responses. IFN-γ is another typical pro-inflammatory cytokine that further stimulates more immune cells, such as natural killer (NK) and T cells. Such pro-inflammatory cytokines are elevated during conditions like IBD and lead to tissue damage from increased inflammation. Therefore, the lowered expression of these pro-inflammatory responses, especially during colitis, help to reduce the inflammation and this would be beneficial in controlling the symptoms seen. The parent strain is seen to have highly elevated expression of these pro-inflammatory cytokines, indicating that there are high levels of inflammation undergoing. Thus, the recombinant strain is seen to be much more protective during colitis compared to the parent strain.

Example 5—Muc2$^{-/-}$ Spontaneous Colitis with *E. coli*

The designer strains were shown to provide protection during DSS-induced colitis; therefore, we examined another model of murine colitis, Muc2$^{-/-}$ spontaneous colitis. Muc2$^{-/-}$ mice develop spontaneous colitis, which is characterized by hyperplasia, crypt abscesses, immune cell infiltration, and sub-mucosal edema (Morampudi V. et al. *Mucosal Immunolgy.* 2016:1-16). These all represent clinical features of active ulcerative colitis. Mucin 2 is the prominent mucin synthesized in the colon and therefore a defective mucus barrier in animal models allows bacterial contact with the intestinal epithelium (Morampudi V. et al. *Mucosal Immunolgy.* 2016:1-16). This results in spontaneous colitis since a defective mucus barrier is seen in ulcerative colitis. Muc2–/– mice can develop rectal prolapse and this would indicate sever inflammation and human endpoint for the mice. Muc2–/– mice bred on a C57BL/6 background were administered either *E. coli* parent stain or designer strain. These animals were split into two cohorts at 3 months of age and at 4 months of age to look at the disease progression with age. Mice were orally gavaged a dose of probiotics once weekly for 4 consecutive weeks. The clinical scores and weight change of these animals was monitored weekly throughout the entire Muc2$^{-/-}$ spontaneous colitis.

The rate of rectal prolapse is summarized in Table 4. The Muc2 control had a 5% rectal prolapse rate, parent strain had a 20% rectal prolapse rate and the designer strain had a 0% rectal prolapse rate. The *E. coli* designer strain had no rectal prolapses in all cohorts of 3 and 4 months of age mice, indicating that the *E. coli* designer strain is providing protection.

TABLE 4

Rate of rectal prolapse in 3 month and 4-month old Muc2$^{-/-}$ mice

| Treatment Groups | Muc2$^{-/-}$ Control | Parent Strain | Designer Strain |
|---|---|---|---|
| Number of rectal prolapses | 1/19 (5%) | 3/15 (20%) | 0/20 (0%) |

Macroscopic images of the distal colon and ceca were taken and, in FIGS. 23A-F, show that in both 3-month (FIGS. 23A-C) and 4-month (FIGS. 23D-F) old Muc2$^{-/-}$ mice, the Muc2$^{-/-}$ control and parent strain groups showed more swollen distal colons compared to the designer strain groups. The ceca of the Muc2$^{-/-}$ control and parent strain mice are more enlarged in size in comparison to the designer strain. This indicates that the administration of the designer strain resulted in less swollen inflamed tissues.

The body weight changes and clinical scores of the Muc2$^{-/-}$ mice at 3 months and 4 months of age are shown in FIGS. 24A-B, 25A-B, 26 and 27. Body weight changes do not show significant changes but when graphing all mice at 3 months of age, the designer strain group shows a slight difference with less body weight loss compared to the Muc2–$^{/-}$ control mice shown in FIG. 26. For clinical scores, parameters such as body movement, stool consistency, weight change, and hydration were examined. Shown in FIGS. 25A-B and 27, at 3 months and 4 months of age, the designer stain group shows lower clinical scores compared to the Muc2$^{-/-}$ control and a slight advantage over the parent strain group. This indicated that the administration of the designer strain in Muc2$^{-/-}$ mice show less clinical symptoms during the disease progression.

To examine if there was a systemic infection, the MLN and spleen was homogenized and then plated on 1.8% LB agar plates to obtain colony counts. Bacterial translocation would result in the passage of viable bacteria from the digestive tract into other body sites that normally would not have bacteria present. Such sites like the MLN and spleen can be used as indicators of bacterial translocation and high amounts of this translocation could result in sepsis. Bacterial translocation indicates that there is dysregulation in either the epithelial layer or the host immune defenses or a combination of both. As shown in FIGS. 28A-B and 29A-B, there are lower colony forming units (CFU) per mL of homogenate plated in the designer strain animal group compared to the parent strain and Muc2$^{-/-}$ control animal groups at both 3 and 4 months of age. This indicates that there can be a leaky gut present in the Muc2$^{-/-}$ mice administered the parent strain and the Muc2$^{-/-}$ control mice that is allowing the passage of bacteria into extra-intestinal sites. Thus, with the rectal prolapse rate at 0%, lower clinical scores, and lower bacterial CFU/mL counts the administration of the *E. coli* designer strain is shown to be more protective during Muc2$^{-/-}$ spontaneous colitis compared to the parent strain and the no probiotic Muc2$^{-/-}$ control.

The results indicate that the *E. coli* and *L. reuteri* designer probiotics were more efficacious during DSS-induced colitis compared to the unmodified parent strains. Macroscopic examination revealed that the modified designer probiotics had less bloody and loose stool in the colon and cecum compared to the unmodified parent strains. The designer probiotics also lost less body weight and had lower clinical scores during the DSS-induced colitis period. The unmodified parent DSS groups lost more of their initial starting body weight and had high clinical scores, indicating humane endpoint in some mice. Histopathologically, the designer strains showed lower histopathological scoring compared to the parent and control groups, as well as fewer gene expression levels of pro-inflammatory markers such as TNF-α, IFN-γ, IL-1β, and IL-17a. In contrast, the unmodified parent strains showed elevated expression of many pro-inflammatory markers, indicating no improvement during IBD. The designer strains also showed a trend of an increase in the expression of the anti-inflammatory cytokine IL-10. The designer strains further showed lower counts of macrophage cell infiltration and the *E. coli* designer strain showed lower counts of neutrophil infiltration, indicating that these designer strains have less damage in the colonic tissue. In terms of protective responses, both the designer strains had an increase of expression in Reg3γ and increased production of the bacterial metabolite butyric acid. The *E. coli* designer strain further had an increase in Muc2 gene expression. Looking at the Muc2$^{-/-}$ spontaneous colitis model with the *E. coli* designer strain, there were no rectal prolapses shown compared to the 5% and 20% for the Muc2 control and parent strain, respectively. There were also lower clinical scores and lower incidence of bacterial translocation in mice that were administered the *E. coli* designer strain as compared to the Muc2 control$^{-/-}$ and mice administered the *E.coli* parent strain. Overall, this shows that the *E. coli* and *L. reuteri* are more protective during DSS-induced colitis. In addition, in the tested *E. coli* designer strain in Muc2$^{-/-}$ spontaneous colitis, the *E. coli* is more protective compared to its parent strain.

All citations are hereby incorporated by reference.

The present invention has been described with regard to one or more embodiments. However, it will be apparent to persons skilled in the art that a number of variations and modifications can be made without departing from the scope of the invention as defined in the claims.

What is claimed is:

1. A recombinant probiotic bacterium expressing a tetrathionate reductase, wherein the tetrathionate reductase is encoded by a tetrathionate respiratory operon, wherein the tetrathionate respiratory operon comprises a nucleotide sequence having at least 98% sequence identity to the nucleic acid sequence set forth in SEQ ID NO: 25.

2. The recombinant probiotic bacterium of claim 1, wherein the recombinant probiotic bacterium is *E. coli* Nissle or *L. reuteri* DSM20016.

3. The recombinant probiotic bacterium of claim 1, wherein the nucleic acid sequence is harmonized for expression in the probiotic bacterium.

4. The recombinant probiotic bacterium of claim 1, wherein the expression of the tetrathionate reductase is chromosomal or plasmid-based.

5. The recombinant probiotic bacterium of claim 1, wherein the tetrathionate respiratory operon is the ttrACBSR operon of *Salmonella enterica*.

6. The recombinant probiotic bacterium of claim 1, wherein the tetrathionate respiratory operon comprises the ttrACB genes of *Salmonella enterica*.

7. The recombinant probiotic bacterium of claim 1, wherein the tetrathionate respiratory operon comprises the ttrSR genes of *Salmonella enterica*.

8. The recombinant probiotic bacterium of claim 1, wherein the tetrathionate respiratory operon comprises the ttrA gene, the ttrC gene and the ttrB gene of *Salmonella enterica*.

9. The recombinant probiotic bacterium of claim 1, wherein the tetrathionate respiratory operon comprises the ttrS gene and the ttrR gene of *Salmonella enterica*.

10. The recombinant probiotic bacterium of claim 8, wherein the ttrA gene of *Salmonella enterica* encodes the amino acid sequence of SEQ ID NO: 34.

11. The recombinant probiotic bacterium of claim 8, wherein the ttrB gene of *Salmonella enterica* encodes the amino acid sequence of SEQ ID NO: 36.

12. The recombinant probiotic bacterium of claim 8, wherein the ttrC gene of *Salmonella enterica* comprises the nucleotide sequence of SEQ ID NO: 37.

13. The recombinant probiotic bacterium of claim 9, wherein the ttrR gene of *Salmonella enterica* encodes the amino acid sequence of SEQ ID NO: 40.

14. The recombinant probiotic bacterium of claim 9, wherein the ttrS gene of *Salmonella enterica* encodes the amino acid sequence of SEQ ID NO: 42.

15. The recombinant probiotic bacterium of claim 1, wherein the tetrathionate respiratory operon comprises the nucleotide sequence set forth in SEQ ID NO: 25.

16. A probiotic composition comprising the recombinant probiotic bacterium of claim 1 and a pharmaceutically acceptable carrier.

17. A method of ameliorating gastrointestinal inflammation in a human or non-human subject in need thereof comprising administering to the subject an effective amount of the composition of claim 16 sufficient to ameliorate the gastrointestinal inflammation.

18. The method of claim 17, wherein the gastrointestinal inflammation is associated with irritable bowel disease.

19. The method of claim 17, wherein the composition is administered orally.

* * * * *